United States Patent
Ohno et al.

(10) Patent No.: US 7,494,989 B2
(45) Date of Patent: Feb. 24, 2009

(54) PYRIDINE COMPOUNDS USEFUL AS N-TYPE CALCIUM CHANNEL ANTAGONISTS

(75) Inventors: Seiji Ohno, Kawasaki (JP); Kayo Otani, Kawasaki (JP); Seiji Niwa, Kawasaki (JP); Satoshi Iwayama, Kawasaki (JP); Akira Takahara, Kawasaki (JP); Hajime Koganei, Kawasaki (JP); Yukitsugu Ono, Kawasaki (JP); Shinichi Fujita, Kawasaki (JP); Tomoko Takeda, Kawasaki (JP); Masako Hagihara, Kawasaki (JP); Akiko Okajima, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/856,339

(22) Filed: Sep. 17, 2007

(65) Prior Publication Data
US 2008/0070903 A1 Mar. 20, 2008

Related U.S. Application Data

(60) Division of application No. 10/387,543, filed on Mar. 14, 2003, now Pat. No. 7,288,544, which is a continuation of application No. PCT/JP01/07841, filed on Sep. 10, 2001.

(30) Foreign Application Priority Data

Sep. 14, 2000 (JP) ............... 2000-280438
Apr. 25, 2001 (JP) ............... 2001-126832

(51) Int. Cl.
C07D 213/82 (2006.01)
C07D 213/80 (2006.01)
C07D 401/06 (2006.01)
A61K 31/455 (2006.01)
A61K 31/496 (2006.01)

(52) U.S. Cl. ............... 514/217.04; 514/235.5; 514/253.13; 514/318; 514/343; 514/355; 514/356; 540/597; 544/124; 544/365; 546/194; 546/279.1; 546/316; 546/321

(58) Field of Classification Search ............... 546/279.1, 546/316, 321, 194; 544/365, 124; 514/355, 514/356, 253.13, 343, 318, 217.04, 235.5; 540/597
See application file for complete search history.

(56) References Cited

U.S. PATENT DOCUMENTS

| 4,698,340 | A | 10/1987 | Takaya et al. |
| 6,274,588 | B1 | 8/2001 | Bös et al. |
| 6,350,762 | B1 | 2/2002 | Niwa et al. |
| 6,350,766 | B1 | 2/2002 | Uneyama et al. |
| 6,610,717 | B2 | 8/2003 | Nakajo et al. |
| 6,855,716 | B2 | 2/2005 | Ohno et al. |
| 6,995,179 | B2 | 2/2006 | Uneyama et al. |
| 7,247,645 | B2 | 7/2007 | Nakanishi et al. |
| 2002/0002167 | A1 | 1/2002 | Niwa et al. |
| 2005/0009814 | A1 | 1/2005 | Iwayama et al. |

FOREIGN PATENT DOCUMENTS

| JP | 2-22266 | 1/1990 |
| WO | 98/49144 | 11/1998 |
| WO | 99/01438 | 1/1999 |
| WO | 00/78730 | 12/2000 |
| WO | WO 2004/080444 | * 9/2004 |

OTHER PUBLICATIONS

H. Takasugi et al, 1990, CAPLUS Abstract 113:40722.
M. Wallace, "Calcium and sodium channel antagonists for the treatment of pain", Jun. 2000, PubMed Abstract, Clin. J. Pain., 16(2 Suppl.):S80-5.
J. Putney, Jr. et al, "Mechanisms of capacitative calcium entry", 2001, Journal of Cell Science, 114 (12), pp. 2223-2229.
A. Damasio, "Alzheimer's Disease and Related Dementias", 1996, Cecil Textbook of Medicine, 20th Ed., vol. 2, pp. 1992-1996.
R. Layzer, "Section Five—Degenerative Diseases of the Nervous System", 1996, Cecil Textbook of Medicine, 20th Ed., vol. 2, pp. 2050-2057.

* cited by examiner

Primary Examiner—Deepak Rao
(74) Attorney, Agent, or Firm—Oblon, Spivak, McClelland, Maier & Neustadt, P.C.

(57) ABSTRACT

Achiral pyrimidine derivatives and pyridine derivatives of the following formulae or analogs thereof have selective N-type calcium channel antagonistic activity and showed analgesic action when they were taken orally. They are useful as therapeutic agents for pains and various diseases associated with the N-type calcium channels.

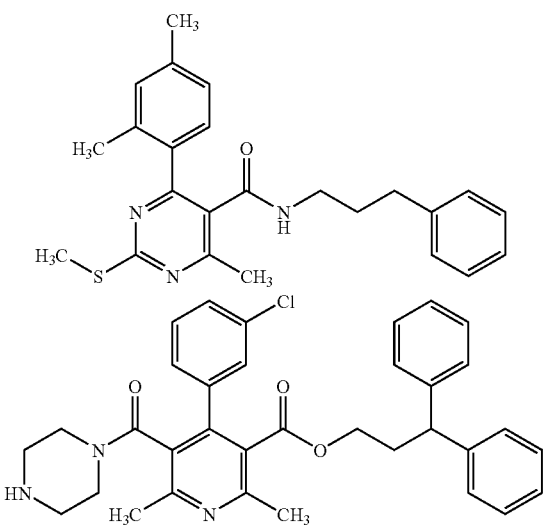

30 Claims, No Drawings

PYRIDINE COMPOUNDS USEFUL AS N-TYPE CALCIUM CHANNEL ANTAGONISTS

CROSS REFERENCE TO RELATED APPLICATIONS

This application is a divisional application of U.S. patent application Ser. No. 10/387,543, filed on Mar. 14, 2003, now U.S. Pat. No. 7,288,544, which was a continuation of International Patent Application No. PCT/JP01/07841, filed on Sep. 10, 2001, and claims priority to Japanese Patent Application No. 2000-280438, filed on Sep. 14, 2000, and Japanese Patent Application No. 2001-126832, filed on Apr. 25, 2001.

BACKGROUND OF THE INVENTION

The present invention relates to new pyrimidine derivatives and the use of the pyrimidine derivatives as medicines. The present invention also relates to new pyridine derivatives and use of the pyridine derivatives as medicines. The association of the activation of N-type calcium channels is suggested in various diseases, for example, acute stage of ischemic cerebrovascular disorders such as cerebral infarction or intracerebral bleeding (including subarachnoidal hemorrhage); progressive neurodegenerative diseases such as Alzheimer's disease, AIDS related dementia, Parkinson's disease, dementia due to cerebrovascular disorder and ALS; neuropathy caused by head injury; various pains such as pains caused by spinal injury, diabetes or thromboangiitis obliterans, neuropathic pain, migraine, visceral pain and cancer pain; bronchial asthma; various diseases associated with psychogenic stress such as unstable angina and irritable colitis; withdrawal symptoms after addiction to drugs such as emotional disorder and ethanol addiction withdrawal symptoms. The compounds of the present invention can inhibit the N-type calcium channels. The present invention relates to the compounds usable as therapeutic agents for these diseases.

Calcium channels are now classified into subtypes of L, N, P, Q, R and T. Each subtype of calcium channels is organ-specifically distributed. It is known that particularly N-type calcium channels are widely distributed in central nerves, peripheral nerves and adrenomedullary cells and participates in neuronal cell death, regulation of blood catecholamine level and control of senses such as perception.

It has been confirmed that omega-conotoxin GVIA and omega-conotoxin MVIIA, which are peptides selectively inhibiting N-type calcium channels, inhibit the release of excitatory neurotransmitters in the sliced brain preparation. It is also confirmed in animal experiments that they inhibit the progress of neuronal necrosis associated with cerebrovascular disorders. It is generally considered that compounds having a N-type calcium channel blocking activity are clinically effective in the treatment of acute stage of ischemic cerebrovascular disorders such as cerebral infarction or intracerebral bleeding (including subarachnoidal hemorrhage); progressive neurodegenerative diseases such as Alzheimer's disease, AIDS related dementia, Parkinson's disease, dementia due to cerebrovascular disorder and ALS; and neuropathy caused by head injury. Further, it is confirmed in animal tests that omega-conotoxin MVIIA relieves a pain induced by formalin, hot plate and peripheral neuropathy (J. Pharmacol. Exp. Ther. 269 (3) 1117-1123, 1994; J. Pharmacol. Exp. Ther. 274 (2) 666-672, 1995). Accordingly, omega-conotoxin MVIIA is considered to be clinically effective against various pains such as pain caused by spinal injury, diabetes or thromboangiitis obliterans, neuropathic pain (for example, post herpetic neuralgia, diabetic nephropathy, complex regional pain syndrome, avulsion injury of the brachial plexus, trigeminal neuralgia, pain from spinal injury, central pain and postoperative pain), migraine, visceral pain and cancer pain. In addition, because omega-conotoxin GVIA inhibits the release of catecholamine from cultured sympathetic ganglion cells, exaltation of catecholamine secretion from canine adrenal medulla and the contraction of the isolated blood vessel by electric stimulation of the perivascular nerve, it is considered that compounds having N-type calcium channel-blocking effects are clinically effective against bronchial asthma, various diseases related to psychogenic stress such as unstable angina and irritable colitis (Neuropharmacol., 32, 1141, 1993).

Some peptidergic and non-peptidergic compounds which selectively affect N-type calcium channels have been ever disclosed (see, for example, WO 9313128, WO 9849144, WO9901438 and WO9932446). However, none of them was actually used as a medicine. Some of the compounds which affect N-type calcium channels are also effective against various types of calcium channels of other than N-type (British Journal of Pharmacology, 122 (1) 37-42, 1997). For example, compounds having an antagonistic effect on L-type calcium channels (the channels that are locally distributed in various organs such as vascular smooth muscles) which are very closely related to hypotensive effect, could not be used for diseases for which N-type calcium channel antagonists will be used (such as cerebral stroke, neuralgia, terminal cancer pain and pain of spinal injury). Under these circumstances, the development of a highly active antagonist selective toward N-type calcium channels (the channels that exist in the nervous system) has been eagerly demanded. Recently, improvement in QOL (Quality of life) of the patients is demanded, and medicines to be taken orally are considered to be necessary. Especially, when the medicines are used as analgesic agents to terminal cancer patients and spinal injury victims, less frequent doses and lower dosage will further improve QOL.

However, N-type calcium channel antagonists well-known in the art were yet unsatisfactory for solving this problem because some of them are peptides which cannot be absorbed in the digestive organs or some of them are chemically unstable and, therefore, decomposed in the digestive organs. Though N-type calcium channel antagonists can be absorbed in the digestive organs, the compounds that have less first-pass effect and high durability of drug efficacy cannot be found yet. In addition, some of the well-known compounds are those which have asymmetric carbons. The compounds having an asymmetric carbon have optical isomers, and the activity, toxicity and pharmacokinetics between the isomers are generally believed to be different from each other. Therefore, the chiral compounds having extremely high optical purity or the achiral compounds without asymmetric carbon have been desired in order to develop the pharmaceutical compounds.

Meanwhile, various pyrimidine derivatives and pyridine derivatives have been reported (WO 9204333, WO 9919302, WO 0073279, Laid-open No. 2000-247957, Laid-open No. Hei 7-101940, Laid-open No. Hei 9-241161, Publication No. Sho 48-21949, J. Med. Chem. 31 (6) 1231-1240, 1988. and Chem. Pharm. Bull. 40 (9) 2423-2431, 1992). However, any prior arts did not describe that the reported compounds and similar pyrimidine derivatives and pyridine derivatives inhibited selectively N-type calcium channels. For instance, Laid-open No. Hei 9-241161 describes that 4-(4-fluorophenyl)-2-methyl-6-(5-piperidinopentyloxy)pyrimidine derivatives inhibit neuronal necrosis and, therefore, are effective in the treatment of post cerebrovascular disorders. However, the said compound is a voltage-dependent $Na^+/Ca^{2+}$ channel inhibitor (Eur. J. Pharmacol. 336, 283-290, 1997) and not expected as selective antagonist to N-type calcium channels.

DISCLOSURE OF THE INVENTION

The object of the present invention is to provide new compounds having a selective antagonistic effect on N-type calcium channels.

Another object of the present invention is to provide antagonists against N-type calcium channels.

A further object of the present invention is to provide a therapeutic agent for any of acute stage of ischemic cerebrovascular disorders such as cerebral infarction or intracerebral bleeding, Alzheimer's disease, AIDS related dementia, Parkinson's disease, progressive neurodegenerative diseases, neuropathy caused by head injury, pain caused by thromboangiitis obliterans, neuropathic pain, migraine, visceral pain, cancer pain, bronchial asthma, unstable angina, irritable colitis and withdrawal symptoms after addiction to drugs.

A further object of the present invention is to provide a pharmaceutical composition.

After synthesizing various compounds, having a pyrimidine nucleus or a pyridine nucleus, which are metabolites of well-known compounds having a dihydropyrimidine nucleus or a dihydropyridine nucleus, and examining the N-type calcium channel inhibiting effect (determined by fluorescent dye method) and L-type calcium channel inhibiting effect (determined by the relaxation after KCl-induced contraction of samples of isolated rat thoracic aorta) of them for the purpose of solving the above-described problems, the inventors have found that specified pyrimidine derivatives and pyridine derivatives have an excellent effect of selectively antagonizing N-type calcium channels. After examining analgesic effect, one of effects against above diseases, for confirming usefulness of the compounds of the present invention, the inventors have found that the said compounds are orally active and their efficacies are durable. The present invention has been completed on the basis of this finding. Further, the compounds of the present invention are more useful pharmaceutical compounds because they are the achiral compounds without an asymmetric carbon.

Namely, the present invention provides pyrimidine derivatives of the following general formula (1) and pharmaceutically acceptable salts thereof.

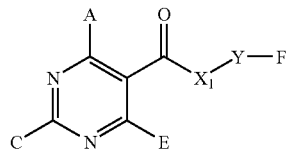
(1)

wherein A represents a group of the following general formula (2), or 1-naphthyl, 2-naphthyl, indole-2-yl, indole-3-yl, thiophene-3-yl, thiophene-2-yl, furan-3-yl, furan-2-yl, pyridine-4-yl, pyridine-3-yl or pyridine-2-yl group:

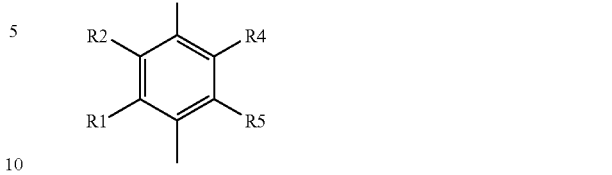
(2)

wherein $R^1$, $R^2$, $R^3$, $R^4$ and $R^5$ may be the same or different from each other and each represents a hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a lower alkoxycarbonyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl-lower alkoxyl group or an aroyl group, C represents a hydrogen atom, a lower alkyl group, a lower alkylamino group, a lower alkylthio group, a lower alkyl sulfinyl group, a lower alkyl sulfonyl group, a lower alkoxyl group, a hydroxy-lower alkyl group, a hydroxy-lower alkylamino group, a hydroxy-lower alkylthio group, a hydroxy-lower alkoxyl group, an amino-lower alkyl group, an amino-lower alkylamino group, an amino-lower alkylthio group, an amino-lower alkoxyl group, an aryl-lower alkyl group, an aryl-lower alkylamino group, an aryl-lower alkylthio group, an aryl-lower alkoxyl group, a heteroaryl-lower alkyl group, a heteroaryl-lower alkylamino group, a heteroaryl-lower alkylthio group, a heteroaryl-lower alkoxyl group, a halogeno-lower alkyl group, a halogeno-lower alkylamino group, a halogeno-lower alkylthio group, a halogeno-lower alkoxyl group, a substituted or unsubstituted aryl group, a substituted or unsubstituted heteroaryl group, a substituted or unsubstituted cyclic alkyl group, a lower alkyl group substituted with a substituted or unsubstituted cyclic alkyl group, a substituted or unsubstituted aryloxy group or a substituted or unsubstituted heteroaryloxy group, E represents a hydrogen atom, a lower alkyl group, dimethoxymethyl group, cyano group, an aryl-lower alkyl group, a heteroaryl-lower alkyl group, a hydroxy-lower alkyl group, an amino-lower alkyl group, a halogeno-lower alkyl group, a substituted or unsubstituted aryl group, a substituted or unsubstituted heteroaryl group or a group of the following general formula (3) or (4):

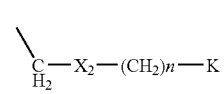
(3)

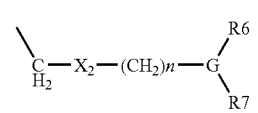
(4)

wherein $X_2$ represents O, S or N—$R_8$, n represents an integer of 1 to 6, K in general formula (3) represents a hydrogen atom, a halogen atom, hydroxyl group, carboxyl group, amino group, cyano group, nitro group or azido group, G in the general formula (4) represents N or C—H, wherein $R^6$ to $R^8$ may be the same or different from each other, and each represents a hydrogen atom, a linear, branched or cyclic, saturated or unsaturated hydrocarbon group having 1 to 6 carbon atoms, a substituted or unsubstituted aryl group, a substituted or unsubstituted heteroaryl group, a hydroxy-lower alkyl group, a hydroxy-lower alkenyl group, an amino-lower alkyl group, an amino-lower alkenyl group, a halogeno-lower alkyl group, a halogeno-lower alkenyl group, an aryl-lower alkyl group, an aryl-lower alkenyl group, a heteroaryl-lower alkyl group, a heteroaryl-lower alkenyl group, a cyano-lower alkyl group or a cyano-lower alkenyl group, and the chains may contain a hetero atom, or $R^6$ and $R^7$ may together form a ring which may contain a hetero atom, F represents a group of the following general formula (5), thiophene-3-yl, thiophene-2-yl, furan-3-yl, furan-2-yl, pyridine-4-yl, pyridine-3-yl, pyridine-2-yl group, cyclopentyl group, cyclohexyl group, morpholine-1-yl, imidazole-1-yl, pyrrolidine-1-yl, pyrrolidinone-1-yl, piperidine-1-yl, piperidinone-1-yl or piperazine-1-yl group:

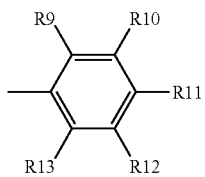

(5)

wherein $R^9$, $R^{10}$, $R^{11}$, $R^{12}$ and $R^{13}$ may be the same or different from each other and each represents a hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl-lower alkyl group, an aryl-lower alkoxyl group, a lower alkoxycarbonyl group, an aroyl group, a substituted or unsubstituted aryl group, a substituted or unsubstituted heteroaryl group or a saturated cyclic hydrocarbon group having 3 to 8 carbon atoms, which may contain a hetero atom in the chain thereof and/or the ring thereof, $X_1$ represents >N—$R^{14}$ wherein $R^{14}$ represents a hydrogen atom, a lower alkyl group which may contain a hetero atom in the chain thereof, a hydroxy-lower alkyl group, an amino-lower alkyl group, a carboxy-lower alkyl group or a lower alkyloxycarbonyl-lower alkyl group, Y represents a saturated or unsaturated linear hydrocarbon group having 1 to 6 carbon atoms, which may contain a hetero atom in the group thereof, or a group of the following general formula (6):

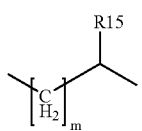

(6)

wherein $R_{15}$ represents a hydrogen atom, a substituted or unsubstituted, saturated or unsaturated linear, branched or cyclic hydrocarbon group having 1 to 6 carbon atoms, a substituted or unsubstituted aryl group, a substituted or unsubstituted heteroaryl group, a hydroxy-lower alkyl group, a hydroxy-lower alkenyl group, an amino-lower alkyl group, an amino-lower alkenyl group, a halogeno-lower alkyl group, a halogeno-lower alkenyl group, an aryl-lower alkyl group, an aryl-lower alkenyl group, a heteroaryl-lower alkyl group, a heteroaryl-lower alkenyl group, a cyano-lower alkyl group or a cyano-lower alkenyl group, and the chains of $R^{15}$ may contain a hetero atom, and m represents an integer of 0 to 5.

The present invention also provides pyridine derivatives of the following general formula (1') and pharmaceutically acceptable salts thereof.

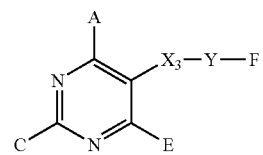

(1')

wherein A represents a group of the following general formula (2), or 1-naphthyl, 2-naphthyl, indole-2-yl, indole-3-yl, thiophene-3-yl, thiophene-2-yl, furan-3-yl, furan-2-yl, pyridine-4-yl, pyridine-3-yl or pyridine-2-yl group:

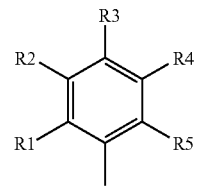

(2)

wherein $R^1$, $R^2$, $R^3$, $R^4$ and $R^5$ may be the same or different from each other and each represents a hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a lower alkoxycarbonyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl-lower alkoxyl group or an aroyl group, C represents a hydrogen atom, a lower alkyl group, a lower alkylamino group, a lower alkylthio group, a lower alkyl sulfinyl group, a lower alkyl sulfonyl group, a lower alkoxyl group, a hydroxy-lower alkyl group, a hydroxy-lower alkylamino group, a hydroxy-lower alkylthio group, a hydroxy-lower alkoxyl group, an amino-lower alkyl group, an amino-lower alkylamino group, an amino-lower alkylthio group, an amino-lower alkoxyl group, an aryl-lower alkyl group, an aryl-lower alkylamino group, an aryl-lower alkylthio group, an aryl-lower alkoxyl group, a heteroaryl-lower alkyl group, a heteroaryl-lower alkylamino group, a heteroaryl-lower alkylthio group, a heteroaryl-lower alkoxyl group, a halogeno-lower alkyl group, a halogeno-lower alkylamino group, a halogeno-lower alkylthio group, a halogeno-lower alkoxyl group, a substituted or unsubstituted aryl group, a substituted or unsubstituted heteroaryl group, a substituted or unsubstituted cyclic alkyl group, a lower alkyl group substituted with a substituted or unsubstituted cyclic alkyl group, a substituted or unsubstituted aryloxy group or a substituted or unsubstituted heteroaryloxy group, E represents a hydrogen atom, a lower alkyl group, dimethoxymethyl group, cyano group, an aryl-lower alkyl group, a heteroaryl-lower alkyl group, a hydroxy-lower alkyl group, an amino-lower alkyl group, a halogeno-lower alkyl group, a substituted or unsubstituted aryl group, a substituted or unsubstituted heteroaryl group or a group of the following general formula (3) or (4):

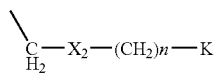
(3)

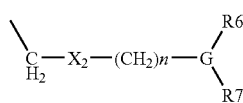
(4)

wherein $X_2$ represents O, S or N—$R_8$, n represents an integer of 1 to 6, K in general formula (3) represents a hydrogen atom, a halogen atom, hydroxyl group, carboxyl group, amino group, cyano group, nitro group or azido group, G in the general formula (4) represents N or C—H, wherein $R^6$ to $R^8$ may be the same or different from each other, and each represents a hydrogen atom, a linear, branched or cyclic, saturated or unsaturated hydrocarbon group having 1 to 6 carbon atoms, a substituted or unsubstituted aryl group, a substituted or unsubstituted heteroaryl group, a hydroxy-lower alkyl group, a hydroxy-lower alkenyl group, an amino-lower alkyl group, an amino-lower alkenyl group, a halogeno-lower alkyl group, a halogeno-lower alkenyl group, an aryl-lower alkyl group, an aryl-lower alkenyl group, a heteroaryl-lower alkyl group, a heteroaryl-lower alkenyl group, a cyano-lower alkyl group or a cyano-lower alkenyl group, and the chains may contain a hetero atom, or $R^6$ and $R^7$ may together form a ring which may contain a hetero atom, F represents a group of the following general formula (5), or thiophene-3-yl, thiophene-2-yl, furan-3-yl, furan-2-yl, pyridine-4-yl, pyridine-3-yl or pyridine-2-yl group, cyclopentyl group, cyclohexyl group, morpholine-1-yl, imidazole-1-yl, pyrrolidine-1-yl, pyrrolidinone-1-yl, piperidine-1-yl, piperidinone-1-yl or piperazine-1-yl group:

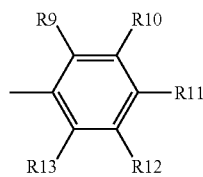
(5)

wherein $R^9$, $R^{10}$, $R^{11}$, $R^{12}$ and $R^{13}$ may be the same or different from each other and each represents a hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl-lower alkyl group, an aryl-lower alkoxyl group, a lower alkoxycarbonyl group, an aroyl group, a substituted or unsubstituted aryl group, a substituted or unsubstituted heteroaryl group or a saturated cyclic hydrocarbon group having 3 to 8 carbon atoms, which may contain a hetero atom in the chain thereof and/or the ring thereof, $X_3$ represents a group of the following general formula (7) or (8):

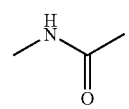
(7)

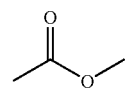
(8)

Y represents a saturated or unsaturated linear hydrocarbon group having 2 to 6 carbon atoms, which may contain a hetero atom in the group thereof, or a group of the following general formula (6):

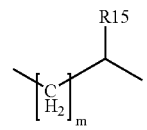
(6)

wherein $R_{15}$ represents a hydrogen atom, a substituted or unsubstituted, saturated or unsaturated linear, branched or cyclic hydrocarbon group having 1 to 6 carbon atoms, a substituted or unsubstituted aryl group, a substituted or unsubstituted heteroaryl group, a hydroxy-lower alkyl group, a hydroxy-lower alkenyl group, an amino-lower alkyl group, an amino-lower alkenyl group, a halogeno-lower alkyl group, a halogeno-lower alkenyl group, an aryl-lower alkyl group, an aryl-lower alkenyl group, a heteroaryl-lower alkyl group, a heteroaryl-lower alkenyl group, a cyano-lower alkyl group or a cyano-lower alkenyl group, and the chains of $R^{15}$ may contain a hetero atom, and m represents an integer of 1 to 5.

The present invention also provides pyrimidine derivatives of the following general formula (1″) and pharmaceutically acceptable salts thereof.

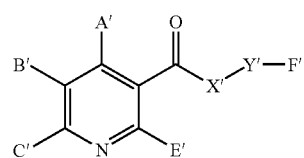
(1″)

wherein A' represents a group of the following general formula (9):

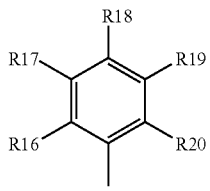
(9)

wherein $R^{16}$, $R^{17}$, $R^{18}$, $R^{19}$ and $R^{20}$ may be the same or different from each other and each represents a hydrogen atom, a halogen atom, hydroxyl group, carboxyl group, amino group, cyano group, nitro group, a lower alkyl group, a lower alkoxyl group or a lower alkylamino group, C' and E' may be the same or different from each other and each represents a hydrogen atom, a lower alkyl group which may contain a hetero atom in the chain thereof, dimethoxymethyl group, cyano group, an aryl-lower alkyl group, a heteroaryl-lower alkyl group, a hydroxy-lower alkyl group, an amino-lower alkyl group, a halogeno-lower alkyl group, a substituted or unsubstituted aryl group, a substituted or unsubstituted heteroaryl group or a group of the following general formula (3) or (4):

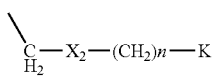
(3)

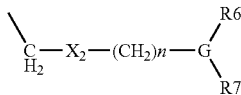
(4)

wherein $X_2$ represents O, S or N—$R_8$, n represents an integer of 1 to 6, K in general formula (3) represents a hydrogen atom, a halogen atom, hydroxyl group, carboxyl group, amino group, cyano group, nitro group, azido group, a substituted or unsubstituted aryl group or a substituted or unsubstituted heteroaryl group, G in the general formula (4) represents N or C—H, wherein $R^6$ to $R^8$ may be the same or different from each other, and each represents a hydrogen atom, a linear, branched or cyclic, saturated or unsaturated hydrocarbon group having 1 to 6 carbon atoms, a substituted or unsubstituted aryl group, a substituted or unsubstituted heteroaryl group, a hydroxy-lower alkyl group, a hydroxy-lower alkenyl group, an amino-lower alkyl group, an amino-lower alkenyl group, a halogeno-lower alkyl group, a halogeno-lower alkenyl group, an aryl-lower alkyl group, an aryl-lower alkenyl group, a heteroaryl-lower alkyl group, a heteroaryl-lower alkenyl group, a cyano-lower alkyl group or a cyano-lower alkenyl group, and the chains may contain a hetero atom, or $R^6$ and $R^7$ may together form a ring which may contain a hetero atom, B' represents a hydrogen atom only when Y' represents the general formula (12) and $R^{26}$ is a substituted or unsubstituted aryl group, a carboxyl group only when Y' represents the general formula (12) or Y' and F' together form the following general formula (12'-1), (12'-2), (12"-1) or (12"-2), or a group of the following general formula (10):

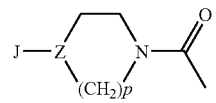
(10)

wherein Z represents a nitrogen atom, an oxygen atom or a carbon atom, p represents an integer of 1 to 3, J represents an unsubstituted group only when Z is an oxygen atom, a hydrogen atom, a lower alkyl group which may contain a hetero atom in the group thereof, a hydroxy-lower alkyl group, an amino-lower alkyl group, a substituted or unsubstituted aryl group, a substituted or unsubstituted heteroaryl group, a substituted or unsubstituted aryl-lower alkyl group or a substituted or unsubstituted heteroaryl-lower alkyl group, F' represents the following general formula (11):

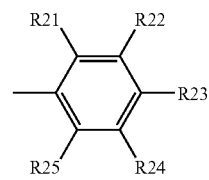
(11)

wherein $R^{21}$, $R^{22}$, $R^{23}$, $R^{24}$ and $R^{25}$ may be the same or different from each other and each represents a hydrogen atom, a halogen atom, hydroxyl group, carboxyl group, amino group, cyano group, nitro group, a lower alkyl group, a lower alkoxyl group, a lower alkylamino group, a substituted or unsubstituted aryl group or a substituted or unsubstituted heteroaryl group, X' represents an oxygen atom or >NH, Y' represents a saturated or unsaturated linear hydrocarbon group having 1 to 6 carbon atoms, which may contain a hetero atom in the group thereof, or a group of the following general formula (12):

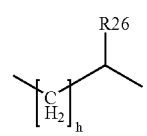
(12)

wherein $R^{26}$ represents a substituted or unsubstituted aryl group or a substituted or unsubstituted heteroaryl group and h represents an integer of 0 to 5, Y' and F' together form a group of the following general formula (12'-1), (12'-2), (12"-1) or (12"-2):

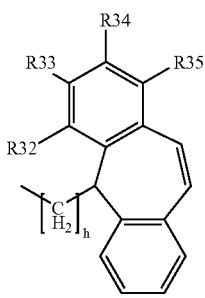

(12'-1)

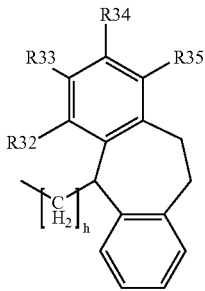

(12'-2)

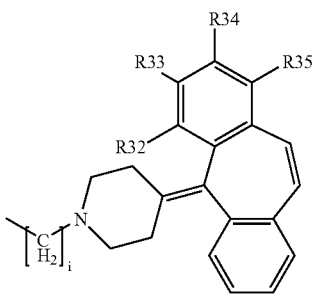

(12"-1)

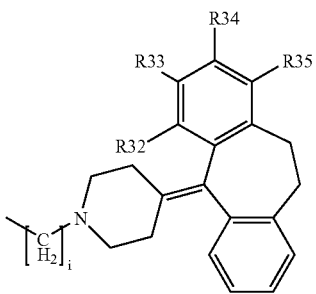

(12"-2)

wherein h represents an integer of 0 to 5, i represents an integer of 2 to 5, $R^{32}$, $R^{33}$, $R^{34}$ and $R^{35}$ may be the same or different from each other and each represents a hydrogen atom, a halogen atom, hydroxyl group, carboxyl group, amino group, cyano group, nitro group, a lower alkyl group, a lower alkoxyl group, a lower alkylamino group, a substituted or unsubstituted aryl group or a substituted or unsubstituted heteroaryl group.

The present invention provides an N-type calcium channel antagonist containing the above-described pyrimidine derivative or pyridine derivative, or a pharmaceutically acceptable salt thereof as the active ingredient.

The present invention also provides a pharmaceutical composition containing the above-described pyrimidine derivative or pyridine derivative, or a pharmaceutically acceptable salt thereof as the active ingredient.

The present invention also provides a therapeutic agent containing the above-described pyrimidine derivative or pyridine derivative, or a pharmaceutically acceptable salt thereof as the active ingredient, for any of acute stage of ischemic cerebrovascular disorders caused by cerebral infarction or intracerebral bleeding, Alzheimer's disease, AIDS related dementia, Parkinson's disease, progressive neurodegenerative diseases, neuropathy caused by head injury, pain caused by thromboangiitis obliterans, neuropathic pain, migraine, visceral pain, cancer pain, bronchial asthma, unstable angina, irritable colitis and withdrawal symptoms after addiction to drugs.

BEST MODE FOR CARRYING OUT THE INVENTION

The term "lower" herein indicates that the group has 1 to 6 carbon atoms. Alkyl groups themselves and also alkyl groups in alkenyl groups, alkynyl groups, alkoxyl groups, alkylamino groups, alkylthio groups, alkanoyl groups, alkyl sulfinyl groups, alkyl sulfonyl groups and the like may be either linear or branched. Examples of these alkyl groups are methyl group, ethyl group, propyl group, isopropyl group, butyl group, secondary and tertiary butyl groups, pentyl group and hexyl group. Among them, those having 1 to 3 carbon atoms are preferred. The aryl-lower alkyl groups include, for example, benzyl group. The heteroaryl-lower alkyl groups include, for example, pyridylmethyl group. The aryl-lower alkoxyl groups include, for example, benzyloxy group. The hetero atoms include nitrogen, oxygen, sulfur, etc. The halogen atoms include fluorine, chlorine, bromine and iodine atoms. In the present specification, the aryl groups are both substituted and unsubstituted aryl groups. They are preferably phenyl group and substituted phenyl group, and the substituents are particularly preferably halogens, alkyl groups and alkoxyl groups. The heteroaryl groups are substituted or unsubstituted heteroaryl groups such as, preferably, pyridyl group, furyl group and thienyl group, and also substituted pyridyl, furyl and thienyl groups. Halogens, alkyl groups and alkoxyl groups are particularly preferred as the substituents. The cyclic alkyl groups include, for example, cyclopentyl groups and cyclohexyl groups. The cyclic alkyl groups which may contain a hetero atom in the ring thereof include, for example, piperidinyl groups, morpholinyl groups and piperazinyl groups. Examples of the cyclic alkyl groups substituted with the cyclic alkyl group are cyclopentylethyl groups and cyclohexylmethyl groups. The cyclic alkyl groups which may contain a hetero atom in the ring thereof include, for example, piperidinylmethyl groups, morpholinylmethyl groups and piperazinylmethyl groups. The aroyl groups include, for example, benzoyl group and pyridylcarbonyl group. The hydrocarbon groups indicate alkyl groups, alkenyl groups and alkynyl groups. The saturated hydrocarbon groups indicate alkyl groups such as methyl group, ethyl group, propyl group, isopropyl group, butyl group, pentyl group, hexyl group and sec. and tert. butyl groups. The unsaturated hydrocarbon groups indicate alkenyl groups and alkynyl groups. The alkenyl groups include propenyl group, butenyl group, pentenyl group, etc. The alkynyl groups include ethynyl group, propinyl group, butynyl group, etc. Examples of the cyclic hydrocarbon groups include cyclopentyl group and cyclohexyl group. Examples of the cyclic hydrocarbon groups which may contain a hetero atom in the chain thereof include piperidyl group, pyrrolidinyl group and piperazinyl group. The hydrocarbon groups and alkyl groups which may contain a hetero atom in the chain or group thereof include, for example, alkoxyl groups, alkylamino groups, alkylthio groups, alkoxymethyl groups and alkylaminoethyl groups.

1-naphthyl group, 2-naphthyl group, indole-2-yl group and indole-3-yl group represented by A in the above general formula (1) are either unsubstituted or substituted. The substituents are those listed above for $R^1$ to $R^5$.

Thiophene-3-yl group, thiophene-2-yl group, furan-3-yl group, furan-2-yl group, pyridine-4-yl group, pyridine-3-yl group and pyridine-2-yl group represented by A are also either unsubstituted or substituted. When two or more substituents are contained therein, they may form a ring together. The substituents are those described above with reference to 1-naphthyl group or the like. The rings formed by those groups include benzothiophene, benzofuran, quinoline, isoquinoline, etc.

A is preferably a group represented by the general formula (2).

$R^1$ to $R^5$ that are substituents of a group of the general formula (2) are preferably a halogen atom, a lower-alkyl group, etc.

The groups represented by C in the general formula (1), namely, lower-alkyl groups, aryl lower-alkyl groups, heteroaryl lower-alkyl groups may contain a hetero atom in the chain thereof, or may form a ring or branch.

Cyclic alkyl groups and lower-alkyl groups substituted with a cyclic alkyl group, which are also the groups represented by C, may contain a hetero atom in the ring thereof. The cyclic alkyl groups include, for example, cyclopentyl groups and cyclohexyl groups. The cyclic alkyl groups which may contain a hetero atom in the ring thereof include piperidinyl groups, morpholinyl groups, piperazinyl groups and so on. Examples of the lower-alkyl groups substituted with the cyclic alkyl group are cyclopentylethyl groups and cyclohexylmethyl groups. The cyclic alkyl groups which may contain a hetero atom in the ring thereof include piperidinylmethyl groups, morpholinylmethyl groups, piperazinylmethyl groups and (piperidine-1-yl)ethoxy groups.

Aryl groups and heteroaryl groups represented by C are either substituted or unsubstituted. Their substituents are those listed above for $R^1$ to $R^5$ in the general formula (1).

Substituted or unsubstituted aryloxy groups and substituted or unsubstituted heteroaryloxy groups, which are the groups represented by C, include phenoxy groups, naphthyloxy groups and pyridyloxy groups. The substituents thereof are those listed above for $R^1$ to $R^5$ in the general formula (1).

Aryl lower-alkyl groups, aryl lower-alkylamino groups, aryl lower-alkylthio groups, aryl lower-alkoxy groups, heteroaryl lower-alkyl groups, heteroaryl lower-alkylamino groups, heteroaryl lower-alkylthio groups and heteroaryl lower-alkoxy groups, which are also represented by C, include, for example, 3-phenylpropyl group, 2-phenylethylamino group, 2-phenylethoxy group, 3-(pyridine-2-yl)propyl group, 2-(pyridine-3-yl)ethylamino group, 2-(pyridine-2-yl)ethoxy group and phenoxymethyl group.

Amino groups in amino lower-alkyl groups, amino lower-alkylamino groups, amino lower-alkylthio groups and amino lower-alkoxy groups, which are also represented by C, may combine with cyclic aliphatic amine, which may contain a hetero atom in the ring thereof. The ring herein indicates 3- to 8-membered ring and its examples are piperidine-1-yl, piperidine-4-yl, pyrrolidine-1-yl, pyrrolidine-3-yl, piperidinone-1-yl, pyrrolidinone-1-yl, piperazine-1-yl and morpholine-4-yl group. Their substituents are, for example, 2-(piperidine-1-yl)ethyl group, 2-(piperidine-1-yl)ethylamino group, 2-(piperidine-1-yl)ethylthio group, 2-(piperidine-1-yl)ethoxy group, aminoethyl group, aminoethylamino group, aminoethylthio group and aminoethoxy group.

A lower-alkyl sulfinyl group, which are also represented by C, includes a methylsulfinyl group. A lower-alkyl sulfonyl group includes, for example, a methylsulfonyl group.

The groups represented by C in the above general formula (1) are preferably lower-alkyl groups, lower-alkylamino groups, lower alkylthio groups or lower-alkoxy groups, and most preferably ethyl groups, propyl groups or methylthio groups.

K represented by the general formula (3) in the groups represented by E in the above general formula (1) represents a hydrogen atom, a halogen atom, hydroxyl group, carboxyl group, amino group, cyano group, nitro group or azido group. K is preferably a hydrogen atom, hydroxyl group, carboxyl group or amino group.

The groups represented by $R^6$ or $R^7$ in the groups represented by the general formula (4) in the groups represented by E in the above general formula (1) each represent a hydrogen atom, a linear, branched or cyclic, saturated or unsaturated hydrocarbon group having 1 to 6 carbon atoms, a substituted or unsubstituted aryl group, a substituted or unsubstituted heteroaryl group, a hydroxy-lower alkyl group, a hydroxy-lower alkenyl group, a halogeno-lower alkyl group, a halogeno-lower alkenyl group, an aryl-lower alkyl group, an aryl-lower alkenyl group, a heteroaryl-lower alkyl group, a heteroaryl-lower alkenyl group, a cyano-lower alkyl group or a cyano-lower alkenyl group, and the chains may contain a hetero atom thereof, or $R^6$ and $R^7$ may together form a ring which may contain a hetero atom thereof. The linear, branched or cyclic, saturated or unsaturated hydrocarbon group having 1 to 6 carbon atoms herein include, for example, methyl group, ethyl group, propyl group, isopropyl group, cyclopentyl group, cyclohexyl group, allyl group and vinyl group. Methyl group and ethyl group are preferred. The substituents in the substituted or unsubstituted aryl groups or substituted or unsubstituted heteroaryl groups represented by $R^6$ or $R^7$ are those described above with reference to $R^1$ to $R^5$ in the general formula (1).

$R^6$ and $R^7$ may be bonded together to form a ring with G. The ring may contain a hetero atom. The rings herein are 3- to 8-membered rings such as cyclopentyl group, cyclohexyl group, piperidine-1-yl group, piperidine-4-yl group, pyrrolidine-1-yl group, pyrrolidine-3-yl group, piperidinone-1-yl group, pyrrolidinone-1-yl group, piperazine-1-yl group and morpholine-4-yl group.

Group E in the general formula (1) is preferably a lower alkyl group, methoxymethyl group, 2-aminoethoxymethyl group, 2-hydroxyethoxymethyl group, 2-carboxyethoxymethyl group, or a group of the general formula (3). Group E is particularly preferably methyl group, a group of the general formula (4) wherein $X_2$ represents an oxygen atom, n represents an integer of 2 or 3 and $R^6$ and $R^7$ are bonded together to form a 5- to 7-membered ring with G (G is preferably N or C—H), such as 2-cyclohexylethoxymethyl group or 2-piperidino-ethoxymethyl group.

Group F is preferably a group of the general formula (5).

A lower-alkyloxycarbonyl lower-alkyl group represented by >N—$R^{14}$ in the group represented by $X_1$ includes an ethoxycarboxymethyl group.

Group $X_1$ is particularly preferably a group represented by >N—$R^{14}$ wherein $R^{14}$ represents a hydrogen atom.

Group Y is preferably a group of the general formula (6) wherein m represents an integer of 1 or 4 and $R^{15}$ represents an aryl groups, or a saturated or unsaturated hydrocarbon group having 3 to 4 carbon atoms. Particularly, 3-phenylpropyl group or 3-phenyl-2-propen-1-yl group is preferred.

In the present invention represented by the general formula (1), F is preferably a group of the general formula (5), thiophene-3-yl group, thiophene-2-yl group, furan-3-yl group or furan-2-yl group, and Y is preferably a saturated or unsaturated linear hydrocarbon group having 2 to 6 carbon atoms, which may contain a hetero atom in the group thereof, or a group of the general formula (6) wherein m is an integer of 1 to 5.

It is preferred in the present invention that A represents a group of the general formula (2), F represents a group of the general formula (5) and $X_1$ represents $>N-R^{14}$ wherein $R^{14}$ represents a hydrogen atom.

It is preferred in the present invention that A represents a group of the general formula (2), C represents a lower-alkyl group, F represents a group of the general formula (5), $X_1$ represents $>N-R^{14}$ wherein $R^{14}$ represents a hydrogen atom, and Y represents a saturated or unsaturated hydrocarbon group having 3 carbon atoms.

It is preferred in the present invention that A represents a group of the general formula (2), C represents a lower-alkylthio group, a lower-alkyl sulfinyl group or a lower-alkyl sulfonyl group, F represents a group of the general formula (5), $X_1$ represents $>N-R^{14}$ wherein $R^{14}$ represents a hydrogen atom, and Y represents a saturated or unsaturated hydrocarbon group having 3 carbon atoms.

It is preferred in the present invention that A represents a group of the general formula (2), C represents a lower-alkyl group, E represents a methyl group, F represents a group of the general formula (5), $X_1$ represents $>N-R^{14}$ wherein $R^{14}$ represents a hydrogen atom, and Y represents a saturated or unsaturated hydrocarbon group having 3 carbon atoms.

It is preferred in the present invention that A represents a group of the general formula (2), C represents a lower-alkylthio group, E represents a methyl group, F represents a group of the general formula (5), $X_1$ represents $>N-R^{14}$ wherein $R^{14}$ represents a hydrogen atom and Y represents a saturated or unsaturated hydrocarbon group having 3 carbon atoms.

It is preferred in the present invention that C represents a hydrogen atom, a lower alkyl group which may contain a hetero atom in the chain thereof, a lower alkylamino group, a lower alkylthio group, a lower alkoxyl group, a hydroxy-lower alkyl group, a hydroxy-lower alkylamino group, a hydroxy-lower alkylthio group, a hydroxy-lower alkoxyl group, an amino-lower alkyl group, an amino-lower alkylamino group, an amino-lower alkylthio group, an amino-lower alkoxyl group, an aryl-lower alkyl group which may contain a hetero atom in the chain thereof, an aryl-lower alkylamino group, an aryl-lower alkylthio group, an aryl-lower alkoxyl group, a heteroaryl-lower alkyl group, a heteroaryl-lower alkylamino group, a heteroaryl-lower alkylthio group, a heteroaryl-lower alkoxyl group, a halogeno-lower alkyl group, a halogeno-lower alkylamino group, a halogeno-lower alkylthio group, a halogeno-lower alkoxyl group, a substituted or unsubstituted aryl group, or a substituted or unsubstituted heteroaryl group.

It is preferred in the present invention that C represents a hydrogen atom, a lower alkyl group which may contain a hetero atom in the chain thereof, a lower alkylamino group, a lower alkylthio group, a lower alkoxyl group, a hydroxy-lower alkyl group, a hydroxy-lower alkylamino group, a hydroxy-lower alkylthio group, a hydroxy-lower alkoxyl group, an amino-lower alkyl group, an amino-lower alkylamino group, an amino-lower alkylthio group, an amino-lower alkoxyl group, an aryl-lower alkyl group which may contain a hetero atom in the chain thereof, an aryl-lower alkylamino group, an aryl-lower alkylthio group, an aryl-lower alkoxyl group, a heteroaryl-lower alkyl group, a heteroaryl-lower alkylamino group, a heteroaryl-lower alkylthio group, a heteroaryl-lower alkoxyl group, a halogeno-lower alkyl group, a halogeno-lower alkylamino group, a halogeno-lower alkylthio group, a halogeno-lower alkoxyl group, a substituted or unsubstituted aryl group, or a substituted or unsubstituted heteroaryl group, A represents a group of the general formula (2), C represents a lower-alkyl group or a lower-alkylthio group, F represents a group of the general formula (5), $X_1$ represents $>N-R^{14}$ wherein $R^{14}$ represents a hydrogen atom, and Y represents a saturated or unsaturated hydrocarbon group having 3 to 4 carbon atoms.

Next, the explanation on the compounds represented by the general formula (1') is given below. 1-naphthyl group, 2-naphthyl group, indole-2-yl group and indole-3-yl group represented by A in the above general formula (1') are either unsubstituted or substituted. The substituents are those listed above for $R^1$ to $R^5$.

Thiophene-3-yl group, thiophene-2-yl group, furan-3-yl group, furan-2-yl group, pyridine-4-yl group, pyridine-3-yl group and pyridine-2-yl group represented by A are also either unsubstituted or substituted. When two or more substituents are contained therein, they may form a ring together. The substituents are those described above with reference to 1-naphthyl group or the like. The rings formed by those groups include benzothiophene, benzofuran, quinoline, isoquinoline, etc.

A is preferably a group represented by the general formula (2).

The groups represented by C in the general formula (1') represents a lower alkyl group, a lower alkylamino group, a lower alkylthio group, a lower alkyl sulfinyl group, a lower alkyl sulfonyl group, a lower alkoxyl group, a hydroxy-lower alkyl group, a hydroxy-lower alkylamino group, a hydroxy-lower alkylthio group, a hydroxy-lower alkoxyl group, an amino-lower alkyl group, an amino-lower alkylamino group, an amino-lower alkylthio group, an amino-lower alkoxyl group, an aryl-lower alkyl group, an aryl-lower alkylamino group, an aryl-lower alkylthio group, an aryl-lower alkoxyl group, a heteroaryl-lower alkyl group, a heteroaryl-lower alkylamino group, a heteroaryl-lower alkylthio group, a heteroaryl-lower alkoxyl group, a halogeno-lower alkyl group, a halogeno-lower alkylamino group, a halogeno-lower alkylthio group, a halogeno-lower alkoxyl group, piperidinyl group, morpholinyl group, piperazinyl groups, piperidinyl-lower alkyl group, morpholinyl-lower alkyl group or piperazinyl-lower alkyl group. The groups may contain a hetero atom in the above chain and also may form a ring or branch.

Aryl groups and heteroaryl groups represented by C are either substituted or unsubstituted. Their substituents are those listed above for $R^1$ to $R^5$ in the general formula (1').

Aryl lower-alkyl groups, aryl lower-alkylamino groups, aryl lower-alkylthio groups, aryl lower-alkoxy groups, heteroaryl lower-alkyl groups, heteroaryl lower-alkylamino groups, heteroaryl lower-alkylthio groups and heteroaryl lower-alkoxy represented by C include 3-phenylpropyl group, 2-phenylethylamino group, 2-phenylethoxy group, 3-(pyridine-2-yl)propyl group, 2-(pyridine-3-yl)ethylamino group, 2-(pyridine-2-yl)ethoxy group and the like.

Amino groups in amino lower-alkyl groups, amino lower-alkylamino groups, amino lower-alkylthio groups and amino lower-alkoxy groups represented by C may combine with cyclic aliphatic amine or may contain a hetero atom in the ring thereof. The ring herein indicates 3- to 8-membered ring and its examples are piperidine-1-yl, piperidine-4-yl, pyrrolidine-1-yl, pyrrolidine-3-yl, piperidinone-1-yl, pyrrolidinone-1-yl, piperazine-1-yl and morpholine-4-yl group. Their substituents are, for example, 2-(piperidine-1-yl)ethyl group, 2-(piperidine-1-yl)ethylamino group, 2-(piperidine-1-yl)ethylthio group, 2-(piperidine-1-yl)ethoxy group, aminoethyl group, aminoethylamino group, aminoethylthio group and aminoethoxy group.

Group C in the general formula (1) is preferably a lower-alkyl group, a lower-alkylamino group, a lower alkylthio group or a lower-alkoxy group, and more preferably ethyl groups, propyl groups or methylthio groups.

K represented by the general formula (3) in the groups represented by E in the above general formula (1') represents a hydrogen atom, a halogen atom, hydroxyl group, carboxyl group, amino group, cyano group, nitro group or azido group. K is preferably a hydrogen atom, hydroxyl group, carboxyl group or amino group.

The group represented by $R^6$ or $R^7$ in the groups represented by the general formula (4) in the groups represented by E in the above general formula (1) each represent a hydrogen atom, a linear, branched or cyclic, saturated or unsaturated hydrocarbon group having 1 to 6 carbon atoms, a substituted or unsubstituted aryl group, a substituted or unsubstituted heteroaryl group, a hydroxy-lower alkyl group, a hydroxy-lower alkenyl group, a halogeno-lower alkyl group, a halogeno-lower alkenyl group, an aryl-lower alkyl group, an aryl-lower alkenyl group, a heteroaryl-lower alkyl group, a heteroaryl-lower alkenyl group, a cyano-lower alkyl group or a cyano-lower alkenyl group, and the chains may contain a hetero atom thereof, or $R^6$ and $R^7$ may together form a ring which may contain a hetero atom thereof. The linear, branched or cyclic, saturated or unsaturated hydrocarbon group having 1 to 6 carbon atoms herein include, for example, methyl group, ethyl group, propyl group, isopropyl group, cyclopentyl group, cyclohexyl group, allyl group and vinyl group. Methyl group, ethyl group and the like are preferred. The substituents in the substituted or unsubstituted aryl groups or substituted or unsubstituted heteroaryl groups represented by $R^6$ or $R^7$ are those described above with reference to $R^1$ to $R^5$ in the general formula (1').

$R^6$ and $R^7$ may be bonded together to form a ring with G. The ring may contain a hetero atom. The rings herein are 3- to 8-membered rings such as cyclopentyl group, cyclohexyl group, piperidine-1-yl group, piperidine-4-yl group, pyrrolidine-1-yl group, pyrrolidine-3-yl group, piperidinone-1-yl group pyrrolidinone-1-yl group, piperazine-1-yl group and morpholine-4-yl group.

Group E in the general formula (1') is preferably a lower alkyl group, methoxymethyl group, 2-aminoethoxymethyl group, 2-hydroxyethoxymethyl group, 2-carboxyethoxymethyl group, or a group of the general formula (3). Group E is particularly preferably methyl group, or a group of the general formula (4) wherein $X_2$ represents an oxygen atom, n represents an integer of 2 or 3 and $R^6$ and $R^7$ are bonded together to form a 5- to 7-membered ring with G (G is preferably N or C—H), such as 2-cyclohexylethoxymethyl group or 2-piperidino-ethoxymethyl group.

Group F is preferably a group of the general formula (5).

Group $X_3$ include a group of the general formula (7) or (8).

Group Y is preferably a group of the general formula (6) wherein m represents an integer of 1 or 4 and $R^{15}$ represents an aryl group, or a saturated or unsaturated hydrocarbon group having 3 to 4 carbon atoms. Particularly, 3-phenylpropyl group or 3-phenyl-2-propen-1-yl group is preferred.

It is preferred in the present invention represented by the general formula (1') that A represents a group of the general formula (2), F represents a group of the general formula (5), $X_3$ represents a group of the general formula (7) or (8) and Y represents a group of the general formula (6) wherein m represents an integer of 1 to 4, and $R^{15}$ represents a substituted or unsubstituted aryl group, or a saturated or unsaturated hydrocarbon group having 2 to 4 carbon atoms.

Next, the explanation on the compounds represented by the general formula (1") is given below. $R^{16}$, $R^7$, $R^8$, $R^{19}$ and $R^{20}$ of the general formula (9) represented by A' in the above general formula (1") may be the same or different from each other and each represents a hydrogen atom, a halogen atom, hydroxyl group, carboxyl group, amino group, cyano group, nitro group, a lower alkyl group, a lower alkoxyl group or a lower alkylamino group. A lower alkyl group, a lower alkoxyl group and a lower alkylamino group may contain a hetero atom in the chain thereof.

B' in the above general formula (1") represents a hydrogen atom only when Y' represents the general formula (12) and $R^{26}$ is a substituted or unsubstituted aryl group, a carboxyl group only when Y' represents the general formula (12) or Y' and F' together form the following general formula (12'-1), (12'-2), (12"-1) or (12"-2), or the general formula (10). The group of the general formula (10) is preferable.

Group Z of the general formula (10) represented by B' in the above general formula (1") represents a nitrogen atom, an oxygen atom or a carbon atom, p represents an integer of 1 to 3, J represents an unsubstituted group only when Z is an oxygen atom, a hydrogen atom, a lower alkyl group which may contain a hetero atom in the group thereof, a hydroxy-lower alkyl group, an amino-lower alkyl group, a substituted or unsubstituted aryl group, a substituted or unsubstituted aryl-lower alkyl group, a substituted or unsubstituted heteroaryl group or a substituted or unsubstituted heteroaryl-lower alkyl group. The substituents of a substituted or unsubstituted aryl group or a substituted or unsubstituted heteroaryl group represented by J are those listed above for $R^1$ to $R^5$ in the general formula (1). It is particularly preferred that Z represents a nitrogen atom and J represents a hydrogen atom in the general formula (10).

K represented by the general formula (3) in the groups represented by C' and E' in the above general formula (1") represents a hydrogen atom, a halogen atom, hydroxyl group, carboxyl group, amino group, cyano group, nitro group, azido group, a substituted or unsubstituted aryl group or a substituted or unsubstituted heteroaryl group. A hydrogen atom, hydroxyl group, a substituted or unsubstituted aryl group or a substituted or unsubstituted heteroaryl group is more preferable. The substituents of a substituted or unsubstituted aryl group or a substituted or unsubstituted heteroaryl group are those listed above for $R^1$ to $R^5$ in the general formula (1).

The group represented by $R^6$ or $R^7$ in the groups represented by the general formula (4) in the groups represented by C' and E' in the above general formula (1") each represent a hydrogen atom, a linear, branched or cyclic, saturated or unsaturated hydrocarbon group having 1 to 6 carbon atoms, a substituted or unsubstituted aryl group, a substituted or unsubstituted heteroaryl group, a hydroxy-lower alkyl group, a hydroxy-lower alkenyl group, a halogeno-lower alkyl group, a halogeno-lower alkenyl group, an aryl-lower alkyl group, an aryl-lower alkenyl group, a heteroaryl-lower alkyl group, a heteroaryl-lower alkenyl group, a cyano-lower alkyl group or a cyano-lower alkenyl group, and the chains may contain a hetero atom thereof, or $R^6$ and $R^7$ may together form a ring which may contain a hetero atom thereof. The linear, branched or cyclic, saturated or unsaturated hydrocarbon group having 1 to 6 carbon atoms herein include, for example, methyl group, ethyl group, propyl group, isopropyl group, cyclopentyl group, cyclohexyl group, allyl group and vinyl group. Methyl group, ethyl group and the like are preferred. The substituents in the substituted or unsubstituted aryl groups or substituted or unsubstituted heteroaryl groups represented by $R^6$ or $R^7$ are those described above with reference to $R^1$ to $R^5$ in the general formula (1).

$R^6$ and $R^7$ may be bonded together to form a ring with G. The ring may contain a hetero atom. The rings herein are 3- to 8-membered rings such as cyclopentyl group, cyclohexyl group, piperidine-1-yl group, piperidine-4-yl group, pyrrolidine-1-yl group, pyrrolidine-3-yl group, piperidinone-1-yl group pyrrolidinone-1-yl group, piperazine-1-yl group and morpholine-4-yl group.

C' and E' in the above general formula (1") may be the same or different from each other and each represents a hydrogen atom, a lower alkyl group which may contain a hetero atom in the chain thereof, dimethoxymethyl group, cyano group, a hydroxy-lower alkyl group or a halogeno-lower alkyl group. A lower alkyl group is particularly preferable.

$R^{21}$, $R^{22}$, $R^{23}$, $R^{24}$ and $R^{25}$ of the general formula (11) represented by F' in the above general formula (1") may be the same or different from each other and each represents a hydrogen atom, a halogen atom, hydroxyl group, carboxyl group, amino group, cyano group, nitro group, a lower alkyl group, a lower alkoxyl group, a lower alkylamino group, a substituted or unsubstituted aryl group or a substituted or unsubstituted heteroaryl group. The substituents in the substituted or unsubstituted aryl groups or substituted or unsubstituted heteroaryl groups represented by $R^{21}$ to $R^{25}$ are those described above with reference to $R^1$ to $R^5$ in the general formula (1).

The groups represented by X' are an oxygen atom or >NH.

The groups represented by Y' are preferably a group of the general formula (12) wherein h represents an integer of 1 to 4 and $R^{26}$ represents an aryl group, or a saturated or unsaturated hydrocarbon group having 3 to 4 carbon atoms. Particularly, 3,3-diphenylpropyl group is preferable.

Y' and F' may together form a group of the general formula (12'-1), (12'-2), (12"-1) or (12"-2).

Further, it is preferable in the present invention represented by the general formula (1") that B' represents a group of the general formula (10).

It is preferable in the present invention that B' represents a group of the general formula (10), Y' represents a group of the general formula (12) and X' represents an oxygen atom.

It is preferable in the present invention that B' represents carboxyl groups and E' represents a group of the general formula (3) or (4).

It is preferable in the present invention that B' represents carboxyl groups, E' represents a group of the general formula (3) or (4), X' represents an oxygen atom and Y' represents a group of the general formula (12).

It is preferable in the present invention that C' and E' may be the same or different from each other and each represents a hydrogen atom, a lower alkyl group which may contain a hetero atom in the chain thereof, dimethoxymethyl group, cyano group, a hydroxy-lower alkyl group or a halogeno-lower alkyl group, and B' represents a group of the general formula (10).

It is preferable in the present invention that B' represents a group of the general formula (10) wherein Z represents a nitrogen atom and J represents a hydrogen atom, C' and E' represent a lower alkyl group, and Y' represents a group of the general formula (12) wherein $R^{26}$ represents a substituted or unsubstituted aryl group and h=2.

It is preferable in the present invention that B' represents a group of the general formula (10) wherein Z represents a nitrogen atom and J represents a hydrogen atom, C' and E' represent a lower alkyl group, Y' represents a group of the general formula (12) wherein $R^{26}$ represents a substituted or unsubstituted aryl group and h=2, and X' represents an oxygen atom.

The compounds of the present invention represented by the general formula (1") are preferably those wherein A' represents 3-chlorophenyl group, B' represents a carboxyl group, C' and E' represent a methyl group, X' represents an oxygen atom, Y' and F' together form a group of the general formula (12"-1), i represents an integer of 3 and $R^2$, $R^{33}$, $R^{34}$ and $R^{35}$ represent a hydrogen atom, and pharmaceutically acceptable salts thereof.

Pyrimidine derivatives and pyridine derivatives of the present invention can be produced by processes described below:

<Production Process 1>

The pyrimidine derivatives (1) of the present invention can be produced by a method described below.

For example, the pyrimidine derivative (1-1) of the general formula (1) wherein E is methyl group and X' is >N—$R_{14}$, in which $R_{14}$ is hydrogen atom, can be produced by the following process:

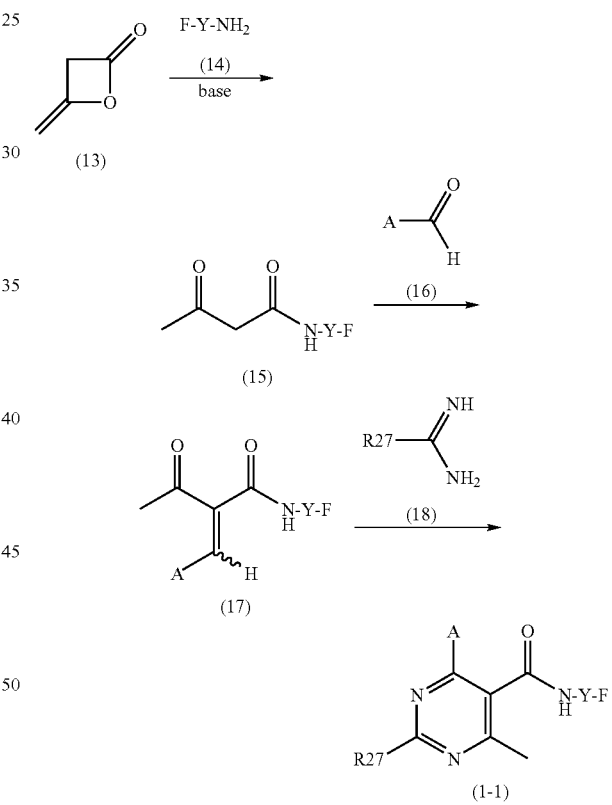

The β-ketocarboxylic acid amide (15) can be obtained by reacting the diketene dimer (13) with the amine derivative (14) in the presence of a base such as triethylamine. As the reaction solvent, aromatic hydrocarbons such as toluene, benzene or xylene can be used. The reaction temperature is 0 to 150° C., preferably 50 to 120° C.

The pyrimidine derivative (1-1) can be obtained by reacting the α, β-unsaturated carbonyl compound (17), obtained by the dehydration condensation of the β-ketocarboxylic acid amide (15) with the aldehyde (16), with the amidine derivative (18).

When the amidine derivative used herein is in the form of hydrochloride or the like, it is preferably converted into the free amine with a base such as potassium carbonate, sodium acetate or sodium hydrogencarbonate. The reaction solvents include aprotic polar solvents such as N,N-dimethylformamide, dimethyl sulfoxide and acetonitrile. The reaction temperature is not particularly limited, and the reaction can be carried out under cooling, at room temperature or under heating.

By this reaction, a dihydropyrimidine derivative (19) of the following formula, wherein A and $R_{27}$ are as defined above, might be produced according to the reaction conditions. In such a case, the intended pyrimidine derivative (1-1) can be obtained by the oxidation reaction of the dihydropyrimidine derivative (19). The oxidizing agents usable for the oxidation reaction include, for example, manganese dioxide, lead tetraacetate, oxygen, hydrogen peroxide, potassium permanganate, DDQ (2,3-dichloro-5,6-dicyano-1,4-benzoquinone) and CAN (cerium diammonium nitrate). The reaction is usually carried out in an ordinary solvent that is inert to the reaction, such as chloroform, methylene chloride, benzene, toluene, pyridine, ethyl acetate, acetone or methyl ethyl ketone. The reaction temperature is not particularly limited, and the reaction is preferably carried out at room temperature or under warming or heating.

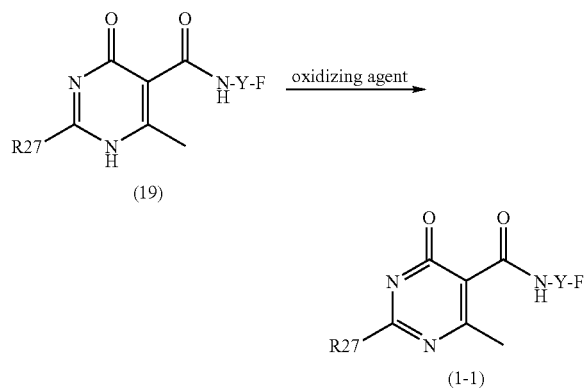

<Production Process 2>

The pyrimidine derivatives (1') of the present invention can be produced by a method described below.

For example, the pyrimidine derivative (1'-1) of the general formula (1') wherein E is methyl group and $X_3$ is represented by the general formula (8) can be produced by the following process:

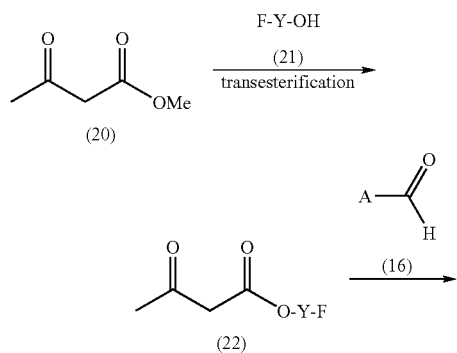

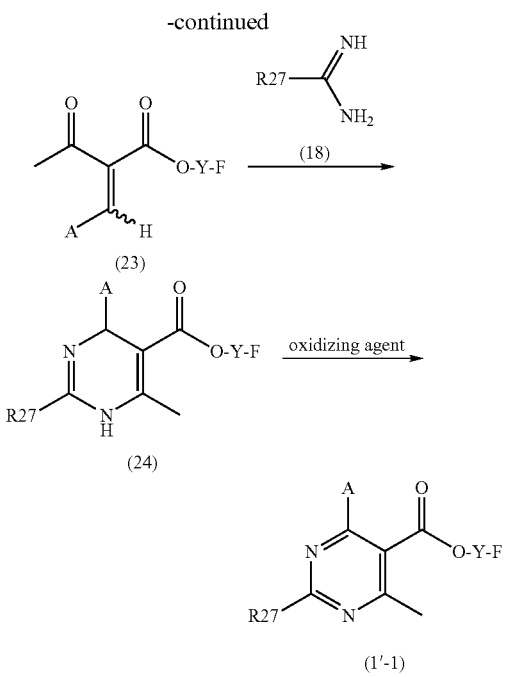

The acetoacetic acid ester derivative (22) can be obtained by the transesterification of the methyl acetoacetate (20) with the alcohol (21). As the reaction solvent, aromatic hydrocarbons such as benzene, toluene or xylene are usually used. However, the intended product can also be obtained by reacting the substrate with the alcohol without any reaction solvent. The reaction temperature is usually 50 to 150° C.

The dihydropyrimidine derivative (24) can be obtained by reacting the α, β-unsaturated carbonyl compound (23), obtained by the dehydration condensation of the acetoacetic acid ester derivative (22) with the aldehyde (16), with the amidine derivative (18).

When the amidine derivative used herein is in the form of hydrochloride or the like, it is preferably converted into the free amine with a base such as potassium carbonate, sodium acetate or sodium hydrogencarbonate. The reaction solvents include aprotic polar solvents such as N,N-dimethylformamide, dimethyl sulfoxide and acetonitrile. The reaction temperature is not particularly limited, and the reaction can be carried out under cooling, at room temperature or under heating.

The intended pyrimidine derivative (1'-1) can be obtained by the oxidation reaction of the dihydropyrimidine derivative (24) with a suitable oxidizing agent. The oxidizing agents usable for the oxidation reaction include, for example, manganese dioxide, lead tetraacetate, oxygen, hydrogen peroxide, potassium permanganate, DDQ (2,3-dichloro-5,6-dicyano-1,4-benzoquinone) and CAN (cerium diammonium nitrate). The reaction is usually carried out in an ordinary solvent that is inert to the reaction, such as chloroform, methylene chloride, benzene, toluene, pyridine, ethyl acetate, acetone or methyl ethyl ketone. The reaction temperature is not particularly limited, and the reaction is preferably carried out at room temperature or under warming or heating.

<Production Process 3>

The pyrimidine derivatives (1') of the present invention can be produced by a method described below.

For example, the pyrimidine derivative (1'-2) of the general formula (1') wherein E is represented by the general formula (3) or (4), in which $X_2$ is an oxygen atom, and $X_3$ is represented by the general formula (8) can be produced by the following process:

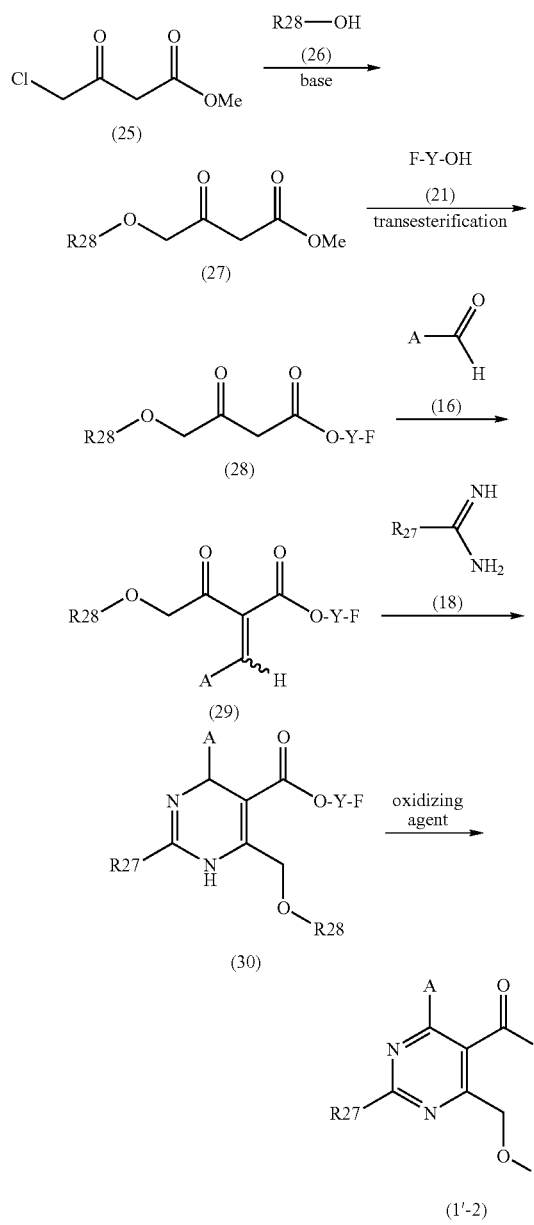

Namely, the methyl β-ketocarboxylate derivative (27) can be obtained by reacting an alkoxide, produced from the alcohol (26) and a base such as potassium carbonate, sodium carbonate or sodium hydride, and commercially available methyl 4-chloroacetoacetate (25). The reaction solvents include aprotic polar solvents such as tetrahydrofuran, N,N-dimethylformamide, dimethyl sulfoxide and acetonitrile. The reaction temperature is not particularly limited, and the reaction can be carried out under cooling, at room temperature or under heating. Then the methyl β-ketocarboxylate derivative (27) is transesterified with the alcohol (21) to obtain the β-ketocarboxylate derivative (28). Aromatic hydrocarbons such as benzene, toluene or xylene are usually used as the reaction solvent. However, the intended product can also be obtained by reacting the substrate with the alcohol without any reaction solvent. The reaction temperature is usually 50 to 150° C.

The dihydropyrimidine derivative (30) can be obtained by reacting the α, β-unsaturated carbonyl compound (29), obtained by the dehydration condensation of the methyl β-ketocarboxylate derivative (28) with the aldehyde (16), with the amidine derivative (18).

When the amidine derivative used herein is in the form of hydrochloride or the like, it is preferably converted into the free amine with a base such as potassium carbonate, sodium acetate or sodium hydrogencarbonate. Aprotic polar solvents such as N,N-dimethylformamide, dimethyl sulfoxide and acetonitrile can be used as the reaction solvent. Although the reaction temperature is not particularly limited, the reaction can be carried out under cooling, at room temperature or under heating.

The intended pyrimidine derivative (1'-2) can be obtained by the oxidation reaction of the dihydropyrimidine derivative (30) with a suitable oxidizing agent. The oxidizing agents usable for the oxidation reaction include, for example, manganese dioxide, lead tetraacetate, oxygen, hydrogen peroxide, potassium permanganate, DDQ (2,3-dichloro-5,6-dicyano-1,4-benzoquinone) and CAN (cerium diammonium nitrate). The reaction is usually carried out in an ordinary solvent that is inert to the reaction, such as chloroform, methylene chloride, benzene, toluene, pyridine, ethyl acetate, acetone or methyl ethyl ketone. Although the reaction temperature is not particularly limited, the reaction is preferably carried out at room temperature or under warming or heating.

<Production Process 4>

The pyrimidine derivatives (1') of the present invention can be produced by a method described below.

For example, the pyrimidine derivative (1'-3) of the general formula (1'), wherein E is methyl group and $X_3$ is represented by the general formula (7), can be produced by the following process:

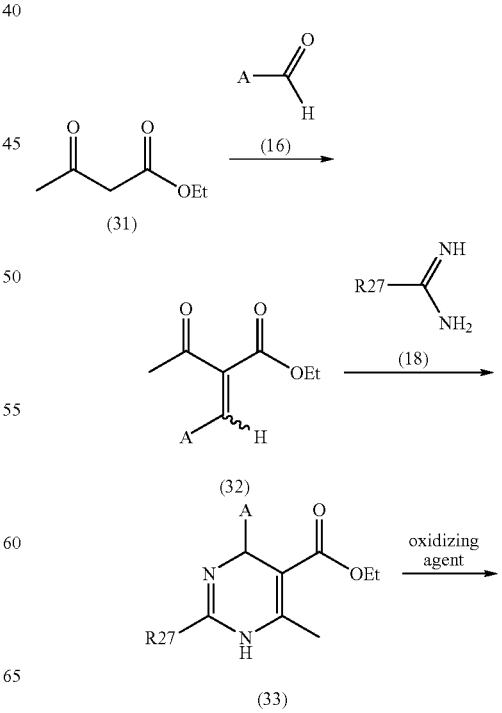

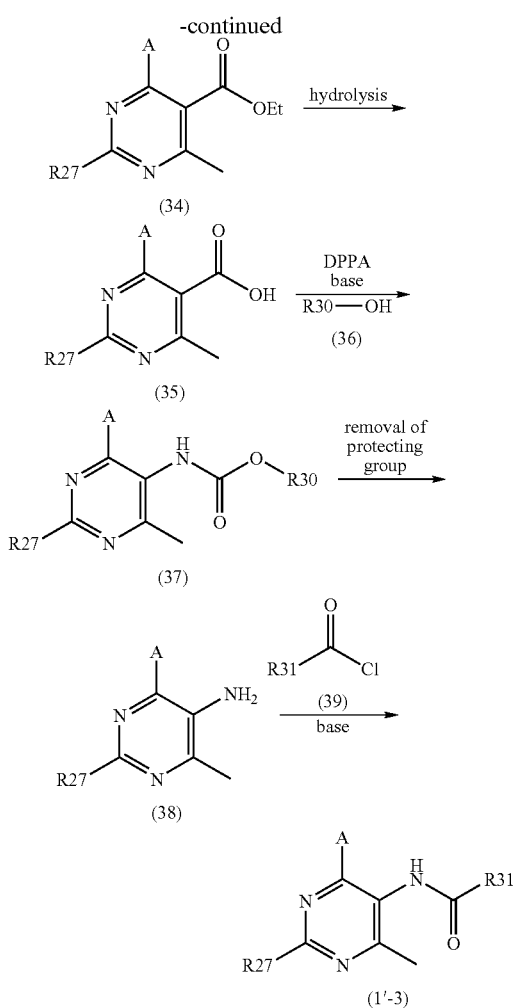

The dihydropyrimidine derivative (33) can be obtained by reacting the α,β-unsaturated carbonyl compound (32), obtained by the dehydration condensation of the ethyl acetoacetate (31) with the aldehyde (16), with the amidine derivative (18).

When the amidine derivative used herein is in the form of hydrochloride or the like, it is preferably converted into the free amine with a base such as potassium carbonate, sodium acetate or sodium hydrogencarbonate. Aprotic polar solvents such as N,N-dimethylformamide, dimethyl sulfoxide and acetonitrile can be used as the reaction solvent. The reaction temperature is not particularly limited, and the reaction can be carried out under cooling, at room temperature or under heating.

The pyrimidine derivative (34) can be obtained by the oxidation reaction of the dihydropyrimidine derivative (33) with a suitable oxidizing agent. The oxidizing agents usable for the oxidation reaction include, for example, manganese dioxide, lead tetraacetate, oxygen, hydrogen peroxide, potassium permanganate, DDQ (2,3-dichloro-5,6-dicyano-1,4-benzoquinone) and CAN (cerium diammonium nitrate). The reaction is usually carried out in an ordinary solvent that is inert to the reaction, such as chloroform, methylene chloride, benzene, toluene, pyridine, ethyl acetate, acetone or methyl ethyl ketone. Although the reaction temperature is not particularly limited, the reaction is preferably carried out at room temperature or under warming or heating.

The obtained pyrimidine derivative (34) is treated with a base such as sodium hydroxide, potassium hydroxide or lithium hydroxide to obtain the carboxylic acid derivative (35). This carboxylic acid derivative (35) is subjected to Crutius rearrangement with diphenylphosphoric azide (DPPA) in the presence of a base such as triethylamine and an alcohol such as t-butyl alcohol to obtain the corresponding carbamate derivative (37). Although a protic polar solvent other than t-butyl alcohol can be used as the reaction solvent, t-butyl alcohol or benzyl alcohol is preferred in view of the removal of the protecting group in the subsequent step. The reaction is usually carried out under heating at 50 to 150° C.

The protecting group is removed from the obtained carbamate derivative (37) to obtain the amine derivative (38), that is then reacted with the corresponding acyl chloride (39) in the presence of a base such as pyridine or triethylamine to obtain the intended pyrimidine derivative (1'-3). When the carbamate derivative (37) is t-butyl carbamate, it is reacted with an acid such as hydrochloric acid or trifluoroacetic acid. When the carbamate derivative (37) is benzyl carbamate, it is catalytically reduced with palladium carbon to obtain the corresponding amine derivative (38). When the acyl chloride (39) is not available on the market, a corresponding carboxylic acid is reacted with a chlorinating agent such as oxalyl chloride or thionyl chloride to obtain the acyl chloride (39). The reaction of the acyl chloride (39) with the amine derivative (38) is carried out in an ordinary solvent inert to the reaction, such as chloroform, methylene chloride, tetrahydrofuran, benzene or toluene. Although the reaction temperature is not particularly limited, the reaction is preferably carried out at room temperature or under warming or heating. The intended pyrimidine derivative (1'-3) can also be synthesized by condensing the amine derivative (38) with a corresponding carboxylic acid in the presence of a condensing agent such as WSC, <Production Process 5>

The pyridine derivatives (1") of the present invention can be produced by a method described below.

The pyridine derivative (1"-1) of the general formula (1"), wherein B' is represented by the general formula (10), C and E are each methyl group and X' is oxygen atom, can be produced by the following process:

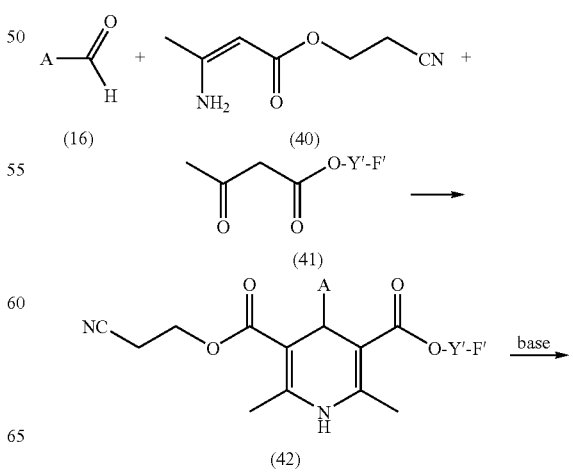

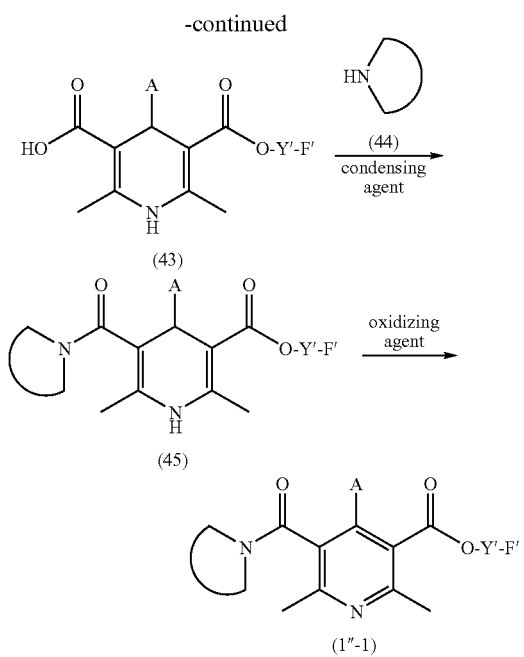

The dihydropyridinecarboxylic acid diester (42) can be obtained by reacting the aldehyde (16), 3-aminocrotonic acid ester (40) and the β-ketocarboxylic acid ester (41). As the reaction solvent, a protic polar solvent such as ethanol or 2-propanol can be used. The reaction temperature is 0 to 150° C., preferably 50 to 120° C.

The dihydropyridinecarboxylic acid diester (42) thus obtained is treated with a base such as sodium hydroxide to obtain a dihydropyridine monocarboxylic acid (43), that is then condensed with the amine derivative (44) in the presence of a condensing agent such as WSC to obtain the dihydropyridine amide derivative (45).

The dihydropyridine amide derivative (45) thus obtained is subjected to the oxidation reaction to obtain the intended pyridine derivative (1″-1). The oxidizing agents usable for the oxidation reaction include, for example, manganese dioxide, lead tetraacetate, oxygen, hydrogen peroxide, potassium permanganate, DDQ (2,3-dichloro-5,6-dicyano-1,4-benzoquinone) and CAN (cerium diammonium nitrate). The reaction is usually carried out in an ordinary solvent that is inert to the reaction, such as chloroform, methylene chloride, benzene, toluene, pyridine, ethyl acetate, acetone or methyl ethyl ketone. Although the reaction temperature is not particularly limited, the reaction is preferably carried out at room temperature or under warming or heating.

<Production Process 6>

The pyridine derivatives (1″-1) of the present invention can be produced by a method shown below.

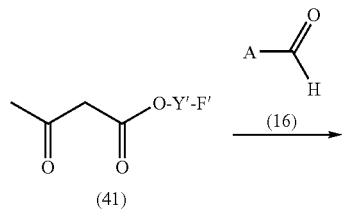

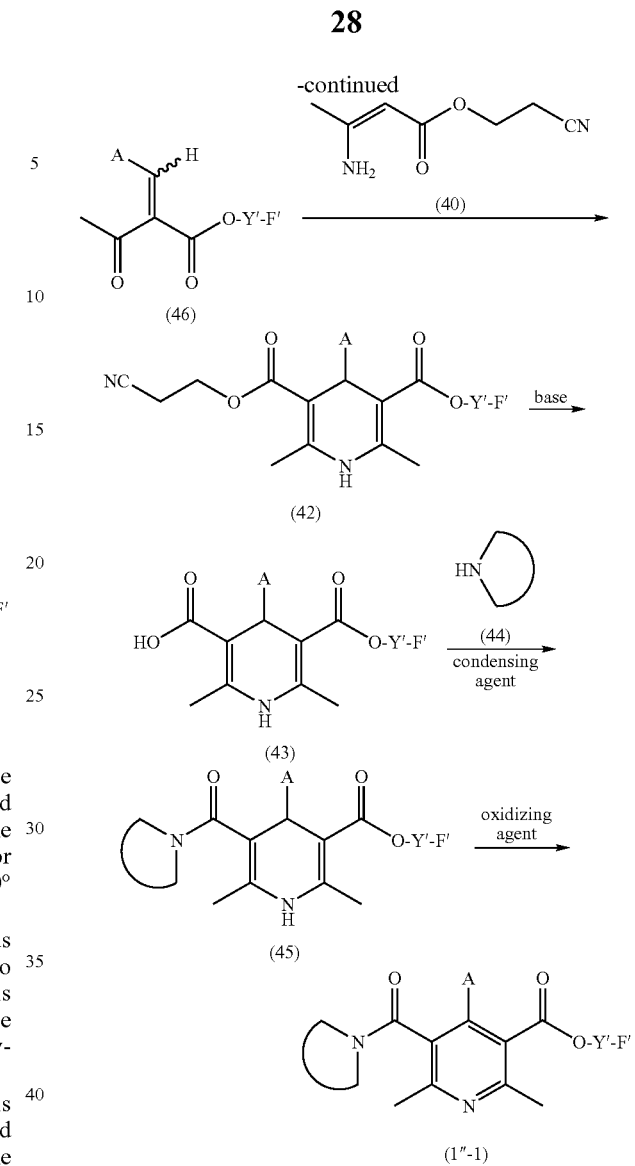

The dihydropyridinecarboxylic acid diester (42) can be obtained by producing the α, β-unsaturated carbonyl compound (46) by the dehydration condensation of the β-ketocarboxylic acid ester (41) with the aldehyde (16) and then reacting this product with the 3-aminocrotonic acid ester (40). The intended pyridine derivative (1″-1) can be produced from the obtained dihydropyridinecarboxylic acid diester (42) by the production process 5.

<Production Process 7>

The pyridine derivatives (1″-1) can also be produced by a method shown below.

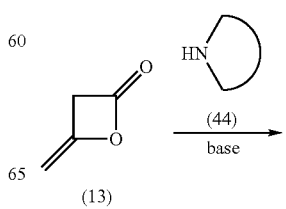

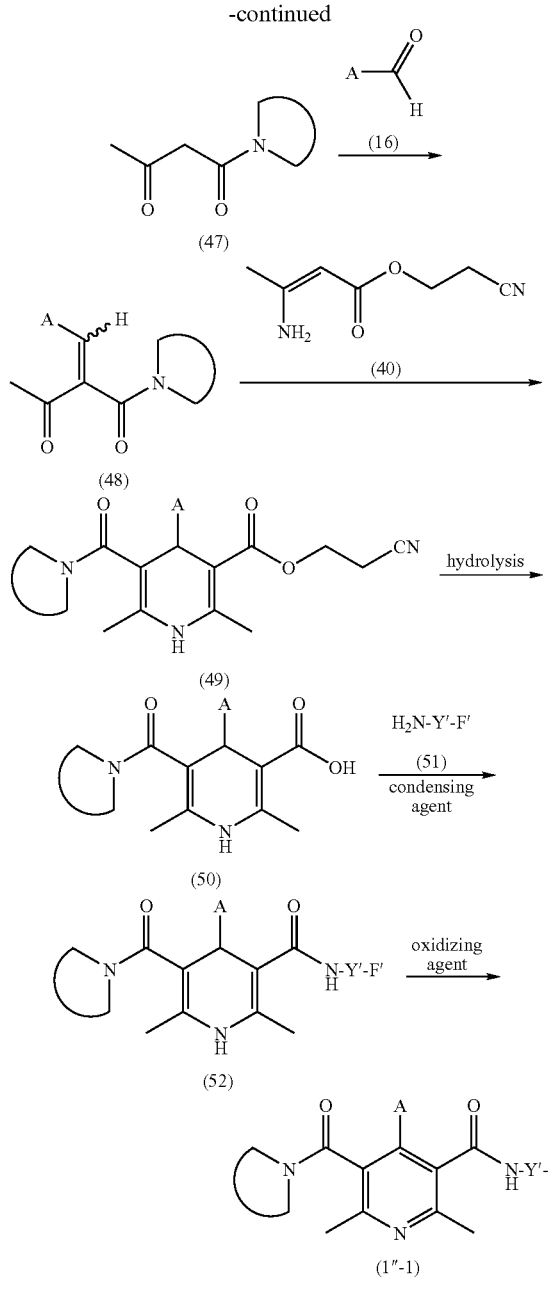

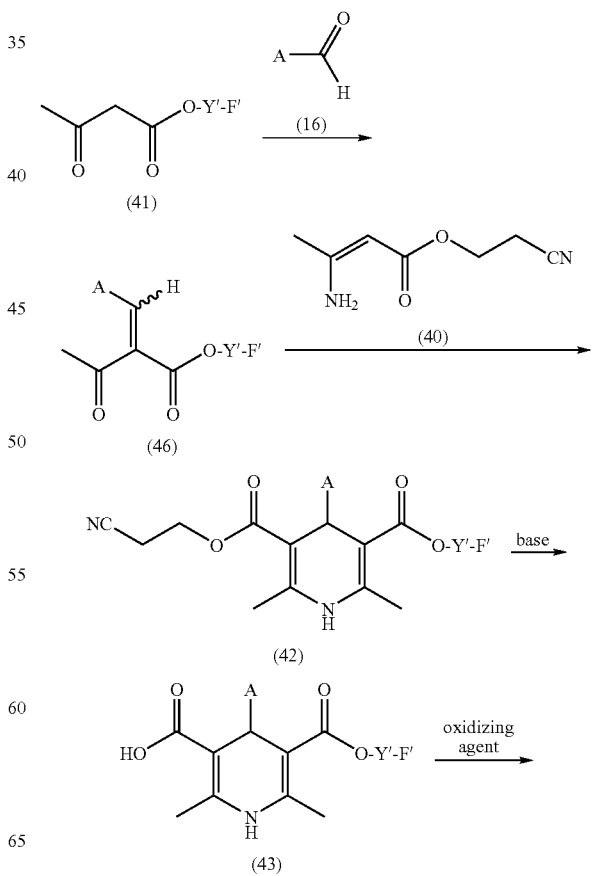

The β-ketocarboxylic acid amide (47) can be obtained by reacting the diketene dimer (13) with the amine derivative (44) in the presence of a base such as triethylamine. As the reaction solvent, aromatic hydrocarbons such as toluene, benzene or xylene can be used. The reaction temperature is 0 to 150° C., preferably 50 to 120° C. The dihydropyridinecarboxylic acid diester (49) can be obtained by producing the α,β-unsaturated carbonyl compound (48) by the dehydration condensation of the β-ketocarboxylic acid amide (47) with the aldehyde (16) and then reacting this compound with the 3-aminocrotonic acid ester (40). As the reaction solvent, a protic polar solvent such as ethanol or 2-propanol can be used. The reaction temperature is not particularly limited, and the reaction is preferably carried out at room temperature or under warming or heating.

The dihydropyridinemonocarboxylic acid (50) can be obtained by treating the obtained dihydropyridinecarboxylic acid diester (49) with a base such as sodium hydroxide. The dihydropyridine amide derivative (52) is formed by condensing the dihydropyridinemonocarboxylic acid (49) with the amine derivative (51) in the presence of a condensing agent such as WSC.

The intended pyridine derivative (1″-1) can be obtained by subjecting the resultant dihydropyridine amide derivative (52) to the oxidation reaction. The oxidizing agent used for the oxidation reaction include, for example, manganese dioxide, lead tetraacetate, oxygen, hydrogen peroxide, potassium permanganate, DDQ (2,3-dichloro-5,6-dicyano-1,4-benzoquinone) and CAN (cerium diammonium nitrate). The reaction is usually carried out in an ordinary solvent that is inert to the reaction, such as chloroform, methylene chloride, benzene, toluene, pyridine, ethyl acetate, acetone or methyl ethyl ketone. Although the reaction temperature is not particularly limited, the reaction is preferably carried out at room temperature or under warming or heating.

<Production Process 8>

The pyridine derivatives (1″) of the present invention can be produced by a method described below.

The pyridine derivative (1″-2) of the general formula (1″), wherein B′ is carboxyl group, C and E are each methyl group and X′ is oxygen atom, can be produced by the following process:

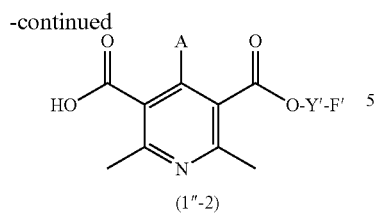

(1″-2)

The dihydropyridinecarboxylic acid diester (42) can be obtained by subjecting the β-ketocarboxylic acid ester (41) and the aldehyde (16) to the dehydration condensation and then reacting the obtained α, β-unsaturated carbonyl compound (46) with 3-aminocrotonic acid ester (40). As the reaction solvent, a protic polar solvent such as ethanol or 2-propanol can be used. Although the reaction temperature is not particularly limited, the reaction is preferably carried out at room temperature or under warming or heating.

The dihydropyridinecarboxylic acid diester (42) thus obtained can be treated with a base such as sodium hydroxide to obtain a dihydropyridine monocarboxylic acid (43), that is then subjected to the oxidation reaction to obtain the intended pyridine derivative (1″-2). The oxidizing agents usable for the oxidation reaction include, for example, manganese dioxide, lead tetraacetate, oxygen, hydrogen peroxide, potassium permanganate, DDQ (2,3-dichloro-5,6-dicyano-1,4-benzoquinone) and CAN (cerium diammonium nitrate). The reaction is usually carried out in an ordinary solvent that is inert to the reaction, such as chloroform, methylene chloride, benzene, toluene, pyridine, ethyl acetate, acetone or methyl ethyl ketone. The reaction temperature is not particularly limited, and the reaction is preferably carried out at room temperature or under warming or heating.

<Production Process 9>

The pyridine derivatives (1″) of the present invention can be produced by a method described below.

The pyridine derivative (1″-3) of the general formula (1″), wherein B' is represented by the general formula (10), C is methyl group, E is represented by the general formula (3) or (4), wherein $X_2$ is oxygen atom, and X' is oxygen atom, can be produced by the following process:

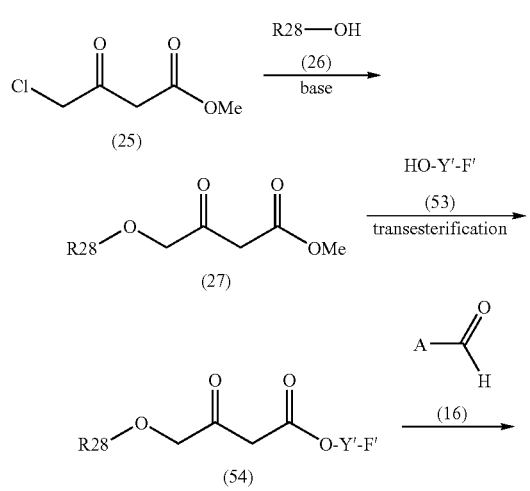

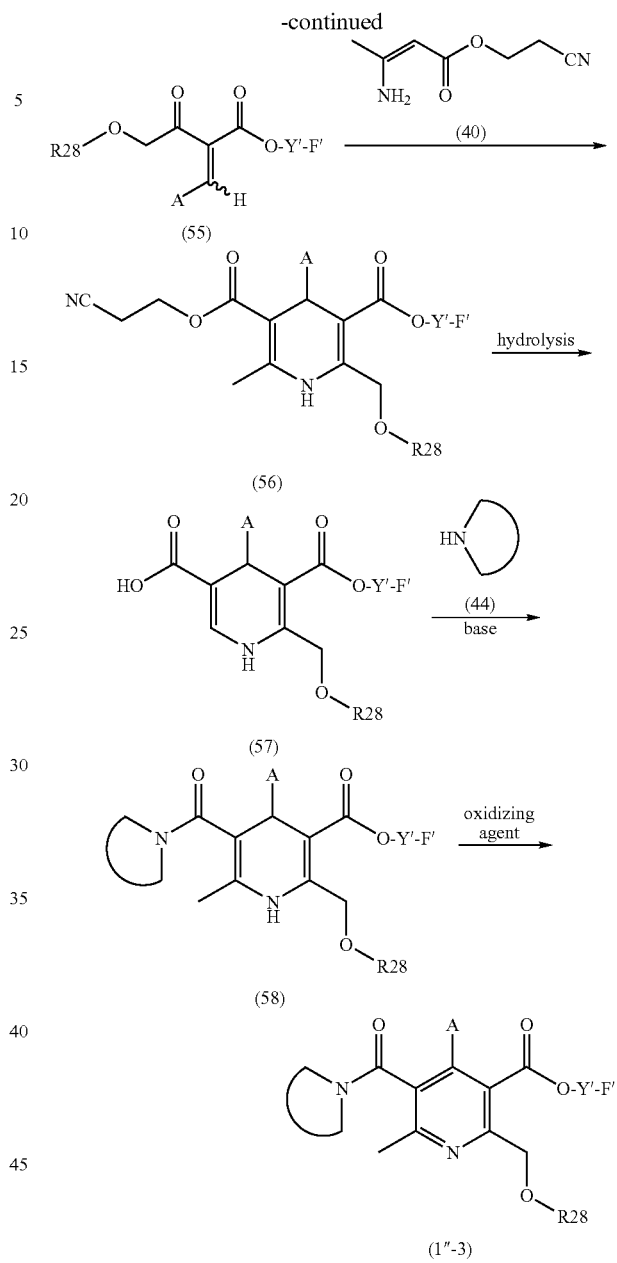

Namely, the methyl β-ketocarboxylate derivative (27) can be obtained by reacting an alkoxide produced from the alcohol (26) and a base such as potassium carbonate, sodium carbonate or sodium hydride with commercially available methyl 4-chloroacetoacetate (25). The reaction solvents include aprotic polar solvents such as tetrahydrofuran, N,N-dimethylformamide, dimethyl sulfoxide and acetonitrile. The reaction temperature is not particularly limited, and the reaction can be carried out under cooling, at room temperature or under heating. Then the methyl β-ketocarboxylate derivative (27) is transesterified with the alcohol (53) to obtain the β-ketocarboxylate derivative (54). Aromatic hydrocarbons such as benzene, toluene or xylene are usually used as the reaction solvent. However, the intended product can also be obtained by reacting the substrate with the alcohol without any reaction solvent. The reaction temperature is usually 50 to 150° C.

The dihydropyridine carboxylic acid diester (56) can be obtained by reacting the α, β-unsaturated carbonyl compound (55), obtained by the dehydration condensation of the β-ketocarboxylate derivative (54) with the aldehyde (16), with the 3-aminocrotonic acid ester (40). As for the reaction solvent, a protic polar solvent such as ethanol or 2-propanol can be used. The reaction temperature is not particularly limited, and the reaction is preferably carried out at room temperature or under warming or heating.

The dihydropyridinemonocarboxylic acid (57) can be obtained by treating the dihydropyridinecarboxylic acid diester (56) with a base such as sodium hydroxide. The dihydropyridine amide derivative (58) is formed by condensing the dihydropyridinemonocarboxylic acid (57) with the amine derivative (44) in the presence of a condensing agent such as WSC. The intended pyridine derivative (1"-3) can be obtained by the oxidation reaction of the dihydropyridine amide derivative (58). The oxidizing agents usable for the oxidation reaction include, for example, manganese dioxide, lead tetraacetate, oxygen, hydrogen peroxide, potassium permanganate, DDQ (2,3-dichloro-5,6-dicyano-1,4-benzoquinone) and CAN (cerium diammonium nitrate). The reaction is usually carried out in an ordinary solvent that is inert to the reaction, such as chloroform, methylene chloride, benzene, toluene, pyridine, ethyl acetate, acetone or methyl ethyl ketone. The reaction temperature is not particularly limited, and the reaction is preferably carried out at room temperature or under warming or heating.

When the compounds of general formulae (1), (1') and (1") can form salts thereof, the salts are pharmaceutically acceptable ones such as ammonium salts, salts thereof with alkali metals, e.g. sodium and potassium, salts thereof with alkaline earth metals, e.g. calcium and magnesium, salts thereof with aluminum and zinc, salts thereof with organic amines, e.g. morpholine and piperidine, and salts thereof with basic amino acids, e.g. arginine and lysine.

The compounds of general formulae (1), (1') and (1") and salts thereof can be administered as they are or in the form of various medicinal compositions to patients. The dosage forms of the medicinal compositions are, for example, tablets, powders, pills, granules, capsules, suppositories, solutions, sugar-coated tablets and depots. They can be prepared with ordinary preparation assistants by an ordinary method. For example, the tablets can be prepared by mixing the pyrimidine derivative, the active ingredient of the present invention, with any of known adjuvants such as inert diluents, e.g. lactose, calcium carbonate and calcium phosphate; binders, e.g. acacia, corn starch and gelatin; extending agents, e.g. alginic acid, corn starch and pre-gelatinized starch; sweetening agents, e.g. sucrose, lactose and saccharin; corrigents, e.g. peppermint, gaultheria leaves oil and cherry; and lubricants, e.g. magnesium stearate, talc and carboxymethyl cellulose.

The N-type calcium channel antagonists containing one of the compounds of above general formulae (1), (1') and (1") or one of salts thereof as active ingredient is usable as a therapeutic agent for various diseases, for example, acute stage of ischemic cerebrovascular disorders such as cerebral infarction or intracerebral bleeding (including subarachnoidal hemorrhage); progressive neurodegenerative diseases such as Alzheimer's disease, AIDS related dementia, Parkinson's disease, dementia due to cerebrovascular disorder and ALS; neuropathy caused by head injury; various pains such as pain caused by spinal injury, diabetes or thromboangiitis obliterans, neurogenic pain, migraine, visceral pain and cancerous pain; various diseases associated with psychogenic stress such as bronchial asthma, unstable angina and irritable colitis; withdrawal symptoms after addiction to drugs such as emotional disorder and ethanol addiction withdrawal symptoms.

The dose of the compound used for the above-described purpose varies depending on the intended therapeutic effect, administration method, period of the treatment, and age and body weight of the patient. The dose is usually 1 μg to 5 g a day for adults in the oral administration, and 0.01 μg to 1 g a day for adults in the parenteral administration.

The following Examples will further illustrate the present invention, which are only preferred embodiments of the invention and which by no means limit the invention.

EXAMPLE 1

Synthesis of 4-(3-chlorophenyl)-6-methyl-2-(methylthio)-N-(3-phenyl-2-propen-1-yl)-5-pyrimidinecarboxamide 1) Synthesis of 3-oxo-N-(3-phenyl-2-propen-1-yl) butylamide 3.06 g (23.0 mmol) of cinnamyl amine, 2.32 ml (30.1 mmol) of diketene and 0.321 ml (2.30 mmol) of triethylamine were heated and stirred in 50 ml of toluene at 70° C. for 3 hours. After saturated aqueous sodium hydrogencarbonate solution was added, the reaction mixture was extracted with ethyl acetate. The organic layer was dried over anhydrous sodium sulfate and concentrated under reduced pressure to obtain the title compound.

Yield: 5.08 g (23.4 mmol) (quantitative yield)
MS (ESI, m/z) 216 (M–H)$^-$
$^1$H-NMR (CDCl3): 2.29 (3H, s), 3.47 (2H, s), 4.07 (2H, t), 6.20 (1H, dt), 6.54 (1H, d), 7.15-7.40 (5H, m).

2) Synthesis of 2-acetyl-3-(3-chlorophenyl)-N-(3-phenyl-2-propen-1-yl) acrylamide 30.0 mg (1.38 mmol) of 3-oxo-N-(3-phenyl-2-propen-1-yl)butylamide and 194 mg (1.38 mmol) of 3-chlorobenzaldehyde were dissolved in 20 ml of 2-propanol. 4.14 mg (0.0690 mmol) of piperidine and 5.67 mg (0.0690 mmol) of acetic acid were added thereto and stirred at room temperature for 2 days. After the solvent was evaporated under reduced pressure, ethyl acetate was added to the reaction mixture. After washing with 1 N hydrochloric acid and then with saturated aqueous sodium hydrogencarbonate solution, the organic layer was dried over anhydrous magnesium sulfate and then concentrated under reduced pressure. The residue was purified by the silica gel chromatography (hexane/ethyl acetate=10/1) to obtain the title compound.

Yield: 413 mg (1.21 mmol) (88%)
MS (ESI, m/z) 340 (M+H)$^+$
$^1$H-NMR (CDCl3): 2.43 (3H, s), 4.10-4.16 (2H, m), 6.05-6.17 (2H, m), 6.70 (1H, d), 7.22-7.32 (7H, m), 7.41-7.45 (2H, m), 7.52 (1H, s).

3) Synthesis of 4-(3-chlorophenyl)-6-methyl-2-(methylthio)-N-(3-phenyl-2-propen-1-yl)-5-pyrimidinecarboxamide 413 mg (1.21 mmol) of 2-acetyl-3-(3-chlorophenyl)-N-(3-phenyl-2-propen-1-yl) acrylamide was dissolved in 10 ml of DMF. 269 mg (0.968 mmol) of methylisothiourea-sulfate and 149 mg of (1.82 mmol) of sodium acetate were added thereto at room temperature and stirred at 100° C. for 2 days. DMF was evaporated under reduced pressure, and the residue was diluted with ethyl acetate and washed with saturated aqueous sodium chloride solution. The organic layer was dried over anhydrous magnesium sulfate and then concentrated under reduced pressure. The residue was purified by the silica gel chromatography (hexane/ethyl acetate=10/1) to obtain the title compound.

Yield: 156 mg (0.379 mmol) (31%)
MS (ESI, m/z) 410 (M+H)$^+$
$^1$H-NMR (CDCl3): 2.58 (3H, s), 2.61 (3H, s), 4.04 (2H, t), 5.52 (1H, br t), 5.89 (1H, dt), 6.31 (1H, d), 7.23-7.40 (7H, m), 7.65-7.68 (1H, m), 7.82 (1H, t).

EXAMPLE 2

Synthesis of 4-(3-chlorophenyl)-N-(3,3-diphenylpropyl)-6-methyl-2-(methylthio)-5-pyrimidinecarboxamide The title compound was obtained by using 157 mg (0.376 mmol) of 2-acetyl-3-(3-chlorophenyl)-N-(3,3-diphenylpropyl)acrylamide, 83.8 mg (0.301 mmol) of methylisothiourea-sulfate and 37.0 mg (0.451 mmol) of sodium acetate, in the same manner as that of Example 1.

Yield: 49.8 mg (0.102 mmol) (27%)
MS (ESI, m/z) 488 (M+H)$^+$
$^1$H-NMR (CDCl3): 2.06-2.13 (2H, m), 2.52 (3H, s), 2.61 (3H, s), 3.22 (2H, q) 3.66 (1H, t), 5.35 (1H, br t), 7.09-7.38 (12H, m), 7.65 (1H, dt), 7.80 (1H, t).

EXAMPLE 3

Synthesis of 4-(3-chlorophenyl)-6-methyl-N-(3-phenyl-2-propen-1-yl)-2-(pyridine-3-yl)-5-pyrimidinecarboxamide 100 mg (0.294 mmol) of 2-acetyl-3-(3-chlorophenyl)-N-(3-phenyl-2-propen-1-yl) acrylamide was dissolved in 5 ml of DMF. 60.1 mg (0.381 mmol) of 3-amidinopyridinium hydrochloride and 28.9 mg of (0.353 mmol) of sodium acetate were added thereto and stirred at room temperature overnight. The reaction mixture was diluted with ethyl acetate and washed with saturated aqueous sodium chloride solution. The organic layer was dried over anhydrous magnesium sulfate and then concentrated under reduced pressure. The obtained residue was stirred at 120° C. overnight, cooled down at room temperature and purified by the silica gel chromatography (hexane/ethyl acetate=1/2) to obtain the title compound.

Yield: 21.8 mg (0.0494 mmol) (17%)
MS (ESI, m/z) 441 (M+H)$^+$, 439 (M−H)$^−$
$^1$H-NMR (CDCl3): 2.74 (3H, s), 4.13 (2H, t), 5.95-6.05 (1H, m), 6.37 (1H, d), 7.07 (1H, s), 7.23-7.47 (8H, m), 7.78 (1H, dd), 7.85 (1H, s), 8.50 (1H, d), 8.65 (1H, t), 9.34 (1H, s).

EXAMPLE 4

Synthesis of 4-(3-chlorophenyl)-6-methyl-2-phenyl-N-(3-phenyl-2-propen-1-yl)-5-pyrimidinecarboxamide The title compound was obtained by using 120 mg (0.353 mmol) of 2-acetyl-3-(3-chlorophenyl)-N-(3-phenyl-2-propen-1-yl) acrylamide, 83.4 mg (0.530 mmol) of benzamidine hydrochloride and 43.5 mg (0.530 mmol) of sodium acetate, in the same manner as that of Example 1.

Yield: 42.0 mg (0.0950 mmol) (27%)
MS (ESI, m/z) 440 (M+H)$^+$, 438 (M−H)$^−$
$^1$H-NMR (CDCl3): 2.70 (3H, s), 4.07 (2H, t), 5.65 (1H, s), 5.87-5.97 (1H, m), 6.32 (1H, d), 7.22-7.42 (7H, m), 7.45-7.52 (3H, m), 7.76 (1H, dd), 7.95 (1H, s), 8.51-8.54 (2H, m).

EXAMPLE 5

Synthesis of 4-(3-chlorophenyl)-N-(3,3-diphenylpropyl)-6-methyl-2-(pyridine-3-yl)-5-pyrimidinecarboxamide The title compound was obtained by using 167 mg (0.400 mmol) of 2-acetyl-3-(3-chlorophenyl)-N-(3,3-diphenylpropyl) acrylamide, 94.5 mg (0.599 mmol) of 3-amidinopyridinium hydrochloride and 49.1 mg (0.599 mmol) of sodium acetate, in the same manner as that of Example 1.

Yield: 72.0 mg (0.138 mmol) (35%)
MS (ESI, m/z) 519 (M+H)$^+$
$^1$H-NMR (CDCl3): 2.20 (2H, q), 2.68 (3H, s), 3.32 (2H, q), 3.79 (1H, t), 7.13-7.40 (13H, m), 7.76 (1H, dt), 7.83 (1H, t), 8.45 (1H, dd), 8.63 (1H, dt), 9.25 (1H, d).

EXAMPLE 6

Synthesis of 4-(3,4-dichlorophenyl)-N-(3,3-diphenylpropyl)-6-methyl-2-(methylthio)-5-pyrimidinecarboxamide The title compound was obtained by using 100 mg (0.221 mmol) of 2-acetyl-3-(3,4-dichlorophenyl)-N-(3,3-diphenylpropyl) acrylamide, 49.2 mg (0.177 mmol) of methylisothiourea-sulfate and 21.8 mg (0.265 mmol) of sodium acetate, in the same manner as that of Example 1.

Yield: 30.1 mg (0.0576 mmol) (26%)
MS (ESI, m/z) 522 (M+H)$^+$
$^1$H-NMR (CDCl3): 2.13 (2H, q), 2.49 (3H, s), 2.59 (3H, s), 3.23 (2H, q), 3.75 (1H, t), 5.56 (1H, br t), 7.63 (1H, dd), 7.93 (1H, d).

EXAMPLE 7

Synthesis of 4-(3,4-dichlorophenyl)-6-methyl-2-(methylthio)-N-(3-phenylpropyl)-5-pyrimidinecarboxamide The title compound was obtained by using 100 mg (0.266 mmol) of 2-acetyl-3-(3,4-dichlorophenyl)-N-(3-phenylpropyl) acrylamide, 59.2 mg (0.213 mmol) of methylisothiourea-sulfate and 26.2 mg (0.319 mmol) of sodium acetate, in the same manner as that of Example 1.

Yield: 22.9 mg (0.0513 mmol) (19%)
MS (ESI, m/z) 446 (M+H)$^+$
$^1$H-NMR (CDCl3): 1.73 (2H, quint), 2.45-2.52 (5H, m), 2.59 (3H, s), 3.30 (2H, q) 5.56 (1H, br t), 7.05 (2H, d), 7.15-7.20 (1H, m), 7.24-7.29 (2H, m), 7.48 (1H, d), 7.65 (1H, dd), 7.93 (1H, d).

EXAMPLE 8

Synthesis of 4-(3,5-dichlorophenyl)-N-(3,3-diphenylpropyl)-6-methyl-2-(methylthio)-5-pyrimidinecarboxamide The title compound was obtained by using 100 mg (0.221 mmol) of 2-acetyl-3-(3,5-dichlorophenyl)-N-(3,3-diphenylpropyl) acrylamide, 49.2 mg (0.177 mmol) of methylisothiourea-sulfate and 21.8 mg (0.265 mmol) of sodium acetate, in the same manner as that of Example 1.

Yield: 25.8 mg (0.0494 mmol) (22%)
MS (ESI, m/z) 522 (M+H)$^+$
$^1$H-NMR (CDCl3): 2.14 (2H, q), 2.50 (3H, s), 2.60 (3H, s), 3.25 (2H, q), 3.69 (1H, t), 5.51 (1H, br t), 7.13-7.35 (11H, m), 7.67 (2H, d).

EXAMPLE 9

Synthesis of 4-(3,5-dichlorophenyl)-6-methyl-2-(methylthio)-N-(3-phenylpropyl)-5-pyrimidinecarboxamide The title compound was obtained by using 100 mg (0.266 mmol) of 2-acetyl-3-(3,5-dichlorophenyl)-N-(3-phenylpropyl) acrylamide, 59.2 mg (0.213 mmol) of methylisothiourea-sulfate and 26.2 mg (0.319 mmol) of sodium acetate, in the same manner as that of Example 1.
Yield: 13.2 mg (0.0296 mmol) (11%)
MS (ESI, m/z) 446 (M+H)$^+$
$^1$H-NMR (CDCl3): 1.74 (2H, quint), 2.48 (2H, t), 2.53 (3H, s), 2.60 (3H, s), 3.32 (2H, q), 5.53 (1H, br t), 7.07 (2H, d), 7.15-7.29 (3H, m), 7.41 (1H, t), 7.69 (2H, d).

EXAMPLE 10

Synthesis of 4-(3,5-dichlorophenyl)-6-methyl-2-(methylthio)-N-(3-phenylpropyl)-5-pyrimidinecarboxamide The title compound was obtained by using 100 mg (0.267 mmol) of 2-acetyl-3-(3,5-dichlorophenyl)-N-(3-phenyl-2-propen-1-yl) acrylamide, 59.5 mg (0.214 mmol) of methyl-isothiourea-sulfate and 26.3 mg (0.320 mmol) of sodium acetate, in the same manner as that of Example 1.
Yield: 36.1 mg (0.0812 mmol) (30%)
MS (ESI, m/z) 444 (M+H)$^+$
$^1$H-NMR (CDCl3): 2.57 (3H, s), 2.60 (3H, s), 4.07 (3H, t), 5.64 (1H, br t), 5.96 (1H, dt), 6.36 (1H, d), 7.24-7.36 (6H, m), 7.69 (2H, d).

EXAMPLE 11

Synthesis of 4-(3,4-dichlorophenyl)-6-methyl-2-(methylthio)-N-(3-phenylpropyl)-5-pyrimidinecarboxamide The title compound was obtained by using 75.7 mg (0.202 mmol) of 2-acetyl-3-(3,4-dichlorophenyl)-N-(3-phenyl-2-propen-1-yl) acrylamide, 45.0 mg (0.162 mmol) of methyl-isothiourea sulfate and 19.9 mg (0.242 mmol) of sodium acetate, in the same manner as that of Example 1.
Yield: 22.4 mg (0.0504 mmol) (25%)
MS (ESI, m/z) 444 (M+H)$^+$
$^1$H-NMR (CDCl3): 2.56 (3H, s), 2.60 (3H, s), 4.06 (2H, t), 5.66 (1H, br t), 5.92 (1H, dt), 6.35 (1H, d), 7.22-7.35 (5H, m), 7.44 (1H, d), 7.64 (1H, dd), 7.95 (1H, d).

EXAMPLE 12

Synthesis of 4-(3,5-dichlorophenyl)-2,6-dimethyl-N-(3-phenylpropyl)-5-pyrimidinecarboxamide The title compound was obtained by using 80.0 mg (0.214 mmol) of 2-acetyl-3-(3,5-dichlorophenyl)-N-(3-phenyl-2-propen-1-yl) acrylamide, 30.3 mg (0.321 mmol) of acetamidine hydrochloride and 21.1 mg (0.257 mmol) of sodium acetate, in the same manner as that of Example 1.

Yield: 45.1 mg (0.109 mmol) (51%)
MS (ESI, m/z) 412 (M+H)$^+$
$^1$H-NMR (CDCl3): 2.61 (3H, s), 2.75 (3H, s), 4.08 (2H, t), 5.64 (1H, br t), 5.96 (1H, dt), 6.37 (1H, d), 7.25-7.36 (6H, m), 7.68 (2H, d).

EXAMPLE 13

Synthesis of 4-(3-chlorophenyl)-6-methyl-2-phenyl-N-(3-phenylpropyl)-5-pyrimidinecarboxamide The title compound was obtained by using 120 mg (0.351 mmol) of 2-acetyl-3-(3-chlorophenyl)-N-(3-phenylpropyl) acrylamide, 82 mg (0.525 mmol) of benzamidine hydrochloride and 34.5 mg (0.421 mmol) of sodium acetate, in the same manner as that of Example 1.
Yield: 28.7 mg (0.0649 mmol) (18%)
MS (ESI, m/z) 442 (M+H)$^+$
$^1$H-NMR (CDCl3): 1.71 (2H, quint), 2.45 (2H, t), 2.66 (3H, s), 3.31 (2H, q), 5.56 (1H, br s), 7.06 (2H, d), 7.15-7.29 (3H, m), 7.34-7.51 (5H, m), 7.77 (1H, d), 7.92 (1H, s), 8.51-8.53 (2H, m)

EXAMPLE 14

Synthesis of 4-(3-chlorophenyl)-6-methyl-N-(3-phenylpropyl)-2-(pyridine-3-yl)-5-pyrimidinecarboxamide The title compound was obtained by using 120 mg (0.351 mmol) of 2-acetyl-3-(3-chlorophenyl)-N-(3-phenylpropyl) acrylamide, 83.0 mg (0.525 mmol) of 3-amidinopyridinium hydrochloride and 34.5 mg (0.421 mmol) of sodium acetate, in the same manner as that of Example 1.
Yield: 85.3 mg (0.193 mmol) (54%)
MS (ESI, m/z) 443 (M+H)$^+$
$^1$H-NMR (CDCl3): 1.81 (2H, quint), 2.52 (2H, t), 2.70 (3H, s), 3.40 (2H, q), 7.09-7.47 (8H, m), 7.76-7.70 (3H, m), 8.40 (1H, d), 8.59 (1H, d), 9.12 (1H, s)

EXAMPLE 15

Synthesis of 4-(3-chlorophenyl)-2,6-dimethyl-N-(3-phenylpropyl)-5-pyrimidinecarboxamide The title compound was obtained by using 120 mg (0.351 mmol) of 2-acetyl-3-(3-chlorophenyl)-N-(3-phenylpropyl) acrylamide, 50.0 mg (0.531 mmol) of acetamidine hydrochloride and 34.5 mg (0.421 mmol) of sodium acetate, in the same manner as that of Example 1.
Yield: 28.6 mg (0.0753 mmol) (22%)
MS (ESI, m/z) 380 (M+H)$^+$
$^1$H-NMR (CDCl3): 1.68 (2H, quint), 2.43 (2H, t), 2.58 (3H, s), 2.75 (3H, s), 3.29 (2H, q), 5.45 (1H, br t), 7.05 (2H, d), 7.15-7.43 (5H, m), 7.79 (1H, m)

EXAMPLE 16

Synthesis of 4-(3-chlorophenyl)-6-methyl-2-(methylthio)-N-(3-phenylpropyl)-5-pyrimidinecarboxamide The title compound was obtained by using 120 mg (0.351 mmol) of 2-acetyl-3-(3-chlorophenyl)-N-(3-phenylpropyl) acrylamide, 146 mg (0.525 mmol) of methylisothiourea-sulfate and 34.5 mg (0.421 mmol) of sodium acetate, in the same manner as that of Example 1.

Yield: 39.0 mg (0.0947 mmol) (27%)

MS (ESI, m/z) 317 (M+H)$^+$ $^1$H-NMR (CDCl3): 1.68 (2H, quint), 2.43 (2H, t), 2.53 (3H, s), 2.60 (3H, s), 3.27 (2H, q), 5.54 (1H, br s), 7.04 (2H, d), 7.15-7.42 (5H, m), 7.66 (1H, d), 7.79 (1H, s).

EXAMPLE 17

Synthesis of 4-(3-chlorophenyl)-2,6-dimethyl-N-(3-phenyl-2-propen-1-yl)-5-pyrimidinecarboxamide The title compound was obtained by using 100 mg (0.294 mmol) of 2-acetyl-3-(3-chlorophenyl)-N-(3-phenyl-2-propen-1-yl) acrylamide, 41.7 mg (0.441 mmol) of acetamidine hydrochloride and 48.2 mg (0.588 mmol) of sodium acetate, in the same manner as that of Example 1.

Yield: 45.5 mg (0.120 mmol) (41%)

MS (ESI, m/z) 378 (M+H)$^+$ $^1$H-NMR (CDCl3): 2.62 (3H, s), 2.76 (3H, s), 4.04 (2H, td), 5.56 (1H, br t), 5.88 (1H, dt), 6.30 (1H, d), 7.22-7.39 (7H, m), 7.64 (1H, dt), 7.81 (1H, t).

EXAMPLE 18

Synthesis of 4-(3,4-dichlorophenyl)-2,6-dimethyl-N-(3-phenylpropyl)-5-pyrimidinecarboxamide The title compound was obtained by using 100 mg (0.266 mmol) of 2-acetyl-3-(3,4-dichlorophenyl)-N-(3-phenylpropyl) acrylamide, 37.7 mg (0.399 mmol) of acetamidine hydrochloride and 43.6 mg (0.532 mmol) of sodium acetate, in the same manner as that of Example 1.

Yield: 91.5 mg (0.221 mmol) (83%)

MS (ESI, m/z) 414 (M+H)$^+$ $^1$H-NMR (CDCl3): 1.72 (2H, quint), 2.48 (2H, t), 2.56 (3H, s), 2.74 (3H, s), 3.31 (2H, q), 5.55 (1H, br t), 7.05 (2H, d), 7.15-7.21 (1H, m), 7.24-7.29 (2H, m), 7.49 (1H, d), 7.62-7.65 (1H, m), 7.93 (1H, d).

EXAMPLE 19

Synthesis of 4-(3,4-dichlorophenyl)-6-methyl-N-(3-phenylpropyl)-2-(pyridine-3-yl)-5-pyrimidinecarboxamide The title compound was obtained by using 100 mg (0.266 mmol) of 2-acetyl-3-(3,4-dichlorophenyl)-N-(3-phenylpropyl) acrylamide, 62.5 mg (0.399 mmol) of benzamidine hydrochloride and 43.6 mg (0.532 mmol) of sodium acetate, in the same manner as that of Example 1.

Yield: 65.3 mg (0.137 mmol) (51%)

MS (ESI, m/z) 477 M+H)$^+$ $^1$H-NMR (CDCl3): 1.83 (2H, quint), 2.56 (2H, t), 2.71 (3H, s), 3.42 (2H, q), 7.10 (2H, d), 7.16-7.31 (3H, m), 7.36-7.40 (1H, m), 7.53 (1H, d), 7.76 (1H, dd), 7.96 (1H, d), 8.48 (1H, br), 8.62 (1H, m), 9.24 (1H, br s).

EXAMPLE 20

Synthesis of 4-(3,5-dichlorophenyl)-6-methyl-2-phenyl-N-(3-phenylpropyl)-5-pyrimidinecarboxamide The title compound was obtained by using 100 mg (0.266 mmol) of 2-acetyl-3-(3,5-dichlorophenyl)-N-(3-phenylpropyl) acrylamide, 62.5 mg (0.399 mmol) of benzamidine hydrochloride and 43.6 mg (0.532 mmol) of sodium acetate, in the same manner as that of Example 1.

Yield: 129 mg (0.271 mmol) (100%)

MS (ESI, m/z) 476 (M+H)$^+$ $^1$H-NMR (CDCl3): 1.78 (2H, quint), 2.51 (2H, t), 2.68 (3H, s), 3.37 (2H, q), 5.52 (1H, br t), 7.09 (2H, d), 7.19-7.30 (3H, m), 7.45 (1H, t), 7.49-7.57 (3H, m), 7.81 (2H, d), 8.52 (2H, m).

EXAMPLE 21

Synthesis of 4-(3,5-dichlorophenyl)-6-methyl-N-(3-phenylpropyl)-2-(pyridine-3-yl)-5-pyrimidinecarboxamide The title compound was obtained by using 100 mg (0.266 mmol) of 2-acetyl-3-(3,5-dichlorophenyl)-N-(3-phenylpropyl) acrylamide, 62.9 mg (0.399 mmol) of 3-amidinopyridinium hydrochloride and 43.6 mg (0.532 mmol) of sodium acetate, in the same manner as that of Example 1.

Yield: 145 mg (0.304 mmol) (111%)

MS (ESI, m/z) 477 (M+H)$^+$ $^1$H-NMR (CDCl3): 1.86 (2H, quint), 2.56 (2H, t), 2.64 (3H, s), 3.44 (2H, q), 7.12-7.37 (6H, m), 7.43-7.44 (1H, m), 7.68 (2H, d), 8.09 (1H, br), 8.37 (1H, br), 8.52-8.56 (1H, m), 9.01 (1H, s).

EXAMPLE 22

Synthesis of 4-(3,5-dichlorophenyl)-2,6-dimethyl-N-(3-phenylpropyl)-5-pyrimidinecarboxamide The title compound was obtained by using 100 mg (0.266 mmol) of 2-acetyl-3-(3,5-dichlorophenyl)-N-(3-phenylpropyl) acrylamide, 37.7 mg (0.399 mmol) of acetamidine hydrochloride and 43.6 mg (0.532 mmol) of sodium acetate, in the same manner as that of Example 1.

Yield: 51.8 mg (0.125 mmol) (48%)

MS (ESI, m/z) 414 (M+H)$^+$ $^1$H-NMR (CDCl3): 1.74 (2H, quint), 2.48 (2H, t), 2.57 (3H, s), 2.75 (3H, s), 3.32 (2H, q), 5.54 (1H, br t), 7.08 (2H, d), 7.16-7.29 (3H, m), 7.41 (1H, m), 7.68 (2H, d).

EXAMPLE 23

Synthesis of 4-(3,4-dichlorophenyl)-6-methyl-2-phenyl-N-(4-phenylbutyl)-5-pyrimidinecarboxamide The title compound was obtained by using 100 mg (0.256 mmol) of 2-acetyl-3-(3,4-dichlorophenyl)-N-(4-phenylbutyl) acrylamide, 60.1 mg (0.384 mmol) of benzamidine hydrochloride and 42.0 mg (0.512 mmol) of sodium acetate, in the same manner as that of Example 1.

Yield: 104 mg (0.212 mmol) (80%)

MS (ESI, m/z) 490 (M+H)$^+$ $^1$H-NMR (CDCl3): 1.38-1.54 (4H, br), 2.57 (2H, t), 2.64 (3H, s), 3.32 (2H, q), 5.60 (1H, br t), 7.10-7.30 (5H, m), 7.48-7.52 (4H, m), 7.73-7.76 (1H, m), 8.04-8.05 (1H, m), 8.49-8.52 (2H, m).

EXAMPLE 24

Synthesis of 4-(3,4-dichlorophenyl)-6-methyl-N-(4-phenylbutyl)-2-(pyridine-3-yl)-5-pyrimidinecarboxamide The title compound was obtained by using 100 mg (0.256 mmol) of 2-acetyl-3-(3,4-dichlorophenyl)-N-(4-phenylbutyl) acrylamide, 60.5 mg (0.384 mmol) of 3-amidinopyridinium hydrochloride and 42.0 mg (0.512 mmol) of sodium acetate, in the same manner as that of Example 1.
Yield: 83.6 mg (0.170 mmol) (65%)
MS (ESI, m/z) 491 (M+H)$^+$
$^1$H-NMR (CDCl3): 1.49-1.58 (4H, br), 2.56-2.64 (2H, br), 2.68 (3H, s), 3.36-3.44 (2H, br), 7.11-7.20 (3H, m), 7.25-7.36 (3H, m), 7.50-7.52 (2H, m), 7.71-7.75 (1H, m), 7.92 (1H, d), 8.32-8.34 (1H, m), 8.56-8.60 (1H, m), 9.12 (1H, m).

EXAMPLE 25

Synthesis of 4-(3,4-dichlorophenyl)-2,6-dimethyl-N-(4-phenylbutyl)-5-pyrimidinecarboxamide The title compound was obtained by using 100 mg (0.256 mmol) of 2-acetyl-3-(3,4-dichlorophenyl)-N-(4-phenylbutyl) acrylamide, 36.3 mg (0.384 mmol) of acetamidine hydrochloride and 42.0 mg (0.512 mmol) of sodium acetate, in the same manner as that of Example 1.
Yield: 53.3 mg (0.124 mmol) (46%)
MS (ESI, m/z) 428 (M+H)$^+$
$^1$H-NMR (CDCl3): 1.36-1.44 (4H, m), 2.53-2.58 (5H, m), 2.74 (3H, s), 3.29 (2H, q), 5.48 (1H, br t), 7.09-7.20 (3H, m), 7.24-7.29 (2H, m), 7.48 (1H, d), 7.62-7.65 (1H, m), 7.93 (1H, d).

EXAMPLE 26

Synthesis of 4-(3,4-dichlorophenyl)-6-methyl-2-(methylthio)-N-(4-phenylbutyl)-5-pyrimidinecarboxamide The title compound was obtained by using 100 mg (0.256 mmol) of 2-acetyl-3-(3,4-dichlorophenyl)-N-(4-phenylbutyl) acrylamide, 53.5 mg (0.192 mmol) of methylisothiourea-sulfate and 42.0 mg (0.512 mmol) of sodium acetate, in the same manner as that of Example 1.
Yield: 57.2 mg (0.124 mmol) (46%)
MS (ESI, m/z) 460 M+H)$^+$
$^1$H-NMR (CDCl3): 1.34-1.52 (4H, br), 2.52-2.60 (8H, m), 3.28 (2H, q), 5.48 (1H, br t), 7.09-7.12 (2H, m), 7.15-7.20 (1H, m), 7.24-7.29 (2H, m), 7.47 (1H, d), 7.63-7.67 (1H, m), 7.93 (1H, d).

EXAMPLE 27

Synthesis of 4-(3,4-dichlorophenyl)-6-methyl-2-phenyl-N-(2-phenylethyl)-5-pyrimidinecarboxamide The title compound was obtained by using 100 mg (0.276 mmol) of 2-acetyl-3-(3,4-dichlorophenyl)-N-(2-phenylethyl) acrylamide, 64.8 mg (0.414 mmol) of benzamidine hydrochloride and 45.3 mg (0.552 mmol) of sodium acetate, in the same manner as that of Example 1.
Yield: 54.6 mg (0.118 mmol) (43%)
MS (ESI, m/z) 462 (M+H)$^+$
$^1$H-NMR (CDCl3): 2.61 (3H, s), 2.74 (2H, t), 3.63 (2H, q), 5.51 (1H, br t), 6.91-6.94 (2H, m), 7.18-7.25 (3H, m), 7.47-7.55 (4H, m), 7.73 (1H, dd), 8.03 (1H, d), 8.48-8.51 (2H, m).

EXAMPLE 28

Synthesis of 4-(3,4-dichlorophenyl)-6-methyl-N-(2-phenylethyl)-2-(pyridine-3-yl)-5-pyrimidinecarboxamide The title compound was obtained by using 100 mg (0.276 mmol) of 2-acetyl-3-(3,4-dichlorophenyl)-N-(2-phenylethyl) acrylamide, 65.2 mg (0.414 mmol) of 3-amidinopyridinium hydrochloride and 45.3 mg (0.552 mmol) of sodium acetate, in the same manner as that of Example 1.
Yield: 114 mg (0.246 mmol) (89%)
MS (ESI, m/z) 463 (M+H)$^+$
$^1$H-NMR (CDCl3): 2.62 (3H, s), 2.82 (2H, t), 3.70 (2H, q), 6.99-7.02 (2H, m), 7.17-7.40 (5H, m), 7.53 (1H, d), 7.72 (1H, dd), 7.90 (1H, d), 8.11-8.17 (1H, br), 8.53-8.56 (1H, m), 9.12 (1H, s).

EXAMPLE 29

Synthesis of 4-(3,4-dichlorophenyl)-2,6-dimethyl-N-(2-phenylethyl)-5-pyrimidinecarboxamide The title compound was obtained by using 100 mg (0.276 mmol) of 2-acetyl-3-(3,4-dichlorophenyl)-N-(2-phenylethyl) acrylamide, 39.1 mg (0.414 mmol) of acetamidine hydrochloride and 45.3 mg (0.552 mmol) of sodium acetate, in the same manner as that of Example 1.
Yield: 43.2 mg (0.108 mmol) (89%)
MS (ESI, m/z) 400 (M+H)$^+$
$^1$H-NMR (CDCl3): 2.50 (3H, s), 2.68-2.72 (5H, m), 3.59 (2H, q), 5.47 (1H, br s), 6.89-6.91 (2H, m), 7.17-7.26 (3H, m), 7.50 (1H, d), 7.59-7.63 (1H, m), 7.89 (1H, d).

EXAMPLE 30

Synthesis of 4-(3,4-dichlorophenyl)-6-methyl-2-(methylthio)-N-(2-phenylethyl)-5-pyrimidinecarboxamide The title compound was obtained by using 100 mg (0.276 mmol) of 2-acetyl-3-(3,4-dichlorophenyl)-N-(2-phenylethyl) acrylamide, 57.6 mg (0.207 mmol) of methylisothiourea-sulfate and 45.3 mg (0.552 mmol) of sodium acetate, in the same manner as that of Example 1.
Yield: 50.3 mg (0.116 mmol) (43%)
MS (ESI, m/z) 432 (M+H)$^+$
$^1$H-NMR (CDCl3): 2.46 (3H, s), 2.58 (3H, s), 2.70 (2H, t), 3.58 (2H, q), 5.46 (1H, br t), 6.89-6.92 (2H, m), 7.18-7.26 (3H, m), 7.49 (1H, d), 7.60-7.64 (1H, m), 7.90 (1H, d).

EXAMPLE 31

Synthesis of 4-(3,4-dichlorophenyl)-2,6-dimethyl-N-(3,3-diphenylpropyl)-5-pyrimidinecarboxamide 120 mg (0.265 mmol) of 2-acetyl-3-(3,4-dichlorophenyl)-N-(3,3-diphenylpropyl) acrylamide was dissolved in 5 ml of DMF. 37.6 mg (0.398 mmol) of acetamidine hydrochloride and 26.1 mg (0.318 mmol) of sodium acetate were added thereto and stirred at 100° C. overnight. After the solvent was evaporated under reduced pressure, the reaction mixture was diluted with ethyl acetate and washed with saturated aqueous sodium chloride solution. The organic layer was dried over anhydrous magnesium sulfate and then concentrated under reduced pressure. The obtained residue was dissolved in 10 ml of toluene. 120 mg (0.530 mmol) of DDQ (2,3-dichloro-5,6-dicyano-1,4-benzoquinone; hereinafter abbreviated as DDQ) was added thereto and stirred at 100° C. overnight. After filtration of insoluble matters and evaporation of the solvent under reduced pressure, the filtrate was diluted with ethyl acetate and washed with saturated aqueous sodium chloride solution. The organic layer was dried over anhydrous magnesium sulfate and then concentrated under reduced pressure. The residue was purified by the silica gel chromatography (hexane/ethyl acetate=10/1 to 1/1) to obtain the title compound.

Yield: 20.0 mg (0.0408 mmol) (15%)
MS (ESI, m/z) 490 (M+H)$^+$
$^1$H-NMR (CDCl3): 2.12 (2H, q), 2.55 (3H, s), 2.75 (3H, s), 3.25 (2H, q), 3.75 (1H, t), 5.43 (1H, br t), 7.11-7.29 (10H, m), 7.47 (1H, d), 7.60-7.64 (1H, m), 7.93 (1H, d).

EXAMPLE 32

Synthesis of 4-(3,5-dichlorophenyl)-2,6-dimethyl-N-(3,3-diphenylpropyl)-5-pyrimidinecarboxamide 111 mg (0.246 mmol) of 2-acetyl-3-(3,5-dichlorophenyl)-N-(3,3-diphenylpropyl) acrylamide was dissolved in 5 ml of DMF. 34.9 mg (0.369 mmol) of acetamidine hydrochloride and 24.2 mg of (0.295 mmol) of sodium acetate were added thereto and stirred at 100° C. overnight. After the solvent was evaporated under reduced pressure, the reaction mixture was diluted with ethyl acetate and washed with saturated aqueous sodium chloride solution. The organic layer was dried over anhydrous magnesium sulfate and then concentrated under reduced pressure. The obtained residue was dissolved in 10 ml of toluene. 112 mg (0.492 mmol) of DDQ was added thereto and stirred at 100° C. overnight. After filtration of insoluble matters and evaporation of the solvent under reduced pressure, the filtrate was diluted with ethyl acetate and washed with saturated aqueous sodium chloride solution. The organic layer was dried over anhydrous magnesium sulfate and then concentrated under reduced pressure. The residue was purified by the silica gel chromatography (hexane/ethyl acetate=10/1 to 1/1) to obtain the title compound.

Yield: 30.2 mg (0.0616 mmol) (25%)
MS (ESI, m/z) 490 (M+H)$^+$
$^1$H-NMR (CDCl3): 2.14 (2H, q), 2.55 (3H, s), 2.75 (3H, s), 3.27 (2H, q), 3.69 (1H, t), 5.41 (1H, br t), 7.13-7.19 (5H, m), 7.24-7.29 (5H, m), 7.34 (1H, d), 7.67 (2H, d).

EXAMPLE 33

Synthesis of 4-(3,4-dichlorophenyl)-6-methyl-N-(3-phenylpropyl)-5-pyrimidinecarboxamide 100 mg (0.224 mmol) of 4-(3,4-dichlorophenyl)-6-methyl-2-(methylthio)-N-(3-phenylpropyl)-5-pyrimidinecarboxamide was dissolved in 5 ml of dichloromethane. 77.3 mg (0.448 mmol) of mCPBA (m-chloroperbenzoic acid; hereinafter abbreviated as mCPBA) was added thereto at 0° C. and stirred at the same temperature for 6 hours. 1 ml of saturated aqueous sodium sulfite solution was added thereto at the same temperature and stirred for 30 minutes heating to room temperature. After the reaction mixture was diluted with dichloromethane, the organic layer was washed with saturated aqueous sodium chloride solution and dried over anhydrous magnesium sulfate and then concentrated under reduced pressure. The obtained residue was dissolved in 5 ml of ethanol and 16.9 mg (0.448 mmol) of sodium borohydride was added at room temperature and stirred for 1 hour. 5 ml of 1N hydrochloric acid was added at the same temperature, stirred at room temperature for 30 minutes and then concentrated under reduced pressure. After the obtained residue was diluted with dichloromethane, the organic layer was washed with saturated aqueous sodium chloride solution and dried over anhydrous magnesium sulfate and then concentrated under reduced pressure. The residue was purified by the silica gel chromatography (hexane/ethyl acetate=3/1) to obtain the title compound.

Yield: 50.8 mg (0.127 mmol) (57%)
MS (ESI, m/z) 400 (M+H)$^+$
$^1$H-NMR (CDCl3): 1.75 (2H, quint), 2.49 (2H, t), 2.62 (3H, s), 3.34 (2H, q), 5.59 (1H, br t), 7.06 (2H, d), 7.15-7.20 (1H, m), 7.24-7.29 (2H, m), 7.52 (1H, d), 7.67 (1H, dd), 7.96 (1H, d).

EXAMPLE 34

Synthesis of 4-(3,4-dichlorophenyl)-2,6-dimethyl-N-[2-(pyridine-3-yl) ethyl]-5-pyrimidinecarboxamide The title compound was obtained by using 140 mg (0.385 mmol) of 2-acetyl-3-(3,4-dichlorophenyl)-N-[2-(pyridine-3-yl)ethyl] acrylamide, 55.3 mg (0.585 mmol) of acetamidine hydrochloride and 64.0 mg (0.780 mmol) of sodium acetate, in the same manner as that of Example 1.

Yield: 37.7 mg (0.0939 mmol) (24%)
MS (ESI, m/z) 401 (M+H)$^+$
$^1$H-NMR (CDCl3): 2.52 (3H, s), 2.72-2.76 (5H, m), 3.59 (2H, q), 5.55 (1H, br t), 7.16-7.20 (1H, m), 7.27-7.31 (1H, m), 7.51 (1H, d), 7.61-7.65 (1H, m), 7.91 (1H, d), 8.28 (1H, s), 8.44-8.45 (1H, m).

EXAMPLE 35

Synthesis of 4-(3,4-dichlorophenyl)-6-methyl-2-(methylthio)-N-[2-(pyridine-3-yl)ethyl]-5-pyrimidinecarboxamide The title compound was obtained by using 140 mg (0.385 mmol) of 2-acetyl-3-(3,4-dichlorophenyl)-N-[2-pyridine-3-yl)ethyl] acrylamide, 81.4 mg (0.292 mmol) of methylisothiourea-sulfate and 64.0 mg (0.780 mmol) of sodium acetate, in the same manner as that of Example 1.

Yield: 45.0 mg (0.104 mmol) (27%)
MS (ESI, m/z) 433 (M+H)$^+$
$^1$H-NMR (CDCl3): 2.44 (3H, s), 2.56 (3H, s), 2.73 (2H, t), 3.57 (2H, q), 6.13 (1H, br s), 7.13-7.17 (1H, m), 7.28-7.32 (1H, m), 7.48 (1H, d), 7.60-7.63 (1H, m), 7.86-7.87 (1H, m), 8.16 (1H, s), 8.33 (1H, d).

EXAMPLE 36

Synthesis of 4-(4-methoxyphenyl)-6-methyl-2-phenyl-N-(3-phenylpropyl)-5-pyrimidinecarboxamide The title compound was obtained by using 131 mg (0.388 mmol) of 2-acetyl-3-(4-methoxyphenyl)-N-(3-phenylpropyl) acrylamide, 91.1 mg (0.582 mmol) of benzamidine hydrochloride and 80.0 mg (0.975 mmol) of sodium acetate, in the same manner as that of Example 1.

Yield: 53.5 mg (0.122 mmol) (31%)
MS (ESI, m/z) 438 (M+H)$^+$ $^1$H-NMR (CDCl3): 1.71 (2H, quint), 2.45 (2H, t), 2.64 (3H, s), 3.32 (2H, q), 3.79 (3H, s), 5.58 (1H, br t), 6.96 (2H, d), 7.05 (2H, d), 7.17-7.28 (3H, m), 7.47-7.50 (3H, m), 7.90 (2H, d), 8.51-8.54 (2H, m).

EXAMPLE 37

Synthesis of 4-(4-methoxyphenyl)-6-methyl-N-(3-phenylpropyl)-2-(pyridine-3-yl)-5-pyrimidinecarboxamide The title compound was obtained by using 137 mg (0.406 mmol) of 2-acetyl-3-(4-methoxyphenyl)-N-(3-phenylpropyl) acrylamide, 96.0 mg (0.609 mmol) of 3-amidinopyridinium hydrochloride and 80.0 mg (0.975 mmol) of sodium acetate, in the same manner as that of Example 1.
Yield: 23.0 mg (0.0524 mmol) (13%)
MS (ESI, m/z) 439 (M+H)$^+$
$^1$H-NMR (CDCl3): 1.79 (2H, quint), 2.51 (2H, t), 2.67 (3H, s), 3.40 (2H, q), 3.81 (3H, s), 6.96-7.36 (8H, m), 7.90 (2H, dt), 8.46 (1H, dd), 8.62 (1H, dt), 9.28 (1H, d).

EXAMPLE 38

Synthesis of 4-methyl-N-(3-phenylpropyl)-2,6-di(pyridine-3-yl)-5-pyrimidinecarboxamide The title compound was obtained by using 177 mg (0.546 mmol) of 2-acetyl-N-(3-phenylpropyl)-3-(pyridine-3-yl) acrylamide, 129 mg (0.819 mmol) of 3-amidinopyridinium hydrochloride and 89.4 mg (1.09 mmol) of sodium acetate, in the same manner as that of Example 1.
Yield: 138 mg (0.337 mmol) (62%)
MS (ESI, m/z) 410 (M+H)$^+$
$^1$H-NMR (CDCl3): 1.81 (2H, quint), 2.53 (2H, t), 2.71 (3H, s), 3.45 (3H, s), 3.41 (2H, q), 7.08-7.11 (2H, m), 7.14-7.20 (1H, m), 7.23-7.28 (2H, m), 7.32-7.39 (2H, m), 7.98 (1H, br t), 8.20 (1H, dt), 8.39 (1H, dd), 8.56 (1H, dt), 8.68 (1H, dd), 9.00-9.01 (1H, m), 9.11-9.12 (1H, m).

EXAMPLE 39

Synthesis of 2,4-dimethyl-N-(3-phenylpropyl)-6-(pyridine-3-yl)-5-pyrimidinecarboxamide The title compound was obtained by using 177 mg (0.546 mmol) of 2-acetyl-N-(3-phenylpropyl)-3-(pyridine-3-yl) acrylamide, 77.0 mg (0.814 mmol) of acetamidine hydrochloride and 89.4 mg (1.09 mmol) of sodium acetate, in the same manner as that of Example 1.
Yield: 82.3 mg (0.238 mmol) (44%)
MS (ESI, m/z) 347 (M+H)$^+$
$^1$H-NMR (CDCl3): 1.70 (2H, quint), 2.45 (2H, t), 2.56 (3H, s), 2.71 (3H, s), 3.29 (2H, q), 6.34 (1H, br t), 7.05 (2H, d), 8.06 (1H, dt), 8.51 (1H, dd), 8.77-8.78 (1H, m).

EXAMPLE 40

Synthesis of 4-(3,4-dichlorophenyl)-6-methyl-2-(methylsulfonyl)-N-(3-phenylpropyl)-5-pyrimidinecarboxamide 214 mg (0.479 mmol) of 4-(3,4-dichlorophenyl)-6-methyl-2-(methylthio)-N-(3-phenylpropyl)-5-pyrimidinecarboxamide synthesized in Example 7 was dissolved in 10 ml of dichloromethane. 165 mg (0.958 mmol) of mCPBA (m-chloroperbenzoic acid) was added thereto at 0° C. and stirred at the same temperature for 6 hours. 5 ml of saturated aqueous sodium bisulfite solution was added thereto at the same temperature and stirred for 30 minutes heating to room temperature. After the reaction mixture was diluted with dichloromethane, the organic layer was washed with saturated aqueous sodium chloride solution and dried over anhydrous magnesium sulfate and then concentrated under reduced pressure. The residue was purified by the silica gel chromatography (hexane/ethyl acetate=5/1) to obtain the title compound.
MS (ESI, m/z) 478 (M+H)$^+$ 476 (M–H)$^-$
$^1$H-NMR (CDCl3): 1.79 (2H, quint), 2.52 (2H, t), 2.72 (3H, s), 3.28 (3H, s), 3.36 (2H, q), 6.34 (1H, br t), 7.07-7.10 (2H, m), 7.16-7.21 (1H, m), 7.25-7.30 (2H, m), 7.52 (1H, d), 7.74 (1H, dd), 8.03 (1H, d).

EXAMPLE 41

Synthesis of 4-methyl-2-phenyl-N-(3-phenylpropyl)-6-(pyridine-3-yl)-5-pyrimidinecarboxamide The title compound was obtained by using 177 mg (0.546 mmol) of 2-acetyl-N-(3-phenylpropyl)-3-(pyridine-3-yl) acrylamide, 128 mg (0.819 mmol) of benzamidine hydrochloride and 89.4 mg (1.09 mmol) of sodium acetate, in the same manner as that of Example 1.
Yield: 116 mg (0.284 mmol) (51%)
MS (ESI, m/z) 409 (M+H)$^+$
$^1$H-NMR (CDCl3): 1.75 (2H, quint), 2.50 (2H, t), 2.67 (3H, s), 3.34 (2H, q), 5.87 (1H, br t), 7.06-7.09 (2H, m), 7.15-7.38 (4H, m), 7.47-7.53 (3H, m), 8.18-8.22 (1H, m), 8.48-8.52 (2H, m), 8.65 (1H, dd), 9.06 (1H, d).

EXAMPLE 42

Synthesis of 4-methyl-2-(methylthio)-N-(3-phenylpropyl)-6-(pyridine-3-yl)-5-pyrimidinecarboxamide The title compound was obtained by using 177 mg (0.546 mmol) of 2-acetyl-N-(3-phenylpropyl)-3-(pyridine-3-yl) acrylamide, 114 mg (0.410 mmol) of methylisothiourea-sulfate and 89.4 mg (1.09 mmol) of sodium acetate, in the same manner as that of Example 1.
Yield: 56.9 mg (0.150 mmol) (27%)
MS (ESI, m/z) 379 (M+H)$^+$
$^1$H-NMR (CDCl3): 1.71 (2H, quint), 2.47 (2H, t), 2.55 (3H, s), 2.60 (3H, s), 3.30 (2H, q), 5.64 (1H, br t), 7.04-7.07 (2H, m), 7.17-7.36 (4H, m), 8.11 (1H, dt), 8.65 (1H, dd), 9.00 (1H, d).

EXAMPLE 43

Synthesis of 2-amino-4-(3,4-dichlorophenyl)-6-methyl-N-(3-phenylpropyl)-5-pyrimidinecarboxamide 114 mg (0.238 mmol) of 4-(3-chlorophenyl)-6-methyl-2-methylsulfonyl-N-(3-phenylpropyl)-5-pyrimidinecarboxamide was dissolved in 10 ml of THF. 5 ml of 28% aqueous ammonia was added at 0° C. and stirred at room temperature for 12 hours. After the reaction mixture was diluted with ethyl acetate, the organic layer was washed with saturated aqueous sodium chloride solution and dried over anhydrous magnesium sulfate and then concentrated under reduced pressure. The residue was purified by the silica gel chromatography (dichloromethane/methanol=100/1 to 10/1) to obtain the title compound.

MS (ESI, m/z) 452 (M+H)+

¹H-NMR (CDCl3): 1.69 (2H, quint), 2.42-2.48 (4H, m), 3.26 (2H, q), 5.25 (2H, br s), 5.45 (1H, br t), 7.04-7.07 (2H, m), 7.07-7.20 (1H, m), 7.23-7.29 (2H, m), 7.46 (1H, d), 7.57 (1H, dd), 7.86 (1H, d).

EXAMPLE 44

Synthesis of 4-(4-methoxyphenyl)-6-methyl-2-(methylthio)-N-(3-phenylpropyl)-5-pyrimidinecarboxamide The title compound was obtained by using 215 mg (0.663 mmol) of 2-acetyl-3-(4-methoxyphenyl)-N-(3-phenylpropyl)acrylamide, 138 mg (0.995 mmol) of methylisothiourea-sulfate and 109 mg (1.33 mmol) of sodium acetate, in the same manner as that of Example 1.

Yield: 38.5 mg (0.0945 mmol) (15%)

MS (ESI, m/z) 408 (M+H)+

¹H-NMR (CDCl3): 1.69 (2H, quint), 2.43 (2H, t), 2.52 (3H, s), 2.60 (3H, s), 3.29 (2H, q), 3.77 (3H, s), 5.49 (1H, br t), 6.91-6.96 (2H, m), 7.03-7.06 (2H, m), 7.14-7.28 (3H, m), 7.78-7.81 (2H, m).

EXAMPLE 45

Synthesis of 4-methyl-6-(3-nitrophenyl)-2-phenyl-N-(3-phenylpropyl)-5-pyrimidinecarboxamide The title compound was obtained by using 100 mg (0.284 mmol) of 2-acetyl-3-(3-nitrophenyl)-N-(3-phenylpropyl)acrylamide, 66.7 mg (0.426 mmol) of benzamidine hydrochloride and 46.6 mg (0.568 mmol) of sodium acetate, in the same manner as that of Example 1.

Yield: 86.0 mg (0.190 mmol) (68%)

MS (ESI, m/z) 453 (M+H)+

¹H-NMR (CDCl3): 1.74 (2H, quint), 2.49 (2H, t), 2.66 (3H, s), 3.33 (2H, q), 5.81 (1H, br t), 7.05 (2H, d), 7.17-7.28 (3H, m), 7.47-7.62 (4H, m), 8.20-8.29 (2H, m), 8.49-8.52 (2H, m), 8.77-8.78 (1H, m).

EXAMPLE 46

Synthesis of 4-methyl-6-(3-nitrophenyl)-N-(3-phenylpropyl)-2-(pyridine-3-yl)-5-pyrimidinecarboxamide The title compound was obtained by using 100 mg (0.284 mmol) of 2-acetyl-3-(3-nitrophenyl)-N-(3-phenylpropyl)acrylamide, 67.1 mg (0.426 mmol) of 3-amidinopyridinium hydrochloride and 46.6 mg (0.568 mmol) of sodium acetate, in the same manner as that of Example 1.

Yield: 74.9 mg (0.165 mmol) (61%)

MS (ESI, m/z) 454 (M+H)+

¹H-NMR (CDCl3): 1.82 (2H, quint), 2.55 (2H, t), 2.74 (3H, s), 3.43 (2H, q), 7.07-7.10 (2H, m), 7.16-7.29 (4H, m), 7.62 (1H, t), 7.89 (1H, br t), 8.23-8.40 (3H, m), 8.59-8.63 (2H, m), 9.12 (1H, d).

EXAMPLE 47

Synthesis of 2,4-dimethyl-6-(3-nitrophenyl)-N-(3-phenylpropyl)-5-pyrimidinecarboxamide The title compound was obtained by using 100 mg (0.284 mmol) of 2-acetyl-3-(3-nitrophenyl)-N-(3-phenylpropyl)acrylamide, 40.3 mg (0.426 mmol) of acetamidine hydrochloride and 46.6 mg (0.568 mmol) of sodium acetate, in the same manner as that of Example 1.

Yield: 31.3 mg (0.0802 mmol) (28%)

MS (ESI, m/z) 391 (M+H)+

¹H-NMR (CDCl3): 1.71 (2H, quint), 2.47 (2H, t), 2.59 (3H, s), 2.77 (3H, s), 3.31 (2H, q), 5.64 (1H, br t), 7.02-7.05 (2H, m), 7.14-7.27 (3H, m), 7.59 (1H, t), 8.11-8.15 (1H, m), 8.25-8.29 (1H, m), 8.68-8.69 (1H, m).

EXAMPLE 48

Synthesis of 4-methyl-2-(methylthio)-6-(3-nitrophenyl)-N-(3-phenylpropyl)-5-pyrimidinecarboxamide The title compound was obtained by using 100 mg (0.284 mmol) of 2-acetyl-3-(3-nitrophenyl)-N-(3-phenylpropyl)acrylamide, 59.3 mg (0.213 mmol) of methylisothiourea-sulfate and 46.6 mg (0.568 mmol) of sodium acetate, in the same manner as that of Example 1.

Yield: 20.0 mg (0.0473 mmol) (17%)

MS (ESI, m/z) 423 (M+H)+

¹H-NMR (CDCl3): 1.71 (2H, quint), 2.47 (2H, t), 2.56 (3H, s), 2.61 (3H, s), 3.31 (2H, q), 5.59 (1H, br t), 7.04 (2H, d), 7.15-7.28 (3H, m), 7.59 (1H, t), 8.13-8.16 (1H, m), 8.26-8.30 (1H, m), 8.69-8.70 (1H, m).

EXAMPLE 49

Synthesis of 4-methyl-6-(3-methylphenyl)-2-phenyl-N-(3-phenylpropyl)-5-pyrimidinecarboxamide The title compound was obtained by using 175 mg (0.544 mmol) of 2-acetyl-3-(3-methylphenyl)-N-(3-phenylpropyl)acrylamide, 127 mg (0.816 mmol) of benzamidine hydrochloride and 88.6 mg (1.08 mmol) of sodium acetate, in the same manner as that of Example 1.

Yield: 11.0 mg (0.0261 mmol) (4.8%)

MS (ESI, m/z) 422 (1+H)+

¹H-NMR (CDCl3): 1.66 (2H, quint), 2.39 (3H, s), 2.40 (2H, t), 2.68 (3H, s), 3.29 (2H, q), 5.43 (1H, br t), 7.04 (2H, d), 7.05-7.28 (4H, m), 7.36 (1H, t), 7.48-7.52 (3H, m), 7.67-7.70 (2H, m), 8.52-8.55 (2H, m).

EXAMPLE 50

Synthesis of 4-methyl-6-(3-methylphenyl)-N-(3-phenylpropyl)-2-(pyridine-3-yl)-5-pyrimidinecarboxamide The title compound was obtained by using 175 mg (0.544 mmol) of 2-acetyl-3-(3-methylphenyl)-N-(3-phenylpropyl)acrylamide, 128 mg (0.816 mmol) of 3-amidinopyridinium hydrochloride and 88.6 mg (1.08 mmol) of sodium acetate, in the same manner as that of Example 1.

Yield: 33.2 mg (0.0786 mmol) (14%)

MS (ESI, m/z) 423 (M+H)+

¹H-NMR (CDCl3): 1.72 (2H, quint), 2.40 (3H, s), 2.44 (2H, t), 2.70 (3H, s), 3.34 (2H, q), 6.61 (1H, br t), 7.04-7.07 (2H, m), 7.15-7.39 (5H, m), 7.66-7.69 (2H, m), 8.54 (1H, dd), 8.69 (1H, dt), 9.43 (1H, d).

EXAMPLE 51

Synthesis of 2,4-dimethyl-6-(3-methylphenyl)-N-(3-phenylpropyl)-5-pyrimidinecarboxamide The title compound was obtained by using 175 mg (0.544 mmol) of 2-acetyl-3-(3-methylphenyl)-N-(3-phenylpropyl)acrylamide, 76.6 mg (0.816 mmol) of acetamidine hydrochloride and 88.6 mg (1.08 mmol) of sodium acetate, in the same manner as that of Example 1.
Yield: 14.8 mg (0.0412 mmol) (7.8%)
MS (ESI, m/z) 360 (M+H)$^+$
$^1$H-NMR (CDCl3): 1.62 (2H, quint), 2.36 (3H, s), 2.37 (2H, t), 2.58 (3H, s), 2.76 (3H, s), 3.25 (2H, q), 5.36 (1H, br t), 7.02 (2H, d), 7.14-7.34 (5H, m), 7.52-7.55 (2H, m).

EXAMPLE 52

Synthesis of 4-methyl-6-(3-methylphenyl)-2-(methylthio)-N-(3-phenylpropyl)-5-pyrimidinecarboxamide The title compound was obtained by using 175 mg (0.544 mmol) of 2-acetyl-3-(3-methylphenyl)-N-(3-phenylpropyl)acrylamide, 113 mg (0.406 mmol) of methylisothiourea-sulfate and 88.6 mg (1.08 mmol) of sodium acetate, in the same manner as that of Example 1.
Yield: 47.7 mg (0.122 mmol) (22%)
MS (ESI, m/z) 392 (M+H)$^+$
$^1$H-NMR (CDCl3): 1.62 (2H, quint), 2.35 (3H, s), 2.37 (2H, t), 2.54 (3H, s), 2.60 (3H, s), 3.24 (2H, q), 5.39 (1H, br t), 7.02 (2H, d), 7.03-7.34 (5H, m), 7.56-7.58 (2H, m).

EXAMPLE 53

Synthesis of 4-(3-fluorophenyl)-6-methyl-2-phenyl-N-(3-phenylpropyl)-5-pyrimidinecarboxamide The title compound was obtained by using 135 mg (0.415 mmol) of 2-acetyl-3-(3-fluorophenyl)-N-(3-phenylpropyl)acrylamide, 97.1 mg (0.623 mmol) of benzamidine hydrochloride and 67.3 mg (0.820 mmol) of sodium acetate, in the same manner as that of Example 1.
Yield: 113 mg (0.266 mmol) (66%)
MS (ESI, m/z) 426 (M+H)$^+$
$^1$H-NMR (CDCl3): 1.70 (2H, quint), 2.45 (2H, t), 2.64 (3H, s), 3.30 (2H, q), 5.65 (1H, br t), 7.03-7.07 (2H, m), 7.12-7.29 (4H, m), 7.36-7.52 (4H, m), 7.63-7.68 (2H, m), 8.49-8.53 (2H, m).

EXAMPLE 54

Synthesis of 4-(3-fluorophenyl)-6-methyl-N-(3-phenylpropyl)-2-(pyridine-3-yl)-5-pyrimidinecarboxamide The title compound was obtained by using 135 mg (0.415 mmol) of 2-acetyl-3-(3-fluorophenyl)-N-(3-phenylpropyl)acrylamide, 97.7 mg (0.623 mmol) of 3-amidinopyridinium hydrochloride and 67.3 mg (0.820 mmol) of sodium acetate, in the same manner as that of Example 1.
Yield: 97.0 mg (0.227 mmol) (56%)
MS (ESI, m/z) 427 (M+H)$^+$
$^1$H-NMR (CDCl3): 1.79 (2H, quint), 2.52 (2H, t), 2.70 (3H, s), 3.40 (2H, q), 7.08-7.46 (9H, m), 7.61-7.71 (2H, m), 8.46 (1H, dd), 8.62 (1H, dt), 9.25 (1H, d).

EXAMPLE 55

Synthesis of 4-(3-fluorophenyl)-2,6-dimethyl-N-(3-phenylpropyl)-5-pyrimidinecarboxamide The title compound was obtained by using 135 mg (0.415 mmol) of 2-acetyl-3-(3-fluorophenyl)-N-(3-phenylpropyl)acrylamide, 58.6 mg (0.623 mmol) of acetamidine hydrochloride and 67.3 mg (0.820 mmol) of sodium acetate, in the same manner as that of Example 1.
Yield: 50.0 mg (0.138 mmol) (34%)
MS (ESI, m/z) 364 (M+H)$^+$
$^1$H-NMR (CDCl3): 1.67 (2H, quint), 2.43 (2H, t), 2.58 (3H, s), 2.75 (3H, s), 3.28 (2H, q), 5.46 (1H, br t), 7.03-7.06 (2H, m), 7.09-7.28 (4H, m), 7.35-7.43 (1H, m), 7.49-7.57 (2H, m).

EXAMPLE 56

Synthesis of 4-(3-fluorophenyl)-6-methyl-2-(methylthio)-N-(3-phenylpropyl)-5-pyrimidinecarboxamide The title compound was obtained by using 135 mg (0.415 mmol) of 2-acetyl-3-(3-fluorophenyl)-N-(3-phenylpropyl)acrylamide, 86.3 mg (0.310 mmol) of methylisothiourea-sulfate and 67.3 mg (0.820 mmol) of sodium acetate, in the same manner as that of Example 1.
Yield: 62.0 mg (0.157 mmol) (39%)
MS (ESI, m/z) 396 (M+H)$^+$
$^1$H-NMR (CDCl3): 1.68 (2H, quint), 2.43 (2H, t), 2.52 (3H, s), 2.59 (3H, s), 3.27 (2H, q), 5.59 (1H, br t), 7.03-7.06 (2H, m), 7.10-7.28 (4H, m), 7.34-7.41 (1H, m), 7.51-7.58 (2H, m).

EXAMPLE 57

Synthesis of 4-(3-methoxyphenyl)-6-methyl-2-(methylthio)-N-(3-phenylpropyl)-5-pyrimidinecarboxamide The title compound was obtained by using 300 mg (0.889 mmol) of 2-acetyl-3-(3-methoxyphenyl)-N-(3-phenylpropyl) acrylamide, 186 mg (0.668 mmol) of methylisothiourea-sulfate and 146 mg (1.78 mmol) of sodium acetate, in the same manner as that of Example 1.
Yield: 194 mg (0.476 mmol) (54%)
MS (ESI, m/z) 408 (M+H)$^+$
$^1$H-NMR (CDCl3): 1.64 (2H, quint), 2.39 (2H, t), 2.53 (3H, s), 2.60 (3H, s), 3.25 (2H, q), 3.78 (3H, s), 5.47 (1H, br t), 6.94-7.05 (3H, m), 7.14-7.37 (6H, m).

EXAMPLE 58

Synthesis of 4-(3-methoxyphenyl)-6-methyl-2-phenyl-N-(3-phenylpropyl)-5-pyrimidinecarboxamide The title compound was obtained by using 200 mg (0.593 mmol) of 2-acetyl-3-(3-methoxyphenyl)-N-(3-phenylpropyl) acrylamide, 139 mg (0.885 mmol) of benzamidine hydrochloride and 96.8 mg (1.18 mmol) of sodium acetate, in the same manner as that of Example 1.
Yield: 56.0 mg (0.128 mmol) (22%)
MS (ESI, m/z) 438 M+H)$^+$ $^1$H-NMR (CDCl3): 1.67 (2H, quint), 2.41 (2H, t), 2.66 (3H, s), 3.29 (2H, q), 3.81 (3H, s), 5.65 (1H, br t), 6.97-7.52 (12H, m), 8.51-8.58 (2H, m).

EXAMPLE 59

Synthesis of 4-(3-methoxyphenyl)-6-methyl-N-(3-phenylpropyl)-2-(pyridine-3-yl)-5-pyrimidinecarboxamide The title compound was obtained by using 200 mg (0.593 mmol) of 2-acetyl-3-(3-methoxyphenyl)-N-(3-phenylpropyl) acrylamide, 140 mg (0.885 mmol) of 3-amidinopyridinium hydrochloride and 96.8 mg (1.18 mmol) of sodium acetate, in the same manner as that of Example 1.
Yield: 39.0 mg (0.0889 mmol) (15%)
MS (ESI, m/z) 439 (M+H)$^+$
$^1$H-NMR (CDCl3): 1.74 (2H, quint), 2.46 (2H, t), 2.70 (3H, s), 3.36 (2H, q), 3.82 (3H, s), 6.70 (1H, br t), 6.99-7.49 (10H, m), 8.55-8.70 (2H, m), 9.42 (1H, br s).

EXAMPLE 60

Synthesis of 4-(3-methoxyphenyl)-2,6-dimethyl-N-(3-phenylpropyl)-5-pyrimidinecarboxamide The title compound was obtained by using 300 mg (0.889 mmol) of 2-acetyl-3-(3-methoxyphenyl)-N-(3-phenylpropyl) acrylamide, 126 mg (1.34 mmol) of acetamidine hydrochloride and 146 mg (1.78 mmol) of sodium acetate, in the same manner as that of Example 1.
Yield: 72.0 mg (0.192 mmol) (21%)
MS (ESI, m/z) 376 (M+H)$^+$
$^1$H-NMR (CDCl3): 1.63 (2H, quint), 2.38 (2H, t), 2.57 (3H, s), 2.74 (3H, s), 3.25 (2H, q), 3.78 (3H, s), 5.47 (1H, br t), 6.93-9.97 (2H, m), 7.14-7.36 (7H, m).

EXAMPLE 61

Synthesis of 2-(t-butyl)-4-(3,5-dichlorophenyl)-6-methyl-N-(3-phenylpropyl)-5-pyrimidinecarboxamide 1) Synthesis of 3-oxo-N-(3-phenylpropyl) butylamide 3.00 g of (22.2 mmol) of 3-phenylpropylamine, 3.39 ml (40.3 mmol) of diketene and 3.37 g (33.3 mmol) of triethylamine were heated and stirred in 20 ml of toluene at 80° C. for 3 hours. After saturated aqueous sodium hydrogencarbonate solution was added, the reaction mixture was extracted with ethyl acetate. The organic layer was dried over anhydrous magnesium sulfate and then concentrated under reduced pressure to obtain the title compound. The residue was purified by the silica gel chromatography (hexane/ethyl acetate=3/1) to obtain the title compound.
Yield: 3.48 g (15.9 mmol) (71%)
MS (ESI, m/z) 218 (M−H)$^−$
$^1$H-NMR (CDCl3): 1.86 (2H, quint), 2.26 (3H, s), 2.66 (2H, t), 3.30 (2H, q), 3.39 (2H, s), 6.96 (1H, br), 7.17-7.21 (3H, m), 7.26-7.31 (2H, m).

2) Synthesis of 2-acetyl-3-(3,5-dichlorophenyl)-N-(3-phenylpropyl) acrylamide 2.22 g (10.1 mmol) of 3-oxo-N-(3-phenylpropyl)butylamide and 1.77 g (10.1 mmol) of 3,5-dichlorobenzaldehyde were dissolved in 30 ml of 2-propanol. 86.0 mg (1.01 mmol) of piperidine and 60.7 mg (1.01 mmol) of acetic acid were added and stirred at room temperature for one day. After the solvent was evaporated under reduced pressure, ethyl acetate was added thereto. The reaction mixture was washed with 1 N hydrochloric acid and then with saturated aqueous sodium hydrogencarbonate solution. The organic layer was dried over anhydrous magnesium sulfate and then concentrated under reduced pressure. The residue was purified by the silica gel chromatography (hexane/ethyl acetate=10/1) to obtain the title compound.
Yield: 2.58 g (6.87 mmol) (68%)
MS (ESI, m/z) 376 (M)$^+$
$^1$H-NMR (CDCl3): 1.86 (2H, quint), 2.41 (3H, s), 2.61 (2H, t), 3.39 (2H, q), 5.84 (1H, br t), 7.11-7.40 (9H, m).

3) Synthesis of 2-(t-butyl)-4-(3,5-dichlorophenyl)-6-methyl-N-(3-phenylpropyl)-5-pyrimidinecarboxamide 100 mg (0.266 mmol) of 2-acetyl-3-(3,5-dichlorophenyl)-N-(3-phenylpropyl) acrylamide was dissolved in 5 ml of DMF. 54.5 mg (0.399 mmol) of t-butyl-carbamidine-hydrochloride and 32.7 mg (0.399 mmol) of sodium acetate were added at room temperature and stirred at 80° C. for one day. After DMF was evaporated under reduced pressure, the reaction mixture was diluted with ethyl acetate and washed with saturated aqueous sodium chloride solution. The organic layer was dried over anhydrous magnesium sulfate and then concentrated under reduced pressure. The residue was purified by the silica gel chromatography (hexane/ethyl acetate=10/1 to 1/1) to obtain the title compound.
Yield: 62.2 mg (0.136 mmol) (51%)
MS (ESI, m/z) 456 (M+H)$^+$ 454 (M−H)$^−$
$^1$H-NMR (CDCl3): 1.42 (9H, s), 1.76 (2H, quint), 2.50 (2H, t), 2.58 (3H, s), 3.35 (2H, q), 5.50 (1H, br s), 7.08 (2H, d), 7.15-7.21 (1H, m), 7.24-7.29 (2H, m), 7.40-7.41 (1H, m), 7.73 (2H, d).

EXAMPLE 62

Synthesis of 2-cyclopropyl-4-(3,5-dichlorophenyl)-6-methyl-N-(3-phenylpropyl)-5-pyrimidinecarboxamide The title compound was obtained by using 100 mg (0.266 mmol) of 2-acetyl-3-(3,5-dichlorophenyl)-N-(3-phenylpropyl) acrylamide, 48.1 mg (0.399 mmol) of cyclopropyl-carbamidine-hydrochloride and 32.7 mg (0.399 mmol) of sodium acetate, in the same manner as that of Example 61.
Yield: 90.4 mg (0.205 mmol) (77%)
MS (ESI, m/z) 440 (M+H)$^+$ 438 (M−H)$^−$
$^1$H-NMR (CDCl3): 1.06-1.14 (2H, m), 1.17-1.22 (2H, m), 1.73 (2H, quint), 2.22-2.30 (1H, m), 2.48 (2H, t), 2.53 (3H, s), 3.31 (2H, q), 5.48 (1H, br t), 7.06-7.08 (2H, m), 7.15-7.20 (1H, m), 7.24-7.29 (2H, m), 7.39-7.40 (1H, m), 7.66-7.68 (2H, m).

EXAMPLE 63

Synthesis of 4-(3,5-dichlorophenyl)-6-methyl-2-(morpholine-4-yl)-N-(3-phenylpropyl)-5-pyrimidinecarboxamide The title compound was obtained by using 100 mg (0.266 mmol) of 2-acetyl-3-(3,5-dichlorophenyl)-N-(3-phenylpropyl) acrylamide, 83.8 mg (0.399 mmol) of morpholino-formamidine-hydrochloride and 32.7 mg (0.399 mmol) of sodium acetate, in the same manner as that of Example 61.

Yield: 59.2 mg (0.122 mmol) (46%)

MS (ESI, m/z) 485 (M+H)$^+$ 483 (M–H)$^-$ $^1$H-NMR (CDCl3): 1.70 (2H, quint), 2.44-2.49 (5H, m), 3.27 (2H, q), 3.76 (4H, br), 3.87 (4H, br), 5.44 (1H, br), 7.07 (2H, d), 7.15-7.29 (3H, m), 7.37 (1H, s), 7.63 (2H, s).

EXAMPLE 64

Synthesis of 4-(3,5-dichlorophenyl)-6-methyl-N-(3-phenylpropyl)-2-(pyridine-2-yl)-5-pyrimidinecarboxamide The title compound was obtained by using 100 mg (0.266 mmol) of 2-acetyl-3-(3,5-dichlorophenyl)-N-(3-phenylpropyl) acrylamide, 62.9 mg (0.399 mmol) of 2-amidinopyridinium hydrochloride and 32.7 mg (0.399 mmol) of sodium acetate, in the same manner as that of Example 61.

Yield: 46.5 mg (0.0974 mmol) (37%)

MS (ESI, m/z) 477 (M+H)$^+$ 475 (M–H)$^-$ $^1$H-NMR (CDCl3): 1.87 (2H, quint), 2.60 (2H, t), 2.70 (3H, s), 3.44 (2H, q), 6.59 (1H, br t), 7.12-7.21 (3H, m), 7.24-7.30 (2H, m), 7.3, 5-7.41 (2H, m), 7.71 (2H, d), 7.88 (1H, td), 8.52 (1H, dt), 8.62-8.65 (1H, m).

EXAMPLE 65

Synthesis of 4-(3,5-dichlorophenyl)-6-methyl-N-(3-phenylpropyl)-2-(pyridine-4-yl)-5-pyrimidinecarboxamide The title compound was obtained by using 100 mg (0.266 mmol) of 2-acetyl-3-(3,5-dichlorophenyl)-N-(3-phenylpropyl) acrylamide, 62.9 mg (0.399 mmol) of 4-amidinopyridinium hydrochloride and 32.7 mg (0.399 mmol) of sodium acetate, in the same manner as that of Example 61.

Yield: 71.8 mg (0.150 mmol) (72%)

MS (ESI, m/z) 477 (M+H)$^+$ 475 (M–H)$^-$ $^1$H-NMR (CDCl3): 1.81 (2H, quint), 2.54 (2H, t), 2.69 (3H, s), 3.40 (2H, q), 6.42 (1H, br t), 7.10-7.12 (2H, m), 7.16-7.21 (1H, m), 7.24-7.30 (2H, m), 7.47 (1H, t), 7.79 (2H, d), 8.24-8.26 (2H, m), 8.61-8.63 (2H, m).

EXAMPLE 66

Synthesis of 4-methyl-2-(methylthio)-6-(2-naphthyl)-N-(3-phenylpropyl)-2-(pyridine-4-yl)-5-pyrimidinecarboxamide The title compound was obtained by using 150 mg (0.420 mmol) of 2-acetyl-3-(2-naphthyl)-N-(3-phenylpropyl) acrylamide, 87.7 mg (0.315 mmol) of methylisothiourea-sulfate and 68.9 mg (0.840 mmol) of sodium acetate, in the same manner as that of Example 1.

Yield: 44.3 mg (0.10 mmol) (24%)

MS (ESI, m/z) 427 (M+H)$^+$ $^1$H-NMR (CDCl3): 1.52 (2H, quint), 2.22 (2H, t), 2.57 (3H, s), 2.64 (3H, s), 3.22 (2H, q), 5.45 (1H, br t), 6.78-6.81 (2H, m), 7.11-7.18 (3H, m), 7.47-7.57 (2H, m), 7.83-7.91 (4H, m), 8.32 (1H, s).

EXAMPLE 67

Synthesis of 4-methyl-6-(4-methylphenyl)-2-phenyl-N-(3-phenylpropyl)-5-pyrimidinecarboxamide The title compound was obtained by using 200 mg (0.622 mmol) of 2-acetyl-3-(4-methylphenyl)-N-(3-phenylpropyl) acrylamide, 146 mg (0.932 mmol) of benzamidine hydrochloride and 102 mg (1.24 mmol) of sodium acetate, in the same manner as that of Example 1.

Yield: 57.0 mg (0.135 mmol) (23%)

MS (ESI, m/z) 422 (M+H)$^+$ $^1$H-NMR (CDCl3): 1.68 (2H, quint), 2.36 (3H, s), 2.41 (2H, t), 2.68 (3H, s), 3.32 (2H, q), 5.45 (1H, br t), 7.03-7.06 (2H, m), 7.15-7.28 (5H, m), 7.47-7.51 (3H, m), 7.80-8.84 (2H, m), 8.51-8.55 (2H, m).

EXAMPLE 68

Synthesis of 4-methyl-6-(4-methylphenyl)-2-(methylthio)-N-(3-phenylpropyl)-5-pyrimidinecarboxamide The title compound was obtained by using 200 mg (0.622 mmol) of 2-acetyl-3-(4-methylphenyl)-N-(3-phenylpropyl) acrylamide, 129 mg (0.463 mmol) of methylisothiourea-sulfate and 102 mg (1.24 mmol) of sodium acetate, in the same manner as that of Example 1.

Yield: 55.0 mg (0.140 mmol) (22%)

MS (ESI, m/z) 392 (M+H)$^+$ $^1$H-NMR (CDCl3): 1.65 (2H, quint), 2.34 (3H, s), 2.38 (2H, t), 2.54 (3H, s), 2.60 (3H, s), 3.27 (2H, q), 5.39 (1H, br t), 7.01-7.04 (2H, m), 7.15-7.28 (5H, m), 7.68-7.72 (2H, m).

EXAMPLE 69

Synthesis of 4-(3,5-dichlorophenyl)-6-methyl-N-(3-phenylpropyl)-2-(1H-pyrazole-1-yl)-5-pyrimidinecarboxamide The title compound was obtained by using 80.0 mg (0.213 mmol) of 2-acetyl-3-(3,5-dichlorophenyl)-N-(3-phenylpropyl )acrylamide, 46.9 mg (0.320 mmol) of 1H-pyrazole-1-carboxamidine-hydrochloride and 26.2 mg (0.320 mmol) of sodium acetate, in the same manner as that of Example 61.

Yield: 35.2 mg (0.0755 mmol) (35%)

MS (ESI, m/z) 466 (M+H)$^+$ 464 (M–H)$^-$ $^1$H-NMR (CDCl3): 1.79 (2H, quint), 2.53 (2H, t), 2.67 (3H, s), 3.37 (2H, q), 5.80 (1H, br t), 6.51-6.53 (1H, m), 7.09-7.11 (2H, m), 7.16-7.21 (1H, m), 7.24-7.30 (3H, m), 7.45 (1H, t), 7.74 (2H, d), 7.81-7.82 (1H, m), 8.64-8.65 (1H, m).

EXAMPLE 70

Synthesis of 4-(3,5-dichlorophenyl)-6-methyl-2-methylamino-N-(3-phenylpropyl)-5-pyrimidinecarboxamide The title compound was obtained by using 80.0 mg (0.213 mmol) of 2-acetyl-3-(3,5-dichlorophenyl)-N-(3-phenylpropyl) acrylamide, 35.1 mg (0.320 mmol) of 1-methylguanidine-hydrochloride and 26.2 mg (0.320 mmol) of sodium acetate, in the same manner as that of Example 61.

Yield: 23.3 mg (0.0543 mmol) (26%)

MS (ESI, m/z) 429 (M+H)$^+$ 427 (M–H)$^-$

¹H-NMR (CDCl3): 1.70 (2H, quint), 2.42-2.49 (5H, m), 3.04 (3H, d), 3.27 (2H, q), 5.38 (1H, t), 7.07-7.10 (2H, m), 7.15-7.20 (1H, m), 7.24-7.29 (2H, m), 7.37-7.42 (1H, m), 7.64 (2H, d), 8.03 (1H, d).

EXAMPLE 71

Synthesis of 4-(3,5-dichlorophenyl)-2-dimethylamino-6-methyl-N-(3-phenylpropyl)-5-pyrimidinecarboxamide The title compound was obtained by using 80.0 mg (0.213 mmol) of 2-acetyl-3-(3,5-dichlorophenyl)-N-(3-phenylpropyl) acrylamide, 87.1 mg (0.320 mmol) of 1,1-dimethylguanidine-hydrochloride and 26.2 mg (0.320 mmol) of sodium acetate, in the same manner as that of Example 61.
Yield: 45.1 mg (0.102 mmol) (48%)
MS (ESI, m/z) 443 (M+H)⁺ 441 (M−H)⁻
¹H-NMR (CDCl3): 1.70 (2H, quint), 2.41 (5H, m), 3.23-3.30 (8H, m), 5.38 (1H, br t), 7.07-7.09 (2H, m), 7.15-7.29 (3H, m), 7.36 (1H, t), 7.64 (2H, d).

EXAMPLE 72

Synthesis of 4-(3,5-dichlorophenyl)-2-(3,5-dimethyl-1H-pyrazole-1-yl)-6-methyl-N-(3-phenylpropyl)-5-pyrimidinecarboxamide The title compound was obtained by using 55.5 mg (0.148 mmol) of 2-acetyl-3-(3,5-dichlorophenyl)-N-(3-phenylpropyl) acrylamide, 44.5 mg (0.221 mmol) of 3,5-dimethylpyrazole-1-carboxamidine-nitrate and 26.2 mg (0.320 mmol) of sodium acetate, in the same manner as that of Example 61.
Yield: 30.9 mg (0.0625 mmol) (43%)
MS (ESI, m/z) 496 (M+H)⁺ 494 (M−H)⁻
¹H-NMR (CDCl3): 1.84 (2H, quint), 2.23 (2H, s), 2.57 (2H, t), 2.65 (6H, s), 3.39 (2H, q), 6.06 (1H, s), 6.25 (1H, br), 7.10-7.20 (3H, m), 7.25-7.29 (2H, m), 7.43-7.44 (1H, m), 7.69-7.70 (2H, m).

EXAMPLE 73

Synthesis of 4-(3-chlorophenyl)-6-methyl-N-(3-phenylpropyl)-2-(piperidine-1-yl)-5-pyrimidinecarboxamide 44.0 mg (0.107 mmol) of 4-(3-chlorophenyl)-6-methyl-2-(methylthio)-N-(3-phenylpropyl)-5-pyrimidinecarboxamide was dissolved in 5 ml of dichloromethane. 36.9 mg (0.213 mmol) of mCPBA (m-chloroperbenzoic acid) was added thereto at 0° C. and stirred at the same temperature for 6 hours. 1 ml of saturated aqueous sodium bisulfite solution was added thereto at the same temperature and stirred for 30 minutes heating to room temperature. After the reaction mixture was diluted with dichloromethane, the organic layer was washed with saturated aqueous sodium chloride solution and dried over anhydrous magnesium sulfate and then concentrated under reduced pressure. The obtained residue was dissolved in 5 ml of toluene and 91.1 mg (1.07 mmol) of piperidine was added at room temperature and stirred at 80° C. for 6 hours. After concentration under reduced pressure, the obtained residue was diluted with ethyl acetate. The organic layer was washed with saturated aqueous sodium chloride solution and dried over anhydrous magnesium sulfate and then concentrated under reduced pressure. The residue was purified by the silica gel chromatography hexane/ethyl acetate=10/1 to 1/1) to obtain the title compound.

Yield: 38.2 mg (0.0851 mmol) (80%)
MS (ESI, m/z) 449 (M+H)⁺ 447 (M−H)⁻
¹H-NMR (CDCl3): 1.57-1.69 (8H, m), 2.38-2.44 (5H, m), 3.23 (2H, q), 3.86 (4H, t), 5.28 (1H, br t), 7.04-7.06 (2H, m), 7.14-7.20 (1H, m), 7.23-7.30 (2H, m), 7.32-7.38 (2H, m), 7.62 (1H, dt), 7.74-7.76 (1H, m).

EXAMPLE 74

Synthesis of 4-(3,5-dichlorophenyl)-6-methyl-N-(3-phenylpropyl)-2-(trifluoromethyl)-5-pyrimidinecarboxamide The title compound was obtained by using 80.0 mg (0.213 mmol) of 2-acetyl-3-(3,5-dichlorophenyl)-N-(3-phenylpropyl) acrylamide, 35.9 mg (0.320 mmol) of trifluoroacetamidine and 26.2 mg (0.320 mmol) of sodium acetate, in the same manner as that of Example 61.
Yield: 25.1 mg (0.0536 mmol) (25%)
MS (ESI, m/z) 466 (M−H)⁻
¹H-NMR (CDCl3): 1.78 (2H, quint), 2.51 (2H, t), 2.71 (3H, s), 3.38 (2H, q), 5.54 (1H, br t), 7.07-7.09 (2H, m), 7.16-7.21 (1H, m), 7.23-7.30 (2H, m), 7.48 (1H, t), 7.76 (2H, d).

EXAMPLE 75

Synthesis of 4-(4-isopropylphenyl)-2,6-dimethyl-N-(3-phenylpropyl)-5-pyrimidinecarboxamide The title compound was obtained by using 150 mg (0.429 mmol) of 2-acetyl-3-(4-isopropylphenyl)-N-(3-phenylpropyl) acrylamide, 61.0 mg (0.645 mmol) of acetamidine hydrochloride and 70.5 mg (0.859 mmol) of sodium acetate, in the same manner as that of Example 1.
Yield: 44.3 mg (0.114 mmol) (26%)
MS (ESI, m/z) 388 (M+H)⁺
¹H-NMR (CDCl3): 1.19 (6H, d), 1.61 (2H, quint), 2.37 (2H, t), 2.57 (3H, s), 2.74 (3H, s), 2.89 (1H, sept), 3.26 (2H, q), 5.38 (1H, br t), 7.02 (2H, d), 7.13-7.30 (5H, m), 7.69 (2H, d).

EXAMPLE 76

Synthesis of 4-(4-isopropylphenyl)-6-methyl-2-(methylthio)-N-(3-phenylpropyl)-5-pyrimidinecarboxamide The title compound was obtained by using 150 mg (0.429 mmol) of 2-acetyl-3-(4-isopropylphenyl)-N-(3-phenylpropyl) acrylamide, 90.0 mg (0.323 mmol) of methylisothioureasulfate and 70.5 mg (0.859 mmol) of sodium acetate, in the same manner as that of Example 1.
Yield: 124 mg (0.296 mmol) (70%)
MS (ESI, m/z) 420 M+H)⁺
¹H-NMR (CDCl3): 1.20 (6H, d), 1.62 (2H, quint), 2.38 (2H, t), 2.53 (3H, s), 2.60 (3H, s), 2.89 (1H, sept), 3.26 (2H, q), 5.40 (1H, br t), 7.01-7.04 (2H, m), 7.13-7.29 (5H, m), 7.71-7.75 (2H, m).

EXAMPLE 77

Synthesis of 4-(4-t-butylphenyl)-2,6-dimethyl-N-(3-phenylpropyl)-5-pyrimidinecarboxamide The title compound was obtained by using 150 mg (0.413 mmol) of 2-acetyl-3-(4-t-butylphenyl)-N-(3-phenylpropyl)

acrylamide, 58.1 mg (0.615 mmol) of acetamidine hydrochloride and 67.3 mg (0.820 mmol) of sodium acetate, in the same manner as that of Example 1.

Yield: 73.8 mg (0.184 mmol) (44%)

MS (ESI, m/z) 402 (M+H)$^+$ $^1$H-NMR (CDCl3): 1.25 (9H, s), 1.60 (2H, quint), 2.36 (2H, t), 2.57 (3H, s), 2.73 (3H, s), 3.26 (2H, q), 5.42 (1H, br t), 7.01-7.03 (2H, m), 7.13-7.25 (3H, m), 7.42-7.46 (2H, m), 7.66-7.71 (2H, m).

EXAMPLE 78

Synthesis of 4-(4-t-butylphenyl)-6-methyl-2-(methylthio)-N-(3-phenylpropyl)-5-pyrimidinecarboxamide The title compound was obtained by using 150 mg (0.413 mmol) of 2-acetyl-3-(4-t-butylphenyl)-N-(3-phenylpropyl) acrylamide, 85.6 mg (0.307 mmol) of methylisothioureasulfate and 67.3 mg (0.820 mmol) of sodium acetate, in the same manner as that of Example 1.

Yield: 107 mg (0.247 mmol) (61%)

MS (ESI, m/z) 434 (M+H)$^+$ $^1$H-NMR (CDCl3): 1.27 (9H, s), 1.61 (2H, quint), 2.38 (2H, t), 2.53 (3H, s), 2.60 (3H, s), 3.25 (2H, q), 5.45 (1H, br t), 7.01-7.04 (2H, m), 7.13-7.26 (3H, m), 7.41-7.45 (2H, m), 7.71-7.76 (2H, m).

EXAMPLE 79

Synthesis of 4-(3,5-dichlorophenyl)-2-isobutylamino-6-methyl-N-(3-phenylpropyl)-5-pyrimidinecarboxamide 83.8 mg (0.203 mmol) of 4-(3-chlorophenyl)-6-methyl-2-(methylthio)-N-(3-phenylpropyl)-5-pyrimidinecarboxamide was dissolved in 5 ml of dichloromethane. 70.2 mg (0.407 mmol) of mCPBA (m-chloroperbenzoic acid) was added thereto at 0° C. and stirred at the same temperature for 6 hours. 1 ml of saturated aqueous sodium bisulfite solution was added thereto at the same temperature and stirred for 30 minutes heating to room temperature. After the reaction mixture was diluted with dichloromethane, the organic layer was washed with saturated aqueous sodium chloride solution and dried over anhydrous magnesium sulfate and then concentrated under reduced pressure. The obtained residue was dissolved in 5 ml of toluene and excessive amounts of 74.2 mg (1.02 mmol) of isobutylamine was added at room temperature and stirred at 80° C. for 6 hours. After concentration under reduced pressure, the obtained residue was diluted with ethyl acetate. The organic layer was washed with saturated aqueous sodium chloride solution and dried over anhydrous magnesium sulfate and then concentrated under reduced pressure. The residue was purified by the silica gel chromatography (hexane/ethyl acetate=10/1 to 1/1) to obtain the title compound.

Yield: 57.5 mg (0.132 mmol) (65%)

MS (ESI, m/z) 437 (M+H)$^+$ 435 (M−H)$^-$ $^1$H-NMR (CDCl3): 0.97 (6H, d), 1.64 (2H, quint), 1.89 (1H, sept), 2.38-2.4 3 (5H, m), 3.23 (2H, q), 3.32 (2H, t), 5.31 (2H, br), 7.04-7.07 (2H, m), 7.14-7. 38 (5H, m), 7.60 (1H, br d), 7.73 (1H, br s).

EXAMPLE 80

Synthesis of 4-(3-chlorophenyl)-2-methoxy-6-methyl-N-(3-phenylpropyl)-5-pyrimidinecarboxamide 62.8 mg (0.153 mmol) of 4-(3-chlorophenyl)-6-methyl-2-(methylthio)-N-(3-phenylpropyl)-5-pyrimidinecarboxamide was dissolved in 5 ml of dichloromethane. 52.7 mg (0.305 mmol) of mCPBA (m-chloroperbenzoic acid) was added thereto at 0° C. and stirred at the same temperature for 6 hours. 1 ml of saturated aqueous sodium bisulfite solution was added thereto at the same temperature and stirred for 30 minutes heating to room temperature. After the reaction mixture was diluted with dichloromethane, the organic layer was washed with saturated aqueous sodium chloride solution and dried over anhydrous magnesium sulfate and then concentrated under reduced pressure. The obtained residue was dissolved in 5 ml of methanol and excessive amounts of 295 mg (1.53 mmol) of sodium methoxide (28% methanol solution) was added at room temperature and stirred at 60° C. for 6 hours. After concentration under reduced pressure, the obtained residue was diluted with ethyl acetate. The organic layer was washed with saturated aqueous sodium chloride solution and dried over anhydrous magnesium sulfate and then concentrated under reduced pressure. The residue was purified by the silica gel chromatography (hexane/ethyl acetate=10/1 to 1/1) to obtain the title compound.

Yield: 42.0 mg (0.106 mmol) (70%)

MS (ESI, m/z) 396 (M+H)$^+$ 394 (M−H)$^-$ $^1$H-NMR (CDCl3): 1.69 (2H, quint), 2.44 (2H, t), 2.54 (3H, s), 3.28 (2H, q), 4.05 (3H, s), 5.48 (1H, br t), 7.04-7.07 (2H, m), 7.14-7.20 (1H, m), 7.23-7.2 8 (2H, m), 7.34 (1H, t), 7.39-7.43 (1H, m), 7.68 (1H, dt), 7.81 (1H, t).

EXAMPLE 81

Synthesis of 2,4-dimethyl-6-(2-naphthyl)-N-(3-phenylpropyl)-5-pyrimidinecarboxamide The title compound was obtained by using 150 mg (0.420 mmol) of 2-acetyl-3-(2-naphthyl)-N-(3-phenylpropyl) acrylamide, 59.6 mg (0.630 mmol) of acetamidine hydrochloride and 68.9 mg (0.840 mmol) of sodium acetate, in the same manner as that of Example 1.

Yield: 29.8 mg (0.0753 mmol) (18%)

MS (ESI, m/z) 396 M+H)$^+$ $^1$H-NMR (CDCl3): 1.51 (2H, quint), 2.21 (2H, t), 2.62 (3H, s), 2.79 (3H, s), 3.23 (2H, q), 5.43 (1H, br t), 6.77-6.80 (2H, m), 7.10-7.18 (3H, m), 7.47-7.5 7 (2H, m), 7.83-7.92 (4H, m), 8.30 (1H, s).

EXAMPLE 82

Synthesis of 2,4-dimethyl-6-(1-naphthyl)-N-(3-phenylpropyl)-5-pyrimidinecarboxamide The title compound was obtained by using 150 mg (0.420 mmol) of 2-acetyl-3-(1-naphthyl)-N-(3-phenylpropyl) acrylamide, 59.6 mg (0.630 mmol) of acetamidine hydrochloride and 68.9 mg (0.840 mmol) of sodium acetate, in the same manner as that of Example 1.

Yield: 24.7 mg (0.0625 mmol) (15%)

MS (ESI, m/z) 396 (M+H)$^+$ $^1$H-NMR (CDCl3): 1.01 (2H, quint), 1.93 (2H, t), 2.66 (3H, s), 2.80 (3H, s), 2.93 (2H, q), 5.16 (1H, br t), 6.76-6.79 (2H, m), 7.11-7.23 (3H, m), 7.46-7.5 3 (4H, m), 7.66-7.70 (1H, m), 7.82-7.87 (2H, m).

EXAMPLE 83

Synthesis of 4-methyl-2-(methylthio)-6-(1-naphthyl)-N-(3-phenylpropyl)-5-pyrimidinecarboxamide The title compound was obtained by using 150 mg (0.420 mmol) of 2-acetyl-3-(1-naphthyl)-N-(3-phenylpropyl) acrylamide, 87.7 mg (0.315 mmol) of methylisothiourea-sulfate and 68.9 mg (0.840 mmol) of sodium acetate, in the same manner as that of Example 1.

Yield: 37.5 mg (0.0877 mmol) (21%)
MS (ESI, m/z) 428 (M+H)$^+$
$^1$H-NMR (CDCl3): 1.01 (2H, quint), 1.94 (2H, t), 2.56 (3H, s), 2.62 (3H, s), 2.91 (2H, q), 5.11 (1H, br t), 6.77-6.80 (2H, m), 7.11-7.23 (3H, m), 7.46-7.5 4 (4H, m), 7.76-7.90 (3H, m).

EXAMPLE 84

Synthesis of 2,6-dimethyl-4-(3,4-dimethylphenyl)-N-(3-phenylpropyl)-5-pyrimidinecarboxamide The title compound was obtained by using 150 mg (0.447 mmol) of 2-acetyl-3-(3,4-dimethylphenyl)-N-(3-phenylpropyl) acrylamide, 63.8 mg (0.675 mmol) of acetamidine hydrochloride and 73.8 mg (0.900 mmol) of sodium acetate, in the same manner as that of Example 1.

Yield: 41.7 mg (0.112 mmol) (24%)
MS (ESI, m/z) 374 (M+H)$^+$
$^1$H-NMR (CDCl3): 1.56-1.66 (2H, m), 2.21 (3H, s), 2.24 (3H, s), 2.34 (2H, t), 2.57 (3H, s), 2.74 (3H, s), 3.27 (2H, q), 5.42 (1H, br t), 7.00-7.02 (2H, m), 7.14-7.28 (4H, m), 7.46-7.53 (2H, m).

EXAMPLE 85

Synthesis of 4-(3,4-dimethylphenyl)-6-methyl-2-(methylthio)-N-(3-phenylpropyl)-5-pyrimidinecarboxamide The title compound was obtained by using 150 mg (0.447 mmol) of 2-acetyl-3-(3,4-dimethylphenyl)-N-(3-phenylpropyl) acrylamide, 94.0 mg (0.338 mmol) of methylisothiourea-sulfate and 73.8 mg (0.900 mmol) of sodium acetate, in the same manner as that of Example 1.

Yield: 89.7 mg (0.221 mmol) (49%)
MS (ESI, m/z) 406 (M+H)$^+$
$^1$H-NMR (CDCl3): 1.62 (2H, quint), 2.22 (3H, s), 2.23 (3H, s), 2.35 (2H, t), 2.52 (3H, s), 2.59 (3H, s), 3.26 (2H, q), 5.49 (1H, br t), 7.00-7.03 (2H, m), 7.15-7.28 (4H, m), 7.50-7.54 (2H, m).

EXAMPLE 86

Synthesis of 4-(3-chlorophenyl)-6-methyl-N-(3-phenylpropyl)-2-(piperazine-1-yl)-5-pyrimidinecarboxamide 83.8 mg (0.203 mmol) of 4-(3-chlorophenyl)-6-methyl-2-(methylthio)-N-(3-phenylpropyl)-5-pyrimidinecarboxamide was dissolved in 5 ml of dichloromethane. 70.2 mg (0.407 mmol) of mCPBA (m-chloroperbenzoic acid) was added thereto at 0° C. and stirred at the same temperature for 6 hours. 1 ml of saturated aqueous sodium bisulfite solution was added thereto at the same temperature and stirred for 30 minutes heating to room temperature. After the reaction mixture was diluted with dichloromethane, the organic layer was washed with saturated aqueous sodium chloride solution and dried over anhydrous magnesium sulfate and then concentrated under reduced pressure. The obtained residue was dissolved in 5 ml of toluene and excessive amounts of 74.2 mg (1.02 mmol) of isobutylamine was added at room temperature and stirred at 80° C. for 6 hours. After concentration under reduced pressure, the obtained residue was diluted with ethyl acetate. The organic layer was washed with saturated aqueous sodium chloride solution and dried over anhydrous magnesium sulfate and then concentrated under reduced pressure. The residue was purified by the basic silica gel chromatography (hexane/ethyl acetate=10/1 to 1/1) to obtain the title compound.

Yield: 82.7 mg (0.184 mmol) (91%)
MS (ESI, m/z) 450 (M+H)$^+$
$^1$H-NMR (CDCl3): 1.64 (2H, quint), 2.38-2.44 (5H, m), 2.91 (4H, t), 3.23 (2H, q), 3.87 (4H, t), 5.33 (1H, br t), 7.04-7.06 (2H, m), 7.14-7.38 (5H, m), 7. 60-7.63 (1H, m), 7.74-7.76 (1H, m).

EXAMPLE 87

Synthesis of 4-(3-chlorophenyl)-6-methyl-N-(3-phenylpropyl)-2-(thiophene-2-yl)-5-pyrimidinecarboxamide The title compound was obtained by using 100 mg (0.266 mmol) of 2-acetyl-3-(3,5-dichlorophenyl)-N-(3-phenylpropyl) acrylamide, 64.9 mg (0.399 mmol) of 2-amidinothiophene hydrochloride and 32.7 mg (0.399 mmol) of sodium acetate, in the same manner as that of Example 61.

Yield: 108 mg (0.224 mmol) (84%)
MS (ESI, m/z) 482 (M+H)$^+$ 480 (M–H)$^-$
$^1$H-NMR (CDCl3): 1.79 (2H, quint), 2.50 (2H, t), 2.62 (3H, s), 3.34 (2H, q), 5.55 (1H, br t), 7.07-7.10 (2H, m), 7.15-7.21 (2H, m), 7.24-7.30 (2H, m), 7. 43 (1H, t), 7.51-7.53 (1H, m), 7.76 (2H, d), 8.07-8.09 (1H, m).

EXAMPLE 88

Synthesis of 4-(3-chlorophenyl)-6-methyl-N-(3-phenylpropyl)-2-[(piperidine-1-yl) ethoxy]-5-pyrimidinecarboxamide 185 mg (0.254 mmol) of 4-(3-chlorophenyl)-6-methyl-2-(methylthio)-N-(3-phenylpropyl)-5-pyrimidinecarboxamide was dissolved in 5 ml of dichloromethane. 87.7 mg (0.508 mmol) of mCPBA (m-chloroperbenzoic acid) was added thereto at 0° C. and stirred at the same temperature for 6 hours. 1 ml of saturated aqueous sodium bisulfite solution was added thereto at the same temperature and stirred for 30 minutes heating to room temperature. After the reaction mixture was diluted with dichloromethane, the organic layer was washed with saturated aqueous sodium chloride solution and dried over anhydrous magnesium sulfate and then concentrated under reduced pressure. The obtained residue was dissolved in 5 ml of DMF. Alkoxide prepared from 146 mg (1.13 mmol) of 1-piperidine ethanol and 45.2 mg (1.13 mmol) of sodium hydride (60% oily substance) was added at 0° C. and stirred heating to room temperature for 1 hour. After concentration under reduced pressure, the obtained residue was diluted with ethyl acetate. The organic layer was washed with saturated aqueous sodium chloride solution and dried over anhydrous magnesium sulfate and then concentrated under reduced pressure. The residue was purified by the basic silica gel chromatography (hexane/ethyl acetate=5/1 to 1/1) to obtain the title compound.

Yield: 78.1 mg (0.158 mmol) (62%)

MS (ESI, m/z) 493 (M+H)$^+$ $^1$H-NMR (CDCl3): 1.40-1.48 (2H, m), 1.54-1.62 (4H, m), 1.69 (2H, quint), 2.41-2.54 (7H, m), 2.80 (2H, t), 3.28 (2H, q), 3.58 (2H, t), 4.56 (2H, t), 5.45 (1H, br t), 7.04-7.06 (2H, m), 7.12-7.42 (5H, m), 7.66-7.69 (1H, m), 7.80-7.82 (1H, m).

EXAMPLE 89

Synthesis of 4-(3,4-dichlorophenyl)-2-methoxy-6-methyl-N-(3-phenylpropyl)-5-pyrimidinecarboxamide 131 mg (0.293 mmol) of 4-(3,4-dichlorophenyl)-6-methyl-2-(methylthio)-N-(3-phenylpropyl)-5-pyrimidinecarboxamide was dissolved in 5 ml of dichloromethane. 101 mg (0.586 mmol) of mCPBA (m-chloroperbenzoic acid) was added thereto at 0° C. and stirred at the same temperature for 6 hours. 1 ml of saturated aqueous sodium bisulfite solution was added thereto at the same temperature and stirred for 30 minutes heating to room temperature. After the reaction mixture was diluted with dichloromethane, the organic layer was washed with saturated aqueous sodium chloride solution and dried over anhydrous magnesium sulfate and then concentrated under reduced pressure. The obtained residue was dissolved in 5 ml of methanol and excessive amounts of 565 mg (2.93 mmol) of sodium methoxide (28% methanol solution) was added at room temperature and stirred at 60° C. for 6 hours. After concentration under reduced pressure, the obtained residue was diluted with ethyl acetate. The organic layer was washed with saturated aqueous sodium chloride solution and dried over anhydrous magnesium sulfate and then concentrated under reduced pressure. The residue was purified by the silica gel chromatography (hexane/ethyl acetate=10/1 to 1/1) to obtain the title compound.

Yield: 20.8 mg (0.0483 mmol) (17%)

MS (ESI, m/z) 430 (M+H)$^+$ 428 (M−H)$^-$ $^1$H-NMR (CDCl3): 1.74 (2H, quint), 2.47-2.54 (5H, m), 3.31 (2H, q), 4.05 (3H, s), 5.55 (1H, br), 7.05-7.08 (2H, m), 7.15-7.29 (3H, m), 7.48 (1H, d), 7.64-7.68 (1H, m), 7.94-7.95 (1H, m).

EXAMPLE 90

Synthesis of 4-(3-chloro-4-methoxyphenyl)-2-cyclopropyl-6-methyl-N-(3-phenylpropyl)-5-pyrimidinecarboxamide The title compound was obtained by using 150 mg (0.419 mmol) of 2-acetyl-3-(3-chloro-4-methoxyphenyl)-N-(3-phenylpropyl)acrylamide, 76.0 mg (0.629 mmol) of cyclopropylcarbamidine hydrochloride and 68.9 mg (0.840 mmol) of sodium acetate, in the same manner as that of Example 1.

Yield: 54.7 mg (0.125 mmol) (31%)

MS (ESI, m/z) 436 (M+H)$^+$ $^1$H-NMR (CDCl3): 1.04-1.11 (2H, m), 1.17-1.22 (2H, m), 1.72 (2H, quint), 2.23-2.32 (1H, m), 2.45 (2H, t), 2.54 (3H, s), 3.32 (2H, q), 3.85 (3H, s), 5.47 (1H, br s), 6.90 (1H, d), 7.04-7.07 (1H, m), 7.15-7.20 (1H, m), 7.23-7.26 (3H, m), 7.70 (1H, dd), 7.88 (1H, d).

EXAMPLE 91

Synthesis of 4-(3-chloro-4-methoxyphenyl)-6-methyl-2-(methylthio)-N-(3-phenylpropyl)-5-pyrimidinecarboxamide The title compound was obtained by using 150 mg (0.419 mmol) of 2-acetyl-3-(3-chloro-4-methoxyphenyl)-N-(3-phenylpropyl) acrylamide, 87.7 mg (0.313 mmol) of methylisothiourea-sulfate and 68.9 mg (0.840 mmol) of sodium acetate, in the same manner as that of Example 1.

Yield: 80.6 mg (0.182 mmol) (43%)

MS (ESI, m/z) 442 (M+H)$^+$ $^1$H-NMR (CDCl3): 1.72 (2H, quint), 2.46 (2H, t), 2.51 (3H, s), 2.59 (3H, s), 3.31 (2H, q), 3.85 (3H, s), 5.60 (1H, br t), 6.90 (1H, d), 7.04-7.07 (2H, m), 7.14-7.28 (3H, m), 7.72 (1H, dd), 7.90 (1H, d).

EXAMPLE 92

Synthesis of 2-cyclopropyl-4-(2,4-dimethylphenyl)-6-methyl-N-(3-phenylpropyl)-5-pyrimidinecarboxamide The title compound was obtained by using 150 mg (0.467 mmol) of 2-acetyl-3-(2,4-dimethylphenyl)-N-(3-phenylpropyl) acrylamide, 84.4 mg (0.700 mmol) of cyclopropyl-carbamidine hydrochloride and 77.1 mg (0.940 mmol) of sodium acetate, in the same manner as that of Example 1.

Yield: 92.9 mg (0.233 mmol) (49%)

MS (ESI, m/z) 400 (M+H)$^+$ $^1$H-NMR (CDCl3): 1.01-1.07 (2H, m), 1.13-1.18 (2H, m), 1.37-1.47 (2H, m), 2.22-2.30 (9H, m), 2.55 (3H, s), 3.15 (2H, q), 5.22 (1H, br t), 6.97-7.05 (3H, m), 7.13-7.28 (5H, m).

EXAMPLE 93

Synthesis of 4-(2,4-dimethylphenyl)-6-methyl-2-(methylthio)-N-(3-phenylpropyl)-5-pyrimidinecarboxamide The title compound was obtained by using 150 mg (0.467 mmol) of 2-acetyl-3-(2,4-dimethylphenyl)-N-(3-phenylpropyl) acrylamide, 97.4 mg (0.350 mmol) of methylisothiourea-sulfate and 77.1 mg (0.940 mmol) of sodium acetate, in the same manner as that of Example 1.

Yield: 92.9 mg (0.229 mmol) (49%)

MS (ESI, m/z) 406 (M+H)$^+$ $^1$H-NMR (CDCl3): 1.43 (2H, quint), 2.23-2.30 (8H, m), 2.55 (3H, s), 2.57 (3H, s), 3.15 (2H, q), 5.15 (1H, br s), 7.01-7.06 (4H, m), 7.15-7.20 (2H, m), 7.24-7.28 (2H, m).

EXAMPLE 94

Synthesis of 4-(2-chlorophenyl)-6-methyl-2-(methylthio)-N-(3-phenylpropyl)-5-pyrimidinecarboxamide The title compound was obtained by using 100 mg (0.293 mmol) of 2-acetyl-3-(2-chlorophenyl)-N-(3-phenylpropyl) acrylamide, 60.5 mg (0.217 mmol) of methylisothiourea-sulfate and 47.6 mg (0.580 mmol) of sodium acetate, in the same manner as that of Example 1.

Yield: 45.6 mg (0.111 mmol) (38%)

MS (ESI, m/z) 412 (M+H)$^+$

¹H-NMR (CDCl3): 1.45 (2H, quint), 2.33 (2H, t), 2.56 (3H, s), 2.57 (3H, s), 3.15 (2H, q), 5.59 (1H, br t), 7.02-7.06 (2H, m), 7.15-7.37 (6H, m), 7.40-7.4 5 (1H, m).

EXAMPLE 95

Synthesis of 4-(3,5-dichloro-4-methoxyphenyl)-6-methyl-2-(methylthio)-N-(3-phenylpropyl)-5-pyrimidinecarboxamide The title compound was obtained by using 100 mg (0.246 mmol) of 2-acetyl-3-(3,5-dichloro-4-methoxyphenyl)-N-(3-phenylpropyl) acrylamide, 52.2 mg (0.188 mmol) of methylisothiourea-sulfate and 41.0 mg (0.500 mmol) of sodium acetate, in the same manner as that of Example 1.

Yield: 57.8 mg (0.121 mmol) (48%)

MS (ESI, m/z) 476 (M+H)+

¹H-NMR (CDCl3): 1.75 (2H, quint), 2.48-2.53 (5H, m), 2.60 (3H, s), 3.34 (2H, q), 3.84 (3H, s), 5.52 (1H, br t), 7.07-7.10 (2H, m), 7.14-7.28 (3H, m), 7. 77 (2H, s).

EXAMPLE 96

Synthesis of 4-(3,5-dichlorophenyl)-6-methyl-2-phenoxy-N-(3-phenylpropyl)-5-pyrimidinecarboxamide 1) Synthesis of 4-(3,5-dichlorophenyl)-6-methyl-2-(methylsulfonyl)-N-(3-phenyl propyl)-5-pyrimidinecarboxamide 1.41 g (3.15 mmol) of 4-(3,5-dichlorophenyl)-6-methyl-2-(methylthio)-N-(3-phenylpropyl)-5-pyrimidinecarboxamide was dissolved in 20 ml of dichloromethane. 1.09 g (6.30 mmol) of mCPBA (m-chloroperbenzoic acid) was added thereto at 0° C. and stirred at the same temperature for 12 hours. 1 ml of saturated aqueous sodium bisulfite solution was added thereto at the same temperature and stirred for 30 minutes heating to room temperature. After the reaction mixture was diluted with dichloromethane, the organic layer was washed with saturated aqueous sodium chloride solution and dried over anhydrous magnesium sulfate and then concentrated under reduced pressure. The residue was purified by the silica gel chromatography (hexane/ethyl acetate=5/1 to 1/1) to obtain the title compound.

Yield: 911 mg (1.90 mmol) (61%)

MS (ESI, m/z) 476 (M−H)−

¹H-NMR (CDCl3): 1.80 (2H, quint), 2.51 (2H, t), 2.72 (3H, s), 3.26 (3H, s), 3.37 (2H, q), 6.52 (1H, t), 7.09-7.12 (2H, m), 7.16-7.21 (1H, m), 7.25-7.30 (2H, m), 7.46 (1H, t), 7.78 (1H, d).

2) Synthesis of 4-(3,5-dichlorophenyl)-6-methyl-2-phenoxy-N-(3-phenylpropyl)-5-pyrimidinecarboxamide 39.3 mg (0.0798 mmol) of phenol was dissolved in DMF. 16.7 mg (0.418 mmol) of sodium hydride (60% oily substance) was added at 0° C. and stirred at the same temperature for 30 minutes. 100 mg (0.209 mmol) of 4-(3,5-dichlorophenyl)-6-methyl-2-methylsulfonyl-N-(3-phenylpropyl)-5-pyrimidinecarboxamide was added at the same temperature and stirred heating to room temperature for 12 hours. After concentration under reduced pressure, the obtained residue was diluted with ethyl acetate. The organic layer was washed with saturated aqueous sodium chloride solution and dried over anhydrous magnesium sulfate and then concentrated under reduced pressure. The residue was purified by the silica gel chromatography (hexane/ethyl acetate=10/1 to 1/1) to obtain the title compound.

Yield: 34.1 mg (1.90 mmol) (33%)

MS (ESI, m/z) 492 (M+H)+ 490 (M−H)−

¹H-NMR (CDCl3): 1.76 (2H, quint), 2.47-2.54 (5H, m), 3.34 (2H, q), 5.52 (1H, br t), 7.06-7.10 (2H, m), 7.17-7.29 (6H, m), 7.39-7.45 (3H, m), 7.65 (2H, d).

EXAMPLE 97

Synthesis of 4-methyl-6-(2-methylphenyl)-2-(methylthio)-N-(3-phenylpropyl)-5-pyrimidinecarboxamide The title compound was obtained by using 150 mg (0.467 mmol) of 2-acetyl-3-(2-methylphenyl)-N-(3-phenylpropyl) acrylamide, 98.1 mg (0.705 mmol) of methylisothiourea-sulfate and 77.1 mg (0.940 mmol) of sodium acetate, in the same manner as that of Example 1.

Yield: 99.8 mg (0.255 mmol) (55%)

MS (ESI, m/z) 392 (M+H)+

¹H-NMR (CDCl3): 1.42 (2H, quint), 2.27-2.32 (5H, m), 2.56 (3H, s), 2.57 (3H, s), 3.12 (2H, q), 5.20 (1H, br t), 7.01-7.04 (1H, m), 7.17-7.31 (8H, m).

EXAMPLE 98

Synthesis of 4-(4-methoxy-3-methylphenyl)-6-methyl-2-(methylthio)-N-(3-phenylpropyl)-5-pyrimidinecarboxamide The title compound was obtained by using 150 mg (0.427 mmol) of 2-acetyl-3-(4-methoxy-3-methylphenyl)-N-(3-phenylpropyl) acrylamide, 90.0 mg (0.323 mmol) of methylisothiourea-sulfate and 70.5 mg (0.859 mmol) of sodium acetate, in the same manner as that of Example 1.

Yield: 91.2 mg (0.216 mmol) (51%)

MS (ESI, m/z) 422 (M+H)+

¹H-NMR (CDCl3): 1.67 (2H, quint), 2.22 (3H, s), 2.40 (2H, t), 2.52 (3H, s), 2.61 (3H, s), 3.29 (2H, q), 3.79 (3H, s), 5.43 (1H, br t), 6.82 (1H, d), 7.01-7.04 (2H, m), 7.14-7.28 (3H, m), 7.62-7.68 (2H, m).

EXAMPLE 99

Synthesis of 4-(3,5-dichlorophenyl)-2-isopropyl-6-methyl-N-(3-phenylpropyl)-5-pyrimidinecarboxamide The title compound was obtained by using 100 mg (0.266 mmol) of 2-acetyl-3-(3,5-dichlorophenyl)-N-(3-phenylpropyl) acrylamide, 48.9 mg (0.399 mmol) of isopropyl-carbamidine hydrochloride and 43.6 mg (0.532 mmol) of sodium acetate, in the same manner as that of Example 61.

Yield: 28.0 mg (0.0663 mmol) (24%)

MS (ESI, m/z) 442 (M+H)+ 440 M−H)−

¹H-NMR (CDCl3): 1.36 (6H, d), 1.75 (2H, quint), 2.49 (2H, t), 2.58 (3H, s), 3.22 (1H, quint), 3.34 (2H, q), 5.49 (1H, br t), 7.07-7.09 (2H, m), 7.15-7.20 (1H, m), 7.24-7.29 (3H, m), 7.40-7.41 (1H, m), 7.70-7.71 (2H, m).

EXAMPLE 100

Synthesis of 4-(3,5-dichlorophenyl)-6-methyl-2-(2-methyl-1,3-thiazole-4-yl)-N-(3-phenylpropyl)-5-pyrimidinecarboxamide The title compound was obtained by using 100 mg (0.266 mmol) of 2-acetyl-3-(3,5-dichlorophenyl)-N-(3-phenylpropyl) acrylamide, 70.9 mg (0.399 mmol) of 2-methylthiazole-4-carbamidine hydrochloride and 43.6 mg (0.532 mmol) of sodium acetate, in the same manner as that of Example 61.

Yield: 65.0 mg (0.131 mmol) (49%)

MS (ESI, m/z) 497 (M+H)$^+$ 495 (M–H)$^-$ $^1$H-NMR (CDCl3): 1.83 (2H, quint), 2.56 (2H, t), 2.66 (3H, s), 2.71 (3H, s), 3.39 (2H, q), 6.23 (1H, br t), 7.10-7.20 (3H, m), 7.23-7.29 (2H, m), 7.42 (1H, t), 7.72 (2H, d), 8.25 (1H, s).

EXAMPLE 101

Synthesis of 4-(3,5-dichlorophenyl)-6-methyl-2-phenoxymethyl-N-(3-phenylpropyl)-5-pyrimidinecarboxamide The title compound was obtained by using 100 mg (0.266 mmol) of 2-acetyl-3-(3,5-dichlorophenyl)-N-(3-phenylpropyl) acrylamide, 88.8 mg (0.399 mmol) of 2-phenoxyacetamidine hydrochloride and 43.6 mg (0.532 mmol) of sodium acetate, in the same manner as that of Example 61.

Yield: 100 mg (0.198 mmol) (75%)

MS (ESI, m/z) 506 (M+H)$^+$ 504 (M–H)$^-$ $^1$H-NMR (CDCl3): 1.76 (2H, quint), 2.49 (2H, t), 2.63 (3H, s), 3.35 (2H, q), 5.32 (2H, s), 5.51 (1H, br t), 6.95-7.09 (5H, m), 7.15-7.20 (1H, m), 7.24-7.3 3 (5H, m), 7.42 (1H, t), 7.67 (2H, d).

EXAMPLE 102

Synthesis of 4-(3,5-dichlorophenyl)-2-ethoxy-6-methyl-N-(3-phenylpropyl)-5-pyrimidinecarboxamide 100 mg (0.209 mmol) of 4-(3,5-dichlorophenyl)-6-methyl-2-(methylsulfonyl)-N-(3-phenylpropyl)-5-pyrimidinecarboxamide was dissolved in 5 ml of DMF. 28.4 mg (0.418 mmol) of sodium ethoxide was added at 0° C. and stirred heating to room temperature for 12 hours. After concentration under reduced pressure, the obtained residue was diluted with ethyl acetate. The organic layer was washed with saturated aqueous sodium chloride solution and dried over anhydrous magnesium sulfate and then concentrated under reduced pressure. The residue was purified by the silica gel chromatography (hexane/ethyl acetate=10/1 to 1/1) to obtain the title compound.

Yield: 22.2 mg (0.0500 mmol) (24%)

MS (ESI, m/z) 444 (M+H)$^+$ 442 (M–H)$^-$ $^1$H-NMR (CDCl3): 1.45 (3H, t), 1.74 (2H, quint), 2.49 (2H, t), 2.54 (3H, s), 3.32 (2H, q), 4.48 (2H, q), 5.52 (1H, br t), 7.07-7.09 (2H, m), 7.15-7.20 (1H, m), 7.23-7.29 (2H, m), 7.40-7.42 (1H, m), 7.69 (2H, d).

EXAMPLE 103

Synthesis of 2-ethyl-4-(3,5-dichlorophenyl)-6-methyl-N-(3-phenylpropyl)-5-pyrimidinecarboxamide

1) Synthesis of 4-(3,5-dichlorophenyl)-6-methyl-2-(methylsulfonyl)-N-(3-phenylpropyl)-5-pyrimidinecarboxamide 1.41 g (3.15 mmol) of 4-(3,5-dichlorophenyl)-6-methyl-2-(methylthio)-N-(3-phenylpropyl)-5-pyrimidinecarboxamide was dissolved in 20 ml of dichloromethane. 1.09 g (6.30 mmol) of mCPBA (m-chloroperbenzoic acid) was added thereto at 0° C. and stirred at the same temperature for 12 hours. 1 ml of saturated aqueous sodium bisulfite solution was added thereto at the same temperature and stirred for 30 minutes heating to room temperature. After the reaction mixture was diluted with dichloromethane, the organic layer was washed with saturated aqueous sodium chloride solution and dried over anhydrous magnesium sulfate and then concentrated under reduced pressure. The residue was purified by the silica gel chromatography (hexane/ethyl acetate=5/1 to 1/1) to obtain the title compound.

Yield: 911 mg (1.90 mmol) (61%)

MS (ESI, m/z) 476 (M–H)$^-$ $^1$H-NMR (CDCl3): 1.80 (2H, quint), 2.51 (2H, t), 2.72 (3H, s), 3.26 (3H, s), 3.37 (2H, q), 6.52 (1H, t), 7.09-7.12 (2H, m), 7.16-7.21 (1H, m), 7.25-7.30 (2H, m), 7.46 (1H, t), 7.78 (1H, d).

2) Synthesis of Synthesis of 2-ethyl-4-(3,5-dichlorophenyl)-6-methyl-N-(3-phenylpropyl)-5-pyrimidinecarboxamide 100 mg (0.209 mmol) of 4-(3,5-dichlorophenyl)-6-methyl-2-(methylsulfonyl)-N-(3-phenylpropyl)-5-pyrimidinecarboxamide was dissolved in 3 ml of THF. 0.314 ml (13% THF solution, 1 mol/l) of ethylmagnesium bromide was added at 0° C. and stirred at the same temperature for 1 hour. 10% hydrochloric acid was added at the same temperature and stirred for 10 minutes. After the reaction mixture was diluted with ethyl acetate, the organic layer was washed with saturated aqueous sodium chloride solution and dried over anhydrous magnesium sulfate and then concentrated under reduced pressure. The residue was purified by the silica gel chromatography (hexane/ethyl acetate=10/1 to 1/1) to obtain the title compound.

Yield: 18.2 mg (0.0425 mmol) (20%)

MS (ESI, m/z) 428 (M+H)$^+$ 426 (M–H)$^-$ $^1$H-NMR (CDCl3): 1.38 (3H, t), 1.75 (2H, quint), 2.49 (2H, t), 2.59 (3H, s), 2.99 (2H, q), 3.34 (2H, q), 5.48 (1H, br t), 7.07-7.09 (2H, m), 7.15-7.20 (1H, m), 7.24-7.29 (2H, m), 7.40-7.41 (1H, m), 7.69-7.70 (2H, m).

EXAMPLE 104

Synthesis of 4-(3,5-dichlorophenyl)-6-methyl-N-(3-phenylpropyl)-2-(n-propyl)-5-pyrimidinecarboxamide 100 mg (0.209 mmol) of 4-(3,5-dichlorophenyl)-6-methyl-2-(methylsulfonyl)-N-(3-phenylpropyl)-5-pyrimidinecarboxamide was dissolved in 3 ml of THF. 0.349 ml (0.90 mol/l, THF solution) of n-propyl magnesium bromide was added at 0° C. and stirred at the same temperature for 1 hour. 10% hydrochloric acid was added at the same temperature and stirred for 10 minutes. After the reaction mixture was diluted with ethyl acetate, the organic layer was washed with saturated aqueous sodium chloride solution and dried over anhydrous magnesium sulfate and then concentrated under reduced pressure. The residue was purified by the silica gel chromatography (hexane/ethyl acetate=10/1 to 1/1) to obtain the title compound.

Yield: 27.3 mg (0.0617 mmol) (30%)

MS (ESI, m/z) 442 (M+H)$^+$ 440 (M−H)$^−$ $^1$H-NMR (CDCl3): 1.02 (3H, t), 1.75 (2H, quint), 1.87 (2H, sext), 2.49 (2H, t), 2.58 (3H, s), 2.94 (2H, t), 3.34 (2H, q), 5.49 (1H, br t), 7.07-7.10 (2H, m), 7.09-7.20 (1H, m), 7.24-7.29 (3H, m), 7.41 (1H, t), 7.69 (2H, d).

EXAMPLE 105

Synthesis of 2-butyl-4-(3,5-dichlorophenyl)-6-methyl-N-(3-phenylpropyl)-2-(n-propyl)-5-pyrimidinecarboxamide 100 mg (0.209 mmol) of 4-(3,5-dichlorophenyl)-6-methyl-2-(methylsulfonyl)-N-(3-phenylpropyl)-5-pyrimidinecarboxamide was dissolved in 3 ml of THF. 0.349 ml (0.90 mol/l, THF solution) of n-butyl magnesium chloride was added at 0° C. and stirred at the same temperature for 1 hour. 10% hydrochloric acid was added at the same temperature and stirred for 10 minutes. After the reaction mixture was diluted with ethyl acetate, the organic layer was washed with saturated aqueous sodium chloride solution and dried over anhydrous magnesium sulfate and then concentrated under reduced pressure. The residue was purified by the silica gel chromatography (hexane/ethyl acetate=10/1 to 1/1) to obtain the title compound.

Yield: 15.6 mg (0.0342 mmol) (16%)

MS (ESI, m/z) 456 (M+H)$^+$ 454 (M−H)$^−$ $^1$H-NMR (CDCl3): 0.96 (3H, t), 1.43 (2H, sext), 1.70-1.86 (4H, m), 2.49 (2H, t), 2.58 (3H, s), 2.96 (2H, t), 3.33 (2H, q), 5.48 (1H, br t), 7.07-7.10 (2H, m), 7.15-7.21 (1H, m), 7.24-7.30 (2H, m), 7.41 (1H, t), 7.69 (2H, d).

EXAMPLE 106

Synthesis of 4-(2,4-dimethylphenyl)-6-methyl-2-(methylsulfinyl)-N-(3-phenylpropyl)-5-pyrimidinecarboxamide The title compound was obtained by using 210 mg (0.52 mmol) of 4-(2,4-dimethylphenyl)-6-methyl-2-(methylthio)-N-(3-phenylpropyl)-5-pyrimidinecarboxamide and 179 mg (1.04 mmol) of mCPBA (m-chloroperbenzoic acid), in the same manner as that of Example 103 1).

Yield: 52 mg (0.12 mmol) (23%)

MS (ESI, m/z) 422 (M+H)$^+$ $^1$H-NMR (CDCl3): 1.51 (2H, quint), 2.25-2.36 (8H, m), 2.74 (3H, s), 3.24 (2H, q), 3.31 (3H, s), 5.62 (1H, br t), 7.01-7.09 (4H, m), 7.15-7.29 (4H, m).

EXAMPLE 107

Synthesis of 4-(2,4-dimethylphenyl)-6-methyl-N-(3-phenylpropyl)2-(n-propyl)-5-pyrimidinecarboxamide The title compound was obtained by using 210 mg (0.518 mmol) of 4-(2,4-dimethylphenyl)-6-methyl-2-(methylthio)-N-(3-phenylpropyl)-5-pyrimidinecarboxamide, 179 mg (1.04 mmol) of mCPBA and 0.49 ml (0.439 mmol) of n-propyl magnesium bromide (0.90 mol/l, THF solution), in the same manner as that of Example 103.

Yield: 49.6 mg (0.124 mmol) (23%)

MS (ESI, m/z) 402 (M+H)$^+$ $^1$H-NMR (CDCl3): 0.99 (3H, t), 1.44 (2H, quint), 1.78-1.91 (2H, m), 2.22 (6H, s), 2.29 (2H, t), 2.61 (3H, s), 2.90-2.95 (2H, m), 2.17 (2H, q), 5.22 (1H, br t), 7.00-7.05 (4H, m), 7.14-7.29 (4H, m).

EXAMPLE 108

Synthesis of 4-(3,5-dichlorophenyl)-6-ethyl-2-(methylthio)-N-(3-phenylpropyl)-5-pyrimidinecarboxamide 1) Synthesis of 3-(3,5-dichlorophenyl)-2-propionyl-acrylic methylester 1.00 g (7.68 mmol) of 3-oxovaleric acid methylester and 1.34 g (7.68 mmol) of 3,5-dichlorobenzaldehyde were dissolved in 20 ml of 2-propanol. 65.4 mg (0.768 mmol) of piperidine and 46.1 mg (0.768 mmol) of acetic acid were added and stirred at room temperature for one day. After the solvent was evaporated under reduced pressure, ethyl acetate was added thereto. The reaction mixture was washed with 1 N hydrochloric acid and then with saturated aqueous sodium hydrogencarbonate solution. The organic layer was dried over anhydrous magnesium sulfate and then concentrated under reduced pressure. The residue was purified by the silica gel chromatography (hexane/ethyl acetate=10/1) to obtain the title compound.

Yield: 1.77 g (23.4 mmol) (83%)

MS (ESI, m/z) 304 (M+NH4)$^+$ $^1$H-NMR (CDCl3): 1.10-1.18 (3H, m), 2.57 and 2.74 (total 2H, ratio 1:1, q, q, respectively), 3.84 (3H, d), 7.21-7.23 (1H, m), 7.28-7.29 (1H, m), 7.37-7.40 (1H, m), 7.46 and 7.55 (total 1H, ratio 1:1, s, s, respectively).

2) Synthesis of 4-(3,5-dichlorophenyl)-6-ethyl-2-(methylthio)-1,4-dihydropyrimidine-5-carboxylic acid methylester 1.00 g (3.48 mmol) of 3-(3,5-dichlorophenyl)-2-propionyl-acrylic methylester was dissolved in 10 ml of DMF. 776 mg (2.79 mmol) of methylisothiourea-sulfate and 428 mg (5.22 mmol) of sodium acetate were added at room temperature and stirred at the same temperature for 2 days. After DMF was evaporated under reduced pressure, the reaction mixture was diluted with ethyl acetate. The organic layer was washed with saturated aqueous sodium chloride solution and dried over anhydrous magnesium sulfate and then concentrated under reduced pressure. The residue was dissolved in toluene and catalytic amount of silica gel was added and stirred at 100° C. for one day. After filtering silica gel, the filtrate was concentrated under reduced pressure. The residue was purified by the silica gel chromatography (hexane/ethyl acetate=10/1 to 2/1) to obtain the title compound.

Yield: 475 mg (1.32 mmol) (38%)

MS (ESI, m/z) 359 (M+H)$^+$ 357 (M−H)$^−$ $^1$H-NMR (CDCl3): 1.20 (3H, t), 2.41 (3H, s), 2.61-2.88 (2H, m), 3.66 (3H, s), 5.65 and 6.36 (total 1H, ratio 1:1, br s, br s, respectively), 7.17-7.21 (3H, m).

3) Synthesis of 4-(3,5-dichlorophenyl)-6-ethyl-2-(methylthio)-pyrimidine-5-carboxylic acid methylester 475 mg (1.32 mmol) of 4-(3,5-dichlorophenyl)-2-(methylthio)-1,4-dihydropyrimidine-5-carboxylic acid methylester was dissolved in 30 ml of chloroform. 1.72 g (19.8 mmol) of manganese dioxide was added and stirred at 80° C. for 3 hours. After filtration of insoluble matters, the filtrate was concentrated under reduced pressure. The residue was purified by the silica gel chromatography (hexane/ethyl acetate=10/1 to 1/1) to obtain the title compound.

Yield: 369 mg (1.03 mmol) (78%)
MS (ESI, m/z) 357 (M+H)$^+$
$^1$H-NMR (CDCl3): 1.32 (3H, t), 2.62 (3H, s), 2.83 (2H, q), 3.75 (3H, s), 7.44-7.46 (1H, m), 7.50-7.51 (2H, m).

4) Synthesis of 4-(3,5-dichlorophenyl)-6-ethyl-2-(methylthio)-pyrimidine-5-carboxylic acid 274 mg (0.768 mmol) of 4-(3,5-dichlorophenyl)-6-ethyl-2-(methylthio)-pyrimidine-5-carboxylic acid methylester was dissolved in 5 ml of THF and 5 ml of water. 38.7 mg (0.922 mmol) of lithium hydroxide monohydrate was added and stirred at 80° C. for 12 hours. 10 ml of water was added thereto and the organic layer was batched off. The obtained aqueous layer was diluted with ethyl acetate and washed with 5 ml of 3 N hydrochloric acid and then with 5 ml of saturated aqueous sodium chloride solution. The organic layer was dried over anhydrous magnesium sulfate and then concentrated under reduced pressure to obtain the title compound.

Yield: 183 mg (0.533 mmol) (70%)
MS (ESI, m/z) 343 (M+H)$^+$ 341 (M−H)$^-$
$^1$H-NMR (CDCl3): 1.32 (3H, t), 2.61 (3H, s), 2.87 (2H, q), 7.42-7.44 (1H, m), 7.58-7.59 (2H, m).

5) Synthesis of 4-(3,5-dichlorophenyl)-6-ethyl-2-(methylthio)-N-(3-phenylpropyl)-5-pyrimidinecarboxamide 183 mg (0.533 mmol) of 4-(3,5-dichlorophenyl)-6-ethyl-2-(methylthio)-pyrimidine-5-carboxylic acid and 86.5 mg (0.640 mmol) of phenylpropylamine were dissolved in 10 ml of dichloromethane. 153 mg (0.800 mmol) of 1-ethyl-3-(3-dimethylaminopropyl)carbodiimide hydrochloride (hereinafter referred to as WSC hydrochloride) was added under cooling with ice and stirred at room temperature overnight. After concentration under reduced pressure, the reaction mixture was diluted with ethyl acetate. The reaction mixture was washed with 1 N hydrochloric acid, saturated aqueous sodium hydrogencarbonate solution and saturated aqueous sodium chloride solution. The organic layer was dried over anhydrous magnesium sulfate and then concentrated under reduced pressure. The residue was purified by the silica gel chromatography (hexane/ethyl acetate=10/1 to 1/1) to obtain the title compound.

Yield: 130 mg (0.283 mmol) (53%)
MS (ESI, m/z) 460 (M+H)$^+$ 458 (M−H)$^-$
$^1$H-NMR (CDCl3): 1.32 (3H, t), 1.72 (2H, quint), 2.47 (2H, t), 2.61 (3H, s), 2.82 (2H, q), 3.31 (2H, q), 5.44 (1H, br t), 7.06-7.08 (2H, m), 7.16-7.20 (1H, m), 7.24-7.29 (2H, m), 7.40-7.41 (1H, m), 7.68-7.69 (2H, m).

EXAMPLE 109

Synthesis of 4-(2,4-dichlorophenyl)-6-methyl-2-(methylthio)-N-(3-phenylpropyl)-5-pyrimidinecarboxamide The title compound was obtained by using 200 mg (0.532 mmol) of 2-acetyl-3-(2,4-dichlorophenyl)-N-(3-phenylpropyl) acrylamide, 111 mg (0.398 mmol) of methylisothiourea-sulfate and 87.0 mg (1.06 mmol) of sodium acetate, in the same manner as that of Example 1.

Yield: 69.0 mg (0.155 mmol) (28%)
MS (ESI, m/z) 446 (M+H)$^+$
$^1$H-NMR (CDCl3): 1.53 (2H, quint), 2.41 (2H, t), 2.55 (3H, s), 2.56 (3H, s), 3.19 (2H, q), 5.56 (1H, br t), 7.05-7.08 (2H, m), 7.16-7.22 (1H, m), 7.25-7.31 (4H, m), 7.46 (1H, t).

EXAMPLE 110

Synthesis of 4-(2,6-dichlorophenyl)-6-methyl-2-(methylthio)-N-(3-phenylpropyl)-5-pyrimidinecarboxamide The title compound was obtained by using 170 mg (0.452 mmol) of 2-acetyl-3-(2,6-dichlorophenyl)-N-(3-phenylpropyl) acrylamide, 94.0 mg (0.338 mmol) of methylisothiourea-sulfate and 74.2 mg (0.904 mmol) of sodium acetate, in the same manner as that of Example 1.

Yield: 35.6 mg (0.081 mmol) (18%)
MS (ESI, m/z) 446 (M+H)$^+$
$^1$H-NMR (CDCl3): 1.51 (2H, quint), 2.37-2.43 (2H, m), 2.57 (3H, s), 2.59 (3H, s), 3.21 (2H, q), 5.79 (1H, br t), 7.05-7.08 (2H, m), 7.16-7.37 (6H, m).

EXAMPLE 111

Synthesis of 4-(2,4-dimethylphenyl)-6-methyl-2-(methylthio)-N-(3-phenyl-2-propen-1-yl)-5-pyrimidinecarboxamide The title compound was obtained by using 453 mg (1.36 mmol) of 2-acetyl-3-(2,4-dimethylphenyl)-N-(3-phenyl-2-propen-1-yl) acrylamide, 284 mg (1.02 mmol) of methylisothiourea-sulfate and 223 mg (2.72 mmol) of sodium acetate, in the same manner as that of Example 1.

Yield: 110 mg (0.273 mmol) (19%)
MS (ESI, m/z) 404 (M+H)$^+$
$^1$H-NMR (CDCl3): 2.24 (3H, s), 2.25 (3H, s), 2.55 (3H, s), 2.60 (3H, s), 3.90 (2H, td), 5.24 (1H, br t), 5.60 (1H, dt), 6.22 (1H, d), 6.99-7.05 (2H, m), 7.16-7.34 (6H, m).

EXAMPLE 112

Synthesis of 4-(2,4-dichlorophenyl)-6-methyl-N-(3-phenylpropyl)-2-(n-propyl)-5-pyrimidinecarboxamide The title compound was obtained by using 200 mg (0.532 mmol) of 2-acetyl-3-(2,4-dichlorophenyl)-N-(3-phenylpropyl) acrylamide, 160 mg (0.797 mmol) of n-propyl-carbamidine-trifluoroacetate and 87.3 mg (1.06 mmol) of sodium acetate, in the same manner as that of Example 61.

Yield: 87.9 mg (0.199 mmol) (37%)
MS (ESI, m/z) 442 (M+H)$^+$ 440 (M−H)$^-$
$^1$H-NMR (CDCl3): 0.99 (3H, t), 1.55 (2H, quint), 1.84 (2H, sext), 2.42 (2H, t), 2.60 (3H, s), 2.93 (2H, t), 3.21 (2H, q), 5.62 (1H, br t), 7.05-7.07 (2H, m), 7.16-7.21 (1H, m), 7.25-7.34 (4H, m), 7.46-7.47 (1H, m).

EXAMPLE 113

Synthesis of 4-(2,5-dimethylphenyl)-6-methyl-2-(methylthio)-N-(3-phenylpropyl)-5-pyrimidinecarboxamide The title compound was obtained by using 284 mg (0.847 mmol) of 2-acetyl-3-(2,5-dimethylphenyl)-N-(3-phenylpropyl) acrylamide, 189 mg (0.678 mmol) of methylisothiourea-sulfate and 139 mg (1.69 mmol) of sodium acetate, in the same manner as that of Example 61.
Yield: 94.8 mg (0.234 mmol) (28%)
MS (ESI, m/z) 406 (M+H)$^+$ 404 (M−H)$^−$
$^1$H-NMR (CDCl3): 1.40 (2H, quint), 2.23-2.31 (8H, m), 2.56 (6H, d), 3.12 (2H, q), 5.18 (1H, br t), 7.00-7.07 (4H, m), 7.13-7.20 (2H, m), 7.23-7.28 (2H, m).

EXAMPLE 114

Synthesis of 4-(2,5-dimethylphenyl)-6-methyl-N-(3-phenylpropyl)-2-(n-propyl)-5-pyrimidinecarboxamide The title compound was obtained by using 284 mg (0.847 mmol) of 2-acetyl-3-(2,5-dimethylphenyl)-N-(3-phenylpropyl) acrylamide, 254 mg (1.27 mmol) of n-propyl-carbamidine-trifluoroacetate and 139 mg (1.69 mmol) of sodium acetate, in the same manner as that of Example 61.
Yield: 155 mg (0.386 mmol) (46%)
MS (ESI, m/z) 402 (M+H)$^+$ 400 (M−H)$^−$
$^1$H-NMR (CDCl3): 0.99 (3H, t), 1.42 (2H, quint), 1.85 (2H, sext), 2.19 (3H, s), 2.24 (3H, s), 2.29 (1H, t), 2.61 (3H, s), 2.93 (2H, t), 3.14 (2H, q), 5.21 (1H, br t), 7.01-7.06 (4H, m), 7.12-7.28 (4H, m).

EXAMPLE 115

Synthesis of 4-(4-chlorophenyl)-6-methyl-2-(methylthio)-N-(3-phenylpropyl)-5-pyrimidinecarboxamide The title compound was obtained by using 210 mg (0.614 mmol) of 2-acetyl-3-(4-chlorophenyl)-N-(3-phenylpropyl) acrylamide, 128 mg (0.460 mmol) of methylisothiourea-sulfate and 101 mg (1.23 mmol) of sodium acetate, in the same manner as that of Example 1.
Yield: 121 mg (0.294 mmol) (48%)
MS (ESI, m/z) 412 (M+H)$^+$
$^1$H-NMR (CDCl3): 1.69 (2H, quint), 2.45 (2H, t), 2.54 (3H, s), 2.60 (3H, s), 3.28 (2H, q), 5.41 (1H, br t), 7.04-7.06 (2H, m), 7.15-7.21 (1H, m), 7.24-7.30 (2H, m), 7.39-7.44 (2H, m), 7.75-7.80 (2H, m).

EXAMPLE 116

Synthesis of 4-(4-chlorophenyl)-6-methyl-N-(3-phenylpropyl)-2-n-propyl-5-pyrimidinecarboxamide The title compound was obtained by using 210 mg (0.614 mmol) of 2-acetyl-3-(4-chlorophenyl)-N-(3-phenylpropyl) acrylamide, 184 mg (0.921 mmol) of n-propyl-amidine-trifluoroacetate and 101 mg (1.23 mmol) of sodium acetate, in the same manner as that of Example 1.
Yield: 20.3 mg (0.0498 mmol) (8.0%)
MS (ESI, m/z) 408 (M+H)$^+$
$^1$H-NMR (CDCl3): 1.02 (3H, t), 1.69 (2H, quint), 1.87 (2H, sext), 2.45 (2H, t), 2.58 (3H, s), 2.91-2.96 (2H, m), 3.30 (2H, q), 5.41 (1H, br t), 7.04-7.07 (2H, m), 7.18-7.20 (1H, m), 7.24-7.30 (2H, m), 7.40-7.44 (2H, m), 7.74-7.78 (2H, m).

EXAMPLE 117

Synthesis of 4-(2,6-dimethylphenyl)-6-methyl-2-(methylthio)-N-(3-phenylpropyl)-5-pyrimidinecarboxamide The title compound was obtained by using 267 mg (0.794 mmol) of 2-acetyl-3-(2,6-dimethylphenyl)-N-(3-phenylpropyl) acrylamide, 177 mg (0.635 mmol) of methylisothiourea-sulfate and 130 mg (1.59 mmol) of sodium acetate, in the same manner as that of Example 61.
Yield: 42.4 mg (0.105 mmol) (13%)
MS (ESI, m/z) 406 (M+H)$^+$ 404 (M−H)$^−$
$^1$H-NMR (CDCl3): 1.38 (2H, quint), 2.10 (6H, s), 2.32 (2H, t), 2.56 (3H, s), 2.59 (3H, s), 3.11 (2H, q), 5.16 (1H, br t), 7.05 (4H, t), 7.13-7.29 (4H, m).

EXAMPLE 118

Synthesis of 4-(2,6-dimethylphenyl)-6-methyl-N-(3-phenylpropyl)-2-(n-propyl)-5-pyrimidinecarboxamide The title compound was obtained by using 267 mg (0.794 mmol) of 2-acetyl-3-(2,6-dimethylphenyl)-N-(3-phenylpropyl) acrylamide, 238 mg (1.19 mmol) of n-propyl-carbamidine-trifluoroacetate and 130 mg (1.59 mmol) of sodium acetate, in the same manner as that of Example 61.
Yield: 24.7 mg (0.0615 mmol) (7.8%)
MS (ESI, m/z) 402 (M+H)$^+$ 400 (M−H)$^−$
$^1$H-NMR (CDCl3): 0.95-1.05 (3H, m), 1.36-1.56 (2H, m), 1.79-1.96 (2H, m), 2.07 (6H, s), 2.30-2.39 (5H, m), 2.63 (3H, s), 2.91-3.00 (2H, m), 3.10-3.20 (2H, m), 5.22 (1H, br), 7.03-7.29 (8H, m).

EXAMPLE 119

Synthesis of 4-(3-chlorophenyl)-5-(3,3-diphenylpropyl) carbamoyl-2,6-dimethylcarboxylic acid 1) Synthesis of 4-(3-chlorophenyl)-2,6-dimethyl-1,4-dihydropyridine-3,5-dicarboxylic acid mono (2-cyanoethyl) ester 3.53 g (22.9 mmol) of 3-aminocrotonate 2-cyanoethyl, 4.40 g (22.9 mmol) of acetoacetic acid benzyl ester and 2.60 ml (23.0 mmol) of 3-chlorobenzaldehyde were heated and stirred at 80° C. for 3 days in 100 ml of 2-propanol. 2-propanol was evaporated under reduced pressure to obtain 4-(3-chlorophenyl)-2,6-dimethyl-1,4-dihydropyridine-3,5-dicarboxylic acid 3-(2-cyanoethyl) ester 5-benzyl ester. 100 ml of ethyl acetate and 10% palladium carbon were added thereto and stirred at room temperature in hydrogen atmosphere under normal pressure for 7 days. After filtering the reaction mixture, the filtrate was evaporated under reduced pressure. The residue was washed with chloroform to obtain the title compound.
Yield: 4.82 g (13.4 mmol) (58%)
MS (ESI, m/z) 359 (M−H)$^−$ ¹H-NMR (DMSO-d6): 2.27 (3H, s), 2.29 (3H, s), 2.79-2.86 (2H, m), 4.15 (2H, t), 4.87 (1H, s), 7.10-7.28 (5H, m), 8.90 (1H, s).

2) Synthesis of 4-(3-chlorophenyl)-2,6-dimethyl-5-(3,3-diphenylpropylcarbamoyl)-1,4-dihydropyridine-3-dicarboxylic acid 2-cyanoethyl ester 219 mg (0.610 mmol) of 4-(3-chlorophenyl)-2,6-dimethyl-1,4-dihydropyridine-3,5-dicarboxylic acid mono (2-cyanoethyl) ester, 138 mg (0.720 mmol) of WSC hydrochloride, 201 mg (0.950 mmol) of 3,3-diphenylpropylamine and 20.0 mg (0.160 mmol) of 4-dimethylaminopyridine were stirred at room temperature overnight in 10 ml of dichloromethane. 2 N hydrochloric acid was added and the reaction mixture was extracted with dichloromethane. The organic layer was dried over anhydrous sodium sulfate and then concentrated under reduced pressure. The residue was purified by the silica gel chromatography (hexane/ethyl acetate=1/1) to obtain the title compound.

Yield: 280 mg (0.510 mmol) (83%)

MS (ESI, m/z) 554 (M+H)+

¹H-NMR (CDCl3): 2.05-2.23 (2H, m), 2.21 (3H, s), 2.32 (3H, s), 2.64 (2H, t), 3.06-3.22 (2H, m), 3.72 (1H, t), 4.20-4.35 (2H, m), 4.73 (1H, s), 5.31 (1H, t), 5.58 (1H, s), 7.09-7.30 (14H, m).

3) Synthesis of 4-(3-chlorophenyl)-2,6-dimethyl-5-(3,3-diphenylpropylcarbamoyl)-1,4-dihydropyridine-3-carboxylic acid 275 mg (0.500 mmol) of 4-(3-chlorophenyl)-2,6-dimethyl-5-(3,3-diphenylpropylcarbamoyl)-1,4-dihydropyridine-3-carboxylic acid 2-cyanoethyl ester was dissolved in 10 ml of methanol. 1 ml of 1 N aqueous sodium hydroxide solution was added and stirred at room temperature for 7.5 hours. After adding 2 N hydrochloric acid, methanol was evaporated under reduced pressure. Water was added to the residue, and precipitates thus formed were taken by the filtration, then washed with water and hexane/ethyl acetate (3/1) and dried under reduced pressure to obtain the title compound.

Yield: 158 mg (0.320 mmol) (63%)

MS (ESI, m/z) 499 (M−H)−

¹H-NMR (DMSO-d6): 2.01 (3H, s), 2.03-2.17 (2H, s), 2.23 (3H, s), 2.82-3.03 (2H, m), 3.84 (1H, t), 4.82 (1H, s), 7.08-7.31 (1H, m), 7.56 (1H, t), 8.26 (1H, s).

4) Synthesis of 4-(3-chlorophenyl)-5-(3,3-diphenylpropyl) carbamoyl-2,6-dimethylcarboxylic acid 2 ml of acetone was added to 57.3 mg (0.110 mmol) of 4-(3-chlorophenyl)-2,6-dimethyl-5-(3,3-diphenylpropylcarbamoyl)-1,4-dihydropyridine-3-carboxylic acid. 178 mg (0.320 mmol) of cerium ammonium nitrate suspended in 1 ml of water was added and stirred at room temperature for 2.5 hours. After adding water and extracting with ethyl acetate, the organic layer was dried over anhydrous sodium sulfate and then concentrated under reduced pressure to obtain the title compound.

Yield: 50.2 mg (0.100 mmol) (88%)

MS (ESI, m/z) 497 (M−H)−

¹H-NMR (DMSO-d6): 1.77 (2H, q), 2.47 (3H, s), 2.54 (3H, s), 2.86 (2H, q), 3.74 (1H, t), 7.13-7.42 (14H, m), 8.34 (1H, br d).

EXAMPLE 120

Synthesis of 4-(3-chlorophenyl)-2,6-dimethylpyridine-3,5-dicarboxylic acid mono (3,3-diphenylpropyl) ester

1) Synthesis of 4-(3-chlorophenyl)-2,6-dimethyl-1,4-dihydropyridine-3,5-dicarboxylic acid 3-(2-cyanoethyl) ester 5-(3,3-diphenylpropane-1-yl) ester 747 mg (2.52 mmol) of acetoacetic acid, 389 mg (2.52 mmol) of 3-aminocrotonate 2-cyanoethyl ester and 0.285 ml (2.52 mmol) of 3-chlorobenzaldehyde were heated and stirred at 80° C. for two nights in 20 ml of 2-propanol. After 2-propanol was evaporated under reduced pressure, the residue was purified by the silica gel chromatography (hexane/ethyl acetate=2/1) to obtain the title compound.

Yield: 814 mg (1.47 mmol) (58%)

MS (ESI, m/z) 553 (M−H)−

¹H-NMR (CDCl3): 2.28-2.42 (2H, m), 2.35 (6H, s), 2.64 (2H, t), 3.91 (1H, t), 3.95-4.02 (2H, m), 4.22-4.39 (2H, m), 5.00 (1H, s), 5.73 (1H, s), 7.08-7.30 (14H, m)

2) Synthesis of 4-(3-chlorophenyl)-2,6-dimethyl-1,4-dihydropyridine-3,5-dicarboxylic acid mono (3,3-diphenylpropyl) ester 808 mg (1.46 mmol) of 4-(3-chlorophenyl)-2,6-dimethyl-1,4-dihydropyridine-3,5-dicarboxylic acid 3-(2-cyanoethyl) ester 5-(3,3-diphenylpropyl) ester was dissolved in 15 ml of methanol. 3 ml of 1 N aqueous sodium hydroxide solution was added and stirred at room temperature for 2 hours. After adding 2 N hydrochloric acid, methanol was evaporated under reduced pressure. Water was added to the residue, and solid matters were taken by the filtration, then washed with water and hexane/ethyl acetate (3/1) and dried under reduced pressure to obtain the title compound.

Yield: 398 mg (0.790 mmol) (54%)

MS (ESI, m/z) 500 (M−H)−

¹H-NMR (DMSO-d6): 2.24-2.34 (2H, m), 2.24 (3H, s), 2.29 (3H, s), 3.81 (2H, t), 3.87 (1H, t), 4.95 (1H, s), 7.09-7.33 (14H, m), 8.85 (1H, s)

3) Synthesis of 4-(3-chlorophenyl)-2,6-dimethylpyridine-3,5-dicarboxylic acid Mono (3,3-diphenylpropyl) ester 2 ml of acetone was added to 50.7 mg (0.100 mmol) of 4-(3-chlorophenyl)-2,6-dimethyl-1,4-dihydropyridine-3,5-dicarboxylic acid mono (3,3-diphenylpropyl) ester. 130 mg (0.240 mmol) of cerium ammonium nitrate suspended in 1 ml of water was added and stirred at room temperature for 10 minutes. After adding water and extracting with ethyl acetate, the organic layer was dried over anhydrous sodium sulfate and then concentrated under reduced pressure to obtain the title compound.

Yield: 398 mg (0.790 mmol) (54%)

MS (ESI, m/z) 498 (M−H)−

¹H-NMR (DMSO-d6): 2.01 (2H, q), 2.48 (3H, s), 2.54 (3H, s), 3.78-3.88 (1H, t), 7.14-7.50 (14H, m).

EXAMPLE 121

Synthesis of 6-(2-aminoethoxy) methyl-4-(3-chlorophenyl)-5-(3,3-diphenylpropylcarbamoyl)-2-methylpyridine-3-carboxylic acid

1) Synthesis of 4-(2-chloroethoxy) acetoacetic acid benzyl ester 4.00 g (21.0 mmol) of acetoacetic acid benzyl ester was dissolved in 40 ml of ether. 1.1 ml (21.0 mmol) of bromine was dropped at 0° C. After stirring at 0° C. for 30 minutes and then at room temperature for 5 hours, about 4 g of ice and sodium carbonate were added so that pH showed 7 or more. The organic layer extracted with ether was washed with water and saturated aqueous sodium chloride solution, dried over anhydrous magnesium sulfate, concentrated and dried in vacuo to obtain 4-bromoacetoacetic acid benzyl ester. 1.68 g (24.0 mmol) of sodium hydride (60% oily substance) was suspended in 20 ml of THF and 11.7 g (21.0 mmol) of 2-chloroethanol was added at −40° C. 4-bromoacetoacetic acid benzyl ester was dropped at −40° C., gradually heated and stirred at room temperature for 16 hours. After adding 1 N hydrochloric acid and extracting with ethyl acetate, the obtained mixture was washed with water and saturated aqueous sodium chloride solution. The mixture was dried over anhydrous magnesium sulfate and then concentrated under reduced pressure. The residue was purified by the silica gel chromatography (hexane/ethyl acetate=7/3) to obtain the title compound.

Yield: 3.75 mg (14.0 mmol) (67%)
$^1$H-NMR (CDCl3): 3.59 (2H, t), 3.59 (2H, s), 3.72 (2H, t), 4.18 (2H, s), 5.18 (2H, s), 7.35-7.38 (5H, m).

2) Synthesis of 2-(2-chloroethoxy) methyl-4-(3-chlorophenyl)-6-methyl-1,4-dihydropyridine-3,5-dicarboxylic acid 3-benzyl ester 5-(2-cyanoethyl) ester 500 mg (1.90 mmol) of 4-(2-chloroethoxy) acetoacetic acid benzyl ester, 260 mg (1.90 mmol) of 3-chlorobenzaldehyde, acetic acid and piperidine were heated and stirred at room temperature for 24 hours in 3 ml of 2-propanol. 280 mg (1.90 mmol) of 3-aminocrotonate 2-cyanoethyl ester was added and further heated and stirred at 50° C. for 48 hours. 2-propanol was evaporated under reduced pressure. The residue was purified by the silica gel chromatography (hexane/ethyl acetate=1/1) to obtain the title compound.

Yield: 340 mg (0.640 mmol) (35%)
MS (ESI, m/z) 531 (M+H)$^+$
$^1$H-NMR (CDCl3): 2.39 (3H, s), 2.59 (2H, t), 3.73 (2H, t), 3.79 (2H, m), 4.22 (2H, m), 4.75 (1H, d), 4.82 (1H, d), 4.98 (1H, s), 5.00 (1H, d), 5.13 (1H, d), 7.11-7.30 (10H, m).

3) Synthesis of 2-(2-chloroethoxy) methyl-4-(3-chlorophenyl)-6-methyl-1,4-dihydropyridine-3,5-dicarboxylic acid 5-(2-cyanoethyl) ester 5 ml of ethyl acetate and 10% palladium carbon were added to 340 mg (0.640 mmol) of 2-(2-chloroethoxy) methyl-4-(3-chlorophenyl)-6-methyl-1,4-dihydropyridine-3,5-dicarboxylic acid 3-benzyl ester 5-(2-cyanoethyl) ester. The obtained solution was stirred at room temperature in hydrogen atmosphere under normal pressure for 8 hours. After filtering the reaction mixture, the filtrate was evaporated under reduced pressure to obtain the title compound.

Yield: 250 mg (0.560 mmol) (87%)
MS (ESI, m/z) 437 (M−H)$^−$
$^1$H-NMR (CDCl3): 2.41 (3H, s), 2.63 (2H, t), 3.74 (2H, m), 3.86 (2H, m), 4.25 (2H, m), 4.75 (1H, d), 4.81 (1H, d), 4.95 (1H, s), 7.13-7.26 (4H, m), 7.47 (1H, s).

4) Synthesis of 6-(2-chloroethoxy) methyl-4-(3-chlorophenyl)-5-(3,3-diphenylpropylcarbamoyl)-2-methyl-1,4-dihydropyridine-3-carboxylic acid (2-cyanoethyl) ester 250 mg (0.560 mmol) of 2-(2-chloroethoxy) methyl-4-(3-chlorophenyl)-6-methyl-1,4-dihydropyridine-3,5-dicarboxylic acid 5-(2-cyanoethyl) ester, 110 mg (0.570 mmol) of WSC hydrochloride and 120 mg (0.570 mmol) of 3,3-diphenylpropylamine were stirred at room temperature for 15 hours in 4 ml of dichloromethane. After evaporating dichloromethane under reduced pressure, 0.1 N hydrochloric acid was added and the reaction mixture was extracted with ethyl acetate. The organic layer was dried over anhydrous magnesium sulfate and then concentrated under reduced pressure. The residue was purified by the silica gel chromatography (hexane/ethyl acetate=1/1) to obtain the title compound.

Yield: 280 mg (0.450 mmol) (80%)
MS (ESI, m/z) 632 (M+H)$^+$
$^1$H-NMR (CDCl3): 2.14 (2H, s), 2.67 (2H, t), 3.10 (2H, m), 3.72 (2H, m), 3.83 (2H, m), 4.31 (2H, m), 4.73 (1H, s), 4.82 (2H, s), 5.56 (1H, t), 7.11-7.26 (15H, m).

5) Synthesis of 6-(2-azidoethoxy) methyl-4-(3-chlorophenyl)-5-(3,3-diphenylpropylcarbamoyl)-2-methyl-1,4-dihydropyridine-3-carboxylic acid (2-cyanoethyl) ester 270 mg (0.430 mmol) of 6-(2-chloroethoxy) methyl-4-(3-chlorophenyl)-5-(3,3-diphenylpropylcarbamoyl)-2-methyl-1,4-dihydropyridine-3-carboxylic acid (2-cyanoethyl) ester was dissolved in 3 ml of 2-propanol. 600 mg (0.400 mmol) of sodium iodide was added thereto and stirred at 60° C. for 20 hours. After the solvent was evaporated under reduced pressure, sodium iodide separated by adding dichloromethane was taken by filtration. The filtrate was concentrated under reduced pressure and stirred together with 33.0 mg (0.490 mmol) of sodium azide at 50° C. for 6 hours in 2 ml of DMF. After adding ethyl acetate, the reaction mixture was washed with water and saturated aqueous sodium chloride solution. The organic layer was dried over anhydrous magnesium sulfate and then concentrated under reduced pressure to obtain the title compound.

Yield: 250 mg (0.390 mmol) (90%)
MS (ESI, m/z) 639 (M+H)$^+$
$^1$H-NMR (CDCl3): 2.15 (2H, m), 2.34 (3H, s), 2.69 (2H, t), 3.10 (2H, m), 3.48 (2H, m), 3.66 (1H, t), 3.75 (2H, m), 4.32 (2H, m), 4.73 (1H, s), 4.83 (2H, s), 5.55 (1H, t), 7.09-7.32 (15H, m).

6) Synthesis of 6-(2-azidoethoxy) methyl-4-(3-chlorophenyl)-5-(3,3-diphenylpropylcarbamoyl)-2-methyl-1,4-dihydropyridine-3-carboxylic acid 250 mg (0.390 mmol) of 6-(2-azidoethoxy) methyl-4-(3-chlorophenyl)-5-(3,3-diphenylpropylcarbamoyl)-2-methyl-1,4-dihydropyridine-3-carboxylic acid (2-cyanoethyl) ester was dissolved in 2 ml of methanol. 0.70 ml of 1 N aqueous sodium hydroxide solution was added and stirred at room temperature for 8 hours. After adding 1 N hydrochloric acid and water, precipitates thus formed were taken by the filtration and dried under reduced pressure to obtain the title compound.

Yield: 190 mg (0.320 mmol) (84%)
MS (ESI, m/z) 584 (M–H)⁻
¹H-NMR (CDCl3): 2.15 (2H, m), 2.34 (3H, s), 3.10 (2H, m), 3.50 (2H, m), 3.66 (1H, t), 3.76 (2H, m), 4.72 (1H, s), 4.87 (2H, s), 5.49 (1H, t), 7.08-7.33 (15H, m).

7) Synthesis of 6-(2-aminoethoxy) methyl-4-(3-chlorophenyl)-5-(3,3-diphenylpropylcarbamoyl)-2-methylpyridine-3-carboxylic acid 3 ml of ethyl acetate and 10% palladium carbon were added to 0.100 g (0.170 mmol) of 6-(2-azidoethoxy) methyl-4-(3-chlorophenyl)-5-(3,3-diphenylpropylcarbamoyl)-2-methyl-1,4-dihydropyridine-3-carboxylic acid and stirred at room temperature in hydrogen atmosphere under normal pressure for 40 hours. The reaction mixture was filtered and the filtrate was evaporated under reduced pressure. The residue thus obtained by evaporating the solvent was subjected to Reversed-phase High-performance Liquid Chromatography using octadodecyl group bounded type silica gel as a filler. Then, the obtained substance was eluted with the mixed solvent of water and acetonitrile. The fraction of the object compound was freeze-dried to obtain the title compound as a by-product material of 6-(2-aminoethoxy) methyl-4-(3-chlorophenyl)-5-(3,3-diphenylpropylcarbamoyl)-2-methyl-1,4-dihydropyridine-3-carboxylic acid.

Yield: 9.10 mg (0.0160 mmol) (10%)
MS (ESI, m/z) 556 (M–H)⁻
¹H-NMR (CD3OD): 1.80 (2H, q), 2.63 (3H, s), 3.00 (2H, t), 3.07 (2H, t), 3.65-3.72 (3H, t), 4.66 (2H, s), 7.10-7.30 (14H, m).

EXAMPLE 122

Synthesis of 4-(3-chlorophenyl)-2,6-dimethyl-5-(piperazine 1-carbonyl)nicotinic acid (3,3-diphenylpropyl) ester 1) Synthesis of 4-(3-chlorophenyl)-2,6-dimethyl-1,4-dihydropyridine-3,5-dicarboxylic acid 3-(2-cyanoethyl) ester 5-(3,3-diphenylpropyl) ester 747 mg (2.52 mmol) of acetoacetic acid 3,3-diphenylpropyl ester, 389 mg (2.52 mmol) of 3-aminocrotonate 2-cyanoethyl ester and 0.285 ml (2.52 mmol) of 3-chlorobenzaldehyde were heated and stirred at 80° C. for two nights in 20 ml of 2-propanol. After 2-propanol was evaporated under reduced pressure, the residue was purified by the silica gel chromatography (hexane/ethyl acetate=2/1) to obtain the title compound.

Yield: 814 mg (1.47 mmol) (58%)
MS (ESI, m/z) 553 (M–H)⁻
¹H-NMR (CDCl3): 2.28-2.42 (2H, m), 2.35 (6H, s), 2.64 (2H, t), 3.91 (1H, t), 3.95-4.02 (2H, m), 4.22-4.39 (2H, m), 5.00 (1H, s), 5.73 (1H, s), 7.08-7.30 (14H, m).

2) Synthesis of 4-(3-chlorophenyl)-2,6-dimethyl-1,4-dihydropyridine-3,5-dicarboxylic acid mono (3,3-diphenylpropyl) ester 808 mg (1.46 mmol) of 4-(3-chlorophenyl)-2,6-dimethyl-1,4-dihydropyridine-3,5-dicarboxylic acid 3-(2-cyanoethyl) ester 5-(3,3-diphenylpropyl) ester was dissolved in 15 ml of methanol. 3 ml of 1 N aqueous sodium hydroxide solution was added and stirred at room temperature for 2 hours. After adding 2 N hydrochloric acid, methanol was evaporated under reduced pressure. Water was added thereto and the solid substance was filtered. The obtained substance was washed with water and then hexane/ethyl acetate (3/1) and dried under reduced pressure to obtain the title compound.

Yield: 398 mg (0.790 mmol) (54%)
MS (ESI, m/z) 500 (M–H)⁻
¹H-NMR (DMSO-d6): 2.24-2.34 (2H, m), 2.24 (3H, s), 2.29 (3H, s), 3.81 (2H, t), 3.87 (1H, t), 4.95 (1H, s), 7.09-7.33 (14H, m), 8.85 (1H, s).

3) Synthesis of 4-[4-(3-chlorophenyl)-5-(3,3-diphenylpropoxycarbonyl)-2,6-dimethyl-1,4-dihydropyridine-3-carbonyl] piperazine-1-carboxylic acid-t-butyl ester 258 mg (0.510 mmol) of 4-(3-chlorophenyl)-2,6-dimethyl-1,4-dihydropyridine-3,5-dicarboxylic acid mono (3,3-diphenylpropyl) ester, 143 mg (0.770 mmol) of 1-t-butoxycarbonylpiperazine, 117 mg (0.610 mmol) of WSC hydrochloride and 18.0 mg (0.140 mol) of 4-dimethylaminopyridine were stirred at room temperature overnight in 15 ml of dichloromethane. After adding water and 1 N hydrochloric acid, the reaction mixture was extracted with dichloromethane. The organic layer was dried over anhydrous sodium sulfate and then concentrated under reduced pressure. The residue was purified by the silica gel chromatography (hexane/ethyl acetate=1/2) to obtain the title compound.

Yield: 259 mg (0.390 mol) (77%)
MS (ESI, m/z) 668 (M–H)⁻
¹H-NMR (CDCl3): 1.40-1.48 (2H, m), 1.43 (9H, s), 1.73 (3H, s), 2.10-2.22 (2H, m), 2.38 (3H, s), 2.85-3.15 (4H, m), 3.62-3.92 (5H, m), 4.96 (1H, s), 5.24 (1H, s), 6.92 (2H, d), 7.08-7.29 (12H, m).

4) Synthesis of 4-(3-chlorophenyl)-2,6-dimethyl-5-(piperazine-1-carbonyl) nicotinic acid (3,3-diphenylpropyl) ester 233 mg (0.350 mol) of 4-(4-(3-chlorophenyl)-5-(3,3-diphenylpropoxycarbonyl)-2,6-dimethyl-1,4-dihydropyridine-3-carbonyl) piperazine-1-carboxylic acid-t-butyl ester was dissolved in 10 ml of dichloromethane. 5 ml of trifluoroacetate was added and stirred at room temperature for 2.5 hours. After concentration under reduced pressure, saturated aqueous sodium hydrogencarbonate solution was added and the reaction mixture was extracted with ethyl acetate. The organic layer was dried over anhydrous sodium sulfate and then concentrated under reduced pressure to obtain the title compound.

Yield: 198 mg (0.350 mol) (100%)
MS (ESI, m/z) 568 (M+H)⁺
¹H-NMR (CDCl3): 1.90-2.04 (2H, m), 2.15-2.27 (1H, m), 2.41-2.65 (2H, m), 2.55 (3H, s), 2.58 (3H, s), 2.73-2.88 (2H, m), 2.98-3.08 (1H, m), 3.40-3.55 (2H, m), 3.71 (1H, t), 3.82-4.05 (2H, m), 7.06-7.29 (14H, m).

EXAMPLE 123

Synthesis of 4-(3-chlorophenyl)-2,6-dimethyl-3-(3-phenylpropyl)-5-(piperazine-1-carbonyl) nicotinamide 1) Synthesis of 4-[4-(3-chlorophenyl)-5-(2-cyanoethoxycarbonyl)-2,6-dimethyl-1,4-dihydropyridine-3-carbonyl] piperazine-1-carboxylic acid-t-butyl ester 1.48 g (7.97 mmol) of 1-(t-butoxycarbonyl) piperazine, 0.74 ml (9.59 mmol) of diketene and 0.22 ml (1.58 mmol) of triethylamine were stirred in 50 ml of toluene at 80° C. for 5 hours. After ethyl acetate was added, the reaction mixture was washed with saturated aqueous sodium hydrogencarbonate solution. The organic layer was dried over anhydrous sodium sulfate and then concentrated under reduced pressure. The obtained substance was dissolved in 50 ml of benzene. 0.94 ml (8.30 mmol) of 3-chlorobenzaldehyde, 0.08 ml of piperidine and catalytic amount of p-toluenesulfonic acid were added and stirred removing water at 120° C. for 7 hours. After adding ethyl acetate, the reaction mixture was washed with 1 N hydrochloric acid and saturated aqueous sodium hydrogencarbonate solution. The organic layer was dried over anhydrous sodium sulfate and then concentrated under reduced pressure. The residue was purified by the silica gel chromatography (hexane/ethyl acetate=3/1). The obtained substance was dissolved in 50 ml of 2-propanol. 929 mg (6.03 mmol) of 3-aminocrotonate (2-cyanoethyl) ester was added and stirred at 80° C. for four nights and then, after the solvent was removed, stirred at 120° C. for 4 hours. The reaction mixture was purified by the silica gel chromatography (chloroform/methanol=100/1) to obtain the title compound.

Yield: 1.67 g (3.15 mmol) (40%)
MS (ESI, m/z) 527 (M–H)⁻
¹H-NMR (CDCl3): 1.43 (9H, s), 1.76 (3H, s), 2.39 (3H, s), 2.42-2.48 (2H, m), 2.60-4.20 (10H, m), 4.87 (1H, s), 5.45 (1H, s), 7.10-7.27 (4H, m).

2) Synthesis of 4-[5-carboxy-4-(3-chlorophenyl)-2,6-dimethyl-1,4-dihydropyridine-3-carbonyl] piperazine-1-carboxylic acid-t-butyl ester 6.30 ml (6.30 mmol) of 1 N aqueous sodium hydroxide solution was added to 1.67 g (3.15 mmol) of 4-[4-(3-chlorophenyl)-5-(2-cyanoethoxycarbonyl)-2,6-dimethyl-1,4-dihydropyridine-3-carbonyl] piperazine-1-carboxylic acid-t-butyl ester in 30 ml of methanol and stirred at room temperature for 2 hours. 6.30 ml (6.30 mmol) of 1 N hydrochloric acid was added and concentrated under reduced pressure. Water was added to the residue and extracted with ethyl acetate. The organic layer was dried over anhydrous sodium sulfate and then concentrated under reduced pressure. The obtained solid substance was filtered, washed with hexane/ethyl acetate (3/1) and dried under reduced pressure to obtain the title compound.

Yield: 1.13 g (2.37 mmol) (75%)
MS (ESI, m/z) 474 (M–H)⁻
¹H-NMR (DMSO-d6): 1.37 (9H, s), 1.68 (3H, s), 2.28 (3H, s), 2.80-3.40 (8H, m), 4.64 (1H, s), 7.02-7.05 (2H, m), 7.19-7.32 (2H, m), 8.28 (1H, s).

3) Synthesis of 4-[4-(3-chlorophenyl)-2,6-dimethyl-5-(3-phenylpropylcarbamoyl) pyridine-3-carbonyl] piperazine-1-carboxylic acid-t-butyl ester 1.13 g (2.37 mmol) of 4-[5-carboxy-4-(3-chlorophenyl)-2,6-dimethyl-1,4-dihydropyridine-3-carbonyl] piperazine-1-carboxylic acid-t-butyl ester, 0.51 ml (3.59 mmol) of 3-phenylpropylamine, 548 mg (2.86 mmol) of WSC hydrochloride and 21 mg (0.17 mmol) of 4-dimethylaminopyridine were stirred in 10 ml of dichloromethane at room temperature overnight. After adding 25 ml of water and 25 ml of 1 N hydrochloric acid, the reaction mixture was extracted with dichloromethane. The organic layer was washed with saturated aqueous sodium hydrogencarbonate solution and dried over anhydrous sodium sulfate and then concentrated under reduced pressure. The residue was purified by the silica gel chromatography (chloroform/methanol=300/1) to obtain the title compound.

Yield: 619 mg (1.05 mmol) (44%)
MS (ESI, m/z) 589 (M–H)⁻
¹H-NMR (CDCl3): 1.35-1.54 (2H, m), 1.41 (9H, s), 2.20-2.39 (2H, m), 2.50 (3H, s), 2.60 (3H, s), 2.70-3.57 (10H, m), 5.43 (1H, t), 7.01-7.47 (9H, m).

4) Synthesis of 4-(3-chlorophenyl)-2,6-dimethyl-3-(3-phenylpropyl)-5-(piperazine-1-carbonyl) nicotinamide 619 mg (1.05 mmol) of 4-[4-(3-chlorophenyl)-2,6-dimethyl-5-(3-phenylpropylcarbamoyl) pyridine-3-carbonyl] piperazine-1-carboxylic acid-t-butyl ester was dissolved in 30 ml of dichloromethane. 15 ml of trifluoroacetate was added and stirred at room temperature for 2 hours. After concentration under reduced pressure, saturated aqueous sodium hydrogencarbonate solution was added and the reaction mixture was extracted with ethyl acetate. The organic layer was dried over anhydrous sodium sulfate and then concentrated under reduced pressure. By adding hexane to the residue, the solid substance was precipitated, filtered and dried under reduced pressure to obtain the title compound.

Yield: 377 mg (0.770 mol) (73%)
MS (ESI, m/z) 489 (M–H)⁻
¹H-NMR (CDCl3): 1.37-1.56 (2H, m), 2.21-2.59 (6H, m), 2.50 (3H, s), 2.59 (3H, s), 2.72-2.78 (2H, m), 2.94-3.06 (2H, m), 3.24-3.35 (1H, m), 3.44-3.47 (2H, m), 5.60 (1H, t), 7.02-7.46 (9H, m).

EXAMPLE 124

Synthesis of 4-(3,5-dichlorophenyl)-2,6-dimethyl-5-(piperazine-1-carbonyl)nicotinic acid (3,3-diphenylpropyl) ester 1) Synthesis of 4-[2-acetyl-3-(3,5-dichlorophenyl)-2-propenoyl] piperazine-1-carboxylic acid-t-butyl ester 2.00 g (10.7 mmol) of 1-(t-butoxycarbonyl), 0.99 ml (12.8 mmol) of diketene and 2.2 ml (16.1 mmol) of triethylamine were stirred in 50 ml of toluene at 80° C. for 2 hours. After adding ethyl acetate, the reaction mixture was washed with saturated aqueous sodium hydrogencarbonate solution. The organic layer was dried over anhydrous magnesium sulfate and then concentrated under reduced pressure. The obtained substance was dissolved in 60 ml of benzene. 1.97 g (11.3 mmol) of 3,5-dichlorobenzaldehyde and 0.11 ml (1.13 mmol) of piperidine were added and stirred removing water at 120° C. for 7 hours. After adding ethyl acetate, the reaction mixture was washed with 1 N hydrochloric acid and saturated aqueous sodium hydrogencarbonate solution. The organic layer was dried over anhydrous magnesium sulfate and then concentrated under reduced pressure. The residue was purified by the silica gel chromatography (hexane/ethyl acetate=3/1) to obtain the title compound.

Yield: 1.52 g (3.56 mmol) (33%)
MS (ESI, m/z)
¹H-NMR (CDCl3): 1.44 (9H, s), 2.43 (3H, s), 2.75-2.88 (1H, m), 3.07-3.18 (2H, m), 3.25-3.47 (2H, m), 3.55-3.71 (2H, m), 3.78-3.90 (1H, m), 7.35 (1H, s), 7.39-7.40 (3H, m).

2) Synthesis of 4-[4-(3,5-dichlorophenyl)-5-(3,3-diphenylpropoxycarbonyl)-2,6-dimethyl-1,4-dihydropyridine-3-carbonyl] piperazine-1-carboxylic acid-t-butyl ester 355 mg (1.20 mmol) of acetoacetic acid 3,3-diphenylpropyl ester and 277 mg (3.59 mmol) of ammonium acetate were stirred in 15 ml of 2-propanol at 55° C. overnight. After evaporating 2-propanol under reduced pressure, ethyl acetate was added and the reaction mixture was washed with saturated aqueous sodium chloride solution. The organic layer was dried over anhydrous magnesium sulfate and then concentrated under reduced pressure. The obtained substance was dissolved in 15 ml of 2-propanol. 513 mg (1.20 mmol) of 4-[2-acetyl-3-(3,5-dichlorophenyl)-2-propenoyl] piperazine-1-carboxylic acid-t-butyl ester was added and stirred at 70° C. overnight. After evaporating 2-propanol under reduced pressure, the residue was purified by the silica gel chromatography (dichloromethane/methanol=100/1 to 50/1) to obtain the title compound.

Yield: 419 mg (0.595 mmol) (49%)
MS (ESI, m/z) 702 (M−H)$^-$
$^1$H-NMR (CDCl3): 1.44 (9H, s), 1.73 (3H, s), 2.13-2.20 (2H, m), 2.36 (3H, s), 2.70-3.92 (1H, m), 4.96 (1H, br s), 5.54 (1H, br s), 6.96 (2H, d), 7.09-7.28 (11H, m).

3) Synthesis of 4-(3,5-dichlorophenyl)-2,6-dimethyl-5-(piperazinylcarbonyl) nicotinic acid (3,3-diphenylpropyl) ester 419 mg (0.595 mmol) of 4-[4-(3,5-dichlorophenyl)-5-(3,3-diphenylpropoxycarbonyl)-2,6-dimethyl-1,4-dihydropyridine-3-carbonyl] piperazine-1-carboxylic acid-t-butyl ester was dissolved in 15 ml of dichloromethane. After adding 7 ml of trifluoroacetate under cooling with ice, the reaction mixture was stirred at room temperature for 2 hours. After concentration under reduced pressure, saturated aqueous sodium hydrogencarbonate solution was added and the reaction mixture was extracted with ethyl acetate. The organic layer was dried over anhydrous magnesium sulfate and then concentrated under reduced pressure. The residue was purified by the silica gel chromatography (dichloromethane) to obtain the title compound.

Yield: 224 mg (0.372 mmol) (63%)
MS (ESI, m/z) 602 (M+H)$^+$
$^1$H-NMR (CDCl3): 2.02-2.10 (3H, m), 2.27-2.35 (1H, m), 2.49-2.55 (4H, m), 2.58 (3H, s), 2.63-2.69 (1H, m), 2.78-2.91 (2H, m), 3.03-3.10 (1H, m), 3.52 (2H, t), 3.73 (1H, t), 3.90-4.08 (2H, m), 7.10-7.30 (14H, m).

EXAMPLE 125

Synthesis of 4-(3-chlorophenyl)-2,6-dimethyl-5-(4-methylpiperazine-1-carbonyl)nicotinic acid (3,3-diphenylpropyl) ester 1.564 g (8.16 mmol) of WSC hydrochloride and 0.905 ml (8.16 mmol) of N-methylpiperazine in the ice bath were added to 3.42 g (6.80 mmol) of 4-(3-chlorophenyl)-2,6-dimethyl-1,4-dihydropyridine-3,5-dicarboxylic acid mono (3,3-diphenylpropane) ester in 100 ml of dichloromethane and stirred at room temperature overnight. 30 ml of trifluoroacetate was added and the reaction mixture was stirred at room temperature overnight. After concentration under reduced pressure, saturated aqueous sodium hydrogencarbonate solution was added to basify. After extracting with ethyl acetate, the organic layer was dried over anhydrous sodium sulfate and then concentrated under reduced pressure. The residue was purified by the silica gel chromatography (chloroform/methanol 50/1) to obtain the title compound.

Yield: 2.67 g (4.58 mmol) (67%)
MS (ESI, m/z) 582 (M+H)$^+$
$^1$H-NMR (CDCl3): 1.72-2.08 (4H, m), 2.17 (3H, s), 2.12-2.38 (2H, m), 2.55 (3H, s), 2.58 (3H, s), 2.76-3.14 (2H, m), 3.40-3.64 (2H, m), 3.71 (1H, t), 3.83-4.05 (2H, m), 7.05-7.30 (14H, m).

EXAMPLE 126

Synthesis of 4-(3-chlorophenyl)-2,6-dimethyl-5-[4-(2-hydroxyethyl) piperazine-1-carbonyl) nicotinic acid (3,3-diphenylpropyl) ester 118 mg (0.620 mmol) of WSC hydrochloride and 80 mg (0.610 mmol) of 1-(2-hydroxyethyl) piperazine in the ice bath were added to 252 mg (0.510 mmol) of 4-(3-chlorophenyl)-2,6-dimethyl-1,4-dihydropyridine-3,5-dicarboxylic acid mono (3,3-diphenylpropyl) ester in 8 ml of dichloromethane and stirred at room temperature overnight. Saturated aqueous sodium hydrogencarbonate solution was added and the reaction mixture was extracted with dichloromethane. The organic layer was dried over anhydrous sodium sulfate and then concentrated under reduced pressure. The residue was dissolved in 8 ml of dichloromethane. 4 ml of trifluoroacetic acid was added in the ice bath and stirred at room temperature for 9 hours. The reaction mixture was concentrated under reduced pressure, followed by basifying with 1N NaOH aq. After extracting it with ethyl acetate, The organic layer was dried over anhydrous sodium sulfate and then concentrated under reduced pressure. The residue was purified by the basic silica gel chromatography (chloroform/methanol=1000/1) to obtain the title compound.

Yield: 206 g (0.340 mmol) (66%)
MS (ESI, m/z) 612 (M+H)$^+$
$^1$H-NMR (CDCl3): 1.82-2.13 (4H, m), 2.24-2.50 (5H, m), 2.55 (3H, s), 2.59 (3H, s), 2.81-3.15 (2H, m), 3.46-3.60 (4H, m), 3.71 (1H, t), 3.84-4.04 (2H, m), 7.05-7.30 (14H, m).

EXAMPLE 127

Synthesis of 4-(3-chlorophenyl)-2,6-dimethyl-5-(pyrrolidine-1-carbonyl)nicotinic acid (3,3-diphenylpropyl) ester 100 mg (0.200 mmol) of 4-(3-chlorophenyl)-2,6-dimethylpyridine-3,5-dicarboxylic acid mono (3,3-diphenylpropyl) ester, 21.3 mg (0.300 mmol) of pyrrolidine, 46.0 mg (0.240 mmol) of WSC hydrochloride and 3.00 mg (0.0250 mmol) of 4-dimethylaminopyridine were stirred in 1.5 ml of dichloromethane at room temperature overnight. 3.7 mg (0.160 mmol) of WSC hydrochloride and 1 ml of DMF were added and further stirred at 60° C. overnight. After adding ethyl acetate and being washed with water, the organic layer was dried over anhydrous magnesium sulfate and then concentrated under reduced pressure. The residue was purified by the thin layer silica gel chromatography (hexane/ethyl acetate=1/3) to obtain the title compound.

Yield: 21.6 mg (0.0391 mmol) (20%)
MS (ESI, m/z) 553 (M+H)$^+$
$^1$H-NMR (CDCl3): 1.45-1.84 (4H, m), 1.91-2.06 (2H, m), 2.56 (3H, s), 2.58 (3H, s), 2.74-7.82 (1H, m), 2.92-3.00 (1H, m), 3.10-3.19 (1H, m), 3.45-3.54 (1H, m), 3.71 (1H, t), 3.84-4.02 (2H, m), 7.06-7.12 (4H, m), 7.13-7.20 (3H, m), 7.22-7.29 (7H, m).

EXAMPLE 128

Synthesis of 4-(3-chlorophenyl)-2,6-dimethyl-5-(piperidine 1-carbonyl)nicotinic acid (3,3-diphenylpropyl) ester The title compound was obtained by using 100 mg (0.200 mmol) of 4-(3-chlorophenyl)-2,6-dimethylpyridine-3,5-dicarboxylic acid mono (3,3-diphenylpropyl) ester, 25.5 mg (0.300 mmol) of piperidine, 76.7 mg (0.400 mmol) of WSC hydrochloride and 3.00 mg of 4-dimethylaminopyridine, in the same manner as that of Example 127.

Yield: 50.8 mg (0.0896 mmol) (45%)

MS (ESI, m/z) 567 (M+H)$^+$ $^1$H-NMR (CDCl3): 0.90-1.54 (1H, br s), 1.54-1.39 (2H, m), 1.39-1.57 (3H, m), 1.86-2.08 (2H, m), 2.55 (3H, s), 2.58 (3H, s), 2.76-2.83 (1H, m), 2.96-3.04 (1H, m), 3.37-3.52 (2H, m), 3.71 (1H, t), 3.83-4.00 (2H, m), 7.06-7.12 (4H, m), 7.13-7.29 (10H, m).

EXAMPLE 129

Synthesis of 5-(azepan-1-carbonyl)-4-(3-chlorophenyl)-2,6-dimethyl-nicotinic acid (3,3-diphenylpropyl) ester The title compound was obtained by using 100 mg (0.200 mmol) of 4-(3-chlorophenyl)-2,6-dimethylpyridine-3,5-dicarboxylic acid mono (3,3-diphenylpropyl) ester, 29.8 mg (0.300 mmol) of hexamethyleneimine, 76.7 mg (0.400 mmol) of WSC hydrochloride and 3.00 mg of 4-dimethylaminopyridine, in the same manner as that of Example 127.

Yield: 51.7 mg (0.0890 mmol) (45%)

MS (ESI, m/z) 581 (M+H)$^+$ $^1$H-NMR (CDCl3): 0.88-1.05 (1H, m), 1.24-1.50 (6H, m), 1.60-1.73 (1H, m), 1.89-2.05 (2H, m), 2.56 (3H, s), 2.58 (3H, s), 2.73-2.81 (1H, m), 3.04 (1H, dt), 3.35-3.43 (2H, m), 3.70 (1H, t), 3.82-4.00 (2H, m), 7.06-7.12 (4H, m), 7.14-7.20 (3H, m), 7.21-7.29 (7H, m).

EXAMPLE 130

Synthesis of 4-(3-chlorophenyl)-2,6-dimethyl-nicotinic acid (3,3-diphenylpropyl) ester 447 mg (2.33 mmol) of WSC hydrochloride and 0.254 ml (2.29 mmol) of N-methylpiperazine in the ice bath were added to 952 mg (1.90 mmol) of 4-(3-chlorophenyl)-2,6-dimethylpyridine-3,5-dicarboxylic acid mono (3,3-diphenylpropyl) ester in 40 ml of dichloromethane and stirred at room temperature for 2 nights. Saturated aqueous sodium hydrogencarbonate solution was added and the reaction mixture was extracted with dichloromethane. The organic layer was dried over anhydrous sodium sulfate and then concentrated under reduced pressure. The residue was purified by the silica gel chromatography (hexane/ethyl acetate=9/1) to obtain the title compound as a by-product.

Yield: 37.0 mg (0.0800 mmol) (4.3%)

MS (ESI, m/z) 456 (M+H)$^+$ $^1$H-NMR (CDCl3): 2.06-2.16 (2H, q), 2.59 (6H, s), 3.77 (1H, t), 4.02 (2H, t), 6.99 (1H, s), 7.08-7.33 (13H, m), 7.38 (1H, m).

EXAMPLE 131

Synthesis of 4-(2,4-dimethylphenyl)-2,6-dimethyl-5-(piperazine-1-carbonyl)nicotinic acid (3,3-diphenylpropyl) ester 1) Synthesis of 4-[2-acetyl-3-(2,4-dimethylphenyl)-2-propenoyl]-1-piperazinecarboxylic acid t-butyl ester 506 mg (2.71 mmol) of 1-(t-butoxycarbonyl)piperazine, 273 mg (3.23 mmol) of diketene and 0.562 ml (4.07 mmol) of trimethylamine were heated and stirred in 10 ml of toluene at 80° C. for 2 hours. After adding saturated aqueous sodium hydrogencarbonate solution, the reaction mixture was extracted with ethyl acetate. The organic layer was dried over anhydrous magnesium sulfate and then concentrated under reduced pressure. 364 mg (2.71 mmol) of 2,4-dimethylbenzaldehyde was dissolved in 20 ml of 2-propanol. 16.3 mg (0.271 mmol) of piperidine and 22.3 mg (0.271 mmol) of acetic acid were added and stirred at room temperature for 2 days. After the solvent was evaporated under reduced pressure, ethyl acetate was added. The obtained substance was washed with 1 N hydrochloric acid and saturated aqueous sodium hydrogencarbonate solution. The organic layer was dried over anhydrous magnesium sulfate and then concentrated under reduced pressure. The residue was purified by the silica gel chromatography (hexane/ethyl acetate=10/1) to obtain the title compound.

Yield: 648 mg (2.40 mmol) (89%)

MS (ESI, m/z) 387 M+H)$^+$ $^1$H-NMR (CDCl3): 1.42 (9H, s), 2.32 (3H, s), 2.36 (3H, s), 2.43 (3H, s), 2.52-2.65 (1H, m), 2.95-3.33 (4H, m), 3.42-3.78 (3H, m), 6.98 (1H, d), 7.04 (1H, s), 7.40 (1H, d) 7.78 (1H, s).

2) Synthesis of 4-[4-(2,4-dimethylphenyl)-5-(3,3-diphenylpropoxycarbonyl)-2,6-dimethyl-1,4-dihydropyridine-3-carbonyl] piperazine-1-carboxylic acid-t-butyl ester 648 mg (1.67 mmol) of 4-[2-acetyl-3-(2,4-dimethylphenyl)-2-propenoyl]-1-piperazinecarboxylic acid t-butyl ester and 493 mg (1.67 mmol) of 3-aminocrotonate (3,3-diphenylpropyl) ester were heated and stirred in 5 ml of 2-propanol at 80° C. for two nights. After evaporating 2-propanol under reduced pressure, the residue was purified by the silica gel chromatography (hexane/ethyl acetate=5/1 to 1/9) to obtain the title compound.

Yield: 274 mg (0.413 mmol) (25%)

MS (ESI, m/z) 664 (M+H)$^+$ 662 (M−H)$^−$ $^1$H-NMR (CDCl3): 1.42 (9H, s), 1.69 (3H, s), 2.06-2.19 (2H, m), 2.23 (3H, s), 2.28 (3H, s), 2.35 (3H, s), 2.65-2.98 (4H, m), 3.10-3.21 (1H, m), 3.62 (2H, br t), 3.73-3.89 (2H, m) 5.13 (1H, br s), 6.83 (1H, s), 6.89-6.97 (2H, m), 7.08-7.27 (10H, m).

3) Synthesis of 4-(2,4-dimethylphenyl)-2,6-dimethyl-5-(piperazine-1-carbonyl) nicotinic acid (3,3-diphenylpropyl) ester 274 mg (0.413 mmol) of 4-[4-(2,4-dimethylphenyl)-5-(3,3-diphenylpropoxycarbonyl)-2,6-dimethyl-1,4-dihydropyridine-3-carbonyl] piperazine-1-carboxylic acid-t-butyl ester was dissolved in 10 ml of dichloromethane. 5 ml of trifluoroacetate was added and stirred at room temperature for 2 hours. After concentration under reduced pressure, saturated aqueous sodium hydrogencarbonate solution was added and

EXAMPLE 132

Synthesis of 4-(3-chlorophenyl)-2,6-dimethyl-5-(morpholine-4-carbonyl)nicotinic acid (3,3-diphenylpropyl) ester 50.0 mg (0.100 mmol) of 4-(3-chlorophenyl)-2,6-dimethylpyridine-3,5-dicarboxylic acid mono (3,3-diphenylpropyl) ester and 5 ml of thionyl chloride were stirred in DMF at room temperature for 1 hour. After concentration under reduced pressure, the residue was dissolved in 3 ml of dichloromethane. 1 ml of morpholine was added and stirred at room temperature for 6 hours. After concentration under reduced pressure, ethyl acetate was added and the residue was washed with water. The organic layer was dried over anhydrous magnesium sulfate and then concentrated under reduced pressure. The residue was purified by the basic silica gel chromatography (hexane/ethyl acetate=20/1 to 1/4) to obtain the title compound.

Yield: 43.9 mg (0.0771 mmol) (77%)
MS (ESI, m/z) 569 (M+H)$^+$
$^1$H-NMR (CDCl3): 1.92-2.08 (2H, m), 2.56 (3H, s), 2.59 (3H, s), 2.77-2.98 (2H, m), 3.02-3.10 (1H, m), 3.18-3.25 (1H, m), 3.38-3.46 (1H, m), 3.49-3.54 (1H, m), 3.57-3.74 (3H, m), 3.85-4.04 (2H, m), 7.06-7.12 (4H, m), 7.14-7.20 (3H, m), 7.24-7.29 (7H, m).

EXAMPLE 133

Synthesis of 4-(3-chlorophenyl)-6-methyl-5-(methylpiperazine-1-carbonyl)-2-[[2-(pyridine-3-yl)ethoxy] methyl] nicotinic acid (3,3-diphenylpropyl) ester 114 mg (0.590 mmol) of WSC hydrochloride and 0.066 ml (0.590 mmol) of N-methylpiperazine were added to 307 mg (0.490 mmol) of 4-(3-chlorophenyl)-2-methyl-6-[2-(3-pyridine) ethoxy] methyl-1,4-dihydropyridine-3,5-dicarboxylic acid 5-(3,3-diphenylpropyl) ester in 10 ml of dichloromethane in the ice bath and stirred at room temperature overnight. 10 ml of trifluoroacetate was added and the reaction mixture was stirred at room temperature overnight. After concentration under reduced pressure, 1 N aqueous sodium hydroxide solution was added to basify and the reaction mixture was extracted with ethyl acetate. The organic layer was dried over anhydrous sodium sulfate and then concentrated under reduced pressure. The residue was purified by the basic silica gel chromatography (hexane/ethyl acetate=1/9 to 0/100) to obtain the title compound.

Yield: 206 mg (0.340 mmol) (66%)
MS (ESI, m/z) 703 (M+H)$^+$
$^1$H-NMR (CDCl3): 1.58-2.06 (4H, m), 2.17 (3H, s), 2.10-2.38 (2H, m), 2.56 (3H, s), 2.73 (2H, t), 2.82-3.14 (2H, m), 3.42-3.64 (2H, m), 3.60 (2H, t), 3.71 (1H, t), 3.76-4.03 (2H, m), 4.60 (1H, d), 4.87 (1H, d), 7.05-7.29 (15H, m), 7.40-7.46 (1H, m), 8.37-8.42 (2H, m).

EXAMPLE 134

Synthesis of 4-(3,5-dichlorophenyl)-N-(3,3-diphenylpropyl)-2,6-dimethyl-5-(1-piperazinylcarbonyl) nicotinamide 1) Synthesis of 4-[5-(2-cyanoethoxycarbonyl)-4-(3,5-dichlorophenyl)-2,6-dimethyl-1,4-dihydropyridine-3-carbonyl] piperazine-1-carboxylic acid-t-butyl ester 1.66 g (3.88 mmol) of 4-[2-acetyl-3-(3,5-dichlorophenyl)-2-propenoyl] piperazine-1-carboxylic acid t-butyl ester and 598 mg (3.88 mmol) of 3-aminocrotonate 2-cyanoethyl ester were stirred in 30 ml of 2-propanol at 80° C. overnight and then stirred at 120° C. for 2 hours. After concentration under reduced pressure, ethyl acetate was added and the residue was washed with saturated aqueous sodium chloride solution. The organic layer was dried over anhydrous magnesium sulfate and then concentrated under reduced pressure. The residue was purified by the silica gel chromatography (dichloromethane/methanol =100/1 to 30/1) to obtain the title compound.

Yield: 1.31 g (2.32 mmol) (60%)
MS (ESI, m/z) 561 (M–H)$^-$
$^1$H-NMR (CDCl3): 1.44 (9H, s), 1.78 (3H, s), 2.40 (3H, s), 2.50 (2H, br t), 2.75-3.82 (6H, m), 4.08-4.15 (4H, m), 4.86 (1H, br s), 5.41 (1H, br s), 7.10 (2H, d), 7.20 (1H, t).

2) Synthesis of 4-[5-carboxy-4-(3,5-dichlorophenyl)-2,6-dimethyl-1,4-dihydropyridine-3-carbonyl] piperazine-1-carboxylic acid t-butyl ester The title compound was obtained by using 1.31 g (2.32 mmol) of 4-[5-(2-cyanoethoxycarbonyl)-4-(3,5-dichlorophenyl)-2,6-dimethyl-1,4-dihydropyridine-3-carbonyl] piperazine-1-carboxylic acid-t-butyl ester and 4.64 ml (4.64 mmol) of 1 N aqueous sodium hydroxide solution, in the same manner as that of Example 123 2).

Yield: 1.10 g (2.16 mmol) (93%)
MS (ESI, m/z) 508 (M–H)$^-$
$^1$H-NMR (DMSO-d6): 1.36 (9H, s), 1.68 (3H, s), 2.25 (3H, s), 2.99-3.56 (8H, m), 4.78 (1H, s), 7.16 (2H, d), 7.27-7.28 (1H, m), 7.64 (1H, br s).

3) Synthesis of 4-[4-(3,5-dichlorophenyl)-2,6-dimethyl-5-(3,3-diphenylpropylcarbamoyl) pyridine-3-carbonyl] piperazine-1-carboxylic acid t-butyl ester 300 mg (0.588 mmol) of 4-[5-carboxy-4-(3,5-dichlorophenyl)-2,6-dimethyl-1,4-dihydropyridine-3-carbonyl] piperazine-1-carboxylic acid t-butyl ester, 0.12 ml (0.882 mmol) of 3,3-diphenylpropylamine and 248 mg (1.29 mmol) of WSC hydrochloride were stirred in 15 ml of dichloromethane and 1 ml of DMF at room temperature overnight. After dichloromethane was evaporated under reduced pressure, ethyl acetate was added. After being washed with saturated aqueous sodium hydrogencarbonate solution and 1 N hydrochloric acid, the organic layer was dried over anhydrous magnesium sulfate and then concentrated under reduced pressure. The residue was dissolved in 8 ml of acetone. 811 mg (1.48 mmol) of diammonium cerium nitrate (IV) suspended in 8 ml of water was dropped and stirred at room temperature for 1 hour. After acetone was evaporated under reduced pressure, ethyl acetate was added. After being washed with water, the organic layer was dried over anhydrous magnesium sulfate and then concentrated under

--- the reaction mixture was extracted with ethyl acetate. The organic layer was dried over anhydrous sodium sulfate and then concentrated under reduced pressure. The residue was purified by the silica gel chromatography (dichloromethane/methanol=100/1 to 10/1) to obtain the title compound.

Yield: 160 mg (0.285 mmol) (69%)
MS (ESI, m/z) 562 (M+H)$^+$
$^1$H-NMR (CDCl3): 1.85-1.97 (2H, m), 2.13-2.19 (6H, m), 2.52-2.58 (7H, m), 2.68-2.78 (2H, m), 3.01-3.27 (3H, m), 3.55-4.02 (5H, m), 6.81-6.96 (2H, m), 7.06-7.28 (11H, m).

reduced pressure. The residue was purified by the silica gel chromatography (dichloromethane/methanol=100/1 to 80/1) to obtain the title compound.

Yield: 369 mg (0.526 mmol) (90%)
MS (ESI, m/z) 699 (M–H)⁻
$^1$H-NMR (CDCl3): 1.42 (9H, s), 1.82-1.96 (2H, m), 2.51 (3H, s), 2.57 (3H, s), 2.66-3.01 (5H, m), 3.20-3.54 (6H, m), 5.35 (1H, br t), 7.08-7.11 (4H, m), 7.15-7.30 (7H, m), 7.36 (2H, br s).

4) Synthesis of 4-(3,5-dichlorophenyl)-N-(3,3-diphenylpropyl)-2,6-dimethyl-5-(1-piperazinylcarbonyl) nicotinamide The title compound was obtained by using 362 mg (0.516 mmol) of 4-[4-(3,5-dichlorophenyl)-2,6-dimethyl-5-(3,3-diphenylpropylcarbamoyl) pyridine-3-carbonyl] piperazine-1-carboxylic acid t-butyl ester and 5 ml of trifluoroacetate, in the same manner as that of Example 124 3).

Yield: 244 mg (0.406 mmol) (79%)
MS (ESI, m/z) 601 (M+H)⁺
$^1$H-NMR (CDCl3): 1.65-1.97 (2H, m), 2.14-2.21 (1H, m), 2.42-2.64 (9H, m), 2.75-2.93 (3H, m), 2.95-3.04 (1H, m), 3.31-3.42 (1H, m), 3.48-3.54 (3H, m), 3.89 (1H, br t), 7.08-7.11 (4H, m), 7.14-7.20 (3H, m), 7.24-7.30 (4H, m), 7.33-7.39 (2H, br s).

EXAMPLE 135

Synthesis of 4-(2,4-dimethylphenyl)-2,6-dimethyl-5-(4-methylpiperazine-1-carbonyl)nicotinic acid (3,3-diphenylpropyl) ester 169 mg (0.301 mmol) of 4-(2,4-dimethylphenyl)-2,6-dimethyl-5-(piperazine-1-carbonyl)nicotinic acid (3,3-diphenylpropyl) ester was dissolved in 10 ml of DMF. 62.4 mg (01.301 mmol) of potassium carbonate was added and stirred for 30 minutes. 51.3 mg (0.361 mmol) of methyl iodide was added under cooling with ice and stirred at the same temperature for 1 hour. The reaction mixture was further stirred for 10 minutes after adding water. After evaporating DMF under reduced pressure, the reaction mixture was diluted with ethyl acetate and washed with saturated aqueous sodium chloride solution. The organic layer was dried over anhydrous magnesium sulfate and then concentrated under reduced pressure. The residue was purified by the silica gel chromatography (dichloromethane/methanol =50/1 to 10/1) to obtain the title compound.

Yield: 9.50 mg (0.0165 mmol) (5.5%)
MS (ESI, m/z) 433 (M+H)⁺
$^1$H-NMR (CDCl3): 1.86-1.99 (2H, m), 2.15-2.24 (12H, m), 2.53-2.59 (6H, m), 3.03-3.22 (3H, m), 3.66-4.02 (5H, m), 6.80-6.98 (2H, m), 7.03-7.28 (11H, m).

EXAMPLE 136

Synthesis of 4-(2,5-dimethylphenyl)-2,6-dimethyl-5-(piperazine-1-carbonyl)nicotinic acid (3,3-diphenylpropyl) ester The title compound was obtained by using 826 mg (2.14 mmol) of 4-[2-acetyl-3-(2,5-dimethylphenyl)-2-propenoyl]-1-piperazinecarboxylic acid t-butyl ester and 632 mg (2.14 mmol) of 3-aminocrotonate (3,3-diphenylpropyl) ester, in the same manner as that of Example 131.

Yield: 329 mg (0.586 mmol) (27%) (2 steps)
MS (ESI, m/z) 562 (M+H)⁺
$^1$H-NMR (CDCl3): 1.78-1.94 (2H, m), 2.12 (3H, s), 2.19 (3H, s), 2.57-2.71 (8H, m), 2.97-3.13 (2H, m), 3.29-3.49 (2H, m), 3.58-3.73 (2H, m), 3.76-3.97 (3H, m), 6.68 (1H, s), 7.03-7.29 (13H, m).

EXAMPLE 137

Synthesis of 4-(4-chlorophenyl)-2,6-dimethyl-5-(piperazine-1-carbonyl)nicotinic acid (3,3-diphenylpropyl) ester The title compound was obtained by using 774 mg (1.97 mmol) of 4-[2-acetyl-3-(4-chlorophenyl)-2-propenoyl]-1-piperazinecarboxylic acid t-butyl ester and 582 mg (1.97 mmol) of 3-aminocrotonate (3,3-diphenylpropyl) ester, in the same manner as that of Example 131.

Yield: 337 mg (0.593 mmol) (30%) (2 steps)
MS (ESI, m/z) 568 (M+H)⁺
$^1$H-NMR (CDCl3): 1.87-2.08 (3H, m), 2.24-2.32 (1H, m), 2.52 (3H, s), 2.58 (3H, s), 2.76-2.84 (1H, m), 3.00-3.05 (2H, m), 3.22-3.31 (1H, m), 3.62-3.78 (3H, m), 3.85-4.00 (2H, m), 7.05-7.30 (14H, m).

EXAMPLE 138

Synthesis of 4-(2,5-dimethylphenyl)-2,6-dimethyl-5-(4-methylpiperazine-1-carbonyl)nicotinic acid (3,3-diphenylpropyl) ester The title compound was obtained by using 236 mg (0.420 mmol) of 4-(2,5-dimethylphenyl)-2,6-dimethyl-5-(piperazine-1-carbonyl)nicotinic acid (3,3-diphenylpropyl) ester, 59.6 mg (0.420 mmol) of methyl iodide and 69.7 mg (0.504 mmol) of potassium carbonate, in the same manner as that of Example 135.

Yield: 126 mg (0.219 mmol) (52%)
MS (ESI, m/z) 576 (M+H)⁺
$^1$H-NMR (CDCl3): 1.81-2.08 (3H, m), 2.12-2.29 (11H, m), 2.52-2.60 (7H, m), 3.04-3.23 (2H, m), 3.30-3.39 (1H, m), 3.52-3.61 (1H, m), 3.73 (1H, t), 3.80-3.94 (2H, m), 6.73 (1H, s), 6.96-7.28 (12H, m).

EXAMPLE 139

Synthesis of 4-(2-chlorophenyl)-2,6-dimethyl-5-(piperazine-1-carbonyl)nicotinic acid (3,3-diphenylpropyl) ester The title compound was obtained by using 731 mg (1.86 mmol) of 4-[2-acetyl-3-(2-chlorophenyl)-2-propenoyl]-1-piperazinecarboxylic acid t-butyl ester and 550 mg (1.86 mmol) of 3-aminocrotonate (3,3-diphenylpropyl) ester, in the same manner as that of Example 131.

Yield: 35.6 mg (0.0627 mmol) (3.4%) (2 steps)
MS (ESI, m/z) 568 (M+H)⁺
$^1$H-NMR (CDCl3): 1.67-2.06 (2H, m), 2.28-2.44 (2H, m), 2.53-2.66 (7H, m), 2.71-2.80 (1H, m), 3.09-3.13 (2H, m), 3.34-3.52 (2H, m), 3.76-3.98 (3H, m), 7.09-7.30 (14H, m).

EXAMPLE 140

Synthesis of 4-(4-chlorophenyl)-2,6-dimethyl-5-(4-methylpiperazine-1-carbonyl)nicotinic acid (3,3-diphenylpropyl) ester The title compound was obtained by using 131 mg (0.231 mmol) of 4-(4-chlorophenyl)-2,6-dimethyl-5-(piperazine-1-carbonyl)nicotinic acid (3,3-diphenylpropyl) ester, 32.7 mg (0.231 mmol) of methyl iodide and 38.3 mg (0.277 mmol) of potassium carbonate, in the same manner as that of Example 135.

Yield: 81.2 mg (0.139 mmol) (60%)

MS (ESI, m/z) 582 (M+H)$^+$ $^1$H-NMR (CDCl3): 1.70-1.76 (2H, m), 1.85-2.13 (3H, m), 2.15 (3H, s), 2.24-2.31 (1H, m), 2.55 (3H, s), 2.58 (3H, s), 2.71-2.78 (1H, m), 3.00-3.08 (1H, m), 3.31-3.39 (1H, m), 3.05-3.68 (1H, m), 3.74 (1H, t), 3.83-3.99 (2H, m), 7.05-7.12 (4H, m), 7.14-7.20 (2H, m), 7.24-7.29 (8H, m).

EXAMPLE 141

Synthesis of 4-(3-chlorophenyl)-5-[(3,3-diphenylpropoxy)carbonyl]-2-methyl-6-[[2-(pyridine-3-yl)ethoxy] methyl] nicotinic acid 2 ml of acetone was added to 80.0 mg (0.130 mmol) of 4-(3-chlorophenyl)-2-methyl-6-[2-(3-pyridine) ethoxy] methyl-1,4-dihydropyridine-3,5-dicarboxylic acid 5-(3,3-diphenylpropyl) ester. 170 mg (0.310 mmol) of diammonium cerium nitrate (IV) suspended in 1 ml of water was added and stirred at room temperature for 30 minutes. After adding water, the reaction mixture was extracted with ethyl acetate. The organic layer was dried over anhydrous sodium sulfate and then concentrated under reduced pressure to obtain the title compound.

Yield: 68.0 mg (0.110 mmol) (85%)

MS (ESI, m/z) 619 (M−H)$^−$ $^1$H-NMR (DMSO-d6): 1.94-2.09 (2H, m), 2.54 (3H, s), 2.93 (2H, t), 3.66 (2H, t), 3.71 (1H, t), 3.84 (1H, t), 4.66 (2H, s), 7.13-7.32 (12H, m), 7.40 (1H, t), 7.46-7.50 (1H, m), 7.96 (1H, t), 8.38 (1H, d), 8.70-8.82 (2H, m).

EXAMPLE 142

Synthesis of 4-(3-fluorophenyl)-2,6-dimethyl-5-piperazine-1-carbonyl)nicotinic acid (3,3-diphenylpropyl) ester The title compound was obtained by using 471 mg (1.25 mmol) of 4-[2-acetyl-3-(3-fluorophenyl)-2-propenoyl]-1-piperazinecarboxylic acid t-butyl ester and 369 mg (1.25 mmol) of 3-aminocrotonate (3,3-diphenylpropyl) ester, in the same manner as that of Example 131.

Yield: 45.8 mg (0.0830 mmol) (6.6%) (2 steps)

MS (ESI, m/z) 552 (M+H)$^+$ $^1$H-NMR (CDCl3): 1.88-2.08 (2H, m), 2.13-2.23 (1H, m), 2.43-2.62 (8H, m), 2.74-2.83 (2H, m), 2.99-3.06 (1H, m), 3.37-3.46 (1H, m), 3.51-3.58 (1H, m), 3.72 (1H, t), 3.84-3.98 (2H, m), 6.93-7.00 (1H, m), 7.06-7.29 (13H, m).

EXAMPLE 143

Synthesis of 4-(3-chlorophenyl)-5-(1,4-diazepan-1-carbonyl)-2,6-dimethylnicotinic acid (3,3-diphenylpropyl) ester 200 mg (0.398 mmol) of 4-(3-chlorophenyl)-2,6-dimethyl-1,4-dihydropyridine-3,5-dicarboxylic acid mono (3,3-diphenylpropyl) ester, 120 mg (1.20 mmol) of homopiperazine and 230 mg (1.20 mmol) of WSC hydrochloride were stirred in 6 ml of dichloromethane at room temperature overnight. 0.8 ml of DMF was added and stirred at 60° C. for 5 hours. After concentration under reduced pressure, chloroform was added. After being washed with saturated aqueous sodium hydrogencarbonate solution, the organic layer was dried over anhydrous magnesium sulfate and then concentrated under reduced pressure. The obtained substance was dissolved in 5 ml of dichloromethane. 2 ml of trifluoroacetate was added and stirred at room temperature for 30 minutes. After concentration under reduced pressure, ethyl acetate was added and the reaction mixture was washed with saturated aqueous sodium hydrogencarbonate solution. The organic layer was dried over anhydrous magnesium sulfate and then concentrated under reduced pressure. The residue was purified by the thin layer silica gel chromatography (dichloromethane/methanol=9/1) to obtain the title compound.

Yield: 36.8 mg (0.0632 mmol) (16%)

MS (ESI, m/z) 582 (M+H)$^+$ $^1$H-NMR (CDCl3): 1.60-1.72 (1H, m), 1.78-2.09 (4H, m), 2.54-2.62 (7H, m), 2.82-2.97 (2H, m), 3.05-3.20 (2H, m), 3.42-3.55 (2H, m), 3.70 (1H, t), 3.88 (2H, dt), 3.93-4.03 (1H, m), 7.05-7.12 (4H, m), 7.14-7.29 (10H, m).

EXAMPLE 144

Synthesis of 4-(3-chlorophenyl)-5-(4-hydroxypiperidine-1-carbonyl)-2,6-dimethylnicotinic acid (3,3-diphenylpropyl) ester The title compound was obtained by using 200 mg (0.398 mmol) of 4-(3-chlorophenyl)-2,6-dimethyl-1,4-dihydropyridine-3,5-dicarboxylic acid mono (3,3-diphenylpropyl) ester, 80.9 mg (0.797 mmol) of 4-hydroxypiperazine and 2.0 ml of trifluoroacetate, in the same manner as that of Example 143.

Yield: 135 mg (0.232 mmol) (58%)

MS (ESI, m/z) 583 (M+H)$^+$ $^1$H-NMR (CDCl3): 1.28-1.43 (1H, m), 1.46-1.70 (3H, m), 1.72-1.84 (1H, m), 1.90-2.06 (2H, m), 2.54 (3H, d), 2.58 (3H, s), 2.63-2.96 (1H, m), 3.08-3.30 (2H, m), 3.71 (1H, t), 3.75-3.81 (1H, m), 3.84-4.02 (3H, m), 7.06-7.29 (14H, m).

EXAMPLE 145

Synthesis of 4-(3-chlorophenyl)-6-methyl-2-(methylthio)-pyrimidine-5-carboxylic acid 3-phenylpropyl ester 1) Synthesis of 4-(3-chlorophenyl)-6-methyl-2-(methylthio)-1,4-dihydropyridine-5-carboxylic acid 3-phenylpropyl ester 200 mg (0.583 mmol) of 2-acetyl-3-(3-chlorophenyl) acrylic acid 3-phenylpropyl ester was dissolved in 10 ml of DMF. 130 mg (0.467 mmol) of methylisothiourea-sulfate and 95.6 mg (1.17 mmol) of sodium acetate was added at room temperature and stirred at 60° C. for 2 days. After DMF was evaporated under reduced pressure, the reaction mixture was diluted with ethyl acetate and washed with saturated aqueous sodium chloride solution. The organic layer was dried over anhydrous magnesium sulfate and then concentrated under reduced pressure. The residue was purified by the silica gel chromatography (hexane/ethyl acetate=10/1 to 2/1) to obtain the title compound.

Yield: 193 mg (0.465 mmol) (80%)
MS (ESI, m/z) 415 (M+H)$^+$ 413 (M–H)$^-$
$^1$H-NMR (CDCl3): 1.84-1.93 (2H, m), 2.36 (3H, s), 2.42 (3H, s), 2.56 (2H, t), 4.02-4.11 (2H, m), 5.72 and 6.26 (total 1H, ratio 1:1, br s, br s, respectively), 7.07-7.10 (2H, m), 7.17-7.31 (7H, m).

2) Synthesis of 4-(3-chlorophenyl)-6-methyl-2-(methylthio)-pyrimidine-5-carboxylic acid 3-phenylpropyl ester 88.5 mg (0.213 mmol) of 4-(3-dichlorophenyl)-2-(methylthio)-1,4-dihydropyrimidine-5-carboxylic acid 3-phenylpropyl ester was dissolved in 5 ml of toluene. 96.8 mg (0.427 mmol) of 2,3-dichloro-5,6-dicyano-1,4-benzochinon (hereinafter abbreviated as DDQ) was added and stirred at 50° C. for 1 hour. After filtration of insoluble matters, the filtrate was diluted with ethyl acetate. The organic layer was washed with saturated aqueous sodium chloride solution and dried over anhydrous magnesium sulfate and then concentrated under reduced pressure. The residue was purified by the silica gel chromatography (hexane/ethyl acetate=10/1 to 3/1) to obtain the title compound.

Yield: 46.0 mg (0.111 mmol) (52%)
MS (ESI, m/z) 413 (M+H)$^+$
$^1$H-NMR (CDCl3): 1.75 (2H, quint), 2.38 (2H, t), 2.58 (3H, s), 2.62 (3H, s), 4.13 (2H, t), 7.04 (2H, d), 7.15-7.28 (3H, m), 7.32-7.43 (2H, m), 7.50 (1H, d), 7.66 (1H, s).

EXAMPLE 146

Synthesis of 4-(3-chlorophenyl)-6-(methoxymethyl)-2-(methylthio)-pyrimidine-5-carboxylic acid 3-phenylpropyl ester The title compound was obtained by using 170 mg (0.456 mmol) of 3-(3-chlorophenyl)-2-(methoxyacetyl)-2-acrylic acid 3-phenylpropyl ester, 96.0 mg (0.345 mmol) of methylisothiourea-sulfate and 75.5 mg (0.920 mmol) of sodium acetate, in the same manner as that of Example 145.

Yield: 39.6 mg (0.0894 mmol) (20%) (2 steps)
MS (ESI, m/z) 443 (M+H)$^+$
$^1$H-NMR (CDCl3): 1.81 (2H, m), 2.43 (2H, t), 2.63 (3H, s), 3.37 (3H, s), 4.14 (2H, t), 4.65 (2H, s), 7.07 (2H, d), 7.18-7.45 (5H, m), 7.51-7.54 (1H, m), 7.67-7.69 (1H, m).

EXAMPLE 147

Synthesis of 4-(3-chlorophenyl)-6-methyl-2-(methylthio)-pyrimidine-5-carboxylic acid (3,3-diphenylpropyl) ester The title compound was obtained by using 500 mg (1.19 mmol) of 2-acetyl-3-(3-chlorophenyl)-2-acrylic acid (3,3-diphenylpropyl) ester, 169 mg (1.79 mmol) of acetamidine hydrochloride and 195 mg (2.38 mmol) of sodium acetate, in the same manner as that of Example 145.

Yield: 253 mg (0.517 mmol) (44%) (2 steps)
MS (ESI, m/z) 489 (M+H)$^+$
$^1$H-NMR (CDCl3): 2.16 (2H, q), 2.55 (3H, s), 2.62 (3H, s), 3.78 (1H, t), 4.08 (2H, t), 7.10-7.21 (6H, m), 7.24-7.29 (5H, m), 7.36 (1H, dt), 7.46 (1H, dt), 7.67 (1H, t).

EXAMPLE 148

Synthesis of N-[4-(3-chlorophenyl)-6-methyl-2-(methylthio)-5-pyrimidinyl]-3-phenylpropanamide 1) Synthesis of 2-acetyl-3-(3-chlorophenyl) acrylic acid ethylester 5.00 g (38.4 mmol) of acetoacetic acid and 5.40 g (38.4 mmol) of 3-chlorobenzaldehyde were dissolved in 50 ml of 2-propanol. 327 mg (3.84 mmol) of piperidine and 231 mg (3.84 mmol) of acetic acid were added and stirred at room temperature for one day. After the solvent was evaporated, ethyl acetate was added and the reaction mixture was washed with 1 N hydrochloric acid and saturated aqueous sodium hydrogencarbonate solution. The organic layer was dried over anhydrous magnesium sulfate and then concentrated under reduced pressure. The residue was purified by the silica gel chromatography (hexane/ethyl acetate=5/1) to obtain the title compound.

Yield: 9.45 g (37.4 mmol) (97%)
MS (ESI, m/z) 253 (M+H)$^+$
$^1$H-NMR (CDCl3): 1.29 (3H, t), 2.42 (3H, s), 4.34 (2H, q), 7.32-7.40 (3H, m), 7.44 (1H, br), 7.50 (1H, s).

2) Synthesis of 4-(3-chlorophenyl)-6-methyl-2-(methylthio)-1,4-dihydropyrimidine-5-carboxylic acid ethylester 3.33 g (13.2 mmol) of 2-acetyl-3-(3-chlorophenyl) acrylic acid ethylester was dissolved in 30 ml of n-butanol. 2.93 g (10.5 mmol) of methylisothiourea-sulfate and 2.00 g (19.8 mmol) of triethylamine were added at room temperature and stirred at 100° C. for one day. After n-butanol was evaporated under reduced pressure, the reaction mixture was diluted with ethyl acetate and washed with saturated aqueous sodium chloride solution. The organic layer was dried over anhydrous magnesium sulfate and then concentrated under reduced pressure. The residue was purified by the silica gel chromatography (hexane/ethyl acetate=10/1) to obtain the title compound.

Yield: 2.09 g (6.42 mmol) (49%)
MS (ESI, m/z) 325 (M+H)$^+$ 323 (M–H)$^-$
$^1$H-NMR (CDCl3): 1.21 (3H, t), 2.32 (3H, s), 2.41 (3H, s), 4.11 (2H, q), 5.70 (1H, s), 6.28 (1H, br s), 7.19-7.28 (4H, m).

3) Synthesis of 4-(3-chlorophenyl)-6-methyl-2-(methylthio)-5-pyrimidinecarboxylic acid ethylester 2.09 g (6.43 mmol) of 4-(3-chlorophenyl)-6-methyl-2-(methylthio)-1,4-dihydropyrimidine-5-carboxylic acid ethylester was dissolved in 30 ml of chloroform. 8.39 g (96.5 mmol) of manganese dioxide was added at room temperature and stirred at 80° C. for 2 hours. After filtration of insoluble matters, the obtained filtrate was concentrated under reduced pressure. The residue was purified by the silica gel chromatography (hexane/ethyl acetate=10/1) to obtain the title compound.

Yield: 1.44 g (4.47 mmol) (70%)
MS (ESI, m/z) 323 (M+H)$^+$
$^1$H-NMR (CDCl3): 1.10 (3H, t), 2.57 (3H, s), 2.61 (3H, s), 4.19 (2H, q), 7.34-7.52 (3H, m), 7.64-6.65 (1H, m).

4) Synthesis of 4-(3-chlorophenyl)-6-methyl-2-(methylthio)-5-pyrimidinecarboxylic acid 1.44 g (4.47 mmol) of 4-(3-chlorophenyl)-6-methyl-2-(methylthio)-5-pyrimidinecarboxylic acid ethylester was dissolved in 10 ml of THF and 5 ml of water. 225 mg (5.36 mmol) of lithium hydroxide monohydrate was added and stirred at 50° C. for 12 hours. 10 ml of water was added thereto and the organic layer was batched off. The obtained aqueous layer was diluted with ethyl acetate and washed with 5 ml of 3 N hydrochloric acid and then with 5 ml of saturated aqueous sodium chloride solution. The organic layer was dried over anhydrous magnesium sulfate and then concentrated under reduced pressure to obtain the title compound.

Yield: 1.21 g (4.11 mmol) (92%)
MS (ESI, m/z) 293 (M−H)⁻
$^1$H-NMR (CDCl3): 2.56 (3H, s), 2.62 (3H, s), 7.38-7.49 (2H, m), 7.54-7.68 (1H, m), 7.70-7.72 (1H, m).

5) Synthesis of t-butyl 4-methyl-6-(methylphenyl)-2-(methylthio)-5-pyrimidinyl carbamate 871 mg (2.95 mmol) of 4-(3-chlorophenyl)-6-methyl-2-(methylthio)-5-pyrimidinecarboxylic acid was dissolved in 20 ml of t-butanol. 448 mg (4.43 mmol) of triethylamine and 1.22 g (4.43 mmol) of diphenylphosphorylazide were added at room temperature and stirred at 100° C. for 3 hours. After t-butanol was evaporated under reduced pressure, the reaction mixture was diluted with ethyl acetate and washed with saturated aqueous sodium chloride solution. The organic layer was dried over anhydrous magnesium sulfate and then concentrated under reduced pressure. The residue was purified by the silica gel chromatography (hexane/ethyl acetate=10/1) to obtain the title compound.

Yield: 140 mg (0.383 mmol) (13%)
MS (ESI, m/z) 366 (M+H)⁺ 364 (M−H)⁻
$^1$H-NMR (CDCl3): 1.45 (9H, s), 2.51 (3H, s), 2.58 (3H, s), 5.75 (2H, br), 7.32-7.43 (2H, m), 7.55-7.58 (1H, m), 7.65 (1H, br s).

6) Synthesis of 4-(3-chlorophenyl)-6-methyl-2-(methylthio)-5-pyrimidinamine 10 ml of 4 N hydrochloric acid-ethyl acetate solution was added to 125 mg (0.342 mmol) of t-butyl 4-methyl-6-(methylphenyl)-2-(methylthio)-5-pyrimidinyl carbamate under cooling with ice and stirred at room temperature for one day. 1 ml of trifluoroacetate was added thereto and stirred at 50° C. for 12 hours. After the solvent was evaporated under reduced pressure, the reaction mixture was diluted with ethyl acetate and washed with saturated aqueous sodium hydrogencarbonate solution and saturated aqueous sodium chloride solution. The organic layer was dried over anhydrous magnesium sulfate and then concentrated under reduced pressure to obtain the title compound.

Yield: 91.0 mg (0.342 mmol) (quantitative yield)
MS (ESI, m/z) 266 (M+H)⁺
$^1$H-NMR (CDCl3): 2.44 (3H, s), 2.56 (3H, s), 7.42-7.43 (2H, m), 7.61-7.63 (1H, m), 7.73-7.74 (1H, m).

7) Synthesis of N-[4-(3-chlorophenyl)-6-methyl-2-(methylthio)-5-pyrimidinyl]-3-phenylpropanamide 51.4 mg (0.342 mmol) of 3-phenylpropionic acid was dissolved in 1 ml of thionyl chloride. A catalytic amount of DMF was added and stirred at room temperature for 3 hours. After the solvent was evaporated under reduced pressure, 45.4 mg (0.171 mmol) of 4-(3-chlorophenyl)-6-methyl-2-(methylthio)-5-pyrimidinamine and 1 ml of pyridine were added and stirred at 50° C. overnight. After the solvent was evaporated under reduced pressure, the reaction mixture was diluted with ethyl acetate and washed with saturated aqueous sodium chloride solution. The organic layer was dried over anhydrous magnesium sulfate and then concentrated under reduced pressure. The residue was purified by the silica gel chromatography (hexane/ethyl acetate=10/1 to 1/1) to obtain the title compound.

Yield: 10.6 mg (0.0266 mmol) (16%)
MS (ESI, m/z) 398 (M+H)⁺ 396 (M−H)⁻
$^1$H-NMR (CDCl3): 2.31 (3H, s), 2.38 (2H, t), 2.57 (3H, s), 2.62 (2H, t), 6.58 (1H, br), 7.17-7.49 (8H, m), 7.56-7.57 (1H, m).

EXAMPLE 149

Synthesis of N-[4-(3-chlorophenyl)-6-methyl-2-(methylthio)-5-pyrimidinyl]-4-phenylbutanamide 56.2 mg (0.342 mmol) of 4-phenylbutyric acid was dissolved in 1 ml of thionyl chloride. A catalytic amount of DMF was added and stirred at room temperature for 3 hours. After the solvent was evaporated under reduced pressure, 45.4 mg (0.171 mmol) of 4-(3-chlorophenyl)-6-methyl-2-(methylthio)-5-pyrimidinamine and 1 ml of pyridine were added and stirred at 50° C. overnight. After the solvent was evaporated under reduced pressure, the reaction mixture was diluted with ethyl acetate and washed with saturated aqueous sodium chloride solution. The organic layer was dried over anhydrous magnesium sulfate and then concentrated under reduced pressure. The residue was purified by the silica gel chromatography (hexane/ethyl acetate=10/1 to 1/1) to obtain the title compound.

Yield: 12.3 mg (0.0299 mmol) (18%)
MS (ESI, m/z) 412 (M+H)⁺ 410 (M−H)⁻
$^1$H-NMR (CDCl3): 2.00 (3H, quint), 2.29 (2H, t), 2.44 (3H, s), 2.58 (3H, s), 2.65 (2H, t), 7.14-7.47 (8H, m), 7.56-7.57 (1H, m).

EXAMPLE 150

Synthesis of 4-(3-chlorophenyl)-6-[(2-hexylethoxy)methyl]-2-phenylpyrimidine-5-carboxylic acid 3,3-diphenylpropyl ester

1) Synthesis of 3-(3-chlorophenyl)-2-[(2-cyclohexylethoxy) acetyl]-2-propenoic acid 3,3-diphenylpropyl ester 1.23 g (2.90 mmol) of 4-(2-cyclohexylethoxy)-3-oxobutanoic acid 3,3-diphenylpropyl ester, 0.33 ml (2.91 mmol) of 3-chlorobenzaldehyde, 0.05 ml (0.51 mmol) of piperidine and catalytic amount of p-toluenesulfonic acid were refluxed in 20 ml of benzene removing water for 1.5 hours. After adding ethyl acetate, the organic layer was washed with 1 N hydrochloric acid and saturated aqueous sodium hydrogencarbonate solution, and dried over anhydrous sodium sulfate and then concentrated under reduced pressure to obtain the title compound.

Yield: 1.59 g (2.91 mmol) (quantitative yield)

2) Synthesis of 4-(3-chlorophenyl)-6-[(2-cyclohexylethoxy) acetyl]-2-phenyl-1,4-dihydropyrimidine-5-carboxylic acid 3,3-diphenylpropyl ester 194 mg (1.24 mmol) of benzamidine hydrochloride and 179 mg (1.30 mmol) of potassium carbonate were heated and stirred in 5 ml of DMF at 60° C. for 1 hour. 670 mg (1.23 mmol) of 3-(3-chlorophenyl)-2-[(2-cyclohexylethoxy) acetyl]-2-propenoic acid 3,3-diphenylpropyl ester dissolved in 5 ml of DMF was added thereto, heated and stirred at 60° C. overnight. After DMF was evaporated under reduced pressure, 1 N hydrochloric acid was added and the reaction mixture was extracted with ethyl acetate. The organic layer was dried over anhydrous sodium sulfate and then concentrated under reduced pressure. The residue was purified by the silica gel chromatography (hexane/ethyl acetate=4/1) to obtain the title compound.

Yield: 245 mg (0.38 mmol) (31%)

MS (ESI, m/z) 645 (M−H)−

1H-NMR (CDCl3): 0.86-1.79 (13H, m), 2.31 (2H, qua), 3.64 (2H, t), 3.88 (1H, t), 3.99 (2H, t), 4.79 (2H, qua), 5.85 (1H, s), 7.04-7.10 (2H, m), 7.12-7.37 (11H, m), 7.40-7.52 (4H, m), 7.70-7.87 (2H, m), 8.21 (1H, s).

3) Synthesis of 4-(3-chlorophenyl)-6-[(2-cyclohexylethoxy) methyl]-2-phenylpyrimidine-5-carboxylic acid 3,3-diphenylpropyl ester 89.8 mg (0.14 mmol) of 4-(3-chlorophenyl)-6-[(2-cyclohexylethoxy)methyl]-2-phenyl-1,4-dihydropyrimidine-5-carboxylic acid 3,3-diphenylpropyl ester and 94.3 mg (0.42 mmol) of 2,3-dichloro-5,6-dicyano-1,4-benzochinon (DDQ) were refluxed in 20 ml of benzene for 3 hours. After adding water, the reaction mixture was extracted with ethyl acetate. The organic layer was dried over anhydrous sodium sulfate and then concentrated under reduced pressure. The residue was purified by the silica gel chromatography (hexane/ethyl acetate=9/1) to obtain the title compound.

Yield: 68 mg (0.105 mmol) (76%)

MS (ESI, m/z) 645 (M+H)+

1H-NMR (CDCl3): 0.74-1.68 (13H, m), 2.24 (2H, qua), 3.48 (2H, t), 3.82 (1H, t), 4.09-4.16 (2H, m), 4.80 (2H, s), 7.11-7.42 (12H, m), 7.47-7.59 (4H, m), 7.79 (1H, t), 8.53-8.58 (2H, m).

EXAMPLE 151

Synthesis of 4-(3-chlorophenyl)-5-(3-(4-(5H-dibenzo[a,d]cyclohepten-5-ylidene) piperidine-1-yl) propoxy) carbonyl-2,6-dimethylnicotinic acid

1) Synthesis of 4-(3-chlorophenyl)-2,6-dimethyl-1,4-dihydropyridine-3,5-dicarboxylic acid 3-(2-cyanoethyl) ester 5-(3-(4-(5H-dibenzo[a,d] cyclohepten-5-ylidene) piperidine-1-yl)propan-1-yl) ester 366 mg (0.88 mmol) of acetoacetic acid 3-(4-(5H-dibenzo[a,d]cyclohepten-5-ylidene) piperidine-1-yl) propyl ester and 136 mg (1.76 mmol) of ammonium acetate were heated and stirred in 10 ml of 2-propanol at 60° C. for 2 days. After 2-propanol was evaporated, ethyl acetate was added and the reaction mixture was washed with saturated aqueous sodium hydrogencarbonate solution. The organic layer was dried over anhydrous sodium sulfate and then concentrated under reduced pressure. 10 ml of 2-propanol and 245 mg (0.88 mmol) of 2-(3-chlorobenzylidene)acetoacetic acid 2-cyanoethyl were added to the residue and the residue was heat-refluxed for 4 hours. After evaporating 2-propanol, the residue was purified by the basic silica gel chromatography (hexane/ethyl acetate=9/1 to 1/9) to obtain the title compound.

Yield: 339 mg (0.503 mmol) (57%)

MS (ESI, m/z) 674 M+H)+

1H-NMR (CDCl3): 1.67-2.39 (10H, m), 2.34 (6H, s), 2.44-2.57 (2H, m), 2.61 (2H, t), 3.98-4.16 (2H, m), 4.17-4.32 (2H, m), 4.93 (1H, s), 5.72 (1H, s), 6.92 (2H, s), 7.06-7.38 (12H, m).

2) Synthesis of 4-(3-chlorophenyl)-2,6-dimethyl-1,4-dihydropyridine-3,5-dicarboxylic acid mono (3-(4-(5H-dibenzo[a,d] cyclohepten-5-ylidene)piperidine-1-yl) propan-1-yl) ester 5 ml of methanol and 0.434 ml of 1 N aqueous sodium hydroxide solution were added to 244 mg (0.36 mmol) of 4-(3-chlorophenyl)-2,6-dimethyl-1,4-dihydropyridine-3,5-dicarboxylic acid 3-(2-cyanoethyl) ester 5-(3-(4-(5H-dibenzo[a,d] cyclohepten-5-ylidene) piperidine-1-yl )propan-1-yl) ester and stirred at room temperature for 5 hours. After adding 1 N hydrochloric acid, precipitates were taken by the filtration and dried under reduced pressure to obtain the title compound.

Yield: 202 mg (0.325 mmol) (90%)

MS (ESI, m/z) 621 (M+H)+

1H-NMR (DMSO): 1.55-1.72 (2H, m), 1.88-2.08 (4H, m), 2.10-2.29 (4H, m), 2.21 (3H, s), 2.25 (3H, s), 2.33-2.46 (2H, m), 3.84-4.05 (2H, m), 4.83 (1H, s), 6.95 (2H, s), 7.05-7.38 (12H, m), 8.79 (1H, s).

3) Synthesis of 4-(3-chlorophenyl)-5-(3-(4-(5H-dibenzo[a,d] cyclohepten-5-ylidene)piperidine-1-yl) propoxy) carbonyl-2,6-dimethylnicotinic acid 5 ml of acetone was added to 132 mg (0.21 mmol) of 4-(3-chlorophenyl)-2,6-dimethyl-1,4-dihydropyridine-3,5-dicarboxylic acid mono (3-(4-(5H-dibenzo[a,d] cyclohepten-5-ylidene) piperidine-1-yl) propan-1-yl) ester. 233 mg (0.43 mmol) of cerium ammonium nitrate suspended in 5 ml of water was added and stirred at room temperature for 2 hours. After acetone was evaporated under reduced pressure, ethyl acetate was added and precipitates were taken by the filtration and dried under reduced pressure to obtain the title compound.

Yield: 130 mg (0.21 mmol) (100%)

MS (ESI, m/z) 619 (M+H)+

1H-NMR (CDCl3): 1.64-2.72 (10H, m), 2.53 (3H, s), 2.59 (3H, s), 3.19-3.34 (2H, m), 3.82-4.01 (2H, m), 6.92 (2H, s), 7.08-7.40 (12H, m).

EXAMPLE 152

Synthesis of 4-(3-chlorophenyl)-2,6-dimethyl-5-(4-methylpiperazine-1-carbonyl)nicotinic acid (2-(5H-dibenzo[a,d] cyclohepten-5-yl) ethyl) ester 1) Synthesis of 4-(3-chlorophenyl)-2,6-dimethyl-1,4-dihydropyridine-3,5-dicarboxylic acid mono 3-(2-cyanoethyl ester 5-(2-(5H-dibenzo[a,d] cyclohepten-5-yl) ethyl) ester 472 mg (2.0 mmol) of 1-(5H-dibenzo[a,d] cyclohepten-5-yl) ethanol, 0.03 ml (0.2 mmol) of triethylamine and 0.345 ml (4.47 mmol) of diketene were heated and stirred in 10 ml of toluene at 80° C. for 3.5 hours. After saturated aqueous sodium hydrogencarbonate solution was added at room temperature, the reaction mixture was extracted with ethyl acetate. The organic layer was dried over anhydrous magnesium sulfate and then concentrated under reduced pressure. 20 ml of 2-propanol, 312 mg (2.02 mmol) of 3-aminocrotonate 2-cyanoethyl and 0.23 ml (2.03 mmol) of 3-chlorobenzaldehyde were added to the residue and the residue was heated and stirred at 80° C. overnight. After evaporating 2-propanol under reduced pressure, saturated aqueous sodium chloride solution was added and the reaction mixture was extracted with ethyl acetate. The organic layer was dried over anhydrous magnesium sulfate and then concentrated under reduced pressure. The residue was purified by the basic silica gel chromatography (hexane/ethyl acetate=9/1 to 1/3) to obtain the title compound.

Yield: 153 mg (0.27 mmol) (13%)
MS (ESI, m/z) 577 (M−H)⁻
1H-NMR (CDCl3): 1.97-2.07 (2H, m), 2.35 (6H, s), 2.67 (2H, t), 3.68 (2H, t), 3.98 (1H, t), 4.24-4.40 (2H, m), 5.03 (1H, s), 5.76 (1H, s), 6.88 (2H, s), 6.90-6.93 (1H, m), 7.10-7.34 (11H, m).

2) Synthesis of 4-(3-chlorophenyl)-2,6-dimethyl-5-(4-methylpiperazine-1-carbonyl)nicotinic acid (2-(5H-dibenzo[a,d] cyclohepten-5-yl) ethyl) ester 4 ml of methanol and 0.32 ml of 1 N aqueous sodium hydroxide solution were added to 153 mg (0.265 mmol) of 4-(3-chlorophenyl)-2,6-dimethyl-1,4-dihydropyridine-3,5-dicarboxylic acid 3-(2-cyanoethyl) ester 5-(2-(5H-dibenzo[a,d] cyclohepten-5-yl) ethyl) ester and stirred at room temperature overnight. After adding 1 N hydrochloric acid, methanol was evaporated under reduced pressure. After water was added, the reaction mixture was extracted with ethyl acetate. The organic layer was dried over anhydrous magnesium sulfate and then concentrated under reduced pressure. 5 ml of dichloromethane, 68 mg (0.352 mmol) of WSC hydrochloride, 0.039 ml (0.352 mmol) of N-methylpiperazine, 0.049 ml (0.352 mmol) of triethylamine and 3.6 mg (0.029 mmol) of dimethylaminopyridine were added to the residue and the residue was stirred at room temperature overnight. 2 ml of trifluoroacetate was added and stirred at room temperature for 4 hours. After concentration under reduced pressure, saturated aqueous sodium hydrogencarbonate solution was added to basify. After extraction with ethyl acetate, the organic layer was dried over anhydrous sodium sulfate and then concentrated under reduced pressure. The residue was purified by the silica gel chromatography (dichloromethane/methanol=9/1) to obtain the title compound.

Yield: 118 mg (0.194 mmol) (73%)
MS (ESI, m/z) 606 (M+H)⁺
1H-NMR (CDCl3): 1.73-1.84 (2H, m), 1.94-2.03 (1H, m), 2.10-2.18 (4H, m), 2.28-2.36 (1H, m), 2.53-2.58 (7H, m), 2.79-2.89 (1H, m), 3.04-3.11 (1H, m), 3.41-3.49 (1H, m), 3.55-3.64 (3H, m), 3.84 (1H, t), 6.86 (2H, s), 7.02-7.05 (1H, m), 7.10-7.15 (1H, m), 7.18-7.31 (10H, m).

The structural formulae of the compounds obtained in Examples 1 to 152 are shown below.

TABLE 1

| Ex. | Structure |
|---|---|
| 1 | (structure) |
| 2 | (structure) |
| 3 | (structure) |
| 4 | (structure) |
| 5 | (structure) |

TABLE 1-continued

| Ex. | Structure |
|---|---|
| 6 | 4-(3,4-dichlorophenyl)-2-(methylthio)-6-methyl-N-(3,3-diphenylpropyl)pyrimidine-5-carboxamide |
| 7 | 4-(3,4-dichlorophenyl)-2-(methylthio)-6-methyl-N-(3-phenylpropyl)pyrimidine-5-carboxamide |
| 8 | 4-(3,5-dichlorophenyl)-2-(methylthio)-6-methyl-N-(3,3-diphenylpropyl)pyrimidine-5-carboxamide |

TABLE 2

| Ex. | Structure |
|---|---|
| 9 | 4-(3,5-dichlorophenyl)-2-(methylthio)-6-methyl-N-(3-phenylpropyl)pyrimidine-5-carboxamide |
| 10 | 4-(3,5-dichlorophenyl)-2-(methylthio)-6-methyl-N-cinnamylpyrimidine-5-carboxamide |

TABLE 2-continued

| Ex. | Structure |
|---|---|
| 11 | 4-(3,4-dichlorophenyl)-2-(methylthio)-6-methyl-N-cinnamylpyrimidine-5-carboxamide |
| 12 | 4-(3,5-dichlorophenyl)-2,6-dimethyl-N-cinnamylpyrimidine-5-carboxamide |
| 13 | 4-(3-chlorophenyl)-2-phenyl-6-methyl-N-(3-phenylpropyl)pyrimidine-5-carboxamide |
| 14 | 4-(3-chlorophenyl)-2-(pyridin-3-yl)-6-methyl-N-(3-phenylpropyl)pyrimidine-5-carboxamide |
| 15 | 4-(3-chlorophenyl)-2,6-dimethyl-N-(3-phenylpropyl)pyrimidine-5-carboxamide |

TABLE 2-continued

| Ex. | Structure |
|---|---|
| 16 | 4-(3-chlorophenyl)-2-(methylthio)-6-methyl-N-(3-phenylpropyl)pyrimidine-5-carboxamide |

TABLE 3

| Ex. | Structure |
|---|---|
| 17 | 4-(3-chlorophenyl)-2,6-dimethyl-N-cinnamylpyrimidine-5-carboxamide |
| 18 | 4-(3,4-dichlorophenyl)-2,6-dimethyl-N-(3-phenylpropyl)pyrimidine-5-carboxamide |
| 19 | 4-(3,4-dichlorophenyl)-6-methyl-N-(3-phenylpropyl)-2-(pyridin-3-yl)pyrimidine-5-carboxamide |
| 20 | 4-(3,5-dichlorophenyl)-6-methyl-2-phenyl-N-(3-phenylpropyl)pyrimidine-5-carboxamide |

TABLE 3-continued

| Ex. | Structure |
|---|---|
| 21 | 4-(3,5-dichlorophenyl)-6-methyl-N-(3-phenylpropyl)-2-(pyridin-3-yl)pyrimidine-5-carboxamide |
| 22 | 4-(3,5-dichlorophenyl)-2,6-dimethyl-N-(3-phenylpropyl)pyrimidine-5-carboxamide |
| 23 | 4-(3,4-dichlorophenyl)-6-methyl-2-phenyl-N-(4-phenylbutyl)pyrimidine-5-carboxamide |
| 24 | 4-(3,4-dichlorophenyl)-6-methyl-N-(4-phenylbutyl)-2-(pyridin-3-yl)pyrimidine-5-carboxamide |

TABLE 4

| Ex. | Structure |
|---|---|
| 25 | 4-(3,4-dichlorophenyl)-2,6-dimethyl-N-(4-phenylbutyl)pyrimidine-5-carboxamide |
| 26 | 4-(3,4-dichlorophenyl)-6-methyl-2-(methylthio)-N-(4-phenylbutyl)pyrimidine-5-carboxamide |
| 27 | 4-(3,4-dichlorophenyl)-6-methyl-2-phenyl-N-(2-phenylethyl)pyrimidine-5-carboxamide |
| 28 | 4-(3,4-dichlorophenyl)-6-methyl-N-(2-phenylethyl)-2-(pyridin-3-yl)pyrimidine-5-carboxamide |
| 29 | 4-(3,4-dichlorophenyl)-2,6-dimethyl-N-(2-phenylethyl)pyrimidine-5-carboxamide |

TABLE 4-continued

| Ex. | Structure |
|---|---|
| 30 | 4-(3,4-dichlorophenyl)-6-methyl-2-(methylthio)-N-(2-phenylethyl)pyrimidine-5-carboxamide |
| 31 | 4-(3,4-dichlorophenyl)-N-(3,3-diphenylpropyl)-2,6-dimethylpyrimidine-5-carboxamide |
| 32 | 4-(3,5-dichlorophenyl)-N-(3,3-diphenylpropyl)-2,6-dimethylpyrimidine-5-carboxamide |

TABLE 5

| Ex. | Structure |
|---|---|
| 33 | 4-(3,4-dichlorophenyl)-6-methyl-N-(3-phenylpropyl)pyrimidine-5-carboxamide |
| 34 | 4-(3,4-dichlorophenyl)-2,6-dimethyl-N-(2-(pyridin-3-yl)ethyl)pyrimidine-5-carboxamide |

TABLE 5-continued

| Ex. | Structure |
|---|---|
| 35 | 4-(3,4-dichlorophenyl)-2-(methylthio)-6-methyl-N-(2-(pyridin-3-yl)ethyl)pyrimidine-5-carboxamide |
| 36 | 4-(4-methoxyphenyl)-6-methyl-2-phenyl-N-(3-phenylpropyl)pyrimidine-5-carboxamide |
| 37 | 4-(4-methoxyphenyl)-6-methyl-N-(3-phenylpropyl)-2-(pyridin-3-yl)pyrimidine-5-carboxamide |
| 38 | 6-methyl-N-(3-phenylpropyl)-2,4-di(pyridin-3-yl)pyrimidine-5-carboxamide |
| 39 | 2,6-dimethyl-N-(3-phenylpropyl)-4-(pyridin-3-yl)pyrimidine-5-carboxamide |

TABLE 5-continued

| Ex. | Structure |
|---|---|
| 40 | 4-(3,4-dichlorophenyl)-6-methyl-2-(methylsulfonyl)-N-(3-phenylpropyl)pyrimidine-5-carboxamide |

TABLE 6

| Ex. | Structure |
|---|---|
| 41 | 6-methyl-2-phenyl-N-(3-phenylpropyl)-4-(pyridin-3-yl)pyrimidine-5-carboxamide |
| 42 | 6-methyl-2-(methylthio)-N-(3-phenylpropyl)-4-(pyridin-3-yl)pyrimidine-5-carboxamide |
| 43 | 2-amino-4-(3,4-dichlorophenyl)-6-methyl-N-(3-phenylpropyl)pyrimidine-5-carboxamide |
| 44 | 4-(4-methoxyphenyl)-6-methyl-2-(methylthio)-N-(3-phenylpropyl)pyrimidine-5-carboxamide |

TABLE 6-continued

| Ex. | Structure |
|---|---|
| 45 | 3-nitrophenyl, phenyl, methyl pyrimidine-5-carboxamide N-(3-phenylpropyl) |
| 46 | 3-nitrophenyl, 3-pyridyl, methyl pyrimidine-5-carboxamide N-(3-phenylpropyl) |
| 47 | 3-nitrophenyl, 2,6-dimethyl pyrimidine-5-carboxamide N-(3-phenylpropyl) |
| 48 | 3-nitrophenyl, 2-methylthio, 6-methyl pyrimidine-5-carboxamide N-(3-phenylpropyl) |

TABLE 7

| Ex. | Structure |
|---|---|
| 49 | 3-methylphenyl, phenyl, methyl pyrimidine-5-carboxamide N-(3-phenylpropyl) |

TABLE 7-continued

| Ex. | Structure |
|---|---|
| 50 | 3-methylphenyl, 3-pyridyl, methyl pyrimidine-5-carboxamide N-(3-phenylpropyl) |
| 51 | 3-methylphenyl, 2,6-dimethyl pyrimidine-5-carboxamide N-(3-phenylpropyl) |
| 52 | 3-methylphenyl, 2-methylthio, 6-methyl pyrimidine-5-carboxamide N-(3-phenylpropyl) |
| 53 | 3-fluorophenyl, phenyl, methyl pyrimidine-5-carboxamide N-(3-phenylpropyl) |
| 54 | 3-fluoropyridyl, 3-pyridyl, methyl pyrimidine-5-carboxamide N-(3-phenylpropyl) |

TABLE 7-continued
| Ex. | Structure |
|---|---|
| 55 | 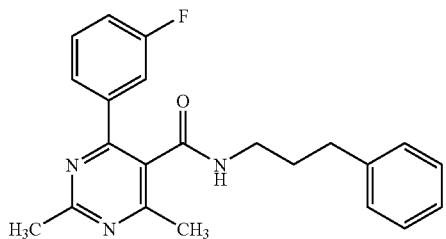 |
| 56 | 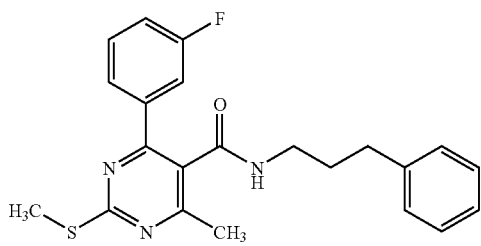 |
TABLE 8
| Ex. | Structure |
|---|---|
| 57 | 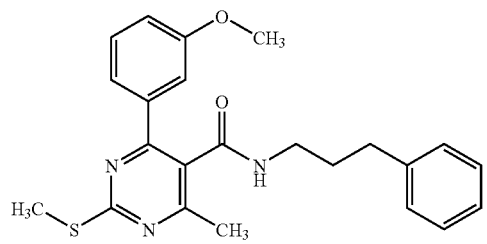 |
| 58 | 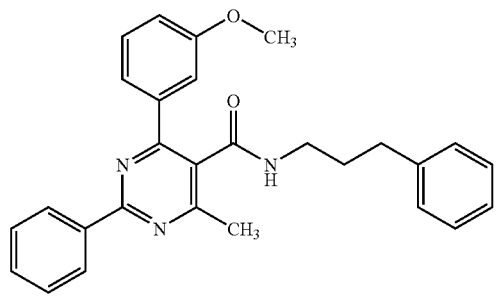 |
| 59 | 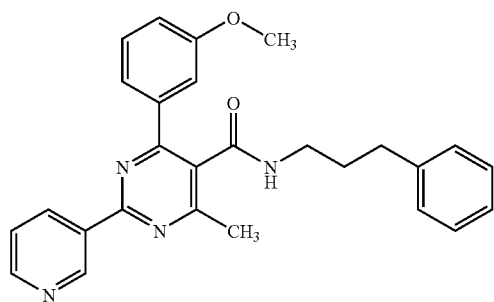 |
TABLE 8-continued
| Ex. | Structure |
|---|---|
| 60 | 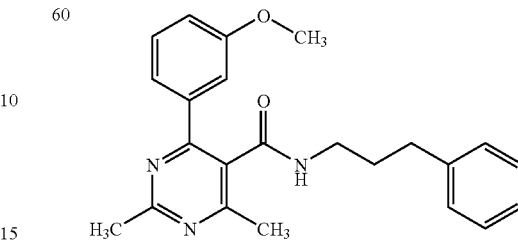 |
| 61 | 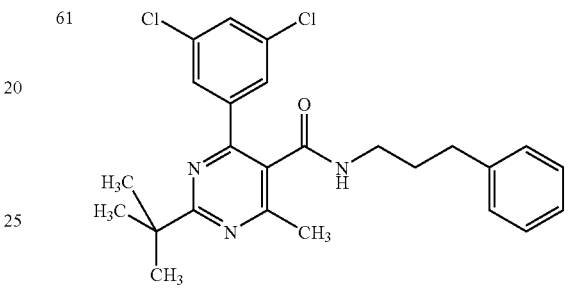 |
| 62 | 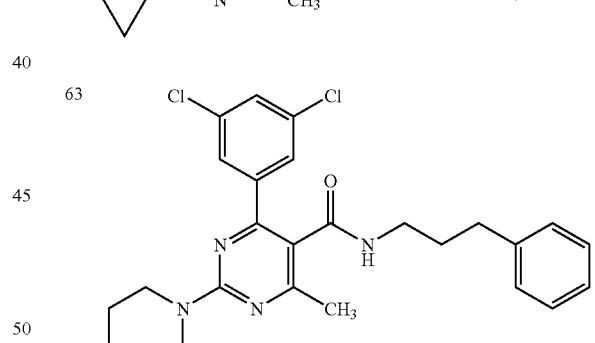 |
| 63 | 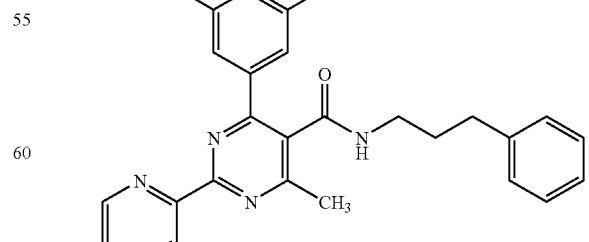 |
| 64 | 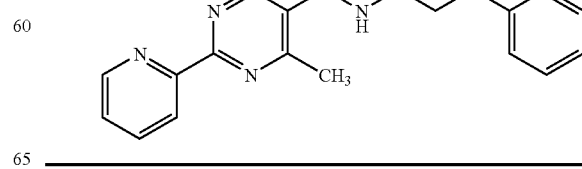 |

TABLE 9

| Ex. | Structure |
|---|---|
| 65 | 4-(3,5-dichlorophenyl)-6-methyl-2-(pyridin-3-yl)-N-(3-phenylpropyl)pyrimidine-5-carboxamide |
| 66 | 6-methyl-2-(methylthio)-4-(naphthalen-2-yl)-N-(3-phenylpropyl)pyrimidine-5-carboxamide |
| 67 | 6-methyl-2-phenyl-N-(3-phenylpropyl)-4-(p-tolyl)pyrimidine-5-carboxamide |
| 68 | 6-methyl-2-(methylthio)-N-(3-phenylpropyl)-4-(p-tolyl)pyrimidine-5-carboxamide |
| 69 | 4-(3,5-dichlorophenyl)-6-methyl-N-(3-phenylpropyl)-2-(1H-pyrazol-1-yl)pyrimidine-5-carboxamide |

TABLE 9-continued

| Ex. | Structure |
|---|---|
| 70 | 4-(3,5-dichlorophenyl)-6-methyl-2-(methylamino)-N-(3-phenylpropyl)pyrimidine-5-carboxamide |
| 71 | 4-(3,5-dichlorophenyl)-2-(dimethylamino)-6-methyl-N-(3-phenylpropyl)pyrimidine-5-carboxamide |
| 72 | 4-(3,5-dichlorophenyl)-2-(3,5-dimethyl-1H-pyrazol-1-yl)-6-methyl-N-(3-phenylpropyl)pyrimidine-5-carboxamide |

TABLE 10

| Ex. | Structure |
|---|---|
| 73 | 4-(3-chlorophenyl)-6-methyl-N-(3-phenylpropyl)-2-(piperidin-1-yl)pyrimidine-5-carboxamide |

TABLE 10-continued
| Ex. | Structure |
|---|---|
| 74 | 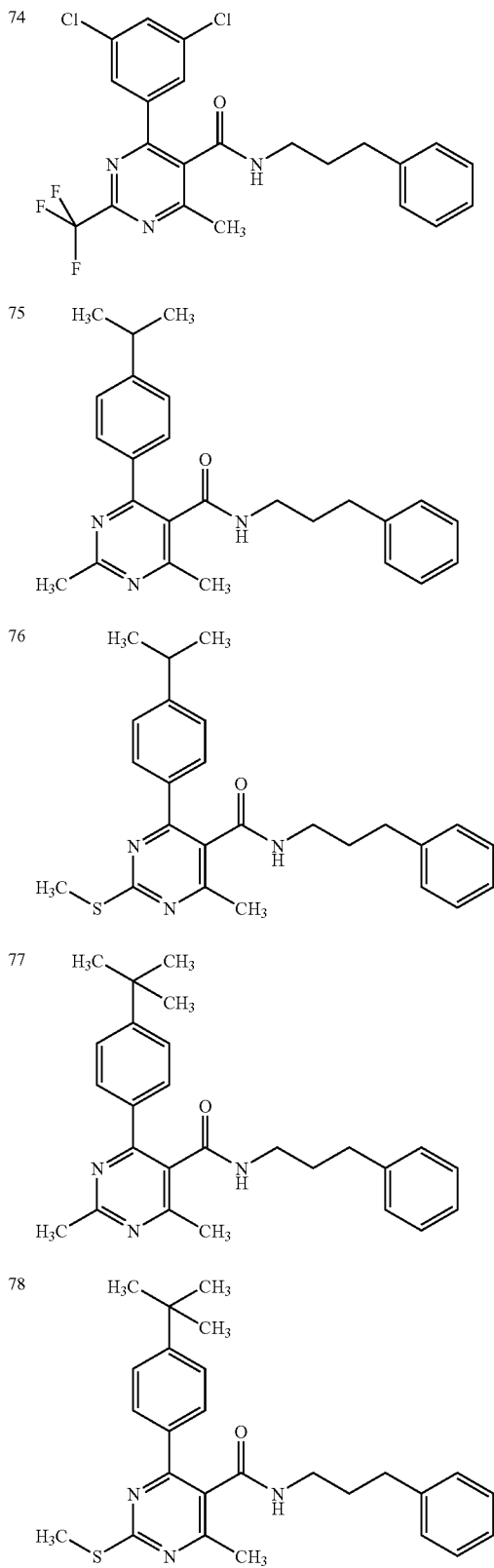 |
| 75 | 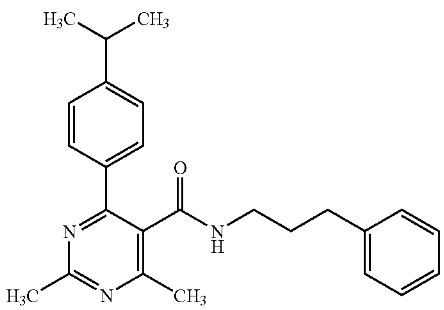 |
| 76 | 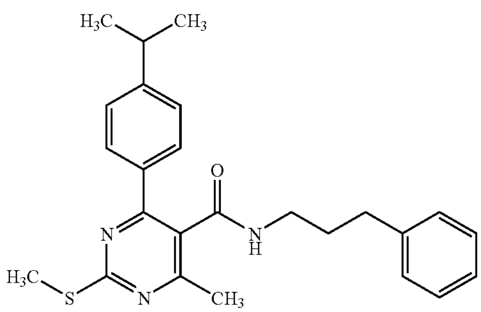 |
| 77 | 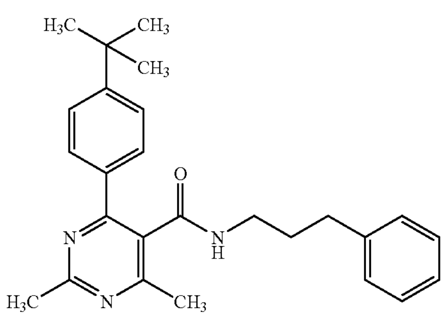 |
| 78 | 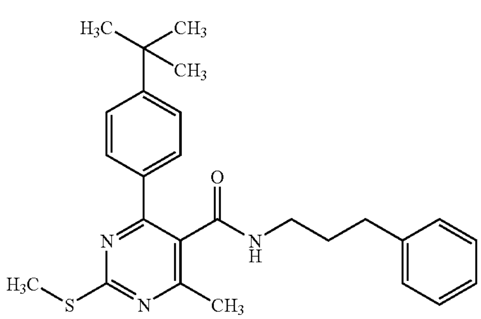 |
TABLE 10-continued
| Ex. | Structure |
|---|---|
| 79 | 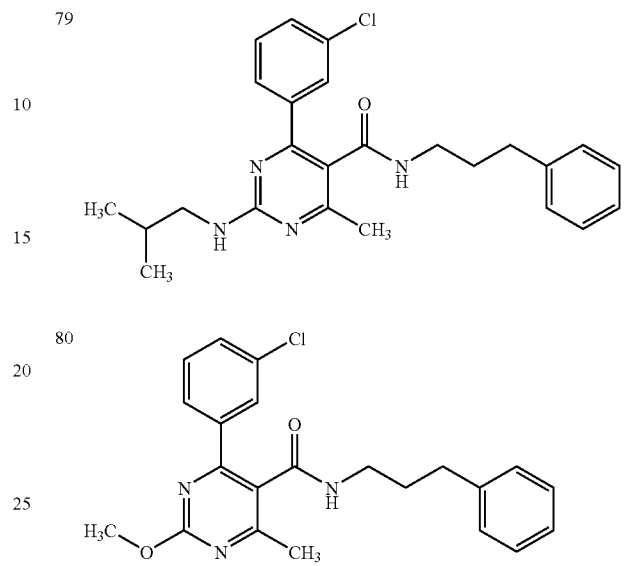 |
| 80 | 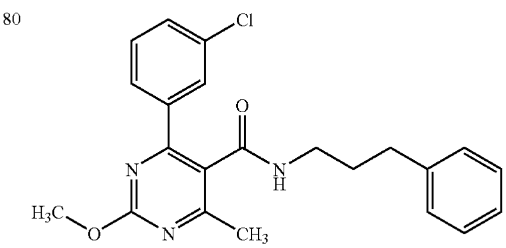 |
TABLE 11
| Ex. | Structure |
|---|---|
| 81 | 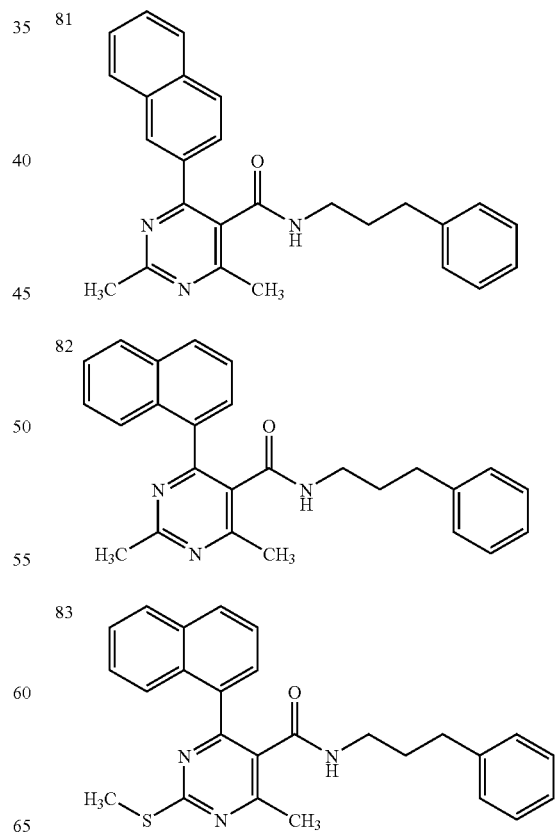 |
| 82 | 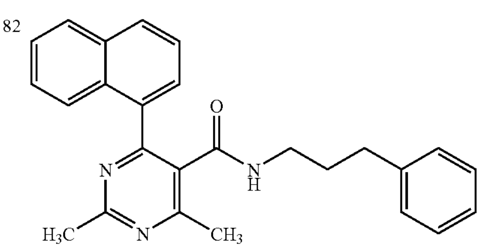 |
| 83 | 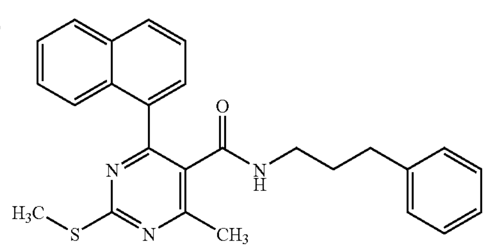 |

TABLE 11-continued
| Ex. | Structure |
|---|---|
| 84 | 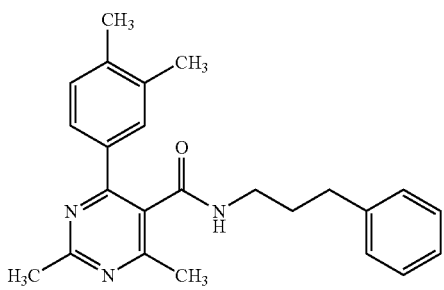 |
| 85 | 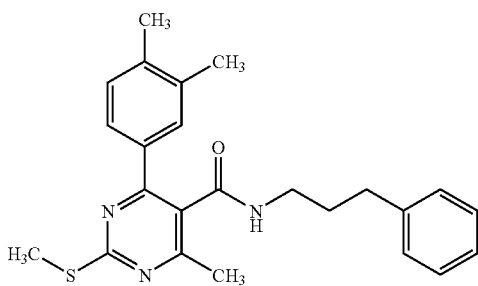 |
| 86 | 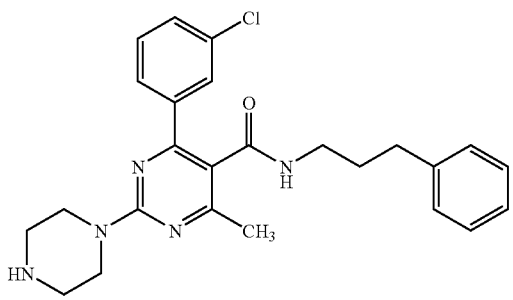 |
| 87 | 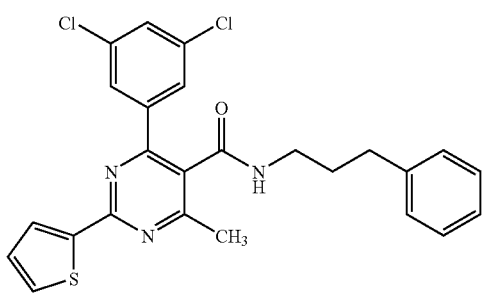 |
| 88 | 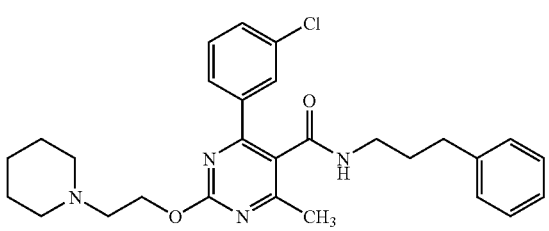 |
TABLE 12
| Ex. | Structure |
|---|---|
| 89 | 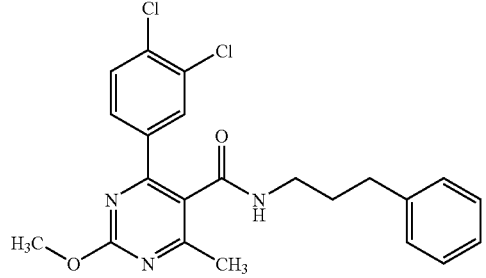 |
| 90 | 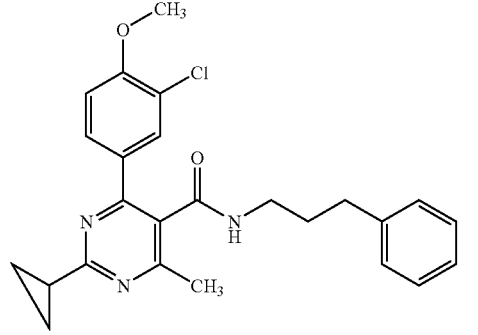 |
| 91 | 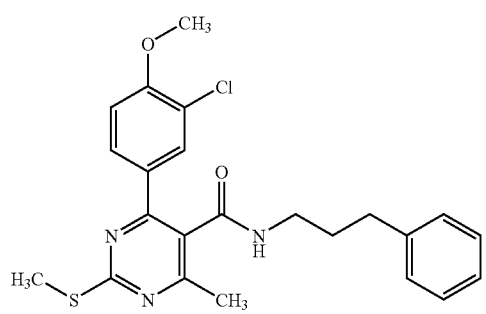 |
| 92 | 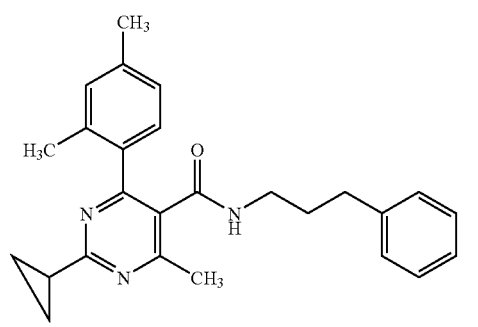 |
| 93 | 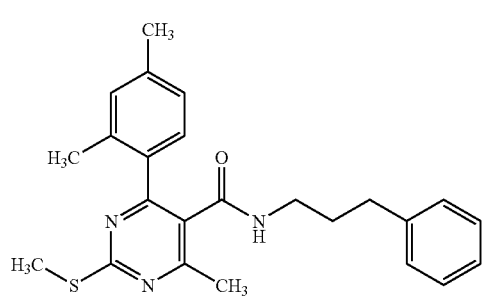 |

TABLE 12-continued
| Ex. | Structure |
|---|---|
| 94 | 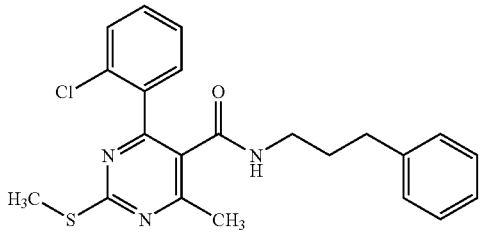 |
| 95 | 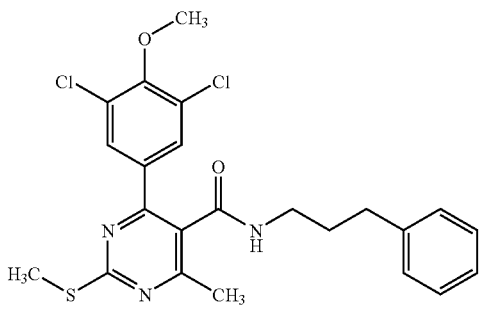 |
| 96 | 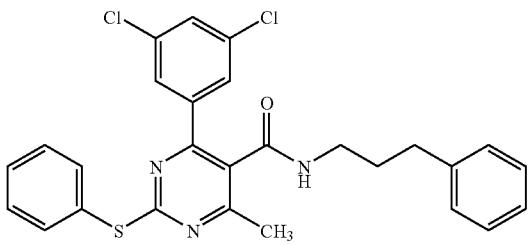 |
TABLE 13
| Ex. | Structure |
|---|---|
| 97 | 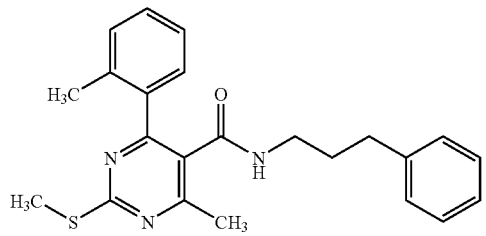 |
| 98 | 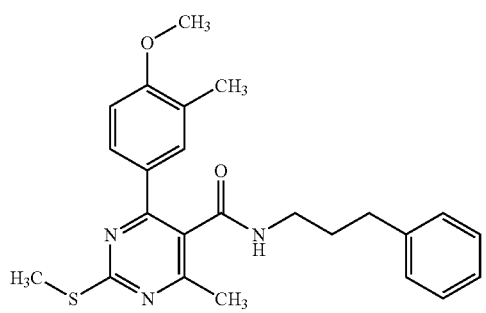 |
TABLE 13-continued
| Ex. | Structure |
|---|---|
| 99 | 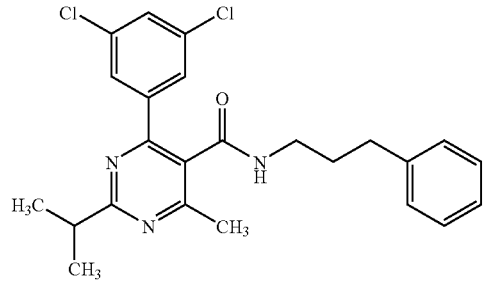 |
| 100 | 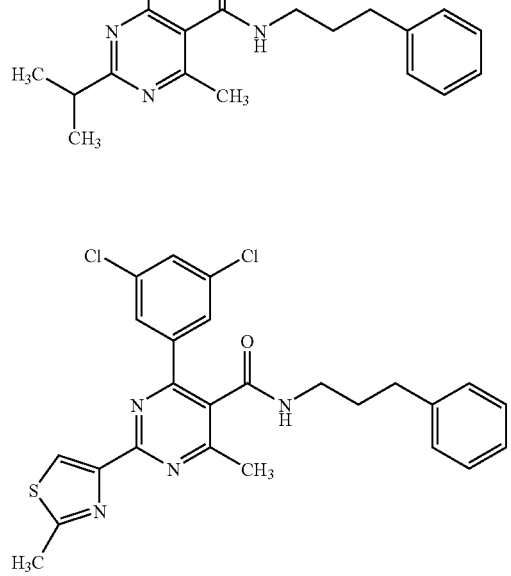 |
| 101 | 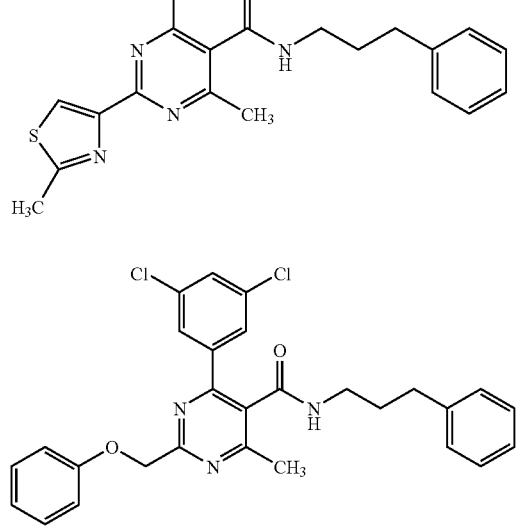 |
| 102 | 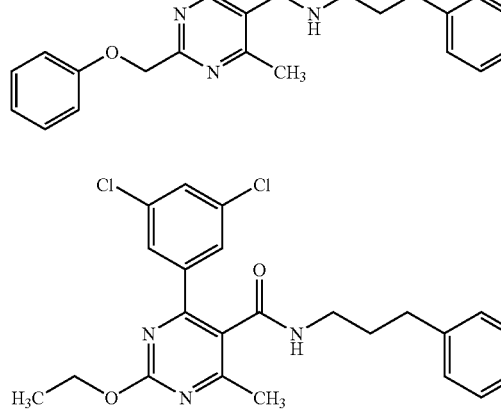 |
| 103 | 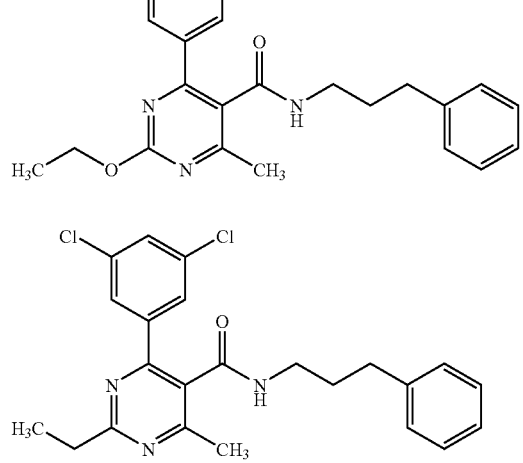 |

TABLE 13-continued
| Ex. | Structure |
|---|---|
| 104 | 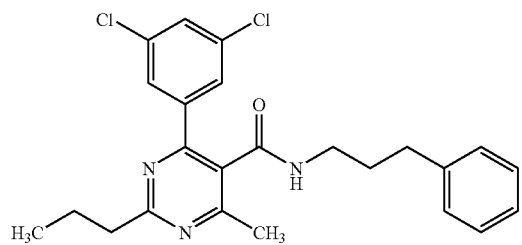 |
TABLE 14
| Ex. | Structure |
|---|---|
| 105 | 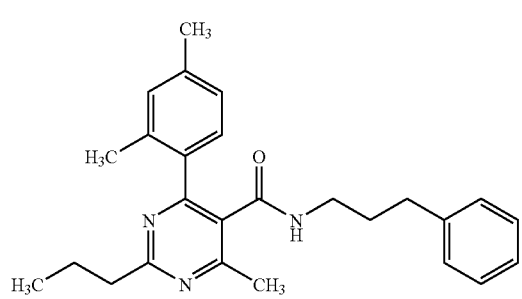 |
| 106 | 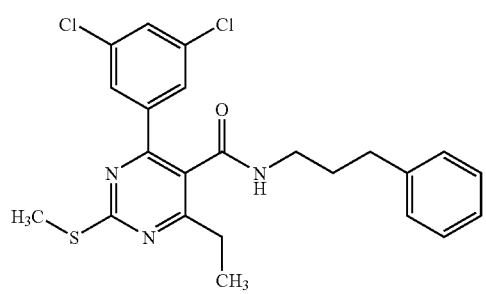 |
| 107 | 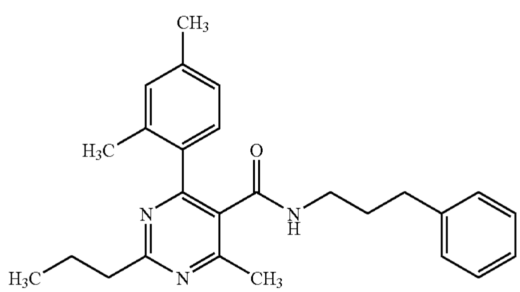 |
TABLE 14-continued
| Ex. | Structure |
|---|---|
| 109 | 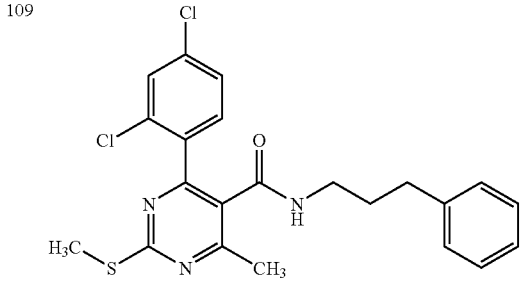 |
| 110 | 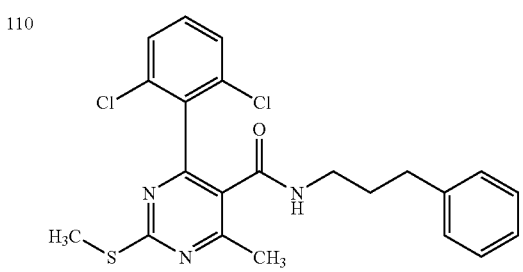 |
| 111 | 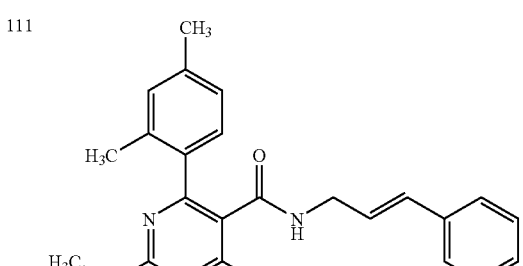 |
| 112 | 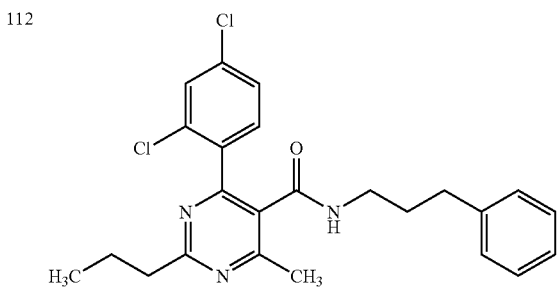 |
TABLE 15
| Ex. | Structure |
|---|---|
| 113 | 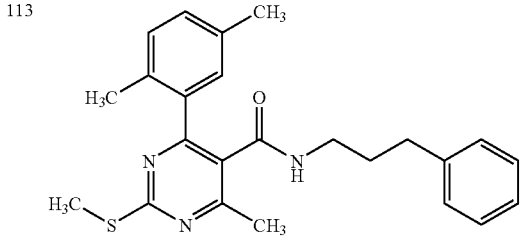 |

TABLE 15-continued
| Ex. | Structure |
|---|---|
| 114 | 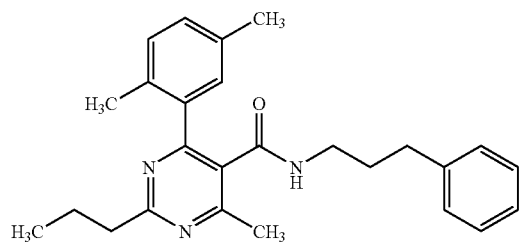 |
| 115 | 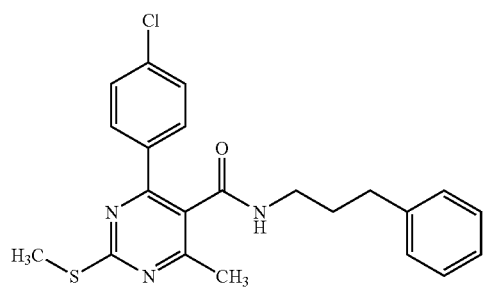 |
| 116 | 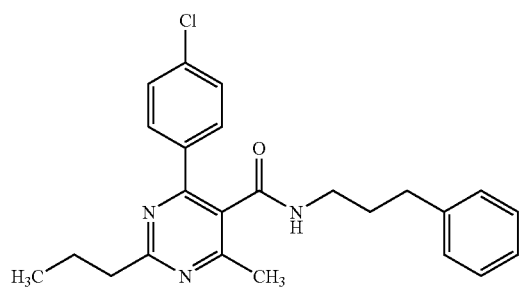 |
| 117 | 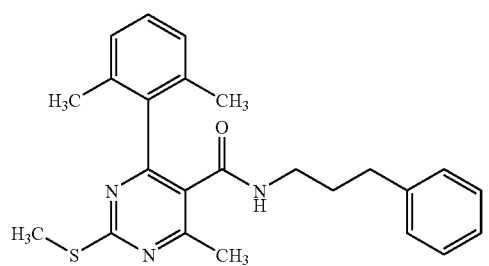 |
TABLE 15-continued
| Ex. | Structure |
|---|---|
| 118 | 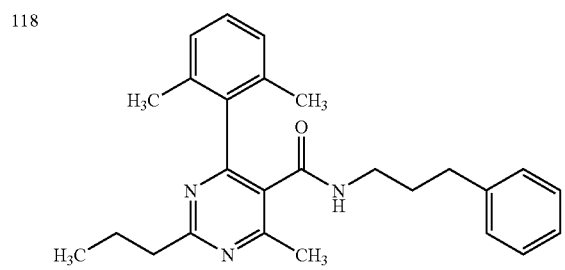 |
| 119 | 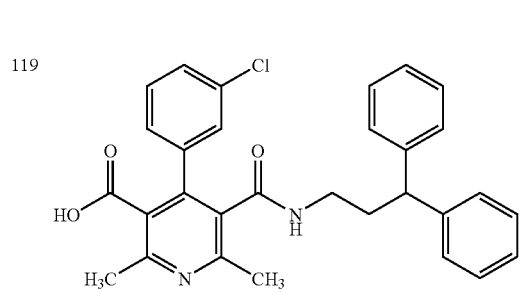 |
| 120 | 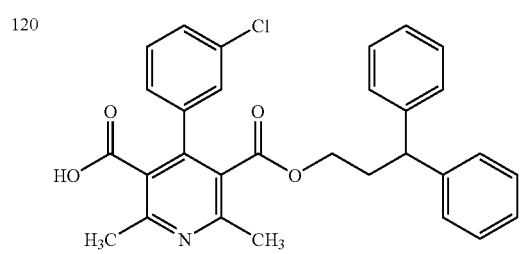 |
TABLE 16
| Ex. | Structure |
|---|---|
| 121 | 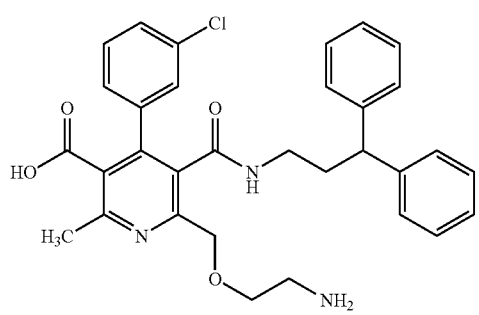 |

TABLE 16-continued
| Ex. | Structure |
|---|---|
| 122 | 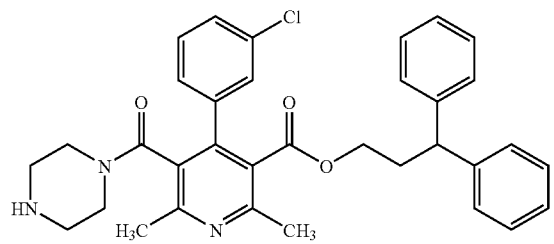 |
| 123 | 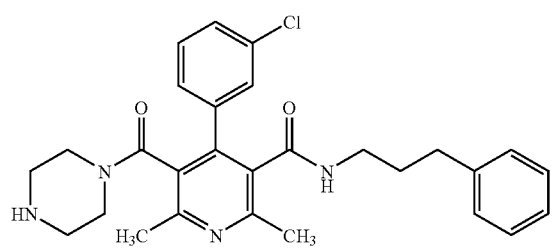 |
| 124 | 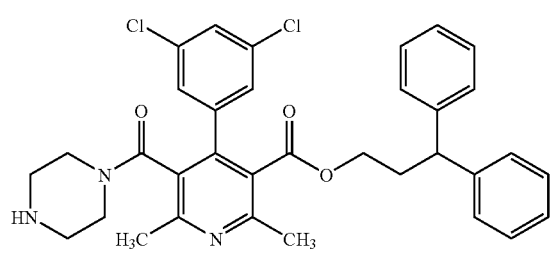 |
| 125 | 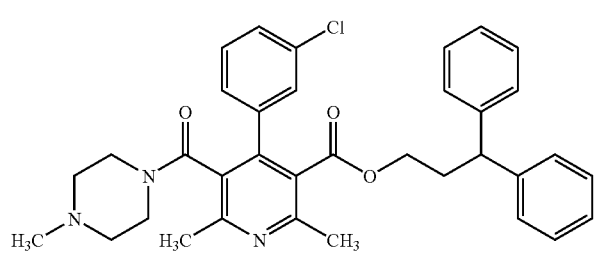 |
| 126 | 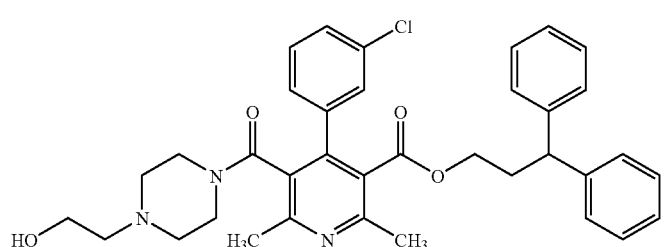 |
| 127 | 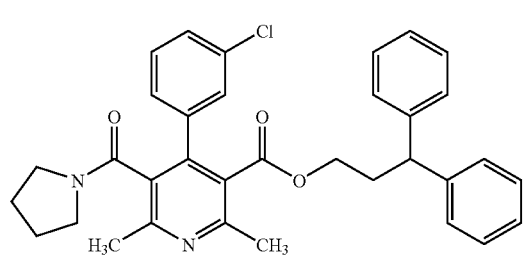 |

TABLE 16-continued
| Ex. | Structure |
|---|---|
| 128 | 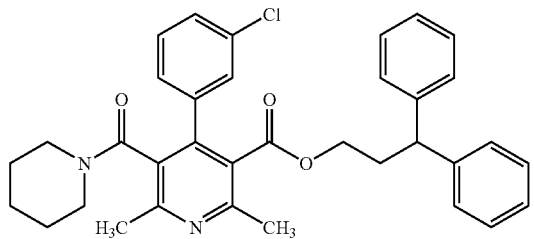 |
TABLE 17
| Ex. | Structure |
|---|---|
| 129 | 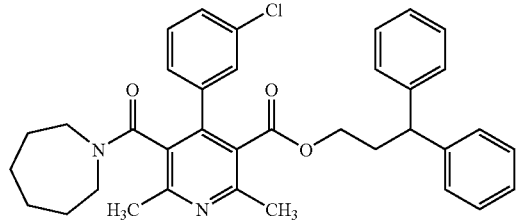 |
| 130 | 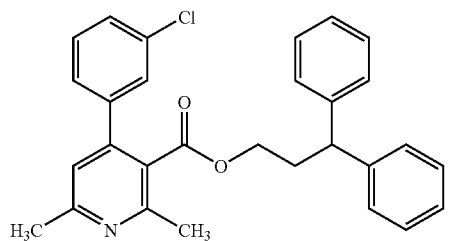 |
| 131 | 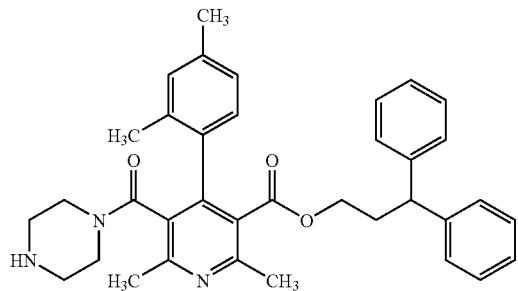 |
| 132 | 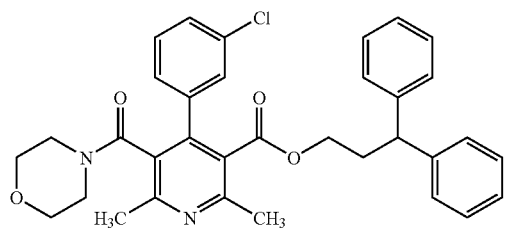 |
TABLE 17-continued
| Ex. | Structure |
|---|---|
| 133 | 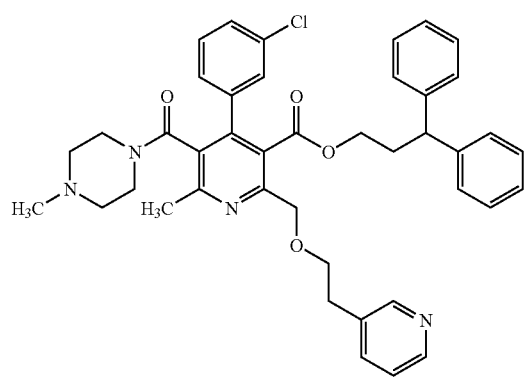 |
| 134 | 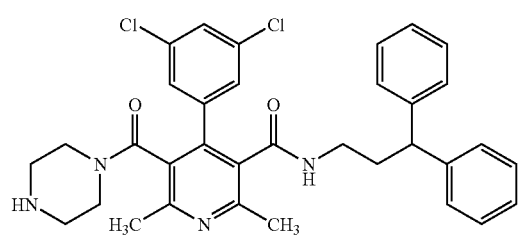 |
| 135 | 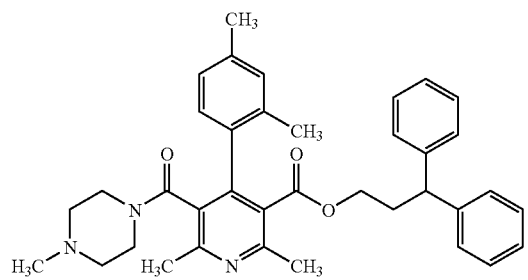 |
| 136 | 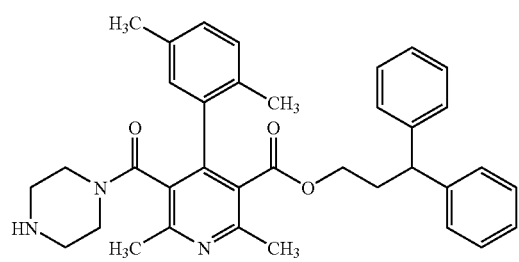 |

TABLE 18
| Ex. | Structure |
|---|---|
| 137 | 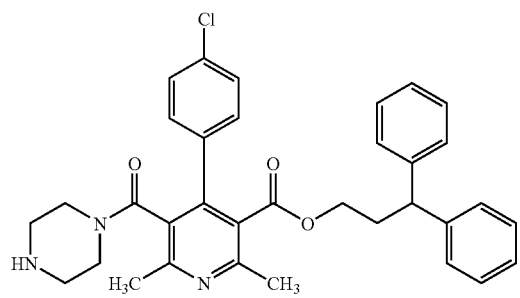 |
| 138 | 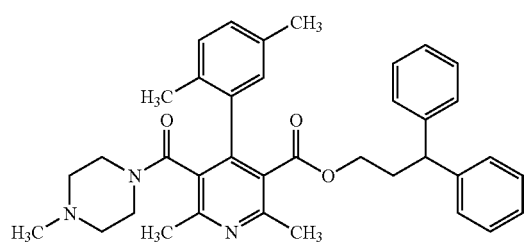 |
| 139 | 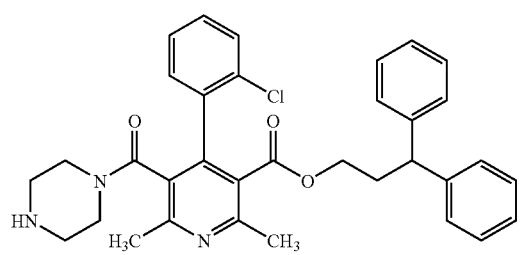 |
| 140 | 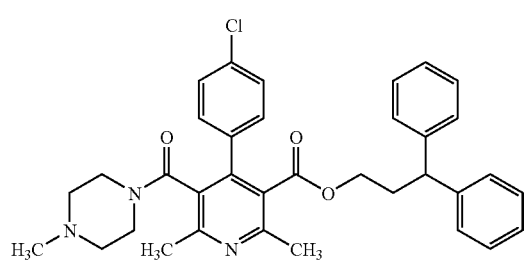 |
| 141 | 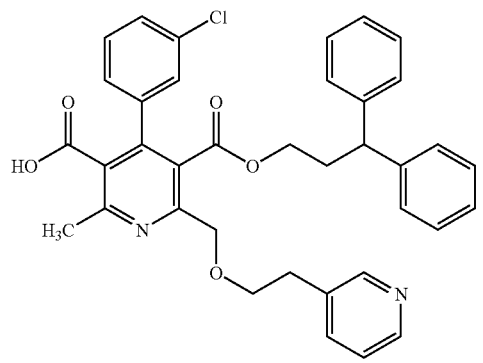 |
TABLE 18-continued
| Ex. | Structure |
|---|---|
| 142 | 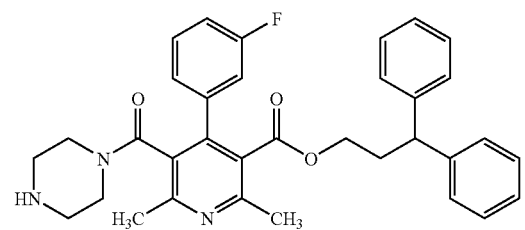 |
| 143 | 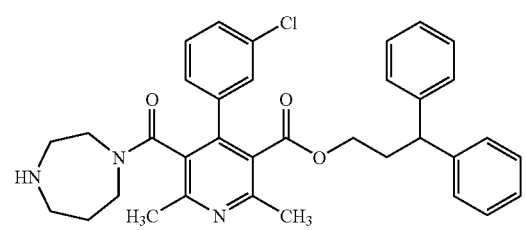 |
| 144 | 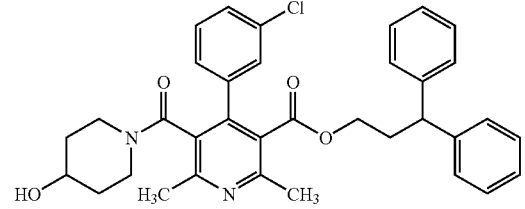 |
TABLE 19
| Ex. | Structure |
|---|---|
| 145 | 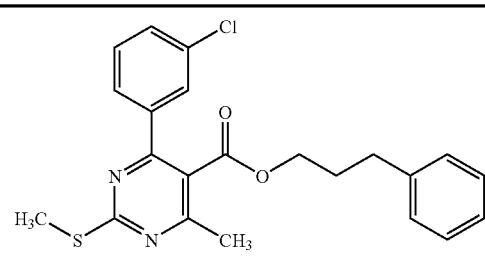 |
| 146 | 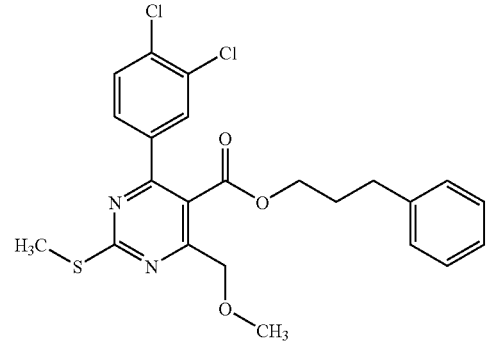 |

TABLE 19-continued

| Ex. | Structure |
|---|---|
| 147 | 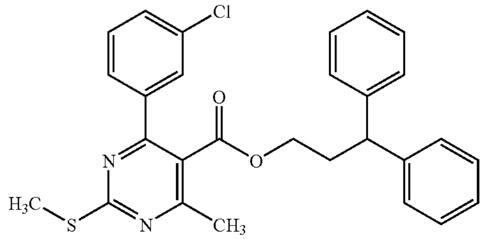 |
| 148 | 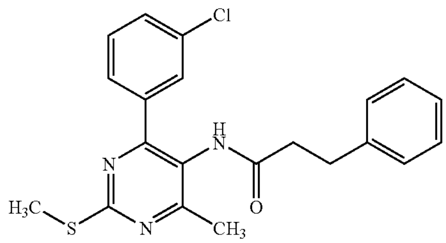 |
| 149 | 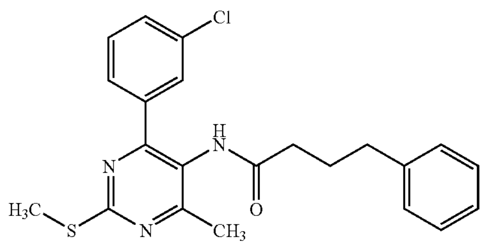 |
| 150 | 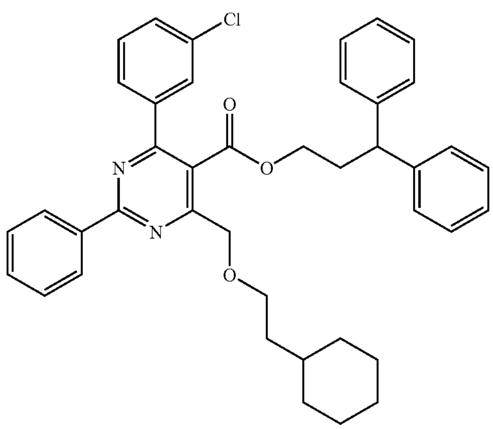 |
| 151 | 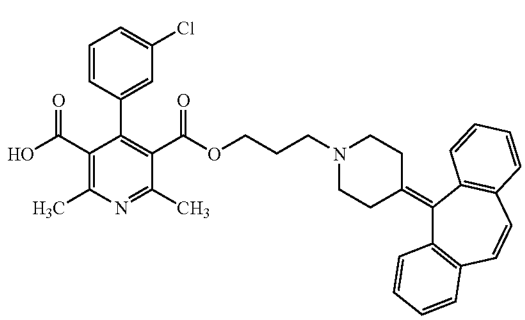 |
| 152 | |

TEST EXAMPLE

Antagonistic Activity on N-Type Calcium Channels (fluorescence dye Method)

Human neuroblastoma cells IMR-32 were obtained from ATCC (American Type Culture Collection). The medium used was a phenol red-free Eagle minimum essential medium containing earle's salts (GIBCO) supplemented with 2 mM of L-glutamine (GIBCO), 1 mM of sodium pyruvate (pH 6.5) (GIBCO), antibiotic/antimicotic mixture (GIBCO) and 10% fetal calf serum (Cell Culture Technologies). Three ml of $1\times10^5$ cells/ml IMR-32 were spread on a 35 mm diameter glass dish (Iwaki Glass Co., Ltd.) which was treated with poly-L-lysin (SIGMA) and collagen (COLLAGEN VITROGEN 100, Collagen Co.). One day after cultivation, 1 mM (final concentration) of dibutyl cAMP and 2.5 µM (final concentration) of 5-bromodeoxyuridine (SIGMA) were added. After the culture for additional 10 to 14 days, the cells were subjected to the activity determination.

The medium for IMR-32 cells thus prepared was replaced with 1 ml of Phenol Red-free Eagle minimum essential medium (GIBCO) containing 2.5 µM fura-2/AM (Dojin Kagaku, Co.) and earle's salts supplement, and the incubation was conducted at 37° C. for 30 minutes. Then the medium was replaced with a recording medium (20 mM of HEPES-KOH, 115 mM of NaCl, 5.4 mM of KCl, 0.8 mM of $MgCl_2$, 1.8 mM of $CaCl_2$ and 13.8 mM of D-glucose). Antagonistic activity on N-type calcium channels was determined and analyzed using a fluorescence microscope (Nikon Corporation) and an image analysis device ARGUS 50 (Hamamatsu Photonics). In particular, a recording medium (20 mM of HEPES-KOH, 115 mM of NaCl, 5.4 mM of KCl, 0.8 mM of $MgCl_2$, 1.8 mM of $CaCl_2$ and 13.8 mM of D-glucose) containing 1 µM of Nifedipine was given to the cells by reflux by a Y-tube method for 2 minutes. Then a stimulating agent containing 60 mM of potassium chloride was rapidly given by the Y-tube method. The calcium concentration change in the cells was examined in terms of N-type calcium channel activity. Stimulating agents containing 60 mM of potassium chloride and 0.1, 1 or 10 µM of test compound were successively and rapidly given to the same cells by the Y-tube method to determine the change in calcium concentration in the cells on this occasion. Antagonistic activity on N-type calcium channel was thus calculated from the inhibition rates.

TEST EXAMPLE

Antagonistic Activity on L-Type Calcium Channels

The activity of the dihydropyrimidine derivatives of the present invention to inhibit L-type calcium channels was determined by the following method in which the relaxation reaction on the KCl-induced contraction of isolated rat thoracic aorta was employed.

1) Method of Preparation of Rat Thoracic Aorta:

The thoracic aorta isolated from a Wistar rat was cut to obtain ring-shaped samples having a width of about 3 mm. The endothelial cells of the samples were mechanically removed. The samples were then suspended in a strain gage in Tyrode's solution (158.3 mM of NaCl, 4.0 mM of KCl, 1.05 mM of $MgCl_2$, 0.42 mM of $NaH_2PO_4$, 10 mM of $NaHCO_3$, 2 mM of $CaCl_2$ and 5 mM of glucose) in which a gaseous mixture of $O_2$ (95%) and $CO_2$ (5%) was introduced. A static tension of 2 g was applied hereto. The tension of the blood vessel was amplified with a transducer and a tension amplifier (EF-601G; Nihon Koden Corporation) and recorded with a multi-pen recorder (Rikadenki Kogyo Co., Ltd.). The experiments were conducted at 37° C.

2) Measurement of Relaxation Response Against KCl-Induced Contraction:

After the tension had been stabilized, the solution in the sample tank was replaced with High $K^+$ Tyrode's solution (112.3 mM of NaCl, 50 mM of KCl, 1.05 mM of $MgCl_2$, 0.42 mM of $NaH_2PO_4$, 10 mM of $NaHCO_3$, 2 mM of $CaCl_2$ and 5 mM of glucose) to conduct the contraction reaction. Thirty minutes after, the solution in the sample tank was replaced with the normal Tyrode's solution. The solution in the sample tank was again replaced with the High $K^+$ Tyrode's solution and the contraction reaction was observed. After attaining the maximum contraction reaction, the test compound was cumulatively added at intervals of 90 minutes to attain concentrations of $10^{-9}$, $10^{-8}$, $10^{-7}$ and $10^{-6}$ M. The inhibitory rate of the test compound on the maximum contraction reaction was employed as the index of the inhibition activity on L-type calcium channels.

Table 20 shows the results of the determination of the antagonistic activity against the N-type calcium channels (pIC50) and the L-type calcium channels (pIC50). The value of pIC50 indicates the antagonistic activity of the test compound Showing a negative logarithm of the concentration of a test compound necessitated for 50% inhibition.

TABLE 20

| Example | N-type inhibition pIC50 | L-type inhibition pIC50 |
|---|---|---|
| 1 | 5.8 | 5.6 |
| 16 | 5.7 | 5.5 |
| 122 | 5.8 | 6.0 |

The same procedure as that of the above-described tests of the N-type calcium channel antagonistic activity of the compounds obtained in the Examples was repeated except for the following changes: stimulating agents containing 60 mM of potassium chloride and 0.1, 1 or 10 µM of test compound were successively and rapidly given by the Y-tube method. A change in calcium concentration in the cells was determined. N-type calcium channel antagonistic activities calculated from the inhibition rates (%) at 10 µM are shown in Table 21.

TABLE 21

| Example | N-type inhibition (inhibition rate (%) at 10 µM) | L-type inhibition pIC50 |
|---|---|---|
| 1 | 52% | 5.6 |
| 16 | 58% | 5.5 |

TABLE 21-continued

| Example | N-type inhibition (inhibition rate (%) at 10 µM) | L-type inhibition pIC50 |
|---|---|---|
| 93 | 63% | 5.3 |
| 103 | 74% | 5.4 |
| 110 | 77% | 5.6 |
| 122 | 56% | 6.0 |
| 125 | 70% | 5.9 |

TEST EXAMPLE

Determination of Analgesic Action (Analgesic action in the formalin test)

1) Preparation of Solution of a Test Compound and its Administration

The compound was weighed and ground in a mortar. While grinding the powder, 0.5% tragacanth solution was added thereto so that a suspension was prepared to have a concentration of 0.6 mg/ml.

Three hours before the formalin injection, the compound suspension was orally administered to SD rats at a volume of 5 ml/kg (dosage; 3 mg/kg, p.o.). In the control group, 0.5% tragacanth solution was orally administered to SD rats at a volume of 5 ml/kg 3 hours before formalin injection.

2) Determination of Analgesic Action in the Formalin Test

The SD rats to which the compound was administered were introduced to a capsule. They were settled under halothane (2 to 4% in 3 L/min of oxygen gas flow rate) and 100 µl of 5% formalin solution was injected subcutaneously to their dorsal surface of left legs. After injection, determination was started when the rats came out from the anesthetic state (based on recovery of righting reflex). The number of flinching under the influence of formalin injection was counted for 60 minutes (Reference: J. Neurosci. 14: 4882-4890 (1994)). The results are shown as "average ±standard error" in Table 22.

TABLE 22

| Example | Flinching (number) |
|---|---|
| Control group | 116 ± 8 |
| 93 | 39 ± 11 |
| 122 | 61 ± 16 |
| 125 | 62 ± 25 |

As is apparent from the results above, the new pyrimidine and pyridine derivatives have excellent selective N-type calcium channel antagonistic activity and that they are useful as a therapeutic agent for pains and various diseases associated with the N-type calcium channels.

The new pyrimidine and pyridine derivatives of the present invention had selective N-type calcium channel antagonistic activity. Thus, the new dihydropyrimidine derivatives of the present invention are effective in the treatment of acute stage of ischemic cerebrovascular disorders such as cerebral infarction or intracerebral bleeding (including subarachnoidal hemorrhage); progressive neurodegenerative diseases such as Alzheimer's disease, AIDS related dementia, Parkinson's disease, dementia due to cerebrovascular disorder and ALS; cerebral disorders caused by head injury; pains and cold flush caused by diabetes or thromboangiitis obliterans; various pains such as neuropathic pain, migraine, visceral pain and cancer pain; bronchial asthma; various diseases associated with psychogenic stress such as unstable angina and irritable colitis; withdrawal symptoms after addiction to drugs such as emotional disorder and ethanol withdrawal symptoms.

What is claimed is:

1. A pyridine compound of formula (1″), or a pharmaceutically acceptable salt thereof:

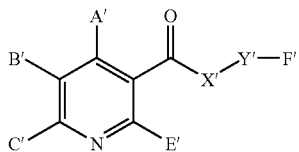

(1″)

wherein A' represents a group of the following general formula (9):

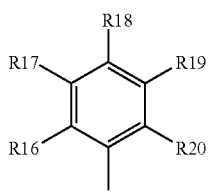

(9)

wherein $R^{16}$, $R^{17}$, $R^{18}$, $R^{19}$ and $R^{20}$ may be the same or different from each other and each represents a hydrogen atom, a halogen atom, hydroxyl group, carboxyl group, amino group, cyano group, nitro group, a lower alkyl group, a lower alkoxyl group or a lower alkylamino group, C' and E' may be the same or different from each other and each represents a hydrogen atom, a lower alkyl group which may contain a hetero atom in the chain thereof, dimethoxymethyl group, cyano group, an aryl-lower alkyl group, a heteroaryl-lower alkyl group, a hydroxy-lower alkyl group, an amino-lower alkyl group, a halogeno-lower alkyl group, a substituted or unsubstituted aryl group, a substituted or unsubstituted heteroaryl group or a group of the following general formula (3) or (4):

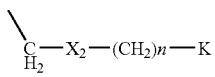

(3)

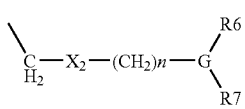

(4)

wherein $X_2$ represents O, S or N—$R_8$, n represents an integer of 1 to 6, K in general formula (3) represents a hydrogen atom, a halogen atom, hydroxyl group, carboxyl group, amino group, cyano group, nitro group, azido group, a substituted or unsubstituted aryl group or a substituted or unsubstituted heteroaryl group, G in the general formula (4) represents N or C—H, wherein $R^6$ to $R^8$ may be the same or different from each other, and each represents a hydrogen atom, a linear, branched or cyclic, saturated or unsaturated hydrocarbon group having 1 to 6 carbon atoms, a substituted or unsubstituted aryl group, a substituted or unsubstituted heteroaryl group, a hydroxy-lower alkyl group, a hydroxy-lower alkenyl group, an amino-lower alkyl group, an amino-lower alkenyl group, a halogeno-lower alkyl group, a halogeno-lower alkenyl group, an aryl-lower alkyl group, an aryl-lower alkenyl group, a heteroaryl-lower alkyl group, a heteroaryl-lower alkenyl group, a cyano-lower alkyl group, a cyano-lower alkyl group or a cyano-lower alkenyl group, and the chains may contain a hetero atom, or $R^6$ and $R^7$ may together form a ring which may contain a hetero atom, B' represents a hydrogen atom only when Y' represents the general formula (12) and $R^{26}$ is a substituted or unsubstituted aryl group, a carboxyl group only when Y' represents the general formula (12) or Y' and F' together form the following general formula (12'-1), (12'-2), (12″-1) or (12″-2), or a group of the following general formula (10):

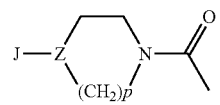

(10)

wherein Z represents a nitrogen atom, an oxygen atom or a carbon atom, p represents an integer of 1 to 3, J is present only when Z is a nitrogen atom or a carbon atom and when present represents a hydrogen atom, a lower alkyl group which may contain a hetero atom in the group thereof, a hydroxy-lower alkyl group, an amino-lower alkyl group, a substituted or unsubstituted aryl group, a substituted or unsubstituted heteroaryl group, a substituted or unsubstituted aryl-lower alkyl group or a substituted or unsubstituted heteroaryl-lower alkyl group, F' represents the following general formula (11):

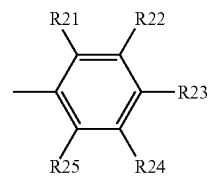

(11)

wherein $R^{21}$, $R^{22}$, $R^{23}$, $R^{24}$ and $R^{25}$ may be the same or different from each other and each represents a hydrogen atom, a halogen atom, hydroxyl group, carboxyl group, amino group, cyano group, nitro group, a lower alkyl group, a lower alkoxyl group, a lower alkylamino group, a substituted or unsubstituted aryl group or a substituted or unsubstituted heteroaryl group, X' represents an oxygen atom or >NH, Y' represents a saturated or unsaturated linear hydrocarbon group having 1 to 6 carbon atoms, which may contain a hetero atom in the group thereof, or a group of the following general formula (12):

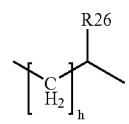

(12)

wherein $R^{26}$ represents a substituted or unsubstituted aryl group or a substituted or unsubstituted heteroaryl group and h represents an integer of 0 to 5, Y' and F' together form a group of the following general formula (12'-1), (12'-2), (12″-1) or (12″-2):

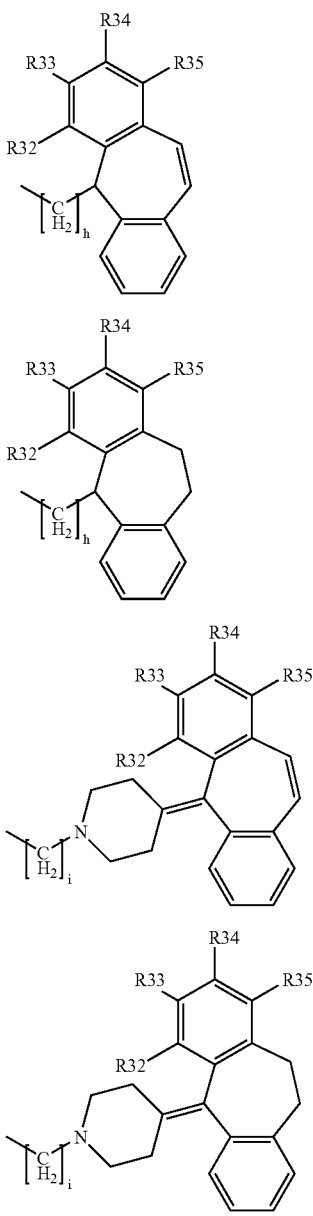

wherein h represents an integer of 0 to 5, i represents an integer of 2 to 5, $R^{32}$, $R^{33}$, $R^{34}$ and $R^{35}$ may be the same or different from each other and each represents a hydrogen atom, a halogen atom, hydroxyl group, carboxyl group, amino group, cyano group, nitro group, a lower alkyl group, a lower alkoxyl group, a lower alkylamino group, a substituted or unsubstituted aryl group or a substituted or unsubstituted heteroaryl group.

2. A pyridine compound or pharmaceutically acceptable salt thereof according to claim 1, excluding the case wherein Y' and F' together form a group of the general formula (12'-1), (12'-2), (12"-1) or (12"-2).

3. A pyridine compound or pharmaceutically acceptable salt thereof according to claim 2, wherein B' represents a group of the general formula (10).

4. A pyridine compound or pharmaceutically acceptable salt thereof according to claim 2, wherein B' represents a group of the general formula (10), Y' represents a group of the general formula (12), and X' represents an oxygen atom.

5. A pyridine compound or pharmaceutically acceptable salt according to claim 2, wherein B' represents carboxyl groups, and E' represents a group of the general formula (3) or (4).

6. A pyridine compound or pharmaceutically acceptable salt thereof according to claim 2, wherein B' represents carboxyl groups, E' represents a group of the general formula (3) or (4), X' represents an oxygen atom, and Y' represents a group of the general formula (12).

7. A pyridine compound or pharmaceutically acceptable salt thereof according to claim 2, wherein C' and E' may be the same or different from each other and each represents a hydrogen atom, a lower alkyl group which may contain a hetero atom in the chain thereof, dimethoxymethyl group, cyano group, a hydroxy-lower alkyl group or a halogeno-lower alkyl group, and B' represents a group of the general formula (10).

8. A pyridine compound or pharmaceutically acceptable salt thereof according to claim 2, wherein B' represents a group of the general formula (10) wherein Z represents a nitrogen atom and J represents a hydrogen atom, C' and E' represent a lower alkyl group, and Y' represents a group of the general formula (12) wherein $R^{26}$ represents a substituted or unsubstituted aryl group and h=2.

9. A pyridine compound or pharmaceutically acceptable salt thereof according to claim 7, wherein B' represents a group of the general formula (10) wherein Z represents a nitrogen atom and J represents a hydrogen atom, C' and E' represent a lower alkyl group, Y' represents a group of the general formula (12) wherein $R^{26}$ represents a substituted or unsubstituted aryl group and h=2, and X' represents an oxygen atom.

10. A pyridine compound or pharmaceutically acceptable salt thereof according to claim 1, wherein A' represents 3-chlorophenyl group, B' represents a carboxyl group, C' and E' represent a methyl group, X' represents an oxygen atom, Y' and F' together form a group of the general formula (12"-1), i represents an integer of 3 and $R^{32}$, $R^{33}$, $R^{34}$ and $R^{35}$ represent a hydrogen atom.

11. A pharmaceutical composition comprising a pyridine compound or pharmaceutically acceptable salt thereof according to claim 1 and a pharmaceutically acceptable carrier.

12. A pharmaceutical composition comprising a pyridine compound or pharmaceutically acceptable salt thereof according to claim 2 and a pharmaceutically acceptable carrier.

13. A pharmaceutical composition comprising a pyridine compound or pharmaceutically acceptable salt thereof according to claim 3 and a pharmaceutically acceptable carrier.

14. A pharmaceutical composition comprising a pyridine compound or pharmaceutically acceptable salt thereof according to claim 4 and a pharmaceutically acceptable carrier.

15. A method for treating neuropathic pain, said method comprising administering an effective amount of a pyridine compound or pharmaceutically acceptable salt thereof according to claim 1 to a subject in need thereof.

16. A method for treating neuropathic pain, said method comprising administering an effective amount of a pyridine compound or pharmaceutically acceptable salt thereof according to claim 2 to a subject in need thereof.

17. A pharmaceutical composition comprising a pyridine compound or pharmaceutically acceptable salt thereof according to claim 5 and a pharmaceutically acceptable carrier.

18. A pharmaceutical composition comprising a pyridine compound or pharmaceutically acceptable salt thereof according to claim 6 and a pharmaceutically acceptable carrier.

19. A pharmaceutical composition comprising a pyridine compound or pharmaceutically acceptable salt thereof according to claim 7 and a pharmaceutically acceptable carrier.

20. A pharmaceutical composition comprising a pyridine compound or pharmaceutically acceptable salt thereof according to claim 8 and a pharmaceutically acceptable carrier.

21. A pharmaceutical composition comprising a pyridine compound or pharmaceutically acceptable salt thereof according to claim 9 and a pharmaceutically acceptable carrier.

22. A pharmaceutical composition comprising a pyridine compound or pharmaceutically acceptable salt thereof according to claim 10 and a pharmaceutically acceptable carrier.

23. A method for treating neuropathic pain, said method comprising administering an effective amount of a pyridine compound or pharmaceutically acceptable salt thereof according to claim 3 to a subject in need thereof.

24. A method for treating neuropathic pain, said method comprising administering an effective amount of a pyridine compound or pharmaceutically acceptable salt thereof according to claim 4 to a subject in need thereof.

25. A method for treating neuropathic pain, said method comprising administering an effective amount of a pyridine compound or pharmaceutically acceptable salt thereof according to claim 5 to a subject in need thereof.

26. A method for treating neuropathic pain, said method comprising administering an effective amount of a pyridine compound or pharmaceutically acceptable salt thereof according to claim 6 to a subject in need thereof.

27. A method for treating neuropathic pain, said method comprising administering an effective amount of a pyridine compound or pharmaceutically acceptable salt thereof according to claim 7 to a subject in need thereof.

28. A method for treating neuropathic pain, said method comprising administering an effective amount of a pyridine compound or pharmaceutically acceptable salt thereof according to claim 8 to a subject in need thereof.

29. A method for treating neuropathic pain, said method comprising administering an effective amount of a pyridine compound or pharmaceutically acceptable salt thereof according to claim 9 to a subject in need thereof.

30. A method for treating neuropathic pain, said method comprising administering an effective amount of a pyridine compound or pharmaceutically acceptable salt thereof according to claim 10 to a subject in need thereof.

* * * * *